US009943577B2

(12) United States Patent
Watkins et al.

(10) Patent No.: US 9,943,577 B2
(45) Date of Patent: *Apr. 17, 2018

(54) AMINOACYL TRNA SYNTHETASES FOR MODULATING INFLAMMATION

(71) Applicant: aTyr Pharma, Inc., San Diego, CA (US)

(72) Inventors: Jeffry Dean Watkins, Encinitas, CA (US); Alain Philippe Vasserot, Carlsbad, CA (US); Leslie Ann Greene, San Diego, CA (US); Ryan Andrew Adams, San Diego, CA (US); Kyle P. Chiang, Cardiff, CA (US); Wei Zhang, San Diego, CA (US); Kristi Helen Piehl, San Diego, CA (US); Fei Hong, San Diego, CA (US); Alina He, San Diego, CA (US)

(73) Assignee: aTyr Pharma, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/365,079

(22) Filed: Nov. 30, 2016

(65) Prior Publication Data

US 2017/0202933 A1 Jul. 20, 2017

Related U.S. Application Data

(63) Continuation of application No. 14/541,792, filed on Nov. 14, 2014, now Pat. No. 9,540,628, which is a continuation of application No. 13/762,151, filed on Feb. 7, 2013, now Pat. No. 9,328,340, which is a continuation of application No. 13/514,952, filed as application No. PCT/US2010/059963 on Dec. 10, 2010, now Pat. No. 9,127,268.

(60) Provisional application No. 61/285,913, filed on Dec. 11, 2009, provisional application No. 61/285,923, filed on Dec. 11, 2009, provisional application No. 61/285,919, filed on Dec. 11, 2009.

(51) Int. Cl.
C12N 9/00 (2006.01)
A61K 38/53 (2006.01)
A61K 45/06 (2006.01)

(52) U.S. Cl.
CPC .............. *A61K 38/53* (2013.01); *A61K 45/06* (2013.01); *C12Y 601/01021* (2013.01)

(58) Field of Classification Search
CPC ........................................................ C12N 9/93
USPC ........................................................ 435/183
See application file for complete search history.

(56) References Cited

U.S. PATENT DOCUMENTS 5,155,214 A 10/1992 Baird et al.
5,484,703 A 1/1996 Raben et al.
5,556,645 A 9/1996 Bockman et al.
5,641,867 A 6/1997 Stern et al.
5,663,066 A 9/1997 Raben et al.
5,981,606 A 11/1999 Martin
6,013,483 A 1/2000 Coleman et al.
6,225,060 B1 5/2001 Clark et al.
6,228,837 B1 5/2001 Stern et al.
6,428,960 B1 8/2002 Clark et al.
6,548,060 B1 4/2003 Kim
6,800,286 B1 10/2004 Olwin et al.
6,812,339 B1 11/2004 Venter et al.
6,864,226 B1 3/2005 Coleman et al.
6,875,749 B2 4/2005 Schwarz et al.
6,903,189 B2 6/2005 Schimmel et al.
6,916,648 B2 7/2005 Goddard et al.
7,037,505 B2 5/2006 Kim et al.
7,045,301 B2 5/2006 Coleman et al.
7,067,126 B2 6/2006 Schimmel et al.
7,144,984 B2 12/2006 Schimmel et al.
7,196,068 B2 3/2007 Kim et al.
7,273,844 B2 9/2007 Schimmel et al.
7,282,208 B2 10/2007 Kim
7,413,885 B2 8/2008 Schimmel et al.
7,459,529 B2 12/2008 Kim
7,476,651 B2 1/2009 Schimmel et al.
7,482,326 B2 1/2009 Coleman et al.
7,521,215 B2 4/2009 Schimmel et al.
7,528,106 B2 5/2009 Friedlander et al.
7,572,452 B2 8/2009 Kim
7,842,467 B1 11/2010 Heidbrink et al.
7,901,917 B2 3/2011 Schimmel et al.
7,902,165 B2 3/2011 Kim
7,981,426 B2 7/2011 Kim
8,003,780 B2 8/2011 Kim et al.

(Continued)

FOREIGN PATENT DOCUMENTS

CN 1341725 3/2002
CN 1341727 3/2002

(Continued)

OTHER PUBLICATIONS

International Preliminary Report on Patentability for International Application No. PCT/US2009/048915, dated Jan. 5, 2011.
International Search Report and Written Opinion for International Application No. PCT/US2009/048915, dated Nov. 2, 2009.
Office Action for U.S. Appl. No. 12/482,151, dated Oct. 11, 2011, 43 pages.
Office Action for U.S. Appl. No. 12/482,151, dated Mar. 18, 2011, 11 pages.
International Preliminary Report on Patentability for International Application No. PCT/US2009/046910, dated Dec. 13, 2010.

(Continued)

Primary Examiner — Tekchand Saidha
(74) Attorney, Agent, or Firm — Cooley LLP

(57) ABSTRACT

Inflammatory and other cellular response-modulating compositions are provided comprising aminoacyl-tRNA synthetase polypeptides, including active fragments and/or variants thereof. Also provided are methods of using such compositions in the treatment of conditions that benefit from the modulation of inflammation, such as inflammatory diseases or conditions.

12 Claims, 25 Drawing Sheets

(56) References Cited

U.S. PATENT DOCUMENTS

| | | |
|---|---|---|
| 8,014,957 B2 | 9/2011 | Radich et al. |
| 8,017,593 B2 | 9/2011 | Schimmel et al. |
| 8,026,088 B2 | 9/2011 | Yang |
| 8,101,566 B2 | 1/2012 | Schimmel et al. |
| 8,148,125 B2 | 4/2012 | Schimmel et al. |
| 8,404,242 B2 | 3/2013 | Zhou et al. |
| 9,127,268 B2 | 9/2015 | Watkins et al. |
| 9,328,340 B2 | 5/2016 | Watkins et al. |
| 9,540,628 B2 | 1/2017 | Watkins et al. |
| 2002/0128187 A1 | 9/2002 | Tang et al. |
| 2002/0160957 A1 | 10/2002 | Stern et al. |
| 2002/0182666 A1 | 12/2002 | Schimmel et al. |
| 2003/0004309 A1 | 1/2003 | Kim et al. |
| 2003/0017564 A1 | 1/2003 | Schimmel et al. |
| 2003/0158400 A1 | 8/2003 | Tang et al. |
| 2003/0165921 A1 | 9/2003 | Tang et al. |
| 2003/0215827 A1 | 11/2003 | Yue et al. |
| 2004/0018505 A1 | 1/2004 | Lee et al. |
| 2004/0048290 A1 | 3/2004 | Lee et al. |
| 2004/0101879 A1 | 5/2004 | Seidel-Dugan et al. |
| 2004/0152079 A1 | 8/2004 | Schimmel et al. |
| 2005/0119175 A1 | 6/2005 | Kim |
| 2005/0181375 A1 | 8/2005 | Aziz et al. |
| 2005/0196754 A1 | 9/2005 | Drmanac et al. |
| 2006/0024288 A1 | 2/2006 | Glidden |
| 2006/0046250 A1 | 3/2006 | Kim |
| 2006/0078553 A1 | 4/2006 | Glidden |
| 2006/0134663 A1 | 6/2006 | Harkin et al. |
| 2006/0204508 A1 | 9/2006 | Champion et al. |
| 2006/0228715 A1 | 10/2006 | Shiffman et al. |
| 2006/0275794 A1 | 12/2006 | Carrino et al. |
| 2007/0037165 A1 | 2/2007 | Venter et al. |
| 2007/0042392 A1 | 2/2007 | Tang et al. |
| 2007/0048322 A1 | 3/2007 | Schimmel et al. |
| 2007/0054278 A1 | 3/2007 | Cargill |
| 2007/0061916 A1 | 3/2007 | Kovalic et al. |
| 2007/0072175 A1 | 3/2007 | Cooper et al. |
| 2007/0093440 A1 | 4/2007 | Champion et al. |
| 2007/0111238 A1 | 5/2007 | Jamieson et al. |
| 2007/0154931 A1 | 7/2007 | Radich et al. |
| 2009/0221437 A1 | 9/2009 | Harkin et al. |
| 2009/0221794 A1 | 9/2009 | Kim et al. |
| 2009/0227662 A1 | 9/2009 | Schimmel et al. |
| 2009/0264453 A1 | 10/2009 | Shiffman et al. |
| 2009/0285792 A1 | 11/2009 | Friedlander et al. |
| 2009/0305973 A1 | 12/2009 | Kim et al. |
| 2010/0003230 A1 | 1/2010 | Glidden |
| 2010/0028352 A1 | 2/2010 | Greene et al. |
| 2010/0041608 A1 | 2/2010 | Kim |
| 2010/0048413 A1 | 2/2010 | Arcus et al. |
| 2010/0092434 A1 | 4/2010 | Belani et al. |
| 2010/0138941 A1 | 6/2010 | Kim et al. |
| 2010/0167997 A1 | 7/2010 | Kim |
| 2010/0310576 A1 | 12/2010 | Adams et al. |
| 2011/0104139 A1 | 5/2011 | Faber |
| 2011/0110917 A1 | 5/2011 | Schimmel et al. |
| 2011/0117572 A1 | 5/2011 | Kim et al. |
| 2011/0124582 A1 | 5/2011 | Kim et al. |
| 2011/0136119 A1 | 6/2011 | Kim et al. |
| 2011/0150885 A1 | 6/2011 | Watkins et al. |
| 2011/0183924 A1 | 7/2011 | Beck et al. |
| 2011/0189195 A1 | 8/2011 | Kim et al. |
| 2011/0250701 A1 | 10/2011 | Kim et al. |
| 2011/0256119 A1 | 10/2011 | Kim et al. |
| 2012/0004185 A1 | 1/2012 | Greene |
| 2012/0015383 A1 | 1/2012 | Park et al. |
| 2012/0058133 A1 | 3/2012 | Whitman et al. |
| 2012/0064082 A1 | 3/2012 | Watkins et al. |
| 2013/0108630 A1 | 5/2013 | Watkins et al. |
| 2013/0273045 A1 | 10/2013 | Watkins et al. |

FOREIGN PATENT DOCUMENTS

| | | |
|---|---|---|
| CN | 1352242 | 6/2002 |
| CN | 1352252 | 6/2002 |
| EP | 0893494 | 1/1999 |
| EP | 0893496 | 1/1999 |
| EP | 0897004 | 2/1999 |
| EP | 1275720 | 1/2003 |
| EP | 1300468 | 4/2003 |
| EP | 1377305 | 1/2009 |
| EP | 1776138 | 10/2009 |
| EP | 1274834 | 7/2010 |
| JP | 2012-520681 | 9/2012 |
| WO | WO 1997/026351 | 7/1997 |
| WO | WO 1997/039017 | 10/1997 |
| WO | WO 1999/045130 | 9/1999 |
| WO | WO 2001/057190 | 8/2001 |
| WO | WO 2001/074841 | 10/2001 |
| WO | WO 2001/075067 | 10/2001 |
| WO | WO 2001/075078 | 10/2001 |
| WO | WO 2001/088188 | 11/2001 |
| WO | WO 2001/090330 | 11/2001 |
| WO | WO 2001/094568 | 12/2001 |
| WO | WO 2002/055663 | 7/2002 |
| WO | WO 2002/059323 | 8/2002 |
| WO | WO 2002/067970 | 9/2002 |
| WO | WO 2002/068579 | 9/2002 |
| WO | WO 2003/009813 | 2/2003 |
| WO | WO 2003/080648 | 10/2003 |
| WO | WO 2003/094848 | 11/2003 |
| WO | WO 2003/094862 | 11/2003 |
| WO | WO 2004/023973 | 3/2004 |
| WO | WO 2004/060262 | 7/2004 |
| WO | WO 2004/063355 | 7/2004 |
| WO | WO 2004/064863 | 8/2004 |
| WO | WO 2005/073250 | 8/2005 |
| WO | WO 2005/087953 | 9/2005 |
| WO | WO 2005/102395 | 11/2005 |
| WO | WO 2005/113812 | 12/2005 |
| WO | WO 2005/117954 | 12/2005 |
| WO | WO 2006/016217 | 2/2006 |
| WO | WO 2006/048219 | 5/2006 |
| WO | WO 2006/057500 | 6/2006 |
| WO | WO 2007/064941 | 6/2007 |
| WO | WO 2008/007818 | 1/2008 |
| WO | WO 2008/016356 | 2/2008 |
| WO | WO 2008/021290 | 2/2008 |
| WO | WO 2008/133359 | 11/2008 |
| WO | WO 2009/114623 | 9/2009 |
| WO | WO 2009/152247 | 12/2009 |
| WO | WO 2009/158649 | 12/2009 |
| WO | WO 2010/021415 | 2/2010 |
| WO | WO 2010/041892 | 4/2010 |
| WO | WO 2010/041913 | 4/2010 |
| WO | WO 2010/090471 | 8/2010 |
| WO | WO 2010/096170 | 8/2010 |
| WO | WO 2010/099477 | 9/2010 |
| WO | WO 2010/107825 | 9/2010 |
| WO | WO 2010/120509 | 10/2010 |
| WO | WO 2011/072265 | 6/2011 |
| WO | WO 2011/072266 | 6/2011 |
| WO | WO 2011/097031 | 8/2011 |
| WO | WO 2011/150279 | 12/2011 |
| WO | WO 2012/021249 | 2/2012 |

OTHER PUBLICATIONS

International Search Report and Written Opinion for International Application No. PCT/US2009/046910, dated Mar. 4, 2010.
Office Action for U.S. Appl. No. 12/085,884, dated Jan. 20, 2011.
International Preliminary Report on Patentability for International Application No. PCT/US2006/046106, dated Jun. 4, 2008.
International Search Report and Written Opinion for International Application No. PCT/US2006/046106, dated Aug. 9, 2007.
International Preliminary Report on Patentability for International Application No. PCT/US2010/025642, dated Aug. 30, 2011.
International Search Report and Written Opinion for International Application No. PCT/US2010/025642, dated Oct. 29, 2010.
Office Action for U.S. Appl. No. 12/751,358, dated Oct. 3, 2011.
Office Action for U.S. Appl. No. 12/751,358, dated Mar. 3, 2011.
International Preliminary Report on Patentability for International Application No. PCT/US2010/029377, dated Oct. 4, 2011.

(56) References Cited

OTHER PUBLICATIONS

International Search Report and Written Opinion for International Application No. PCT/US2010/029377, dated Jan. 26, 2011.
Supplementary European Search Report for European Application No. 10753998, dated Nov. 21, 2012.
Office Action for U.S. Appl. No. 12/725,272, dated Jul. 13, 2012, 9 pages.
International Preliminary Report on Patentability for International Application No. PCT/US2010/027525, dated Sep. 20, 2011.
International Search Report and Written Opinion for International Application No. PCT/US2010/027525, dated Jan. 10, 2011.
International Search Report and Written Opinion for International Application No. PCT/US2010/059964, dated Aug. 25, 2011.
Communication Pursuant to Article 94(3) EPC for European Application No. 10793402.8, dated Mar. 27, 2013.
Office Action for U.S. Appl. No. 13/514,952, dated Jul. 18, 2014, 11 pages.
Office Action for U.S. Appl. No. 13/514,952, dated Nov. 14, 2014, 8 pages.
International Preliminary Report on Patentability for International Application No. PCT/US2010/059963, dated Jun. 12, 2012, 18 pages.
International Search Report and Written Opinion for International Application No. PCT/US2010/059963, dated May 12, 2011.
Office Action for U.S. Appl. No. 13/762,151, dated Sep. 10, 2014, 12 pages.
Office Action for U.S. Appl. No. 13/762,151, dated Jan. 2, 2015, 14 pages.
International Search Report and Written Opinion for International Application No. PCT/US2011/000210, dated Aug. 12, 2011.
Adams, M. D. et al., "The genome sequence of *Drosophila melanogaster*," Science, 287(5961):2185-2195 (2000).
Aderem, A. et al., "Toll-like receptors in the induction of the innate immune response," Nature, 406:782-787 (2000).
Amaar, Y. G. et al., "Cloning and characterization of the C.elegans histidyl-tRNA synthetase gene," Nucleic Acids Research, 21(18):4344-4347 (1993).
Ascherman, D. P. et al., "Critical Requirement for Professional APCs in Eliciting T Cell Responses to Novel Fragments of Histidyl-tRNA Synthetase (Jo-1) in Jo-1 Antibody-Positive Polymyositis," J. Immunol., 169:7127-7134 (2002).
Ascherman, D. P., "The Role of Jo-1 in the Immunopathogenesis of Polymyositis: Current Hypotheses," Current Rheumatology Reports, 5:425-430 (2003).
Barbasso, S. et al., "Sera From Anti-Jo-1-Positive Patients with Polymyositis and Interstitial Lung Disease Induce Expression of Intercellular Adhesion Molecule 1 in Human Lung Endothelial Cells," Arthritis & Rheumatism, 60(8):2524-2530 (2009).
Bernstein, R. M. et al., "Anti-Jo-1 antibody: a marker for myositis with interstitial lung disease," British Medical Journal, 289:151-152 (1984).
Blechynden, L.M. et al., "Sequence and polymorphism analysis of the murine gene encoding histidyl-tRNA synthetase," Gene, 178:151-156 (1996).
Blechynden, L.M. et al., "Myositis Induced by Naked DNA Immunization with the Gene for Histidyl-tRNA Synthetase," Human Gene Therapy, 8:1469-1480 (Aug. 10, 1997).
Blum, D. et al., "Extracellular toxicity of 6-hydroxydopamine on PC12 cells," Neuroscience Letters, 283(3):193-196 (2000).
Brightbill, H. D. et al., "Toll-like receptors: molecular mechanisms of the mammalian immune response," Immunology, 101:1-10 (2000).
Broun, P. et al., "Catalytic plasticity of fatty acid modification enzymes underlying chemical diversity of plant lipids," Science, 282:1315-1317 (1998).
Brown, M. V. et al., "Mammalian aminoacyl-tRNA synthetases: Cell signaling functions of the protein translation machinery," Vascular Pharmacology, 52(1-2):21-26 (2010).
Casciola-Rosen, L. et al., "Cleavage by Granzyme B Is Strongly Predictive of Autoantigen Status: Implications for Initiation of Autoimmunity," J. Exp. Med., 190(6):815-825 (1999).
Casciola-Rosen, L., "Histidyl-Transfer RNA Synthetase: A Key Participant in Idiopathic Inflammatory Myopathies," Arthritis and Rheumatism, 63(2):331-333 (2011).
Chica, R. A. et al., "Semi-rational approaches to engineering enzyme activity: combining the benefits of directed evolution and rational design," Curr. Opin. Biotechnol., 16:378-384 (2005).
Choi, W. S. et al., "Two Distinct Mechanisms Are Involved in 6-Hydroxydopamine-and MPP+-Induced Dopaminergic Neuronal Cell Death: Role of Caspases, ROS, and JNK," Journal of Neuroscience Research, 57(1):86-94 (1999).
Delgado, C. et al., "The uses and properties of PEG-linked proteins," Critical Reviews in Therapeutic Drug Carrier Systems, 9(3,4):249-304 (1992).
Devos, D. et al., "Practical limits of function prediction," Proteins: Structure, Function, and Genetics, 41:98-107 (2000).
Ewalt, K. L. et al., "Activation of Angiogenic Signaling Pathways by Two Human tRNA Synthetases," Biochemistry, 41(45):13344-13349 (2002).
Felden, B. et al., "Resected RNA pseudoknots and their recognition by histidyl-tRNA synthetase," Proc. Natl. Acad. Sci. USA, 95:10431-10436 (1998).
Francklyn, C. et al., "Histidyl-tRNA Synthetase," Eurekah Bioscience, 1(3):265-277 (2005).
Frommhold, D. et al., "Sialyltransferase ST3Gal-IV controls CXCR2-mediated firm leukocyte arrest during inflammation," Journal of Experimental Medicine, 205(6):1435-1446 (2008).
GenBank Accession No. AA984229, published May 27, 1998.
GenBank Accession No. AK055917, published Jan. 19, 2008.
GenBank Accession No. AK124831, published Jul. 3, 2008.
GenBank Accession No. AK225776, published Jul. 22, 2006.
GenBank Accession No. AK293154, published Jul. 24, 2008.
GenBank Accession No. AK293531, published Jul. 24, 2008.
GenBank Accession No. AK295219, published Jul. 24, 2008.
GenBank Accession No. AK302295, published Jul. 24, 2008.
GenBank Accession No. AK303778, published Jul. 24, 2008.
GenBank Accession No. AU129836, published Feb. 18, 2011.
GenBank Accession No. BE872272, published Jan. 13, 2011.
GenBank Accession No. BF791754, published Jan. 13, 2011.
GenBank Accession No. BG108830, published Jun. 1, 2001.
GenBank Accession No. BP268250, published Feb. 10, 2011.
GenBank Accession No. DA083923, published Feb. 17, 2011.
GenBank Accession No. DB146646, published Feb. 16, 2011.
GenBank Accession No. Q7QD89, Anopheles gambiae Sequence Committee, submitted Apr. 2002, [Retrieved from the Internet Apr. 24, 2007], <URL: http://www.ncbi.nlm.nih.gov/entrez/viewer.fcgi?db=protein&val=74803944>.
GenBank Accession No. Q9VV60, published May 1, 2000.
GenBank Accession No. Z11518, published Oct. 7, 2008.
Goldgur, Y. et al., "The crystal structure of phenylalanyl-tRNA synthetase from Thermus thermophilus complexed with cognate tRNA," Structure, 5:59-68 (1997).
Greenberg, Y. et al., "The novel fragment of tyrosyl tRNA synthetase, mini-TyrRS, is secreted to induce an angiogenic response in endothelial cells," FASEB Journal, 22(5):1597-1605 (2008).
Grundtman, C. et al., "Immune mechanisms in the pathogenesis of idiopathic inflammatory myopathies," Arthritis Research & Therapy, 9:208 (2007).
Guijarro, J. I. et al., "Structure and Dynamics of the Anticodon Arm Binding Domain of *Bacillus stearothermophilus* Tyrosyl-tRNA Synthetase," Structure, 10:311-317 (2002).
Guo, R-T. et al., "Crystal structures and biochemical analyses suggest a unique mechanism and role for human glycyl-tRNA synthetase in Ap4A homeostasis," Journal of Biological Chemistry, 284(42):28968-28976 (2009).
Guo, M. et al., "Functional expansion of human tRNA synthetases achieved by structural inventions," FEBS Letters, 584(2):434-442 (2010).
Hanrott, K. et al., "6-Hydroxydopamine-induced Apoptosis Is Mediated via Extracellular Auto-oxidation and Caspase 3-depen-

(56) References Cited

OTHER PUBLICATIONS dent Activation of Protein Kinase C8," The Journal of Biological Chemistry, 281(9):5373-5382 (2006).
Hartl, D. et al., "Infiltrated neutrophils acquire novel chemokine receptor expression and chemokine responsiveness in chronic inflammatory lung diseases," J. Immunol., 181:8053-8067 (2008).
Hausmann, C. D. et al., "Aminoacyl-tRNA synthetase complexes: molecular multitasking revealed," FEMS Microbiol. Rev., 32(4):705-721 (2008).
Hengstman, G. J. D. et al., "Anti-Jo-1 positive inclusion body myositis with a marked and sustained clinical improvement after oral prednisone," J. Neurol. Neurosurg. Psychiatry, 70(5):706 (2001).
Hou, Y-M. et al., "Sequence determination and modeling of structural motifs for the smallest monomeric aminoacyl-tRNA synthetase," Proc. Nat. Acad. Sci., 88(3):976-980 (1991).
Howard, O. M. Z. et al., "Histidyl-tRNA Synthetase and Asparaginyl-tRNA Synthetase, Autoantigens in Myositis, Activate Chemokine Receptors on T Lymphocytes and Immature Dendritic Cells," The Journal of Experimental Medicine, 196(6):781-791 (2002).
Howard, O. M. Z. et al., "Autoantigens signal through cheokine receptors: uveitis antigens induce CXCR3- and CRCR5-expressing lymphocytes and immature dendritic cells to migrate", Blood, 105(11) 4207-4214 (2005).
Ivakhno, S. S. et al., "Cytokine-Like Activities of Some Aminoacyl-tRNA Synthetases and Auxiliary p43 Cofactor of Aminoacylation Reaction and Their Role in Oncogenesis," Exp. Oncol., 26(4):250-255 (2004).
Izumi, Y. et al., "p-Quinone Mediates 6-Hydroxydopamine-Induced Dopaminergic Neuronal Death and Ferrous Iron Accelerates the conversion of p-Quinone Into Melanin Extracellularly," Journal of Neuroscience Research, 79(6):849-860 (2005).
Jacobo-Molina, A. et al., "cDNA Sequence, Predicted Primary Structure, and Evolving Amphiphilic Helix of Human Aspartyl-tRNA Synthetase," Journal of Biological Chemistry, 264(28):16608-16612 (1989).
Jura, M. et al., "Comprehensive Insight into human aminoacyl-tRNA synthetases as autoantigens in idiopathic inflammatory myopathies," Critical Reviews in Immunology, 27(6):559-572 (2007).
Kapoor, M. et al., "Mutational separation of aminoacylation and cytokine activities of human tyrosyl-tRNA synthetase," Chemistry & Biology, 16(5):531-539 (2009).
Katsumata, Y. et al., "Species-specific immune responses generated by histidyl-tRNA synthetase immunization are associated with muscle and lung inflammation," Journal of Autoimmunity, 29:174-186 (2007).
Katsumata, Y. et al., "Animal models in myositis," Current Opinion in Rheumatology, 20:681-685 (2008).
Katsumata, Y. et al., "Attenuation of experimental autoimmune myositis by blocking ICOS-ICOS ligand interaction," J. Immunol., 179:3772-3779 (2007).
Kimchi-Sarfaty, C. et al., "A 'Silent' polymorphism in the MDR1 gene changes substrate specificty," Science, 315:525-528 (2007).
Kise, Y. et al., "A short peptide insertion crucial for angiostatic activity of human tryptophanyl-tRNA synthetase," Nature Structural & Molecular Biology, 11(2):149-156 (2004).
Kochendoerfer, G. G., "Site-specific polymer modification of therapeutic proteins," Current Opinion in Chemical Biology, 9:555-560 (2005).
Kovaleski, B. J. et al.,"In vitro characterization of the interaction between HIV-1 Gag and human lysyl-tRNA synthetase," J. Bio. Chem., 281(28):19449-19456 (2006).
Kucharzik, T. et al., "Neutrophil transmigration in inflammatory bowel disease is associated with differential expression of epithelial intercellular junction proteins," American Journal of Pathology, 159(6):2001-2009 (2001).

Levine, S. M. et al., "Anti-aminoacyl tRNA synthetase immune responses: insights into the pathogenesis of the idiopathic inflammatory myopathies," Current Opinion in Rheumatology, 15(6):708-713 (2003).
Levine, S. M., et al., "Novel Conformation of Histidyl-Transfer RNA Synthetase in the Lung", Arthritis & Rheumatism, 56(8): 2729-2739, 2007.
Link, A. J. et al., "Discovery of aminoacyl-tRNA synthetase activity through cell-surface display of noncanonical amino acids," Proc. Nat. Acad. Sci., 103(27):10180-10185 (2006).
Martin, A. et al., "Epitope studies indicate that histidyl-tRNA synthetase is a stimulating antigen in idiopathic myositis," The FASEB Journal, 9:1226-1233 (1995).
Miller, F. W., et al., "Origin and Regulation of a Disease-specific Autoantibody Response, Antigenic Epitopes, Spectrotype Stability, and Isotype Restriction of Anti-Jo-1 Autoantibodies," J. Clin. Invest., 85:468-475 (1990).
Miller, F. W. et al., "The role of an autoantigen, histidyl-tRNA synthetase, in the induction and maintenance of autoimmunity," Proc. Natl. Acad. Sci. USA, 87:9933-9937 (1990).
Molecular Modeling Database (MMDB), "Solution Structures of the Whep-trs domain of human histidyl-trna synthetase," MMDB ID No. 35920, available for www.ncbi.nlm.nih.gov/Structure/mmdb, accessed Aug. 24, 2012.
Mozaffar, T. et al., "Myopathy with anti-Jo-1 antibodies: pathology in perimysium and neighbouring muscle fibres," J. Neurol. Neurosurg. Psychiatry, 68:472-478 (2000).
Moldoveanu, B. et al., "Inflammatory mechanisms in the lung," Journal of Inflammation Research, 2:1-11 (2009).
Nackley, A. G. et al., "Human Caechol-O-Methytransferase haplotypes modulate protein expression by altering mRNA secondary structure," Science, 314:1930-1933 (2006).
Naito, Y. et al., "Neutrophil-dependent oxidative stress in ulcerative colitis," J. Clin. Biochem. Nutr., 41:18-26 (2007).
Ngo, J. T. et al., "Computational complexity, protein structure prediction, and the Levinthal paradox," In The Protein Folding Problem and Tertiary Structure Prediction, Merz et al. (ed.), Birkhauser, Boston, MA, pp. 433 and 492-495 (1994).
Nichols, R. C. et al., "Human isoleucyl-tRNA synthetase: sequence of the cDNA, alternative mRNA splicing, and the characteristics of an unusually long C-terminal extension," Gene, 155(2):299-304 (1995).
Nishikai, M. et al., "Heterogeneity of Precipitating Antibodies in Polymyositis and Dermatomyositis," Arthritis and Rheumatism, 23(8):881-888 (1980).
O'Hanlon, T. P. et al., "Genomic organization, transcriptional mapping, and evolutionary implications of the human bi-directional histidyl-tRNA synthetase locus (HARS/HARSL)," Biochemical and Biophysical Research Communications, 294:609-614 (2002).
Oppenheim, J. J. et al., "Autoantigens act as tissue-specific chemoattractants," Journal of Leukocyte Biology, 77:854-861 (2005).
Park, S. G., et al., "Aminoacyl tRNA synthetases and their connections to disease," PNAS, 105(32):11043-11049 (2008).
Park, C-K. et al., "Development of antisynthetase syndrome in a patient with rheumatoid arthritis," Rheumatol. Int., 31:529-532 (2011).
Park, S. G. et al., "Dose-dependent biphasic activity of tRNA synthetase-associating factor, p43, in angiogenesis," The Journal of Biological Chemistry, 277(47):45243-45248 (2002).
Park, S. G. et al., "Is there an answer? Do aminoacyl-tRNA synthetases have biological functions other than in protein biosynthesis?" IUBMB Life, 58(9):556-558 (2006).
Parker, L. C. et al., "Toll-Like Receptor (TLR)2 and TLR4 Agonists Regulate CCR Expression in Human Monocytic Cells," The Journal of Immunology, 172:4977-4986 (2004).
Pierce, S. B. et al., "Mutations in mitochondrial histidyl tRNA synthetase HARS2 cause ovarian dysgenesis and sensorineural hearing loss of Perrault syndrome," PNAS, 108(16):6543-6548 (2011).
Puffenberger, E. G. et al., "Genetic mapping and exome sequencing identify variants associated with five novel diseases," PLoS, 7(1):e28936 (2012).

(56) References Cited

OTHER PUBLICATIONS

Quesniaux, V. F.J. et al., "Hematopoiesis, including lymphocyte developmet and maturation," Principles of Immunopharmacology, pp. 3-17 (2005).
Raben, N. et al., "A Motif in Human Histidyl-tRNA Synthetase Which Is Shared among Several Aminoacyl-tRNA Synthetases Is a Coiled-coil That is Essential for Enzymatic Activity and Contains the Major Autoantigenic Epitope," The Journal of Biological Chemistry, 269(39): 24277-24283 (1994).
Reed, V. S. et al., "Characterization of a Novel N-terminal Peptide in Human Aspartyl-tRNA Synthetase," Journal of Biological Chemistry, 269(52):32937-32941 (1994).
Richardson, R. M. et al., "Role of the cytoplasmic tails of CXCR1 and CXCR2 in mediating leukocyte migration, activation, and regulation," Journal of Immunology, 170(6):2904-2911 (2003).
Rosenberg, N. L. et al., "Experimental autoimmune myositis in SJL/J mice," Clin. Exp. Immunol., 68:117-129 (1987).
Sauna, Z. E. et al., "Silent polymorhisms speak: How they affect pharmacogenomics and the treatment of cancer," Cancer Res., 67(20):9609-9612 (2007).
Seburn, K. L. et al., "An active dominant mutation of glycyl-tRNA synthetase causes neuropathy in a Charcot-Marie-Tooth 2D mouse model," Neuron, 51(6):715-726 (2006).
Sen, S. et al., "Developments in directed evolution for improving enzyme functions," Appl. Biochem. Biotechnol., 143:212-223 (2007).
Smith, D. F. et al., "Leukocyte phosphoinositide-3 kinase γ is required for chemokine-induced, sustained adhesion under flow in vivo," Journal of Leukocyte Biology, 80(6):1491-1499 (2006).
Soejima, M. et al., "Role of Innate Immunity in a Murine Model of Histidyl-Transfer RNA Snythetase (Jo-1)-Mediated Myositis," Arthritis and Rheumatism, 63(2):479-487 (2011).
Stone, K. D. et al., "Immunomodulatory therapy of eosinophil-associated gastrointestinal diseases," Clin. Exp. Allergy, 38(12):1858-1865 (2008).
Sultan, S. M. et al., "Re-classifiyng myositis," Rheumatology, 49:831-833 (2010).
Tarabishy, A. B. et al., "Retinal Vasculitis Associated with the Anti-Synthetase Syndrome," Ocular Immunology & Inflamation, 18(1):16-18 (2010).
Targoff, I. N., "Update on myositis-specific and myositis-associated autoantibodies," Current Opinion in Rheumatology, 12:475-481 (2000).
Traves, S. L. et al., "Specific CXC but not CC chemokines cause elevated monocyte migration in COPD: a role for $CXCR_2$," Journal of Leukocyte Biology, 76(2):441-450 (2004).
Tsui, H. W. et al., "Transcriptional analyses of the gene region that encodes human histidyl-tRNA sysnthetase: identification of a novel bidirectional regulatory element," Gene, 131:201-208 (1993).
Tzioufas, A. G. et al., "Antisynthetase syndrome," Orphanet Encyclopedia, http://www.orpha.net/data/patho/GB/uk-antisynthetase.pdf, pp. 1-5 Nov. 2001.
Veronese, F. M. et al., "Preface: Introduction and overview of peptide and protein pegylation," Advanced Drug Delivery Reviews, 54:453-456 (2002).
Vestergaard, C. et al., "Expression of CCR2 on monocytes and macrophages in chronically inflamed skin in atopic dermatitis and psoriasis," Acta Derm. Venereol., 84:353-358 (2004).
Wakasugi, K. et al., "Two distinct cytokines released from a human aminoacyl-tRNA synthetase," Science, 284:147-151 (1999).
Wakasugi, K. et al., "A human aminoacyl-tRNA synthetase as a regulator of angiogenesis," Proc. Natl. Acad. Sci., 99(1):173-177 (2002).
Wakasugi, K. et al., "Induction of angiogenesis by a frament of human tyrosyl-tRNA synthetase," The Journal of Biological Chemistry, 277(23):20124-20126 (2002).
Wallace, E. A. et al., "Diagnosis and management of inflammatory muscle disease," The Journal of Musculoskeletal Medicine, 27(12):1-7 (2010).
Whisstock, J. C. et al., "Prediction of protein function from protein sequence," Q. Rev. Biophysics., 36(3):307-340 (2003).
Wishart, M. J. et al., "A single mutation converts a novel phosphotyrosine binding domain into a dual-specificity phosphatase," J. Biol. Chem., 270(45):26782-26785 (1995).
Witkowski, A. et al., "Conversion of β-ketoacyl synthase to a Malonyl Decarboxylase by replacement of the active cysteine with glutamine," Biochemistry, 38:11643-11650 (1999).
WPI Database Accession No. 2002-090149 (2013).
Woolhouse, I. S. et al., "Endothelial interactions of neutrophils under flow in chronic obstructive pulmonary disease," Eur. Respir. J., 25:612-617 (2005).
Xie, W. et al., "Long-range structural effects of a Charcot-Marie-Tooth disease-causing mutation in human glycyl-tRNA synthetase," PNAS, 104(24):9976-9981 (2007).
Xu, Z. et al., "Internally deleted human tRNA synthetase suggest evolutionary pressure for repurposing," Structure, 20(9):1470-1477 (2012).
Yang, X-L et al., "Crystal structure of a human aminoacyl-tRNA synthetase cytokine," PNAS, 99(24):15369-15374 (2002).
Yang, X-L et al., "Relationship of two human tRNA synthetases used in cell signaling," Trends in Biochemical Sciences, 29(5):250-256 (2004).
Yang, X-L et al., "Gain-of-Function Mutational Activation of Human tRNA Synthetase Procytokine," Chemistry & Biology, 14(12):1323-1333 (2007).
Yousem, S. A. et al., "The pulmonary histopathologic manifestations of the anti-Jo-1 tRNA synthetase syndrome," Modern Pathology, 23:874-880 (2010).
Yu, Y. et al., "Crystal structure of human tryptophanyl-tRNA synthetase catalytic fragment," The Journal of Biological Chemistry, 279(9):8378-8388 (2004).
Zalipsky, S. et al., "Use of functionalized poly(ethylene glycol)s for modification of polypeptides," Polyethylene glycol chemistry: Biotechnical and Biomedical Applications, pp. 347-370, Plenum Press, New York (1992).
Zhang, L. et al., "Chemical activation of innate and specific immunity in contact dermatitis," J. Invest. Dermatol., 115:168-176 (2000).
Zhou, Q. et al., "Orthogonal use of a human tRNA synthetase active site to achieve multifunctionality," Nature Structural & Molecular Biology, 17(1):57-62 (2010).
Zwijnenburg, P. J. G. et al., B-1426, "Tyrosyl tRNA synthetase is a chemotactic factor in cerebrospinal fluid from patients with bacterial meningitis," Abstracts of the 42nd Interscience Conference on Antimicrobial Agents and Chemotherapy, San Diego, California, Sep. 27-30, 2002, Session 156(B), p. 55.
Supplementary European Search Report for European Application No. 15152652.2, dated Sep. 11, 2015.
Kim, T. et al., "Catalytic Peptide of Human Glutaminyl-tRNA Synthetase Is Essential for Its Assembly to the Aminoacyl-tRNA Synthetase Complex," Journal of Biological Chemistry, 275(28):21768-21772 (2000).
Ko, Y-G. et al., "Glutamine-dependent Antiapoptotic Interaction of Human Glutaminyl-tRNA Synthetase with Apoptosis Signal-regulating Kinase 1," Journal of Biological Chemistry, 276(8):6030-6036 (2001).
Koh, Y. T. et al., "Role of Nucleic Acid-Sensing TLR's in Diverse Autoantibody Specifics and Anti-Nuclear Antibody-Producing B Cells," J Immunol., vol. 190(10):4982-4990, May 15, 2013.
Rubtsov, A., et al., "TLR7 Drives Accumulation of ABC's and Autoantibody Production in Autoimmune-prone Mice," Immonol Res. Mar. 2013, vol. 55(0); 210-216, 12 pages.
Schray, B. et al., "Glutaminyl-tRNA synthetase as a component of the high-molecular weight complex of human aminoacyl-tRNA synthetases. An immunological study," Biochimica et Biophysica Acta, 1087(2):226-234 (1990).
Targoff, I. N. et al., "Reaction of Anti-OJ Autoantibodies with Components of the Multi-enzyme Complex of Aminoacyl-tRNA Synthetases in Addition to Isoleucyl-tRNA Synthetases in Addition to Isoleucyl-tRNA Synthetase," Journal of Clinical Investigation, 91:2556-2564 (1993).

(56) References Cited

OTHER PUBLICATIONS

Zhu, J., et al., "Toll-Like Receptor Signaling Pathways—Therapeutic Opportunities," Hindawa Publishing Corporation, Mediators of Inflammation, vol. 2010, Article ID 781235, 7 pages.

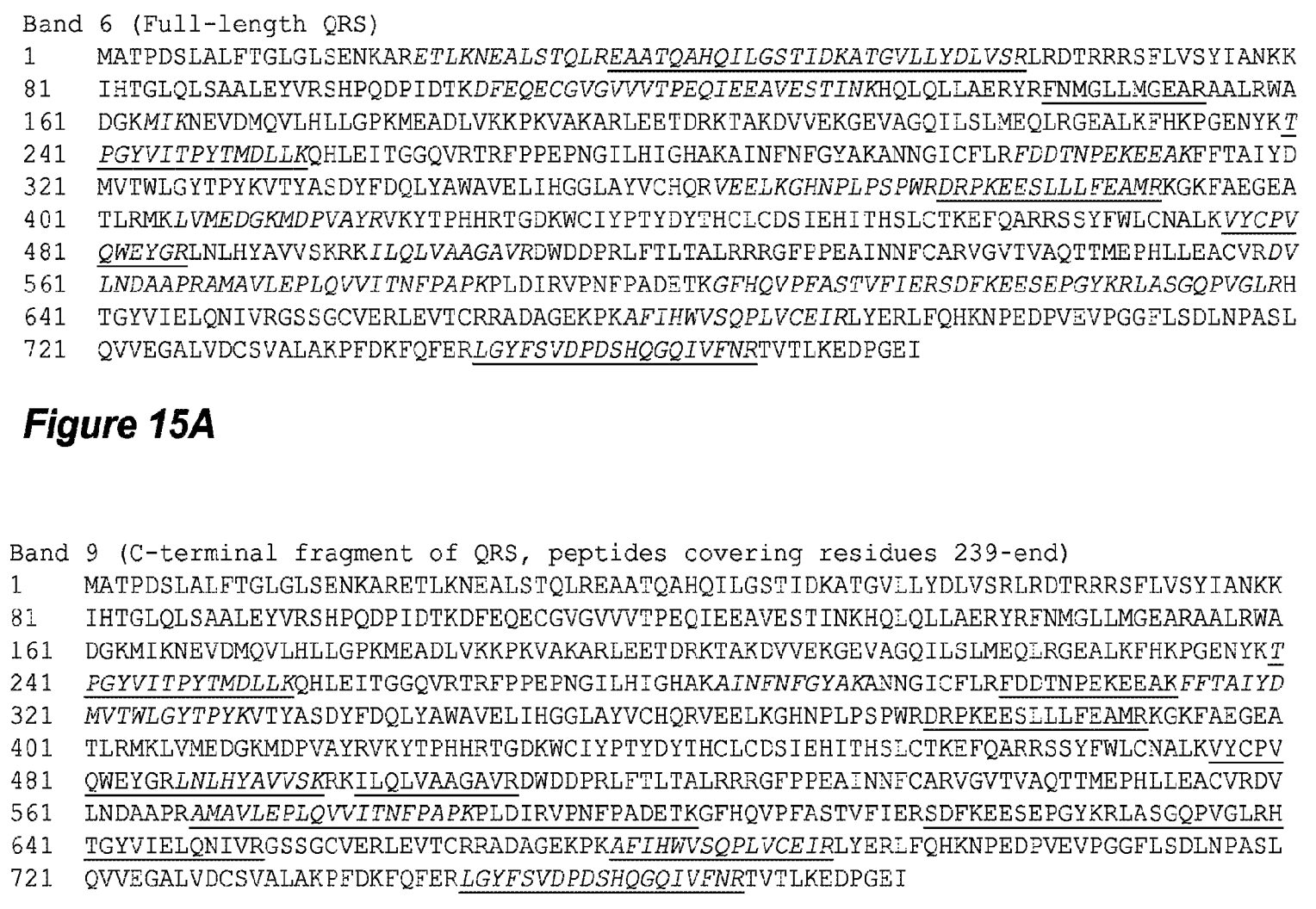

Band 6 (Full-length QRS)

```
  1  MATPDSLALFTGLGLSENKARETLKNEALSTQLREAATQAHQILGSTIDKATGVLLYDLVSRLRDTRRSFLVSYIANKK
 81  IHTGLQLSAALEYVRSHPQDPIDTKDFEQECGVGVVTPEQIEEAVESTINKHQLQLLAERYRFNMGLLMGEARAALRWA
161  DGKMIKNEVDMQVLHLLGPKMEADLVKKPKVAKARLEETDRKTAKDVVEKGEVAGQILSLMEQIRGEALKFHKPGENYKT
241  PGYVITPYTMDLLKQHLEITGGQVRTRFPPEPNGILHIGHAKAINFNFGYAKANNGICFLRFDDTNPEKEEAKFFTAIYD
321  MVTWLGYTPYKVTYASDYFDQLYAWAVELIHGGLAYVCHQRVEELKGHNPLPSPWRDRPKEESLLFEAMRKGKFAEGEA
401  TLRMKLVMEDGKMDPVAYRVKYTPHHRTGDKWCIYPTYDYTHCLCDSIEHITHSLCTKEFQARRSSYFWLCNALKVYCPV
481  QWEYGRLNLHYAVVSKRKILQLVAAGAVRDWDDPRLFTLALRRGFFPEAINNFCARVGVTVAQTTMEPHLLEACVRDV
561  LNDAAPRAMAVLEPLQVITNFPAPKPLDIRVPNFPADETKGFHQVPFASTVFIERSDFKEESEPGYKRLASGQPVGLRH
641  TGYVIELQNIVRGSSGCVERLEVTCRRADAGEKPKAFIHWVSQPLVCEIRLYERLFQHKNPEDPVEVPGGFLSDLNPASL
721  QVVEGALVDCSVALAKPFDKFQFERLGYFSVDPDSHQGQIVFNRTVTLKEDPGEI
```

*Figure 15A*

Band 9 (C-terminal fragment of QRS, peptides covering residues 239-end)

```
  1  MATPDSLALFTGLGLSENKARETLKNEALSTQLREAATQAHQILGSTIDKATGVLLYDLVSRLRDTRRSFLVSYIANKK
 81  IHTGLQLSAALEYVRSHPQDPIDTKDFEQECGVGVVTPEQIEEAVESTINKHQLQLLAERYRFNMGLLMGEARAALRWA
161  DGKMIKNEVDMQVLHLLGPKMEADLVKKPKVAKARLEETDRKTAKDVVEKGEVAGQILSLMEQERGEALKFHKPGENYKT
241  PGYVITPYTMDLLKQHLEITGGQVRTRFPPEPNGILHIGHAKAINFNFGYAKANNGICFLRFDDTNPEKEEAKFFTAIYD
321  MVTWLGYTPYKVTYASDYFDQLYAWAVELIHGGLAYVCHQRVEELKGHNPLPSPWRDRPKEESLLFEAMRKGKFAEGEA
401  TLRMKLVMEDGKMDPVAYRVKYTPHHRTGDKWCIYPTYDYTHCLCDSIEHITHSLCTKEFQARRSSYFWLCNALKVYCPV
481  QWEYGRLNLHYAVVSKRKILQLVAAGAVRDWDDPRLFTLALRRGFFPEAINNFCARVGVTVAQTTMEPHLLEACVRDV
561  LNDAAPRAMAVLEPLQVITNFPAPKPLDIRVPNFPADETKGFHQVPFASTVFIERSDFKEESEPGYKRLASGQPVGLRH
641  TGYVIELQNIVRGSSGCVERLEVTCRRADAGEKPKAFIHWVSQPLVCEIRLYERLFQHKNPEDPVEVPGGFLSDLNPASL
721  QVVEGALVDCSVALAKPFDKFQFERLGYFSVDPDSHQGQIVFNRTVTLKEDPGEI
```

*Figure 15B*

Band 19 (N-terminal fragment of QRS peptides covering beginning - 180)

```
  1   MATPDSLALFTGLGLSENKARETLKNEALSTQLREAATQAHQILGSTIDKATGVLLYDLVSRLRDTRRSFLVSYIANKK
 81   IHTGLQLSAALEYVRSHPQDPIDTKDFEQECGVGVVTPEQIEEAVESTINKHQLQLLAERYRFNMGLLMGEARAALRWA
161   DGKMIKNEVDMQVLHLLGPKMEADLVKKPKVAKARLEETDRKTAKDVVEKGEVAGQILSLMEQLRGEALKFHKPGENYKT
241   PGYVITPYTMDLLKQHLEITGGQVRTRFPPEPNGILHIGHAKAINFNFSYAKANNGICFLRFDDTNPEKEEAKFFTAIYD
321   MVTWLGYTPYKVTYASDYFDQLYAWAVELIHGGLAYVCHQRVEELKGHNFLPSPWRDRPKEESLLFEAMRKGKFAEGEA
401   TLRMKLVMEDGKMDPVAYRVKYTPHHRTGDKWCIYPTYDYTHCLCDSIEHITHSECTKEFQARRSSYFWLCNALKVYCPV
481   QWEYGRLNLHYAVVSKRKILQLVAAGAVRDWDDPRLFTLTALRRRGFPPEAINFCARVGVTVAQTTMEPHLLEACVRDV
561   LNDAAPRAMAVLEPLQVVITNFPAPKPLDIRVPNFPADETKGFHQVPFASTVFIERSDFKEESEPGYKRLASGQPVGLRH
641   TGYVIELQNIVRGSSGCVERLEVTCRRADAGEKPKAFIHWVSQPLVCEIRLYERLFQHKNPEDPVEVPGGFLSDLNPASL
721   QVVEGALVDCSVALAKPFDKFQFERLGYFSVDPDSHQGQIVFNRTVTLKEDPGEI
```

*Figure 15C*

Band 20 (N-terminal fragment of QRS peptides covering beginning - 180)

```
  1   MATPDSLALFTGLGLSENKARETLKNEALSTQLREAATQAHQILGSTIDKATGVLLYDLVSRLRDTRRSFLVSYIANKK
 81   IHTGLQLSAALEYVRSHPQDPIDTKDFEQECGVGVVTPEQIEEAVESTINKHQLQLLAERYRFNMGLLMGEARAALRWA
161   DGKMIKNEVDMQVLHLLGPKMEADLVKKPKVAKARLEETDRKTAKDVVEKGEVAGQILSLMEQLRGEALKFHKPGENYKT
241   PGYVITPYTMDLLKQHLEITGGQVRTRFPPEPNGILHIGHAKAINFNFSYAKANNGICFLRFDDTNPEKEEAKFFTAIYD
321   MVTWLGYTPYKVTYASDYFDQLYAWAVELIHGGLAYVCHQRVEELKGHNFLPSPWRDRPKEESLLFEAMRKGKFAEGEA
401   TLRMKLVMEDGKMDPVAYRVKYTPHHRTGDKWCIYPTYDYTHCLCDSIEHITHSECTKEFQARRSSYFWLCNALKVYCPV
481   QWEYGRLNLHYAVVSKRKILQLVAAGAVRDWDDPRLFTLTALRRRGFPPEAINFCARVGVTVAQTTMEPHLLEACVRDV
561   LNDAAPRAMAVLEPLQVVITNFPAPKPLDIRVPNFPADETKGFHQVPFASTVFIERSDFKEESEPGYKRLASGQPVGLRH
641   TGYVIELQNIVRGSSGCVERLEVTCRRADAGEKPKAFIHWVSQPLVCEIRLYERLFQHKNPEDPVEVPGGFLSDLNPASL
721   QVVEGALVDCSVALAKPFDKFQFERLGYFSVDPDSHQGQIVFNRTVTLKEDPGEI
```

*Figure 15D*

Human Jurkat T-cells treated with Staurospaurine (STS) 4 hours

Band 18

| | |
|---|---|
| 1 | MPTCRLGPKFLLVSGVSAMAALDSLSLFTSLGLSEQKARETLKNSALSAQLREAATQAQQTLGSTIDKATGILLYGLASR |
| 81 | LRDTRRLSFLVSYIASKKIHTEPQLSAALEYVRSHPLDPIDTVDFERECGVGVIVTPEQIEEAVEAAINRHRPQLLVERY |
| 161 | HFNMGLLMGEARAVLKWADGKMIKNEVDMQVLHLLGPKLEADLEKKFKVAKARLEETDRRTAKDVVENGETADQTLSLME |
| 241 | QLRGEALKFHKPGENYKTPGYVVTPHTMNLLKQHLEITGGQVRTRFPPEPNGILHIGHAKAINFNFGYAKANNGICFLRF |
| 321 | DDTNPEKEEAKFFTAICDMVAWLGYTPFKVTYASDYFDQLYAWAVELIRRGLAYVCHQRGEELKGHNTLPSPWRDRPMEE |
| 401 | SLLLFEAMRKGKFSEGEATLRMKLVMEDGRMDPVAYRVKYTPHERTGDKWCIYPTYDYTHCLCDSIEHITHSLCTKEFQA |
| 481 | RRSSYFWLCNALDVYCPVQWEYGRLNLHYAVVSKRKILQLVATGAVRDWDDPRLFTLALRRGFPPEAINNFCARVGVT |
| 561 | VAQTTMEPHLLEACVRDVLNDTAPRAMAVLESLRVTIINFPAAKSLDIQVPNFPADETKGFHQVPFAPIVFIERTDFKEE |
| 641 | PEPGFKRLAWGQPVGLRHTGYVIELQHVVKGPSGCVESLEVTCRRADAGEKPKAFIHWVSQPLMCEVRLYERLFQHKNPE |
| 721 | DPTEVPGGFLSDLNLASLHVVDRAALVDCSVALAKPFDKFQFERLGYFSVDPDSHQGKLVFNRTVTLKEDPGKV |

*Figure 16A*

Band 19

| | |
|---|---|
| 1 | MPTCRLGPKFLLVSGVSAMAALDSLSLFTSLGLSEQKARETLKNSALSAQLREAATQAQQTLGSTIDKATGILLYGLASR |
| 81 | LRDTRRLSFLVSYIASKKIHTEPQLSAALEYVRSHPLDPIDTVDFERECGVGVIVTPEQIEEAVEAAINRHRPQLLVERY |
| 161 | HFNMGLLMGEARAVLKWADGKMIKNEVDMQVLHLLGPKLEADLEKKFKVAKARLEETDRRTAKDVVENGETADQTLSLME |
| 241 | QLRGEALKFHKPGENYKTPGYVVTPHTMNLLKQHLEITGGQVRTRFPPEPNGILHIGHAKAINFNFGYAKANNGICFLRF |
| 321 | DDTNPEKEEAKFFTAICDMVAWLGYTPFKVTYASDYFDQLYAWAVELIRRGLAYVCHQRGEELKGHNTLPSPWRDRPMEE |
| 401 | SLLLFEAMRKGKFSEGEATLRMKLVMEDGKMDPVAYRVKYTPHERTGDKWCIYPTYDYTHCLCDSIEHITHSLCTKEFQA |
| 481 | RRSSYFWLCNALDVYCPVQWEYGRLNLHYAVVSKRKILQLVATGAVRDWDDPRLFTLTALRRGFPPEAINNFCARVGVT |
| 561 | VAQTTMEPHLLEACVRDVLNDTAPRAMAVLESLRVTIINFPAAKSLDIQVPNFPADETKGFHQVPFAPIVFIERTDFKEE |
| 641 | PEPGFKRLAWGQPVGLRHTGYVIELQHVVKGPSGCVESLEVTCRRADAGEKPKAFIHWVSQPLMCEVRLYERLFQHKNPE |
| 721 | DPTEVPGGFLSDLNLASLHVVDRAALVDCSVALAKPFDKFQFERLGYFSVDPDSHQGKLVFNRTVTLKEDPGKV |

*Figure 16B*

Human Jurkat T-cells treated with Staurosporine STS 6 hours
Band 18

```
  1  MPTCRLGPKFLLVSGVSAMAALDSLSLFTSLGLSEQKARETLKNSALSAQLREAATQAQQTLGSTIDKATGILLYGLASR
 81  LRDTRRLSFLVSYIASKKIHTEPQLSAALEYVRSHPLDPIDTVDFERECGVGVIVTPEQIEEAVEAAINRHRPQLLVERY
161  HFNMGLIMGEARAVLKWADGKMIKNEVDMQVLHLLGPKLEADLEKKFKVAKARLEETDRRTAKDVVENGETADQTLSIME
241  QLRGEALKFHKPGENYKTPGYVVTPHTMNLLKQHLEITGGQVRTRFPPEPNGILHIGHAKAINFNFGYAKANNGICFLRF
321  DDTNPEKEEAKFFTAICDMVAWLGYTPYKVTYASDYFDQLYAWAVELIRRGLAYVCHQRGEELKGHNTLPSPWRDRPMEE
401  SLLLFEAMRKGKFSEGEATLRMKLVMEDGKMDPVAYRVKYTPHHRTGDKWCIYPTYDYTHCLCDSIEHITHSLCTKEFQA
481  RRSSYFWLCNALDVYCPVQWEYGRLNLHYAVVSKRKILQLVATGAVRDWDDPRLFTLTALRRGFPPEAINNFCARVGVT
561  VAQTTMEPHLLEACVRDVLNDTAPRAMAVLESLRVIITNFPAAKSLDIQVPNFPADETKGFHQVPFAPIVETERTDFKEE
641  PEPGFKRLAWGQPVGLRHTGYVIELQHVVKGPSGCVESLEVTCRRADAGEKPKAFIHWVSQPLMCEVRLYERLFQHKNPE
721  DPTEVPGGFLSDLNLASLHVVDAALVDCSVALAKPFDKFQFERLGYFSVDPDSHQGKLVFNRTVTLKEDPGKV
```

*Figure 16C*

AMINOACYL TRNA SYNTHETASES FOR MODULATING INFLAMMATION

CROSS REFERENCE TO RELATED APPLICATIONS

This application is a continuation of U.S. application Ser. No. 14/541,792, filed Nov. 14, 2014; which is a Continuation of U.S. application Ser. No. 13/762,151, filed Feb. 7, 2013, now granted U.S. Pat. No. 9,328,340, issued May 3, 2016; which is a continuation application of U.S. application Ser. No. 13/514,952, filed Sep. 14, 2012, which is now granted U.S. Pat. No. 9,127,268, issued Sep. 8, 2015; which is a U.S. national phase application of International Patent Application No. PCT/US2010/059963, filed Dec. 10, 2010, which claims benefit under 35 U.S.C. § 119(e) to U.S. Provisional Application No. 61/285,913, filed Dec. 11, 2009; U.S. Provisional Application No. 61/285,923, filed Dec. 11, 2009; and U.S. Provisional Application No. 61/285,919, filed Dec. 11, 2009, which are incorporated by reference in their entireties.

STATEMENT REGARDING SEQUENCE LISTING

The Sequence Listing associated with this application is provided in text format in lieu of a paper copy, and is hereby incorporated by reference into the specification. The name of the text file containing the Sequence Listing is ATYR_020_04US_ST25.txt. The text file is 118 KB, was created on Nov. 30, 2016, and is being submitted electronically via EFS-Web.

BACKGROUND

Technical Field

The present invention relates generally to compositions comprising aminoacyl-tRNA synthetase polypeptides, including truncations, proteolytic fragments, and/or variants thereof, and methods of using such compositions for modulating inflammation and other cellular responses.

Description of the Related Art

Aminoacyl-tRNA synthetases, which catalyze the aminoacylation of tRNA molecules, are essential for decoding genetic information during the process of translation. In higher eukaryotes, aminoacyl-tRNA synthetases associate with other polypeptides to form supramolecular multienzyme complexes. Each of the eukaryotic tRNA synthetases consists of a core enzyme, which is closely related to the prokaryotic counterpart of the tRNA synthetase, and one or more additional domains that are appended to the amino-terminal or carboxyl-terminal end of the core enzyme. Human tyrosyl-tRNA synthetase (YRS), for example, has a carboxyl-terminal domain that is not part of prokaryotic and lower eukaryotic YRS molecules.

Aminoacyl tRNA synthetases, such as tyrosyl-tRNA synthetase, tryptophan-tRNA synthetase, and others, are associated with expanded functions in mammalian cells, including activities in signal transduction pathways, among others.

BRIEF SUMMARY

Embodiments of the present invention stem from the unexpected finding that compositions comprising aminoacyl-tRNA synthetase (AARS) polypeptides, including truncated fragments, proteolytic fragments, and variants thereof, modulate inflammatory responses, and thereby modulate inflammation. These AARS polypeptides are therefore useful in treating a variety of inflammatory diseases or conditions.

Accordingly, embodiments of the present invention relate generally to compositions for modulating inflammation, comprising one or more isolated aminoacyl-tRNA synthetase (AARS) polypeptides, or biologically active fragments or variants thereof, wherein the polypeptides modulate inflammation. In certain embodiments, the AARS polypeptide is a tyrosyl-tRNA synthetase (YRS), a tryptophanyl-tRNA synthetase (WRS), a glutaminyl-tRNA synthetase (QRS), a glycyl-tRNA synthetase (GlyRS), a histidyl-tRNA synthetase (HisRS), a seryl-tRNA synthetase, a phenylalanyl-tRNA synthetase, an alanyl-tRNA synthetase, an asparaginyl-tRNA synthetase (AsnRS), an aspartyl-tRNA synthetase (AspRS), a cysteinyl-tRNA synthetase (CysRS), a glutamyl-tRNA synthetase, a prolyl-tRNA synthetase (ProRS), an arginyl-tRNA synthetase, an isoleucyl-tRNA synthetase, a leucyl-tRNA synthetase, a lysyl-tRNA synthetase, a threonyl-tRNA synthetase, a methionyl-tRNA synthetases, or a valyl-tRNA synthetase.

Certain embodiments include a proteolytic fragment of the AARS polypeptide. In certain embodiments, the sequence of the proteolytic fragment is derived by incubating the polypeptide with a protease in vitro. In certain embodiments, the sequence of the proteolytic fragment is derived by recombinantly expressing the AARS polypeptide in a cell, wherein the cell comprises one or more recombinant or endogenous proteases. In certain embodiments, the proteolytic fragment comprises the sequence of an endogenous, naturally-occurring human or mouse AARS proteolytic fragment.

In certain embodiments, the aminoacyl-tRNA synthetase is a YRS polypeptide. In certain embodiments, the YRS polypeptide is truncated at its C-terminus. In certain embodiments, the YRS polypeptide comprises the amino acid sequence of SEQ ID NO: 1, 2, 3, 6, 8, 10, 12, or 14, wherein at least about 1-50, 50-100, 100-150, 150-200, or about 200-250 amino acid residues are truncated from its C-terminus.

In certain embodiments, the YRS polypeptide is truncated at its N-terminus. In certain embodiments, the YRS polypeptide comprises the amino acid sequence of SEQ ID NO: 1, 2, 3, 6, 8, 10, 12, or 14, wherein at least about 1-50, 50-100, 100-150, 150-200, or about 200-250 amino acid residues are truncated from its N-terminus.

In certain embodiments, the YRS polypeptide comprises an amino acid sequence at least 80%, 90%, 95%, 98%, or 100% identical to the amino acid sequence set forth in SEQ ID NO:2, wherein the alanine at position 341 is not substituted with a tyrosine. In certain embodiments, the YRS polypeptide comprises an amino acid sequence at least 80%, 90%, 95%, 98%, or 100% identical to the amino acid sequence set forth in SEQ ID NO: 1, 2, 3, 6, 8, 10, 12, or 14.

In certain embodiments, the aminoacyl-tRNA synthetase is a GlyRS polypeptide. In certain embodiments, the GlyRS polypeptide is a fragment of the full length human glycyl-tRNA synthetase sequence set forth in SEQ ID NO:16. In certain embodiments, the fragment comprises amino acid residues 367-438 of SEQ ID NO:16, or an active variant thereof. In certain embodiments, the GlyRS polypeptide comprises an amino acid sequence at least 80%, 90%, 95%, 98%, or 100% identical to the amino acid sequence set forth in SEQ ID NO:16. In certain embodiments, the GlyRS polypeptide comprises amino acid residues 57-685, 214-685, 239-685, 311-685, 439-685, 511-658, 214-438, 367-438, 214-420, 214-338, 85-127 1-213, 1-61, 85-214, 333-

685, 128-685, 265-685, 483-685 or 25-56 of SEQ ID NO:16, or an active fragment thereof.

In certain embodiments, the aminoacyl-tRNA synthetase is a QRS polypeptide. In certain embodiments, the QRS polypeptide comprises an amino acid sequence at least 80%, 90%, 95%, 98%, or 100% identical to the amino acid sequence set forth in SEQ ID NO:25. In certain embodiments, the QRS polypeptide is truncated at its C-terminus. In certain embodiments, the QRS polypeptide comprises the amino acid sequence of SEQ ID NO:25, wherein at least about 1-50, 50-100, 50-100, 100-150, 150-200, 200-250, 250-300, 300-350, 350-400, 400-450, 450-500, or about 500-550 amino acid residues are truncated from its C-terminus. In certain embodiments, the QRS polypeptide comprises amino acid residues 1-183, 1-220, 1-249, or 1-200 of SEQ ID NO:25, or any one or more of SEQ ID NOS:36-103 or 109-115.

In certain embodiments, the aminoacyl-tRNA synthetase is a HisRS polypeptide. Certain embodiments comprise HisRS splice variant polypeptide. In certain embodiments, the HisRS polypeptide comprises at least the WHEP domain of HisRS. In certain embodiments, the HisRS polypeptide comprises at least the anticodon binding domain of HisRS. In certain embodiments, the HisRS polypeptide lacks a functional aminoacylation domain. In certain embodiments, the HisRS polypeptide comprises at least the WHEP domain of HisRS and the anticodon binding domain of HisRS but lacks a functional aminoacylation domain. In certain embodiments, the HisRS polypeptide comprises the sequence set forth in SEQ ID NO:-28, 30, or 32. In certain embodiments, the HisRS polypeptide comprises an amino acid sequence at least 80%, 90%, 95%, 98%, or 100% identical to the amino acid sequence set forth in SEQ ID NO:28, 30, or 32. In certain embodiments, the HisRS polypeptide comprises at least 20 contiguous amino acid residues of the sequence set forth in SEQ ID NO:28, 30, or 32.

In certain embodiments, the aminoacyl-tRNA synthetase is a WRS polypeptide. In certain embodiments, the WRS polypeptide comprises an amino acid sequence at least 80%, 90%, 95%, 98%, or 100% identical to the amino acid sequence set forth in any one or more of SEQ ID NOS:33-35. In certain embodiments, the WRS polypeptide comprises a biologically active fragment of any one or more of SEQ ID NOS:33-35.

In certain embodiments, the AARS polypeptide is an aspartyl-tRNA synthetase (AspRS). In certain embodiments, the AspRS polypeptide comprises an amino acid sequence at least 80%, 90%, 95%, 98%, or 100% identical to the amino acid sequence set forth in SEQ ID NO:105. In certain embodiments, the AspRS polypeptide consists essentially of amino acids 1-154 of SEQ ID NO:105.

Certain embodiments include pharmaceutical compositions for modulating an inflammatory response in a subject, comprising an aminoacyl-tRNA synthetase (AARS) polypeptide as described herein and a pharmaceutically acceptable carrier.

Certain embodiments include methods of modulating an inflammatory response, comprising contacting a cell with an effective concentration of an aminoacyl-tRNA synthetase (AARS) polypeptide having an inflammatory response-modulating activity, thereby modulating the inflammatory response.

In certain embodiments, the cell is an immune cell or a vascular cell. In certain embodiments, the immune cell is a granulocyte, lymphocyte, monocyte/macrophage, dendritic cell, or mast cell. In certain embodiments, the granulocyte is a neutrophil, eosinophil, or basophil. In certain embodiments, the lymphocyte is a B-cell, CD8+ T-cell, CD4+ T-cell, natural killer cell, or γδ T-cell. In certain embodiments, the vascular cell is a smooth muscle cell, endothelial cells, or fibroblast.

Certain embodiments include contacting the cell in vitro or ex vivo. Certain embodiments include administering the cell to a subject. Certain embodiments include contacting the cell in a subject by directly administering the AARS polypeptide to the subject.

Certain embodiments include reducing an acute inflammatory response, reducing a chronic inflammatory response, or both. Certain embodiments include increasing an acute inflammatory response, increasing a chronic inflammatory response, or both. Certain embodiments include modulating the activation, inflammatory molecule secretion, proliferation, activity, migration, or adhesion of one or more immune cells or vascular cells. Certain embodiments include modulating the levels or activity of one or more inflammatory molecules.

In certain embodiments, the one or more inflammatory molecules comprise plasma-derived inflammatory molecules of any one or more of the complement system, kinin system, coagulation system, or fibrinolysis system. In certain embodiments, the one or more inflammatory molecules comprise cell-derived inflammatory molecules of any one or more of lysosome granules, vasoactive amines, eicosanoids, cytokines, acute-phase proteins, or nitric oxide. In certain embodiments, the one or more cytokines are selected from the cytokines in Tables J and K. Certain embodiments include modulating the levels or activity of any one or more of TNF-α, IL-2, MIP-1β, IL-12(p40), KC, MIP-2, or IL-10.

Certain embodiments include modulating an inflammatory response or inflammatory condition associated with one or more tissues, tissue systems, or organs selected from skin, hair follicles, nervous system, auditory system or balance organs, respiratory system, gastroesophogeal tissues, gastrointestinal system, vascular system, liver, gallbladder, lymphatic/immune system, uro-genital system, musculoskeletal system, adipose tissue, mammaries, and endocrine system.

Certain embodiments include treating hypersensitivity selected from type I hypersensitivity, type II hypersensitivity, type III hypersensitivity, type IV hypersensitivity, immediate hypersensitivity, antibody mediated hypersensitivity, immune complex mediated hypersensitivity, T-lymphocyte mediated hypersensitivity, and delayed type hypersensitivity.

Certain embodiments include treating an auto-inflammatory condition selected from familial Mediterranean fever, TNF receptor associated periodic syndrome (TRAPS), Hyper-IgD syndrome (HIDS), CIAS1-related diseases such as Muckle-Wells syndrome, familial cold auto-inflammatory syndrome, and neonatal onset multisystem inflammatory disease, PAPA syndrome (pyogenic sterile arthritis, pyoderma gangrenosum, acne), and Blau syndrome.

Certain embodiments include treating inflammation associated with a cancer selected from prostate cancer, breast cancer, colon cancer, rectal cancer, lung cancer, ovarian cancer, testicular cancer, stomach cancer, bladder cancer, pancreatic cancer, liver cancer, kidney cancer, brain cancer, melanoma, non-melanoma skin cancer, bone cancer, lymphoma, leukemia, thyroid cancer, endometrial cancer, multiple myeloma, acute myeloid leukemia, neuroblastoma, glioblastoma, and non-Hodgkin's lymphoma.

Certain embodiments include treating inflammation associated with systemic inflammatory response syndrome (SIRS). Certain embodiments include treating inflammation associated with cytokine storm. Certain embodiments include treating inflammation associated with any one or more of granulomatous inflammation, fibrinous inflammation, purulent inflammation, serous inflammation, or ulcerative inflammation. Certain embodiments include treating inflammation associated with one or more wounds. Certain embodiments include treating inflammation associated with chronic obstructive pulmonary disorder (COPD).

Certain embodiments include increasing the inflammatory response to treat a primary or secondary immunodeficiency. In certain embodiments, the primary immunodeficiency is a combined T-cell and B-cell immunodeficiency, antibody deficiency, well-defined syndrome, immune dysregulation disease, phagocyte disorder, innate immunity disorder, or a complement deficiency.

Certain embodiments include modulating an inflammatory condition associated with activity one or more immune cells or vascular cells. In certain embodiments, the immune cell is a granulocyte, lymphocyte, monocyte/macrophage, dendritic cell, or mast cell. In certain embodiments, the granulocyte is a neutrophil, eosinophil, or basophil. In certain embodiments, the lymphocyte is a B-cell, T-cell, natural killer cell. In certain embodiments, the vascular cell is a smooth muscle cell, endothelial cells, or fibroblast. In certain embodiments, the inflammatory condition is a neutrophil-mediated condition, a macrophage-mediated condition, or a lymphocyte-mediated condition.

Certain aspects of the present invention stem from the discovery that certain glutaminyl-tRNA synthetase (QRS) polypeptides possess non-canonical biological activities of therapeutic relevance. Therefore, according to one aspect, the present invention provides isolated QRS polypeptides having at least one non-canonical biological activity, as well active fragments and variants thereof which substantially retain said non-canonical activity. "Non-canonical" activity," as used herein, refers generally to an activity possessed by a QRS polypeptide of the invention that is other than aminoacylation and, more specifically, other than the addition of glutamine onto a tRNA$^{Gln}$ molecule. As detailed herein, in certain embodiments, a non-canonical biological activity exhibited by a QRS polypeptide of the invention may include, but is not limited to, modulation of cell proliferation, modulation of apoptosis, modulation of cell signaling (e.g., via Akt), modulation of angiogenesis, modulation of cell migration, modulation of cell binding, modulation of cellular metabolism, modulation of cytokine production (e.g., IL-12, TNF-α), and the like.

In certain embodiments, the QRS polypeptide of the invention is a contiguous fragment of a full length mammalian QRS protein. In a more specific embodiment, the QRS polypeptide is a contiguous fragment of the human or mouse QRS protein sequence set forth in SEQ ID NOS:25, 36-103, or 109-115. Illustratively, the fragments may be of essentially any length, provided they are not full length and further provided they retain at least one non-canonical biological activity of interest. In certain illustrative embodiments, a QRS polypeptide of the invention will range in size from about 10-50, 10-100, 10-150, 10-200, 10-250, 10-300, 10-350, 10-400, 10-450, 10-500, 10-550, 10-600, 10-650, 10-700, or 10-750 amino acids in length. In certain illustrative embodiments, a QRS polypeptide of the invention will range in size from about 20-50, 20-100, 20-150, 20-200, 20-250, 20-300, 20-350, 20-400, 20-450, 20-500, 20-550, 20-600, 20-650, 20-700, or 20-750 amino acids in length. In other embodiments, the QRS polypeptide of the invention will range in size from about 50-100, 50-150, 50-200, 50-250, 50-300, 50-350, 50-400, 50-450, 50-500, 50-550, 50-600, 50-650, 50-700, or 50-750 amino acids in length. In other embodiments, the QRS polypeptide of the invention will range in size from about 100-150, 100-200, 100-250, 100-300, 100-350, 100-400, 100-450, 100-500, 100-550, 100-600, 100-650, 100-700, or 100-750 amino acids in length. In still other illustrative embodiments, the QRS polypeptide of the invention will range in size from about 200-250, 200-300, 200-350, 200-400, 200-450, 200-500, 200-550, 200-600, 200-650, 200-700, or 200-750 amino acids in length.

In further embodiments of the invention, a QRS polypeptide comprises an active variant (i.e., retains at least one non-canonical biological activity of interest) of a fragment of a QRS protein sequence, such as the human QRS protein sequence set forth in SEQ ID NO:25. In a more specific embodiment, the active variant is a polypeptide having at least 70%, 80%, 90%, 95%, 98% or 99% identity along its length to a human or mouse QRS sequence set forth in SEQ ID NOS: 25, 36-103, or 109-115.

Other embodiments of the invention provide QRS splice variants and point mutants, whether naturally or non-naturally occurring, that possess one or more non-canonical activities. Other embodiments of the invention provide QRS proteolytic fragments, whether produced endogenously (i.e., in a cell) or in vitro, that possess one or more non-canonical activities. In certain embodiments, the sequence of the proteolytic fragment is identified by incubating the QRS polypeptide with a protease in vitro. In certain embodiments, the sequence of the proteolytic fragment is identified by recombinantly expressing the QRS polypeptide in a cell, wherein the cell comprises one or more recombinant or endogenous proteases. In certain embodiments, the proteolytic fragment comprises the sequence of an endogenous, naturally-occurring human or mouse QRS proteolytic fragment.

In a more specific embodiment of the invention, a QRS polypeptide comprises a fragment of the human QRS sequence of SEQ ID NO:25, comprising or consisting essentially of amino acid residues 1-183 (Q1), 1-220 (Q2), 1-249 (Q3), or 1-200 (Q4), or an active fragment or variant thereof that substantially retains at least one non-canonical biological activity of interest. In certain embodiments, a QRS polypeptide fragment comprises or consists essentially of any one of SEQ ID NOS:36-103 or 109-115.

According to another aspect of the invention, there are provided fusion proteins comprising at least one QRS polypeptide as described herein and a heterologous fusion partner.

According to another aspect of the invention, there are provided isolated polynucleotides encoding the polypeptides and fusion proteins as described herein, as well as expression vectors comprising such polynucleotides, and host cell comprising such expression vectors.

According to yet another aspect of the invention, there are provided compositions, e.g., pharmaceutical compositions, comprising physiologically acceptable carriers and at least one of the isolated polypeptides, fusion proteins, antibodies, isolated polynucleotides, expression vectors, host cells, etc., of the invention, as described herein.

Also provided by the present invention, in other aspects, are methods for modulating a cellular activity by contacting a cell or tissue with a composition of the invention, as described herein, wherein the cellular activity to be modulated is selected from the group consisting of cell proliferation, apoptosis, cell signaling, cellular metabolism, angiogenesis, cell migration, cell binding, cytokine production, and the like.

In other aspects, the present invention provides methods for treating a disease, disorder or other condition in a subject in need thereof by administering a composition according to the present invention. By way of illustration, such diseases, disorders or conditions may include, but are not limited to, cancer, inflammatory disease or condition, immune disease (including autoimmune disease) and/or conditions associated with abnormal angiogenesis.

SEQUENCE LISTING

SEQ ID NO:1 is the full-length amino acid sequence of human tyrosyl-tRNA synthetase (YRS).

SEQ ID NO:2 is the amino acid sequence of a Y341A variant of full-length human YRS.

SEQ ID NO:3 is the amino acid sequence of a C-terminally truncated (amino acids 1-364) human YRS.

SEQ ID NO:4 is a polynucleotide sequence that encodes the full-length amino acid sequence of human YRS (SEQ ID NO:1).

SEQ ID NO:5 shows the sequence of an eight amino acid tag.

SEQ ID NO:6 is the amino acid sequence of the SP1 human YRS splice variant.

SEQ ID NO:7 is the polynucleotide sequence that encodes the SP1 human YRS splice variant (SEQ ID NO:6).

SEQ ID NO:8 is the amino acid sequence of the SP2 human YRS splice variant.

SEQ ID NO:9 is the polynucleotide sequence that encodes the SP2 human YRS splice variant (SEQ ID NO:8)

SEQ ID NO:10 is the amino acid sequence of the SP3 human YRS splice variant.

SEQ ID NO:11 is the polynucleotide sequence that encodes the SP3 human YRS splice variant (SEQ ID NO:10).

SEQ ID NO:12 is the amino acid sequence of the SP4 human YRS splice variant.

SEQ ID NO:13 is the polynucleotide sequence that encodes the SP4 human YRS splice variant (SEQ ID NO:12).

SEQ ID NO:14 is the amino acid sequence of the SP5 human YRS splice variant.

SEQ ID NO:15 is the polynucleotide sequence that encodes the SP5 human YRS splice variant (SEQ ID NO:14).

SEQ ID NO:16 is the full length amino acid sequence of human cytoplasmic glycyl-tRNA synthetase (GlyRS).

SEQ ID NO:17 is a nucleic acid sequence encoding the GlyRS polypeptide of SEQ ID NO:16.

SEQ ID NOS:18-24 represent illustrative peptide sequences analyzed in determining GlyRS fragment boundaries.

SEQ ID NO:25 is the full-length amino acid sequence of human glutaminyl-tRNA synthetase (QRS).

SEQ ID NOS:26 and 27 represent illustrative peptide sequences analyzed in determining QRS fragment boundaries.

SEQ ID NO:28 is the full-length amino acid sequence of the histidyl-tRNA synthetase (HisRS) protein (NP_002100.2).

SEQ ID NO:29 is a nucleic acid coding sequence of the HisRS-SV9 splice variant.

SEQ ID NO:30 is the amino acid sequence of the HisRS-SV9 splice variant polypeptide encoded by SEQ ID NO:29.

SEQ ID NO:31 is a nucleic acid coding sequence of the HisRS-SV11 splice variant.

SEQ ID NO:32 is the amino acid sequence of the HisRS-SV11 splice variant polypeptide encoded by SEQ ID NO:31.

SEQ ID NO:33 is the amino acid sequence of the main isoform of human tryptophanyl-tRNA synthetase (WRS).

SEQ ID NO:34 is the amino acid sequence of a truncated variant (T2) of human WRS.

SEQ ID NO:35 is the amino acid sequence of a truncated variant (Toltrup) of human WRS.

SEQ ID NOS:36-103 represent various endogenous peptide fragments of human QRS.

SEQ ID NO:104 is the amino acid sequence of a human phenylalanyl-tRNA synthetase (PheRS) splice variant (PheRS_SV1P).

SEQ ID NO:105 is the amino acid sequence of a full-length human aspartyl-tRNA synthetase (AspRS) polypeptide.

SEQ ID NO:106 is the amino acid sequence of an N-terminal fragment (F1; amino acids 1-471) of human WRS.

SEQ ID NO:107 is the amino acid sequence of a splice variant (mini-WRS; amino acids 48-471) of human WRS.

SEQ ID NO:108 is the amino acid sequence of a fragment (T1; amino acids 71-471) of human WRS).

SEQ ID NOS:109-115 are naturally-occurring, endogenous human QRS proteolytic fragments obtained from human Jurkat T-cells.

SEQ ID NO:116 is the full-length amino acid sequence of mouse glutaminyl-tRNA synthetase (mQRS).

SEQ ID NO:117 is a nucleic acid sequence encoding the human QRS polypeptide of SEQ ID NO:25.

BRIEF DESCRIPTION OF THE DRAWINGS

FIG. 1A shows the effects for Y341A, and FIG. 1B shows the effects for mini-YRS, as compared to dexamethasone treated positive control cells and untreated control cells (see Example 1).

FIG. 2A shows reduced migration of neutrophils, and FIG. 2B shows reduced migration of eosinophils (see Example 1).

FIG. 5A shows circulating serum levels of TNF-α and IL-10 in mice injected intravenously with 10 mg/kg D1. TNF-α is increased at early time points but is rapidly cleared while the anti-inflammatory cytokine, IL-10, shows a prolonged time course. FIG. 5B shows in vivo serum levels for five cytokines from mice injected with D1. FIG. 5C shows in vitro analysis of PBMCs stimulated with D1, with an increase in TNF-α at 4 hours that is markedly higher than the full length DRS. FIG. 5D shows that secreted IL-10 levels are significantly increased at 24 hrs after D1 treatment of PBMCs.

FIG. 13A shows the inhibitory effects of HisRS on THP-1 migration to the chemoattractant CCL-23, FIG. 13B shows the inhibitory effects of AspRS on THP-1 migration to the chemoattractant CCL-23, and FIG. 13C shows the inhibitory effects of p43 polypeptide on THP-1 migration to the chemoattractant CCL-5.

FIGS. 15A-15D show the amino acid sequences of naturally-occurring, endogenous QRS peptides fragments that correspond to the PROTOMAP of FIG. 14. In these figures, (blue; italicized) corresponds to peptides detected in the cytosol, (red; underlined) corresponds to peptides detected in the conditioned media, and (purple; italicized and underlined) corresponds to peptides detected in both samples. FIG. 15A shows the peptide fragments for band 6 (full-length QRS), FIG. 15B shows the peptide fragments for band 9 (C-terminal QRS fragment), and FIGS. 15C-D show the peptide fragments for bands 19 and 20 (N-terminal QRS fragment).

FIGS. 16A-16C show the amino acid sequences of endogenous QRS peptides (blue; italicized) that were obtained from human Jurkat T-cells treated with staurosporine. FIGS. 16A and 16B show the peptides for bands 18 and 19, respectively, obtained from Jurkat T-cells treated with Staurospaurine (STS) for 4 hours. FIG. 16C shows the peptides for band 18, obtained from Jurkat T-cells treated with STS for 6 hours.

DETAILED DESCRIPTION

Figure 1A:
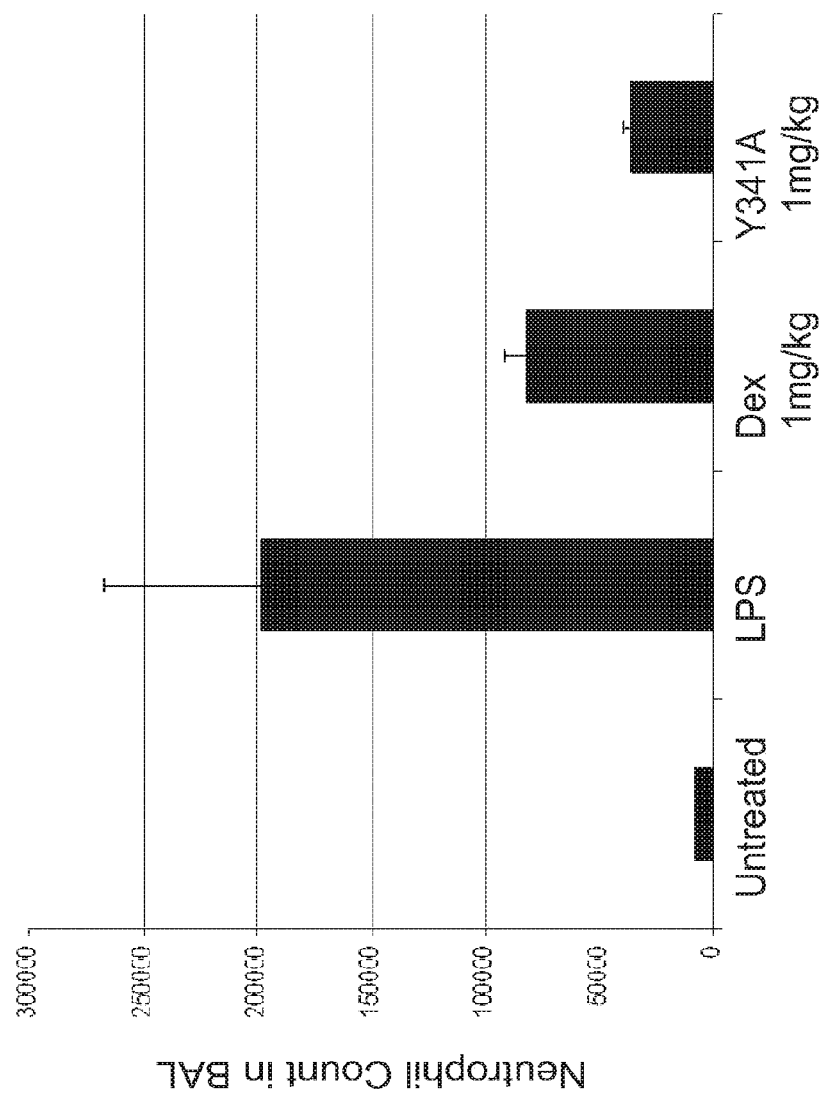
FIGS. 1A-1B show the effects of tyrosyl-tRNA synthetase polypeptides on neutrophil migration into the lungs.

The present invention stems from the discovery that aminoacyl-tRNA synthetases (AARS) and certain polypeptides derived therefrom possess non-canonical biological activities of therapeutic relevance. Therefore, according to one aspect, the present invention provides isolated AARS polypeptides having at least one non-canonical biological activity, as well as active fragments and variants thereof which substantially retain said non-canonical activity.

"Non-canonical" activity," as used herein, refers generally to an activity possessed by a AARS polypeptide of the invention that is other than the addition of an amino acid onto a tRNA molecule. As detailed herein, in certain embodiments, a non-canonical biological activity exhibited by an AARS polypeptide of the invention may include, but is not limited to, the modulation of inflammatory responses, including acute and chronic inflammatory responses, systemic inflammatory responses, local inflammatory responses, and inflammatory responses at the cellular level, whether in vivo, ex vivo, or in vitro. Examples of inflammatory response-modulating activities include, without limitation, modulating the growth, activity, or trafficking of various immune cells, and modulating the production or secretion of various cytokines. Hence, embodiments of the present invention include AARS polypeptides, including truncations, splice variants, proteolytic fragments, and variants thereof, which modulate inflammation, such as by increasing or decreasing an inflammatory response, and thereby possess therapeutically beneficial activity in the treatment and prophylaxis of diseases or conditions associated with inflammation.

Advantages of the use of AARS polypeptides over other treatments include, for example, a different mechanism of action than traditional treatments, synergism with inflammatory-based signaling, higher potency, and the benefits associated with using a de-immunized molecule. Other advantages will be apparent to a person skilled in the art.

The practice of the present invention will employ, unless indicated specifically to the contrary, conventional methods of molecular biology and recombinant DNA techniques within the skill of the art, many of which are described below for the purpose of illustration. Such techniques are explained fully in the literature. See, e.g., Sambrook, et al., *Molecular Cloning: A Laboratory Manual* (3rd Edition, 2000); *DNA Cloning: A Practical Approach*, vol. I & II (D. Glover, ed.); *Oligonucleotide Synthesis* (N. Gait, ed., 1984); *Oligonucleotide Synthesis: Methods and Applications* (P. Herdewijn, ed., 2004); *Nucleic Acid Hybridization* (B. Hames & S. Higgins, eds., 1985); *Nucleic Acid Hybridization: Modern Applications* (Buzdin and Lukyanov, eds., 2009); *Transcription and Translation* (B. Hames & S. Higgins, eds., 1984); *Animal Cell Culture* (R. Freshney, ed., 1986); Freshney, R. I. (2005) *Culture of Animal Cells, a Manual of Basic Technique*, 5th Ed. Hoboken N.J., John Wiley & Sons; B. Perbal, *A Practical Guide to Molecular Cloning* (3rd Edition 2010); Farrell, R., *RNA Methodologies: A Laboratory Guide for Isolation and Characterization* (3rd Edition 2005).

All publications, patents and patent applications cited herein are hereby incorporated by reference in their entirety.

Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e., to at least one) of the grammatical object of the article. By way of example, "an element" means one element or more than one element.

By "about" is meant a quantity, level, value, number, frequency, percentage, dimension, size, amount, weight or length that varies by as much as 30, 25, 20, 25, 10, 9, 8, 7, 6, 5, 4, 3, 2 or 1% to a reference quantity, level, value, number, frequency, percentage, dimension, size, amount, weight or length.

The term "biologically active fragment", as applied to fragments of a reference polynucleotide or polypeptide sequence, refers to a fragment that has at least about 0.1, 0.5, 1, 2, 5, 10, 12, 14, 16, 18, 20, 22, 24, 26, 28, 30, 35, 40, 45, 50, 55, 60, 65, 70, 75, 80, 85, 90, 95, 96, 97, 98, 99, 100, 110, 120, 150, 200, 300, 400, 500, 600, 700, 800, 900, 1000% or more of the activity of a reference sequence. Included within the scope of the present invention are biologically active fragments of at least about 18, 19, 20, 21, 22, 23, 24, 25, 26, 27, 28, 29, 30, 40, 50, 60, 70, 80, 90, 100, 120, 140, 160, 180, 200, 220, 240, 260, 280, 300, 320, 340, 360, 380, 400, 420, 440, 460, 480, 500 or more contiguous nucleotides or amino acid residues in length, including all integers in between, which comprise or encode a inflammatory response-modulating activity of a reference amino-acyl tRNA transferase polynucleotide or polypeptide, such as the exemplary reference polypeptide sequences of SEQ ID NOS: 1, 2, 3, 6, 8, 10, 12, 14, 16, 25, 28, 30, 32-108, and 109-115, or exemplary the reference nucleotide sequences of SEQ ID NOS: 4, 7, 9, 11, 13, 15, 17, 19, and 31.

Biologically active fragments also include naturally occurring splice variants of a reference AARS sequence, as well as proteolytic fragments of AARS polypeptides.

"Proteolytic fragments," or the sequence of proteolytic fragments, can be identified or derived according to a variety of techniques. For instance, as exemplified herein, proteolytic fragments can be identified in vitro, such as by incubating AARS polypeptides with selected proteases, or they can be identified endogenously (i.e., in vivo). In certain embodiments, endogenous proteolytic fragments can be generated or identified, for instance, by recombinantly expressing AARS polypeptides in a selected microorganism or eukaryotic cell that has been either modified to contain one or more selected proteases, or that naturally contains one or more proteases that are capable of acting on an AARS polypeptide, and isolating and characterizing the endogenously produced proteolytic fragments therefrom. Examples of such proteolytic fragments include Q1-Q4, as described herein, as well as the proteolytic fragments illustrated in Tables C-I, including variants thereof.

In certain embodiments, naturally-occurring endogenous proteolytic fragments can be generated or identified, for instance, from various cellular fractions (e.g., cytosolic, membrane, nuclear) and/or growth medium of various cell-types, including, for example, macrophages such as RAW macrophages (e.g., RAW 264.7 macrophages; see Example 5), T-cells, including primary T-cells and T-cell lines such as Jurkats, and natural killer (NK) cells, among others. In certain embodiments, endogenous proteolytic fragments, however generated, can be identified by techniques such as mass-spectrometry, or equivalent techniques. Once an in vitro or endogenously identified proteolytic fragment has been generated or identified, then it can be sequenced and cloned into an expression vector for recombinant production, or produced synthetically.

Representative biologically active fragments generally participate in an interaction, e.g., an intramolecular or an inter-molecular interaction. An inter-molecular interaction can be a specific binding interaction or an enzymatic interaction. An inter-molecular interaction can be between an AARS polypeptide and a target molecule, such as another AARS polypeptide or a target molecule involved in modulating the process of inflammation (e.g., cytokine production or secretion, immune cell migration or recruitment, immune cell response to self or foreign antigens, adhesion). Biologically active fragments of an AARS polypeptide include polypeptide fragments comprising amino acid sequences with sufficient similarity or identity to, or which are derived from, the amino acid sequences of any of SEQ ID NOS: 1, 2, 3, 6, 8, 10, 12, 14, 16, 25, 28, 30, 32-108, or 109-115, including biologically active portions thereof, or are encoded by a nucleotide sequences of SEQ ID NOS: 4, 7, 9, 11, 13, 15, 17, 19, or 31.

By "coding sequence" is meant any nucleic acid sequence that contributes to the code for the polypeptide product of a gene. By contrast, the term "non-coding sequence" refers to any nucleic acid sequence that does not contribute to the code for the polypeptide product of a gene.

Throughout this specification, unless the context requires otherwise, the words "comprise," "comprises," and "comprising" will be understood to imply the inclusion of a stated step or element or group of steps or elements but not the exclusion of any other step or element or group of steps or elements.

By "consisting of" is meant including, and limited to, whatever follows the phrase "consisting of" Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

The terms "complementary" and "complementarity" refer to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands.

By "corresponds to" or "corresponding to" is meant (a) a polynucleotide having a nucleotide sequence that is substantially identical or complementary to all or a portion of a reference polynucleotide sequence or encoding an amino acid sequence identical to an amino acid sequence in a peptide or protein; or (b) a peptide or polypeptide having an amino acid sequence that is substantially identical to a sequence of amino acids in a reference peptide or protein.

By "derivative" is meant a polypeptide that has been derived from the basic sequence by modification, for example by conjugation or complexing with other chemical moieties (e.g., pegylation) or by post-translational modification techniques as would be understood in the art. The term "derivative" also includes within its scope alterations that have been made to a parent sequence including additions or deletions that provide for functionally equivalent molecules.

As used herein, the terms "function" and "functional" and the like refer to a biological, enzymatic, or therapeutic function.

By "gene" is meant a unit of inheritance that occupies a specific locus on a chromosome and consists of transcriptional and/or translational regulatory sequences and/or a coding region and/or non-translated sequences (i.e., introns, 5' and 3' untranslated sequences).

"Homology" refers to the percentage number of amino acids that are identical or constitute conservative substitutions. Homology may be determined using sequence comparison programs such as GAP (Deveraux et al., 1984, *Nucleic Acids Research* 12, 387-395), which is incorporated herein by reference. In this way sequences of a similar or substantially different length to those cited herein could be compared by insertion of gaps into the alignment, such gaps being determined, for example, by the comparison algorithm used by GAP.

The term "host cell" includes an individual cell or cell culture that can be or has been a recipient of any recombinant vector(s) or isolated polynucleotide of the invention. Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vivo or in vitro with a recombinant vector or a polynucleotide of the invention. A host cell which comprises a recombinant vector of the invention is a recombinant host cell.

By "isolated" is meant material that is substantially or essentially free from components that normally accompany it in its native state. For example, an "isolated polynucleotide," as used herein, includes a polynucleotide that has been purified from the sequences that flank it in its naturally-occurring state, e.g., a DNA fragment which has been removed from the sequences that are normally adjacent to the fragment. Alternatively, an "isolated peptide" or an "isolated polypeptide" and the like, as used herein, includes the in vitro isolation and/or purification of a peptide or polypeptide molecule from its natural cellular environment, and from association with other components of the cell; i.e., it is not significantly associated with in vivo substances.

By "obtained from" is meant that a sample such as, for example, a polynucleotide extract or polypeptide extract is isolated from, or derived from, a particular source of the subject. For example, the extract can be obtained from a tissue or a biological fluid isolated directly from the subject.

The term "oligonucleotide" as used herein refers to a polymer composed of a multiplicity of nucleotide residues (deoxyribonucleotides or ribonucleotides, or related structural variants or synthetic analogues thereof) linked via phosphodiester bonds (or related structural variants or synthetic analogues thereof). Thus, while the term "oligonucleotide" typically refers to a nucleotide polymer in which the nucleotide residues and linkages between them are naturally occurring, it will be understood that the term also includes within its scope various analogues including, but not restricted to, peptide nucleic acids (PNAs), phosphoramidates, phosphorothioates, methyl phosphonates, 2-O-methyl ribonucleic acids, and the like. The exact size of the molecule can vary depending on the particular application. An oligonucleotide is typically rather short in length, generally from about 10 to 30 nucleotide residues, but the term can refer to molecules of any length, although the term "polynucleotide" or "nucleic acid" is typically used for large oligonucleotides.

The term "operably linked" as used herein means placing a structural gene under the regulatory control of a promoter, which then controls the transcription and optionally translation of the gene. In the construction of heterologous promoter/structural gene combinations, it is generally preferred to position the genetic sequence or promoter at a distance from the gene transcription start site that is approximately the same as the distance between that genetic sequence or promoter and the gene it controls in its natural setting; i.e., the gene from which the genetic sequence or promoter is derived. As is known in the art, some variation in this distance can be accommodated without loss of function. Similarly, the preferred positioning of a regulatory sequence element with respect to a heterologous gene to be placed under its control is defined by the positioning of the element in its natural setting; i.e., the genes from which it is derived.

The recitation "polynucleotide" or "nucleic acid" as used herein designates mRNA, RNA, cRNA, cDNA or DNA. The term typically refers to polymeric form of nucleotides of at least 10 bases in length, either ribonucleotides or deoxynucleotides or a modified form of either type of nucleotide. The term includes single and double stranded forms of DNA.

The terms "polynucleotide variant" and "variant" and the like refer to polynucleotides displaying substantial sequence identity with a reference AARS polynucleotide sequence or polynucleotides that hybridize to an AARS reference sequence under stringent conditions that are defined hereinafter. These terms also encompass polynucleotides that are distinguished from a reference polynucleotide by the addition, deletion or substitution of at least one nucleotide. Accordingly, the terms "polynucleotide variant" and "variant" include polynucleotides in which one or more nucleotides have been added or deleted, or replaced with different nucleotides. In this regard, it is well understood in the art that certain alterations inclusive of mutations, additions, deletions and substitutions can be made to a reference polynucleotide whereby the altered polynucleotide retains the biological function or activity of the reference polynucleotide. Polynucleotide variants include, for example, polynucleotides having at least 50% (and at least 51% to at least 99% and all integer percentages in between) sequence identity with the sequence set forth in SEQ ID NO:4, 7, 9, 11, 13, 15, 17, 19, or 31, or portions thereof that encode a biologically active fragment of an AARS polypeptide. The terms "polynucleotide variant" and "variant" also include naturally occurring allelic variants.

"Polypeptide," "polypeptide fragment," "peptide" and "protein" are used interchangeably herein to refer to a polymer of amino acid residues and to variants and synthetic analogues of the same. Thus, these terms apply to amino acid polymers in which one or more amino acid residues are synthetic non-naturally occurring amino acids, such as a chemical analogue of a corresponding naturally occurring amino acid, as well as to naturally-occurring amino acid polymers.

The term "aminoacyl-tRNA synthetase" (AARS) refers generally to enzymes that in their natural or wild-type form are capable of catalyzing the esterification of a specific amino acid or its precursor to one of all its compatible cognate tRNAs to form an aminoacyl-tRNA. In this "canonical" activity, aminoacyl-tRNA synthetases catalyse a two-step reaction: first, they activate their respective amino acid by forming an aminoacyl-adenylate, in which the carboxyl of the amino acid is linked in to the alpha-phosphate of ATP by displacing pyrophosphate, and then, when the correct tRNA is bound, the aminoacyl group of the aminoacyl-adenylate is transferred to the 2' or 3' terminal OH of the tRNA.

Class I aminoacyl-tRNA synthetases typically have two highly conserved sequence motifs. These enzymes aminoacylate at the 2'-OH of an adenosine nucleotide, and are usually monomeric or dimeric. Class II aminoacyl-tRNA synthetases typically have three highly conserved sequence motifs. These enzymes aminoacylate at the 3'-OH of the same adenosine, and are usually dimeric or tetrameric. The active sites of class II enzymes are mainly made up of a seven-stranded anti-parallel β-sheet flanked by α-helices. Although phenylalanine-tRNA synthetase is class II, it aminoacylates at the 2'-OH.

AARS polypeptides include tyrosyl-tRNA synthetases (YRS), tryptophanyl-tRNA synthetases (WRS), glutaminyl-tRNA synthetases (QRS), glycyl-tRNA synthetases (GlyRS), histidyl-tRNA synthetases, seryl-tRNA synthetases, phenylalanyl-tRNA synthetases, alanyl-tRNA synthetases, asparaginyl-tRNA synthetases (AsnRS), aspartyl-tRNA synthetases (AspRS), cysteinyl-tRNA synthetases (CysRS), glutamyl-tRNA synthetases, prolyl-tRNA synthetases (ProRS), arginyl-tRNA synthetases, isoleucyl-tRNA synthetases, leucyl-tRNA synthetases, lysyl-tRNA synthetases, threonyl-tRNA synthetases, methionyl-tRNA synthetases, and valyl-tRNA synthetases. The full-length wild-type sequences of these AARS polypeptides are known in the art. Also included within the meaning of AARS polypeptides are aminoacyl tRNA synthetase-interacting multifunctional proteins (AIMPs), including AIMP-1 (or p43), AIMP-2 (or p38), and AIMP-3 (or p18).

The recitations "polypeptides," "polypeptide fragments," "truncated polypeptides" or "variants thereof" encompass, without limitation, polypeptides having the amino acid sequence that shares at least 50% (and at least 51% to at least 99% and all integer percentages in between) sequence identity with a reference AARS sequence, such as the amino acid sequence of a human or mouse AARS polypeptide, including biologically active fragments thereof, such as fragments having at least about 10, 20, 30, 40, 50, 60, 70, 80, 90, 100, 120, 140, 160, 180, 200, 220, 240, 260, 280, 300, 350, 400, 450, 500, 550, 600, 650, 700 or more contiguous amino acids of the reference sequences, including all integers in between. These recitations further encompass natural allelic variation of AARS polypeptides that may exist and occur from one genus or species to another. Illustrative reference sequences include those set forth in any one of SEQ ID NOS: 1, 2, 3, 6, 8, 10, 12, 14, 16, 25, 28, 30, 32-108, and 109-115.

AARS polypeptides, including truncations, fragments, and/or variants thereof, encompass polypeptides that exhibit at least about 10%, 20%, 30%, 40%, 50%, 60%, 70%, 80%, 90%, 100%, 110%, 120%, 130%, 140%, 150%, 200%, 300%, 400%, 500%, 600%, 700%, 800%, 900%, 1000% or more of the specific biological activity of a reference AARS polypeptide (e.g., an inflammatory response-modulating activity in a subject or in vitro). Merely by way of illustration, AARS-related non-canonical biological activity may be quantified, for example, by measuring the ability of an AARS polypeptide to reduce migration of immune cells such as granulocytes to a site of inflammation, including the lungs, or by measuring the effect of an AARS polypeptide on an immune cells response to a given antigen, whether self or foreign. In certain embodiments, AARS polypeptides desensitize immune cells such as neutrophils to an antigen, and thereby reduce the recruitment of these cells to sites of inflammation. In certain embodiments, AARS polypeptides modulate inflammatory response of immune cells, or modulate the levels or activities of various inflammatory molecules, among others. Suitable in vitro models for assaying immune cell are described herein (see Example 1) and known in the art. AARS polypeptides, including truncations and/or variants thereof, having substantially reduced biological activity relative to a reference AARS polypeptide are those that exhibit less than about 25%, 10%, 5% or 1% of the specific activity of a biologically active reference AARS polypeptide (i.e., having a non-canonical activity).

The recitation polypeptide "variant" refers to polypeptides that are distinguished from a reference polypeptide by the addition, deletion or substitution of at least one amino acid residue. In certain embodiments, a polypeptide variant is distinguished from a reference polypeptide by one or more substitutions, which may be conservative or non-conservative. In certain embodiments, the polypeptide variant comprises conservative substitutions and, in this regard, it is well understood in the art that some amino acids may be changed to others with broadly similar properties without changing the nature of the activity of the polypeptide. Polypeptide variants also encompass polypeptides in which one or more amino acids have been added or deleted, or replaced with different amino acid residues.

The present invention contemplates the use in the methods described herein of variants of full-length AARS polypeptides (e.g., a full-length YRS polypeptide having a Y341A substitution), truncated fragments of full-length AARS polypeptides, splice variants, proteolytic fragments, including endogenous proteolytic fragments, and variants of such fragments, as well as their related biologically active fragments. Biologically active fragments of an AARS polypeptide include peptides comprising amino acid sequences sufficiently similar to, or derived from, the amino acid sequences of a (putative) full-length AARS polypeptide sequence, such as SEQ ID NO:1, or portions thereof, or the polypeptides of SEQ ID NOS:2, 3, 6, 8, 10, 12, 14, 16, 25, 28, 30, 32-108, or 109-115.

Typically, biologically active fragments comprise a domain or motif with at least one activity of an AARS polypeptide and may include one or more (and in some cases all) of the various active domains, and include fragments having an inflammatory response-modulating activity. In some cases, biologically active fragments of an AARS polypeptide have a biological activity (e.g., modulating cytokine secretion, modulating migration of immune cells) that is unique to the particular, truncated fragment, such that the full-length AARS polypeptide may not have that activity. In certain cases, the biological activity may be revealed by separating the biologically active AARS polypeptide fragment from the other full-length AARS polypeptide sequences, or by altering certain residues (e.g., Y341A of the YRS polypeptide) of the full-length AARS wild-type polypeptide sequence to unmask the biologically active domains. A biologically active fragment of a truncated AARS polypeptide can be a polypeptide fragment which is, for example, 10, 11, 12, 13, 14, 15, 16, 17, 18, 19, 20, 21, 22, 23, 24, 25, 26, 27, 28, 29, 30, 40, 50, 60, 70, 80, 90, 100, 110, 120, 130, 140, 150, 160, 170, 180, 190, 200, 220, 240, 260, 280, 300, 320, 340, 360, 380, 400, 450, 500, 550, 600, 650, 700, 750 or more contiguous or non-contiguous (e.g., splice variants are sometimes non-contiguous) amino acids, including all integers in between, of the amino acid sequences set forth in any one of SEQ ID NOS: 1, 2, 3, 6, 8, 10, 12, 14, 16, 25, 28, 30, 32-108, or 109-115, or the known amino acid sequences of the various human AARS polypeptides. In certain embodiments, a biologically active fragment comprises an inflammatory response-modulating sequence, domain, or motif. Suitably, the biologically-active fragment has no less than about 1%, 10%, 25%, or 50% of an activity of the biologically active (i.e., non-canonical biological activity) polypeptide from which it is derived.

The recitations "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity.

Terms used to describe sequence relationships between two or more polynucleotides or polypeptides include "reference sequence", "comparison window", "sequence identity", "percentage of sequence identity" and "substantial identity". A "reference sequence" is at least 12 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., 1997, *Nucl. Acids Res.* 25:3389. A detailed discussion of sequence analysis can be found in Unit 19.3 of Ausubel et al., "Current Protocols in Molecular Biology," John Wiley & Sons Inc, 1994-1998, Chapter 15.

A "subject," as used herein, includes any animal that exhibits a symptom, or is at risk for exhibiting a symptom, which can be treated with either an AARS polypeptide of the invention, cells (e.g., stem cells) that have been treated ex vivo or in vitro with an AARS polypeptide, or both. Suitable subjects (patients) include laboratory animals (such as mouse, rat, rabbit, or guinea pig), farm animals, and domestic animals or pets (such as a cat or dog). Non-human primates and, preferably, human patients, are included. Certain embodiments include subjects that exhibit, or are at risk for exhibiting, an increased or pathological inflammatory response, or an insufficient inflammatory response.

An "effective concentration" of an aminoacyl-tRNA synthetase polypeptide refers to an amount that is capable of modulating or regulating an inflammatory response or inflammation in any desired way, as compared to a control polypeptide or no polypeptide, whether in a cell in vitro or ex vivo, in a tissue, or in a subject. One example of a inflammatory response-modulating activity includes reducing migration of immune cells such as granulocytes (e.g., neutrophils, eosinophils) or lymphocytes to selected tissues, such as the lung. Another example includes desensitizing immune cells to an antigen. A further example of an inflammatory response-modulating activity includes the modulation of cytokine production. Other examples will be apparent from the description provided herein and the understanding in the art.

An "immune cell" includes any cell of the vertebrate immune system, including lymphocytes such as B-cells, killer T-cells (i.e., CD8+ T-cells), helper T-cells (i.e., CD4+ T-cells, including $T_h1$ and $T_h2$ cells), natural killer cells, and γδ T-cells, monocytes, macrophages, neutrophils, dendritic cells, mast cells, eosinophils, and basophils.

A "megakaryocyte" refers generally to a bone marrow cell that is responsible for the production of blood thrombocytes (i.e., platelets), which are necessary for normal blood clotting. Megakaryocytes typically account for 1 out of 10,000 bone marrow cells. Megakaryocytes are derived from pluripotent hematopoietic stem cell precursor cells in the bone marrow. Thrombopoietin (TPO) is the primary signal for megakaryocyte production, i.e., TPO is sufficient but not absolutely necessary for inducing differentiation of progenitor cells in the bone marrow towards a final megakaryocyte phenotype. Other molecular signals for megakaryocyte differentiation include GM-CSF, IL-3, IL-6, IL-11, chemokines (SDF-1; FGF-4), and erythropoietin.

Megakaryocytes are believed to develop through the following lineage: CFU-Me (pluripotential hematopoietic stem cell or hemocytoblast)->megakaryoblast->promegakaryocyte->megakaryocyte. At the megakaryoblast stage, the cell loses its ability to divide, but is still able to replicate its DNA and continue development, becoming polyploid. Upon maturation, megakaryocytes begin the process of producing platelets, or thrombocytes. Thrombopoietin plays a role in inducing the megakaryocyte to form small proto-platelet processes, or cytoplasmic internal membranes for storing platelets prior to release. Upon release, each of these proto-platelet processes can give rise to 2000-5000 new platelets. Overall, about ⅔ of the newly-released platelets will remain in circulation and about ⅓ will be sequestered by the spleen. After releasing the platelets, the remaining cell nucleus typically crosses the bone marrow barrier to the blood and is consumed in the lung by alveolar macrophages. Megakaryocytopenia, also referred to as megakaryophthisis, is a scarcity of megakaryocytes in the bone marrow.

An "erythrocyte" refers to a red blood cell that consists mainly of hemoglobin, a complex metalloprotein containing heme groups whose iron atoms temporarily link to oxygen molecules (02) in the lungs. Erythrocytes are produced by a process called erythropoiesis, in which they develop from committed stem cells through reticulocytes to mature erythrocytes in about 7 days and live a total of about 100-120 days. "Polycythemias" (or erythrocytoses) are diseases characterized by a surplus of erythrocytes, in which the increased viscosity of the blood can cause a number of symptoms. "Anemias" are diseases characterized by low oxygen transport capacity of the blood, because of low red cell count or some abnormality of the red blood cells or the hemoglobin.

A "granulocyte" refers to a white blood cell that is characterized by the presence of granules in its cytoplasm. Granulocytes are also referred to as polymorphonuclear leukocytes (PMN or PML), because of the varying shapes of the nuclei. Examples of granulocytes include neutrophils, eosinophils, and basophils. A "neutrophil," or neutrophil granulocyte, refers generally to an abundant type of white blood cells in humans, which, together with basophils and eosinophils, form part of the polymorphonuclear cell family (PMNs). Neutrophils can be readily identified according to their unique staining characteristics on hematoxylin and eosin (H&E) histological or cytological preparations. Neutrophils are normally found in the blood stream, but are one of the first group of inflammatory cells to migrate toward inflammation sites during the beginning (i.e., acute) phase of inflammation, mainly as a result of infection or cancer. Typically, neutrophils first migrate through the blood vessels, and then through interstitial tissues, following chemical signals (e.g., interleukin-8 (IL-8), interferon-gamma (IFN-gamma), and C5a) that originate at the site of inflammation. "Neutropenia" refers to the presence of low neutrophil counts, which may result from a congenital (genetic) disorder, or may develop due to other conditions, as in the case of aplastic anemia or some kinds of leukemia. "Neutrophilia" refers to an abnormally high neutrophil count.

"Eosinophils," also called eosinophilic leukocytes, refer to leukocytes that have coarse round granules of uniform size within their cytoplasm, and which typically have a bilobate (two-lobed) nucleus. The cytoplasmic granules of eosinophils stain red with the dye eosin. Eosinophils normally constitute about 1% to about 3% of the peripheral blood leukocytes, at a count of about 350 to 650 per cubic millimeter. Eosinophil counts in blood often rise above the normal range during allergic reactions and parasitic infections, such as worms. "Eosinopenia" refers to a form of agranulocytosis in which the number of eosinophil granulocyte is lower than expected. "Eosinophilia" refers to an abnormally high number of eosinophils in the blood. For example, eosinophilia can be categorized as mild (less than about 1500 eosinophils per cubic millimeter), moderate (about 1500 to about 5000 per cubic millimeter), or severe (more than about 5000 per cubic millimeter). In primary eosinophilia, the increased production of eosinophils is typically due to an abnormality in hematopoietic stem cells, such as in eosinophilic leukemia. In secondary eosinophilia, the increased production of eosinophils is typically due to a reactive process driven by cytokines.

Basophils, also called basophilic leukocytes, refer to leukocytes that have coarse bluish-black granules of uniform size within the cytoplasm, and which typically have a bilobate (two-lobed) nucleus. The cytoplasmic granules of basophils stain with basic dyes. Basophils normally constitute about 0.5% to 3% of the peripheral blood leukocytes. Basophils store and release histamine and serotonin, among other chemicals. Basophils are capable of ingesting foreign particles, and also produce, store and release heparin, serotonin, and histamine. The release of inflammatory chemicals such as heparin and histamine is often associated with asthma and allergies. Basophils are produced continually by stem cells in the bone marrow. "Basopenia" refers to a low basophil count (e.g., less than about $0.01 \times 10^9$ per liter of blood), and "basophilia" refers to a high basophil count (e.g., more than about $10^{10}$ per liter of blood).

"Lymphocytes" refer generally to white blood cells of the vertebrate immune system, and include B-cells, T-cells (e.g., helper T-cells, cytotoxic T-cells, γδ T-cells), and natural killer (NK) cells. Generally, and merely for illustrative purposes, B-cells produce and secrete antibodies, T-helper cells release cytokines and growth factors that regulate other immune cells, cytotoxic T-cells (CTLs) lyse virally infected cells, tumour cells and allografts, and NK cells lyse virally infected cells and tumour cells. "Lymphocytopenia" is characterized by abnormally low level of lymphocytes in the blood. The normal total lymphocyte count is typically about 1000 to 4800/4 in adults, and about 3000 to 9500/μL in children younger than 2 years. At age 6, the lower limit of normal total lymphocyte count is about 1500/4. Lymphocytopenia is often characterized by a total lymphocyte count of <1000/μL in adults or <3000/μL in children younger than 2 years. Specific examples of lymphocytopenia include T-lymphocytopenia, in which there are too few T-cells (e.g., CD4+ T-cell counts below about 300 cells/4) but often normal numbers of other lymphocytes, B lymphocytopenia, in which there are too few B lymphocytes but often normal numbers of other lymphocytes, and NK lymphocytopenia, in which there are there are too few natural killer cells but often normal numbers of other lymphocytes.

"Lymphocytosis" refers to an abnormally high lymphocyte count, often characterized by a total lymphocyte count that is more than 40% above normal. In adults, absolute lymphocytosis is typically present when the absolute lymphocyte count is greater than 4000 per microliter, in older children greater than 7000 per microliter, and in infants greater than 9000 per microliter. Relative lymphocytosis may occur when there is a higher proportion (greater than 40%) of lymphocytes among the white blood cells, and when lymphocyte count (ALC) is normal (less than about 4000 per microliter).

The term "modulating" includes "increasing" or "stimulating," as well as "decreasing" or "reducing," typically in a statistically significant or a physiologically significant amount.

The terms "enhance" or "enhancing," or "increase" or "increasing," or "stimulate" or "stimulating," refer generally to the ability of one or agents or compositions to produce or cause a greater physiological response (i.e., downstream effects) in a cell, as compared to the response caused by either no AARS polypeptide or a control molecule/composition. A measurable physiological response may include greater cell growth, expansion, adhesion, or migration, among others apparent from the understanding in the art and the description herein. Among other methods known in the art, in vitro colony formation assays represent one way to measure cellular responses to agents provided herein. A measurable physiological response may also include a clinical response, such as altered inflammation, as measured, for example, by body temperature, redness, swelling, or other clinical marker of inflammation. An "increased" or "enhanced" amount is typically a "statistically significant" amount, and may include an increase that is 1.1, 1.2, 2, 3, 4, 5, 6, 7, 8, 9, 10, 15, 20, 30 or more times (e.g., 500, 1000 times) (including all integers and decimal points in between and above 1), e.g., 1.5, 1.6, 1.7. 1.8, etc.) the amount produced by no AARS polypeptide (the absence of an agent) or a control composition.

The term "reduce" may relate generally to the ability of one or more AARS polypeptides of the invention to "decrease" a relevant physiological or cellular response, such as a symptom of a disease or condition described herein, as measured according to routine techniques in the diagnostic art. Examples include decreased migration of immune cells such as granulocytes to the lung, and decreased inflammation of the lung. A measurable physiological response may include decreased inflammation, as measured, for example, by body temperature, redness, swelling, or other clinical marker of inflammation. Relevant physiological or cellular responses (in vivo or in vitro) will be apparent to persons skilled in the art. A "decrease" in a response may be statistically significant as compared to the response produced by no AARS polypeptide or a control composition, and may include, for example, a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% decrease, including all integers in between.

"Migration" refers to cellular migration, a process that can be measured according to routine in vitro assays, as described herein and known in the art (see, e.g., Example 8). Migration also refers to in vivo migration, such as the migration of cells from one tissue to another tissue (e.g., from bone marrow to peripheral blood, or from peripheral blood to lung tissue), or from a site within one tissue to another site within the same tissue. Migration in vivo (e.g., chemotaxis) often occurs in a response to infection or damaged/irritated tissue.

"Differentiation" refers to the process by which a less specialized (e.g., pluripotent, totipotent, multipotent, etc.) cell becomes a more specialized cell type.

"Treatment" or "treating," as used herein, includes any desirable effect on the symptoms or pathology of a disease or condition associated with the modulation of inflammation, or on the outcome of other primary treatments (e.g., infections, allergies) that may benefit from the modulation of inflammation, and may include even minimal changes or improvements in one or more measurable markers of the disease or condition being treated. "Treatment" or "treating" does not necessarily indicate complete eradication or cure of the disease or condition, or associated symptoms thereof. The subject receiving this treatment is any animal in need, including primates, in particular humans, and other mammals such as equines, cattle, swine and sheep; and poultry and pets in general. Also included are "prophylactic" treatments, which reduce the risk of developing a relevant disease or condition, or of developing symptoms associated with the disease or condition. Exemplary markers of clinical improvement include without limitation altered body temperature, alterations in immune cell count, and alterations in bacterial counts, whether following administration of an AARS polypeptide, following administration of cells that have been treated ex vivo or in vitro with an AARS polypeptide, or both.

By "vector" is meant a polynucleotide molecule, preferably a DNA molecule derived, for example, from a plasmid, bacteriophage, yeast or virus, into which a polynucleotide can be inserted or cloned. A vector preferably contains one or more unique restriction sites and can be capable of autonomous replication in a defined host cell including a target cell or tissue or a progenitor cell or tissue thereof, or be integrable with the genome of the defined host such that the cloned sequence is reproducible. Accordingly, the vector can be an autonomously replicating vector, i.e., a vector that exists as an extra-chromosomal entity, the replication of which is independent of chromosomal replication, e.g., a linear or closed circular plasmid, an extra-chromosomal element, a mini-chromosome, or an artificial chromosome. The vector can contain any means for assuring self-replication. Alternatively, the vector can be one which, when introduced into the host cell, is integrated into the genome and replicated together with the chromosome(s) into which it has been integrated. A vector system can comprise a single vector or plasmid, two or more vectors or plasmids, which together contain the total DNA to be introduced into the genome of the host cell, or a transposon. The choice of the vector will typically depend on the compatibility of the vector with the host cell into which the vector is to be introduced. In the present case, the vector is preferably one which is operably functional in a bacterial cell. The vector can also include a selection marker such as an antibiotic resistance gene that can be used for selection of suitable transformants.

The terms "wild-type" and "naturally occurring" are used interchangeably to refer to a gene or gene product that has the characteristics of that gene or gene product when isolated from a naturally occurring source. A wild-type gene or gene product (e.g., a polypeptide) is that which is most frequently observed in a population and is thus arbitrarily designed the "normal" or "wild-type" form of the gene.

Aminoacyl-tRNA Polypeptides and Variants Thereof

The present invention relates in part to the observation that aminoacyl-tRNA synthetase polypeptides, including truncations and variants thereof, modulate inflammatory responses both in vivo and ex vivo (or in vitro). Accordingly, polypeptides of the present invention include a full-length aminoacyl-tRNA synthetase polypeptide, in addition to any biologically active fragments, or variants or modifications thereof, of an aminoacyl-tRNA synthetase polypeptide, wherein the polypeptide is capable of modulating an inflammatory response, either in a subject, in vitro, or ex vivo.

Aminoacyl-tRNA synthetases typically catalyze the aminoacylation of tRNA with their cognate amino acid. Because of their central role in linking amino acids with nucleotide triplets contained in tRNAs, aminoacyl-tRNA synthetases are thought to be among the first proteins that appeared in evolution.

As noted above, examples of aminoacyl-tRNA synthetases include tyrosyl-tRNA synthetases (YRS), tryptophanyl-tRNA synthetases (WRS), glutaminyl-tRNA synthetases (QRS), glycyl-tRNA synthetases (GlyRS), histidyl-tRNA synthetases (HisRS), seryl-tRNA synthetases (SRS), phenylalanyl-tRNA synthetases (PheRS), alanyl-tRNA synthetases (AlaRS), asparaginyl-tRNA synthetases (AsnRS), aspartyl-tRNA synthetases (AspRS), cysteinyl-tRNA synthetases (CysRS), glutamyl-tRNA synthetases (ERS), prolyl-tRNA synthetases (ProRS), arginyl-tRNA synthetases (RRS), isoleucyl-tRNA synthetases (IRS), leucyl-tRNA synthetases (LRS), lysyl-tRNA synthetases (KRS), threonyl-tRNA synthetases (TRS), methionyl-tRNA synthetases (MRS), and valyl-tRNA synthetases (VRS).

Tyrosyl-tRNA synthetases (YRS) belong to the class I tRNA synthetase family, which has two highly conserved sequence motifs at the active site, HIGH and KMSKS. Class I tRNA synthetases aminoacylate at the 2'-OH of an adenosine nucleotide, and are usually monomeric or dimeric (one or two subunits, respectively).

The human tyrosyl-tRNA synthetase is composed of three domains: 1) an amino-terminal Rossmann fold domain that is responsible for formation of the activated E.Tyr-AMP intermediate and is conserved among bacteria, archeae, and eukaryotes; 2) a tRNA anticodon recognition domain that has not been conserved between bacteria and eukaryotes; and 3) a carboxyl-terminal domain that is unique to the human tyrosyl-tRNA synthetase, and whose primary structure is 49% identical to the putative human cytokine endothelial monocyte-activating protein II, 50% identical to the carboxyl-terminal domain of methionyl-tRNA synthetase from *Caenorhabditis elegans*, and 43% identical to the carboxyl-terminal domain of Arc1p from *Saccharomyces cerevisiae*.

The first two domains of the human tyrosyl-tRNA synthetase are 52, 36, and 16% identical to tyrosyl-tRNA synthetases from *S. cerevisiae*, *Methanococcus jannaschii*, and *Bacillus stearothermophilus*, respectively. Nine of fifteen amino acids known to be involved in the formation of the tyrosyl-adenylate complex in *B. stearothermophilus* are conserved across all of the organisms, whereas amino acids involved in the recognition of $tRNA^{Tyr}$ are not conserved. Kinetic analyses of recombinant human and *B. stearothermophilus* tyrosyl-tRNA synthetases expressed in *Escherichia coli* indicate that human tyrosyl-tRNA synthetase aminoacylates human but not *B. stearothermophilus* $tRNA^{Tyr}$, and vice versa. It is believed that the carboxyl-terminal domain of human tyrosyl-tRNA synthetase evolved from gene duplication of the carboxyl-terminal domain of methionyl-tRNA synthetase and may direct tRNA to the active site of the enzyme.

Biological fragments of eukaryotic tyrosyl-tRNA synthetases connect protein synthesis to cell-signaling pathways. These fragments may be produced naturally by either alternative splicing or proteolysis, or by artificial proteolytic treatment. For example, as provided in the present invention, the N-terminal fragment mini-YRS is capable of modulating inflammatory responses in vivo. In addition, certain mutations in the full-length YRS polypeptide sequence confer increased inflammatory response-modulating activity on the reference sequence (e.g., Y341A). Examples of truncated splice variants of the full-length YRS polypeptide sequence include the SP1-SP5 polypeptides.

The full-length amino acid sequence of human tyrosyl-tRNA synthetase is set forth in SEQ ID NO:1. The structure of human mini-YRS (i.e., SEQ ID NO:3; or mini-Tyr), which contains both the catalytic and the anticodon recognition domain, has been reported to a resolution of 1.18 Å. Whereas the catalytic domains of the human and bacterial enzymes superimpose, the spatial disposition of the anticodon recognition domain relative to the catalytic domain is unique in mini-YRS relative to the bacterial orthologs. Without wishing to be bound by any one theory, the unique orientation of the anticodon-recognition domain may explain why the fragment mini-YRS is more active in various cell-signaling pathways.

Specific examples of YRS polypeptide variants include full-length YRS polypeptides, or truncations or splice variants thereof, having one or more amino acid substitutions selected from an R93Q substitution, an I14L substitution, an N17G substitution, an L271 substitution, an A85S substitution, and a V156L substitution, in addition to combinations thereof. Particular examples of YRS polypeptide variants include, but are not limited to, a YRS polypeptide having amino acids 1-364 of SEQ ID NO:1 with an R93Q substitution, a YRS polypeptide having amino acids 1-353 of SEQ ID NO:1 with an I14L substitution, a YRS polypeptide having amino acids 1-353 of SEQ ID NO:1 with an N17G substitution, a YRS polypeptide having amino acids 1-353 of SEQ ID NO:1 with an L271 substitution, a YRS polypeptide having amino acids 1-353 of SEQ ID NO:1 with an A85S substitution, and a YRS polypeptide having amino acids 1-353 of SEQ ID NO:1 with a V156L substitution.

Particular examples of biologically active YRS fragments include, but are not limited to, C-terminally truncated tyrosyl-tRNA synthetase polypeptides comprising or consisting of amino acids 1-343, amino acids 1-344, amino acids 1-350, amino acids 1-353, or amino acids 1-364 of the amino acid sequence set forth in SEQ ID NO:1, in addition to the polypeptides of SEQ ID NOS:3 and 6. Additional examples of biologically active fragments include, but are not limited to, N-terminally truncated tyrosyl-tRNA synthetase polypeptides comprising or consisting of the amino acid sequences set forth in SEQ ID NOS: 6, 10, 12, and 14. These and other YRS polypeptides are included within the AARS polypeptides of the present invention.

Histidyl-tRNA synthetases (HRS or HisRS) are α2 dimers that belong to the class IIa tRNA synthetase family. A compilation of primary structures of HisRSs shows that the subunits of these homo-dimeric enzymes consist of 420-550 amino acid residues. This represents a relatively short chain length among AARSs, whose peptide chain sizes range from about 300 to 1100 amino acid residues. SEQ ID NO:28 is the amino acid sequence of the full length HisRS protein (NP_002100.2). SEQ ID NO:30 is the amino acid sequence of the HRS-SV9 splice variant, and SEQ ID NO:32 is the amino acid sequence of the HRS-SV11 splice variant.

Examples of histidyl-tRNA synthetase polypeptides, and variants or truncations thereof, include HisRS fragments comprising at least the WHEP domain of HisRS, e.g., amino acid residues 3-43 of the human full length HisRS protein and HisRS fragments comprising at least the anticodon binding domain of HisRS, e.g., amino acid residues 406-501 of the full length human HisRS protein. Further examples include HisRS fragments that lack a functional aminoacylation domain, e.g., amino acid residues 54-398 of the human full length HisRS protein or HisRS splice variant polypeptides that comprise at least the WHEP domain and the anticodon binding domain but lack a functional aminoacylation domain.

In certain embodiments, the HisRS polypeptide of the invention comprises a sequence set forth in SEQ ID NOS: 28, 30, or 32, or is a contiguous or non-contiguous (e.g., splice variants may be non-contiguous) fragment of a polypeptide set forth in SEQ ID NOS:28, 30, or 32. Illustratively, the fragments may be of essentially any length, provided they retain at least one non-canonical biological activity of interest. For example, as further described herein, such a fragment may comprise at least about 5, 10, 15, 20, 25, 50, 75 or 80, or more, contiguous amino acid residues of SEQ ID NOS:28, 30, or 32.

In further embodiments of the invention, a HisRS polypeptide comprises an active variant (i.e., retains at least one non-canonical biological activity of interest) of a sequence set forth in SEQ ID NOS:28, 30, or 32. In certain embodiments, the active variant is a polypeptide having at least 70%, 80%, 90%, 95% or 99% identity along its length to a sequence set forth in SEQ ID NOS:28, 30, or 32. In certain embodiment, the HisRS polypeptide of the invention is not a polypeptide consisting of residues 1-48 of the full length human HisRS protein. These and other HisRS polypeptides are included within the AARS polypeptides of the present invention.

Tryptophanyl-tRNA synthetases (WRS), also referred to as tryptophan-tRNA ligases, belong to the class I tRNA synthetase family. Tryptophanyl-tRNA synthetase catalyzes the aminoacylation of $tRNA^{trp}$ with tryptophan, an essential function in protein synthesis. Human WRS has a kinase domain in the N-terminal region and a serine phosphorylation site near the C-terminus.

Two main forms of human tryptophanyl-tRNA synthetase are produced in vivo through alternative mRNA splicing, to yield the full-length protein (SEQ ID NO: 33), and a fragment thereof, often designated mini-WRS (SEQ ID NO:107). Also included are human T1-WRS (SEQ ID NO:108) and T2-WRS (SEQ ID NO:34), alternate splice variants that are produced from an IFN-gamma-sensitive promoter, the latter being an N-terminally truncated fragment of WRS, as well as an N-terminal fragment (F1; SEQ ID NO:106) and fragment of WRS referred to as "Tolstrup" (SEQ ID NO:35). Other splice variants of human WRS are known in the art (see, e.g., Liu et al., *Nucleic Acids Research*, 32(2):719-27, 2004, herein incorporated by reference).

Structurally, full-length WRS contains three parts, a canonical dinucleotide-binding fold, a dimer interface, and a helical domain. This enzyme has enough structural homology to tyrosyl-tRNA synthetase (YRS) that the two enzymes can be described as conformational isomers. Structural elements interacting with the activated amino acid, tryptophanyl-5' AMP, are almost exactly as seen in the tyrosyl-5' AMP complex. Also, side chains that recognize indole are also highly conserved, and require reorientation of a "specificity-determining" helix containing a conserved aspartate to assure selection of tryptophan versus tyrosine. The carboxy terminus, which is disordered and therefore not seen in YRS, forms part of the dimer interface in WRS (see Doublie et al., *Structure*. 3:17-31, 1995).

The crystal structure of human T2-WRS has been reported at 2.5 Å resolution. This variant shares a very low sequence homology of 22% with *Bacillus stearothermophilus* WRS (bWRS), however their overall structures are strikingly similar. Structural comparison of T2-WRS with bWRS reveals substantial structural differences in the substrate-binding pocket and at the entrance to the pocket that play important roles in substrate binding and tRNA binding. T2-WRS has a wide opening to the active site and adopts a compact conformation similar to the closed conformation of bWRS. Modeling studies indicate that tRNA binds with the dimeric enzyme and interacts primarily with the connective polypeptide 1 of human WRS via its acceptor arm and the α-helical domain of WRS via its anticodon loop.

The amino acid sequence of the full-length WRS polypeptide (or the main splice variant) is shown in SEQ ID NO:33. The amino acid sequence of various splice variants or fragments are shown in SEQ ID NOS:34 and 35. Accordingly, these and other variants or fragments of WRS polypeptides are included within the AARS polypeptides of the present invention.

Glutaminyl-tRNA synthetases (QRS) belong to the class I tRNA synthetase family, and the human protein is one of several mammalian aminoacyl-tRNA synthetases that form a macromolecular protein complex. The eukaryote-specific N-terminal appendix of QRS appears to stabilize the association of other components in the multi-ARS complex, whereas the C-terminal catalytic domain is necessary for QRS association with the multi-AARS complex.

The human QRS enzyme differs from both the bacterial and yeast enzymes, suggesting that a considerable part of human QRS has evolved to perform functions other than the charging of tRNA. For instance, at least two distinct regions (part I and part II) within the eukaryotic QRS (EC 6.1.1.18) N-terminal region have no counterpart in *Escherichia coli*. Even though these regions are thought to bind RNA in a non-specific manner, enhancing interactions between the tRNA and enzyme, they are not essential for enzyme function (see, e.g., Wang et al., *J. Biol. Chem.* 274:16508-12, 1999). Further, human and mouse cells express at least one QRS variant that contains a deletion in part 1 of the N-terminal region, possibly due to an alternate start codon or alternate splicing. However, the available sequence data for yeast suggests that these microorganisms do not express such a QRS variant, but rather only express a QRS polypeptide that contains both part I and part II of the N-terminal region.

Molecular phylogenetic studies of QRS suggest that it has relatively recently evolved from the closely related enzyme glutamyl-tRNA synthetase. As evidence, selected glutaminyl-tRNA synthetase mutants display enhanced glutamic acid recognition. For instance, mutagenesis of two residues proximal to the active site, Phe-90 and Tyr-240, improves glutamic acid recognition 3-5-fold in vitro and results in the misacylation of tRNA$^{gln}$ with glutamic acid.

QRS has been crystallised in a variety of complexes, most importantly with its cognate tRNA$^{gln}$. The enzyme makes extensive contacts with the concave face of the tRNA, and makes specific interactions with the CUG anticodon at positions 34 to 36, and with the base pairs between the 5' end and the 3' end of the tRNA, just before the aminoacyl acceptor.

Certain QRS polypeptides possess anti-apoptotic activities. For instance, human QRS interacts with Fas ligation activated apoptosis signal-regulating kinase 1 (ASK1) in a glutamine-dependent manner. This interaction involves the catalytic domains of the two enzymes, and is dissociated by Fas ligand. This interaction also inhibits both ASK1 activity, as measured by in vitro kinase and transcription assays, and cell death induced by ASK1, an effect that is weakened by glutamine deprivation. The anti-apoptotic interaction of QRS with ASK1 is therefore enhanced by the cellular concentration of glutamine and reduced by Fas ligation. This anti-apoptotic activity is believed to lie in the C-terminal 539 amino acids of human QRS.

The amino acid sequence of the full-length QRS polypeptide is shown in SEQ ID NO:25. Certain specific examples of QRS variants, truncations, or fragments include QRS polypeptides that comprise or consist essentially of amino acids 1-183 (QRS1 or Q1), 1-220 (QRS2 or Q2), 1-249 (QRS3 or Q3), 1-200 (QRS4 or Q4), 1-(181-293), e.g., 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, etc., of SEQ ID NO:25 (see Table 2). Also included are peptides of SEQ ID NOS: 36-103 and 109-115. Accordingly, these and other variants of QRS polypeptides are included within the AARS polypeptides of the present invention.

Glycyl-tRNA synthetase (GlyRS) is an α2 dimer that belongs to the class II family of tRNA synthetases (see, e.g., U.S. application Ser. No. 12/492,925, herein incorporated by reference). The approximately 2462 bp cDNA for this gene contains a large open reading frame (ORF) encoding 685 amino acids with predicted M(r)=77,507 Da. The protein sequence of human GlyRS has approximately 60% identity with *B. mori* GlyRS and 45% identity with *S. cerevisiae* GlyRS, and contains motifs 2 and 3 characteristic of Class II tRNA synthetases The amino acid sequence of the full-length GlyRS polypeptide is shown in SEQ ID NO:16. SEQ ID NOS:18-24 represent illustrative peptide sequences analyzed in determining GlyRS fragment boundaries.

Certain examples of GlyRS proteolytic fragments include polypeptides that comprise, consist essentially of, or consist of amino acid residues 57-685, 214-685, 239-685, 311-685, 439-685, 511-658, 214-438, 367-438, 214-420, 214-338, 85-127 1-213, 1-61, 85-214, 333-685, 128-685, 265-685, 483-685 or 25-56 of SEQ ID NO:16, including biologically active truncations or variants thereof (e.g., variants having about 80%, 85%, 90%, 95%, 98% sequence identity to the fragments) that substantially retain at least one non-canonical biological activity of interest. In certain specific embodiments, the GlyRS polypeptide is not a polypeptide as set forth in any one of NCBI # CR594947, U09587 and/or U09510. Accordingly, these and other variants of GlyRS polypeptides are included within the AARS polypeptides of the present invention.

Additional examples of AARS polypeptides having non-canonical activities include phenylalanyl-tRNA synthetase (PheRS) splice variant polypeptides (PheRS_SV1P) (SEQ ID NO:104), which have a unique amino acid sequence in the C-terminal end that is different from the full-length human PheRS protein sequence, including variants and fragments of those PheRS polypeptides; and aspartyl-tRNA synthetase (AspRS) polypeptides (SEQ ID NO:105), including fragments thereof that consist essentially of amino acid residues 1-154, 1-174, 1-31, 399-425, 413-476 or 397-425 of SEQ ID NO:105.

Embodiments of the present invention contemplate the use of compositions comprising AARS polypeptides, including truncated fragments, splice variants, proteolytic fragments, and variants and/or modified polypeptides thereof, for modulating inflammation in a subject. Included are AARS polypeptides that reduce migration of immune cells such as granulocytes to the lung, desensitize immune cells such as granulocytes to a given antigen or irritant, or both, among other inflammatory-modulating activities described herein and known in the art. Variant proteins encompassed by the present application are biologically active, that is, they continue to possess the inflammatory response-modulating activity of a reference AARS polypeptide sequence (e.g., SEQ ID NOS: 1, 2, 3, 6, 8, 10, 12, 14, 16, 25, 28, 30, and 32-108, 109-115 etc.). Such variants may result from, for example, genetic polymorphism or from human manipulation.

Biologically active variants of a reference AARS polypeptide fragment will have at least 40%, 50%, 60%, 70%, generally at least 75%, 80%, 85%, usually about 90% to 95% or more, and typically about 98% or more sequence similarity or identity with the amino acid sequence of a reference protein as determined by sequence alignment programs described elsewhere herein using default parameters. A biologically active variant of a reference AARS polypeptide may differ from that protein generally by as much 200, 100, 50 or 20 amino acid residues or suitably by as few as 1-15 amino acid residues, as few as 1-10, such as 6-10, as few as 5, as few as 4, 3, 2, or even 1 amino acid residue. In some embodiments, an AARS polypeptide differs from the reference sequences in SEQ ID NOS: 1, 2, 3, 6, 8, 10, 12, 14, 16, 25, 28, 30, 32-108, or 109-115 by at least one but by less than 15, 10 or 5 amino acid residues. In other embodiments, it differs from the reference sequences in SEQ ID NOS: 1, 2, 3, 6, 8, 10, 12, 14, 16, 25, 28, 30, 32-108, or 109-115 by at least one residue but less than 20%, 15%, 10% or 5% of the residues.

An AARS polypeptide may be altered in various ways including amino acid substitutions, deletions, truncations, and insertions. Methods for such manipulations are generally known in the art. For example, amino acid sequence variants of a truncated and/or variant AARS polypeptide can be prepared by mutations in the DNA. Methods for mutagenesis and nucleotide sequence alterations are well known in the art. See, for example, Kunkel (1985, *Proc. Natl. Acad. Sci. USA*. 82: 488-492), Kunkel et al., (1987, *Methods in Enzymol*, 154: 367-382), U.S. Pat. No. 4,873,192, Watson, J. D. et al., ("Molecular Biology of the Gene", Fourth Edition, Benjamin/Cummings, Menlo Park, Calif., 1987) and the references cited therein. Guidance as to appropriate amino acid substitutions that do not affect biological activity of the protein of interest may be found in the model of Dayhoff et al., (1978) *Atlas of* Protein Sequence and Structure (Natl. Biomed. Res. Found., Washington, D.C.). Methods for screening gene products of combinatorial libraries made by point mutations or truncation, and for screening cDNA libraries for gene products having a selected property are known in the art. Such methods are adaptable for rapid screening of the gene libraries generated by combinatorial mutagenesis of AARS polypeptides. Recursive ensemble mutagenesis (REM), a technique which enhances the frequency of functional mutants in the libraries, can be used in combination with the screening assays to identify AARS polypeptide variants (Arkin and Yourvan (1992) *Proc. Natl. Acad. Sci. USA* 89: 7811-7815; Delgrave et al., (1993) *Protein Engineering*, 6: 327-331). Conservative substitutions, such as exchanging one amino acid with another having similar properties, may be desirable as discussed in more detail below.

Biologically active truncated and/or variant AARS polypeptides may contain conservative amino acid substitutions at various locations along their sequence, as compared to a reference AARS amino acid sequence (e.g., SEQ ID NOS: 1, 2, 3, 6, 8, 10, 12, 14, 16, 25, 28, 30, 32-108, and 109-115). A "conservative amino acid substitution" is one in which the amino acid residue is replaced with an amino acid residue having a similar side chain. Families of amino acid residues having similar side chains have been defined in the art, which can be generally sub-classified as follows:

Acidic: The residue has a negative charge due to loss of H ion at physiological pH and the residue is attracted by aqueous solution so as to seek the surface positions in the conformation of a peptide in which it is contained when the peptide is in aqueous medium at physiological pH. Amino acids having an acidic side chain include glutamic acid and aspartic acid.

Basic: The residue has a positive charge due to association with H ion at physiological pH or within one or two pH units thereof (e.g., histidine) and the residue is attracted by aqueous solution so as to seek the surface positions in the conformation of a peptide in which it is contained when the peptide is in aqueous medium at physiological pH. Amino acids having a basic side chain include arginine, lysine and histidine.

Charged: The residues are charged at physiological pH and, therefore, include amino acids having acidic or basic side chains (i.e., glutamic acid, aspartic acid, arginine, lysine and histidine).

Hydrophobic: The residues are not charged at physiological pH and the residue is repelled by aqueous solution so as to seek the inner positions in the conformation of a peptide in which it is contained when the peptide is in aqueous medium. Amino acids having a hydrophobic side chain include tyrosine, valine, isoleucine, leucine, methionine, phenylalanine and tryptophan.

Neutral/polar: The residues are not charged at physiological pH, but the residue is not sufficiently repelled by aqueous solutions so that it would seek inner positions in the conformation of a peptide in which it is contained when the peptide is in aqueous medium. Amino acids having a neutral/polar side chain include asparagine, glutamine, cysteine, histidine, serine and threonine.

This description also characterizes certain amino acids as "small" since their side chains are not sufficiently large, even if polar groups are lacking, to confer hydrophobicity. With the exception of proline, "small" amino acids are those with four carbons or less when at least one polar group is on the side chain and three carbons or less when not. Amino acids having a small side chain include glycine, serine, alanine and threonine. The gene-encoded secondary amino acid proline is a special case due to its known effects on the secondary conformation of peptide chains. The structure of proline differs from all the other naturally-occurring amino acids in that its side chain is bonded to the nitrogen of the α-amino group, as well as the α-carbon. Several amino acid similarity matrices are known in the art (see e.g., PAM120 matrix and PAM250 matrix as disclosed for example by Dayhoff et al., 1978, A model of evolutionary change in proteins). Matrices for determining distance relationships In M. O. Dayhoff, (ed.), Atlas of protein sequence and structure, Vol. 5, pp. 345-358, National Biomedical Research Foundation, Washington D.C.; and by Gonnet et al., (Science, 256: 14430-1445, 1992), however, include proline in the same group as glycine, serine, alanine and threonine. Accordingly, for the purposes of the present invention, proline is classified as a "small" amino acid.

The degree of attraction or repulsion required for classification as polar or nonpolar is arbitrary and, therefore, amino acids specifically contemplated by the invention have been classified as one or the other. Most amino acids not specifically named can be classified on the basis of known behaviour.

Amino acid residues can be further sub-classified as cyclic or non-cyclic, and aromatic or non-aromatic, self-explanatory classifications with respect to the side-chain substituent groups of the residues, and as small or large. The residue is considered small if it contains a total of four carbon atoms or less, inclusive of the carboxyl carbon, provided an additional polar substituent is present; three or less if not. Small residues are, of course, always non-aromatic. Dependent on their structural properties, amino acid residues may fall in two or more classes. For the naturally-occurring protein amino acids, sub-classification according to this scheme is presented in Table A.

TABLE A

Amino acid sub-classification

| Sub-classes | Amino acids |
|---|---|
| Acidic | Aspartic acid, Glutamic acid |
| Basic | Noncyclic: Arginine, Lysine; Cyclic: Histidine |
| Charged | Aspartic acid, Glutamic acid, Arginine, Lysine, Histidine |
| Small | Glycine, Serine, Alanine, Threonine, Proline |
| Polar/neutral | Asparagine, Histidine, Glutamine, Cysteine, Serine, Threonine |
| Polar/large | Asparagine, Glutamine |
| Hydrophobic | Tyrosine, Valine, Isoleucine, Leucine, Methionine, Phenylalanine, Tryptophan |
| Aromatic | Tryptophan, Tyrosine, Phenylalanine |
| Residues that influence chain orientation | Glycine and Proline |

Conservative amino acid substitution also includes groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. For example, it is reasonable to expect that replacement of a leucine with an isoleucine or valine, an aspartate with a glutamate, a threonine with a serine, or a similar replacement of an amino acid with a structurally related amino acid will not have a major effect on the properties of the resulting variant polypeptide. Whether an amino acid change results in a functional truncated and/or variant AARS polypeptide can readily be determined by assaying its activity, as described herein (see, e.g., Examples 1, 2, 10, and 11). Conservative substitutions are shown in Table B under the heading of exemplary substitutions. Amino acid substitutions falling within the scope of the invention, are, in general, accomplished by selecting substitutions that do not differ significantly in their effect on maintaining (a) the structure of the peptide backbone in the area of the substitution, (b) the charge or hydrophobicity of the molecule at the target site, (c) the bulk of the side chain, or (d) the biological function. After the substitutions are introduced, the variants are screened for biological activity.

TABLE B

Exemplary Amino Acid Substitutions

| Original Residue | Exemplary Substitutions | Preferred Substitutions |
|---|---|---|
| Ala | Val, Leu, Ile | Val |
| Arg | Lys, Gln, Asn | Lys |
| Asn | Gln, His, Lys, Arg | Gln |
| Asp | Glu | Glu |
| Cys | Ser | Ser |
| Gln | Asn, His, Lys, | Asn |
| Glu | Asp, Lys | Asp |
| Gly | Pro | Pro |
| His | Asn, Gln, Lys, Arg | Arg |
| Ile | Leu, Val, Met, Ala, Phe, Norleu | Leu |
| Leu | Norleu, Ile, Val, Met, Ala, Phe | Ile |
| Lys | Arg, Gln, Asn | Arg |
| Met | Leu, Ile, Phe | Leu |
| Phe | Leu, Val, Ile, Ala | Leu |
| Pro | Gly | Gly |
| Ser | Thr | Thr |
| Thr | Ser | Ser |
| Trp | Tyr | Tyr |
| Tyr | Trp, Phe, Thr, Ser | Phe |
| Val | Ile, Leu, Met, Phe, Ala, Norleu | Leu |

Alternatively, similar amino acids for making conservative substitutions can be grouped into three categories based on the identity of the side chains. The first group includes glutamic acid, aspartic acid, arginine, lysine, histidine, which all have charged side chains; the second group includes glycine, serine, threonine, cysteine, tyrosine, glutamine, asparagine; and the third group includes leucine, isoleucine, valine, alanine, proline, phenylalanine, tryptophan, methionine, as described in Zubay, G., Biochemistry, third edition, Wm.C. Brown Publishers (1993).

Thus, a predicted non-essential amino acid residue in a truncated and/or variant AARS polypeptide is typically replaced with another amino acid residue from the same side chain family. Alternatively, mutations can be introduced randomly along all or part of an AARS coding sequence, such as by saturation mutagenesis, and the resultant mutants can be screened for an activity of the parent polypeptide to identify mutants which retain that activity. Following mutagenesis of the coding sequences, the encoded peptide can be expressed recombinantly and the activity of the peptide can be determined. A "non-essential" amino acid residue is a residue that can be altered from the reference sequence of an embodiment polypeptide without abolishing or substantially altering one or more of its activities. Suitably, the alteration does not substantially abolish one of these activities, for example, the activity is at least 20%, 40%, 60%, 70% or 80% 100%, 500%, 1000% or more of a reference AARS polypeptide. An "essential" amino acid residue is a residue that, when altered from the reference AARS polypeptide, results in abolition of an activity of the parent molecule such that less than 20% of the reference activity is present. For example, such essential amino acid residues include those that are conserved in AARS polypeptides across different species, including those sequences that are conserved in the active binding site(s) or motif(s) of AARS polypeptides from various sources.

Accordingly, the present invention also contemplates variants of the naturally-occurring AARS polypeptide sequences or their biologically-active fragments, wherein the variants are distinguished from the naturally-occurring sequence by the addition, deletion, or substitution of one or more amino acid residues. In general, variants will display at least about 30, 40, 50, 55, 60, 65, 70, 75, 80, 85, 90, 91, 92, 93, 94, 95, 96, 97, 98, 99% similarity or sequence identity to a reference AARS polypeptide sequence, for example, as set forth in SEQ ID NOS: 1, 2, 3, 6, 8, 10, 12, 14, 16, 25, 28, 30, 32-108, and 109-115. Moreover, sequences differing from the native or parent sequences by the addition, deletion, or substitution of 1, 2, 3, 4, 5, 6, 7, 8, 9, 10, 11, 12, 13, 14, 15, 16, 17, 18, 19, 20, 30, 40, 50, 60, 70, 80, 90, 100, 110, 120, 130, 140, 150 or more amino acids but which retain the properties of a parent or reference AARS polypeptide sequence are contemplated. In certain embodiments, the C-terminal or N-terminal region of any AARS polypeptide, including the AARS polypeptides of SEQ ID NOS: 1, 2, 3, 6, 8, 10, 12, 14, 16, 25, 28, 30, 32-108, or 109-115, may be truncated by about 1, 2, 3, 4, 5, 6, 7, 8, 9, 10, 15, 20, 25, 30, 35, 40, 45, 50, 60, 70, 80, 90, 100, 110, 120, 130, 140, 150, 160, 170, 180, 190, 200, 250, 300, 350, 400, 450, 500, 550, 600, 650, or 700 or more amino acids, or by about 10-50, 20-50, 50-100, 100-150, 150-200, 200-250, 250-300, 300-350, 350-400, 400-450, 450-500, 500-550, 550-600, 600-650, 650-700 or more amino acids, including all integers and ranges in between (e.g., 101, 102, 103, 104, 105), so long as the truncated AARS polypeptide is capable of modulating an inflammatory response, either in vivo, in vitro, or ex vivo (e.g., reducing migration of immune cells such as granulocytes, including neutrophils and eosinophils).

In some embodiments, variant polypeptides differ from a reference AARS sequence by at least one but by less than 50, 40, 30, 20, 15, 10, 8, 6, 5, 4, 3 or 2 amino acid residue(s). In other embodiments, variant polypeptides differ from the corresponding sequences of SEQ ID NOS: 1, 2, 3, 6, 8, 10, 12, 14, 16, 25, 28, 30, 32-108, or 109-115 by at least 1% but less than 20%, 15%, 10% or 5% of the residues. (If this comparison requires alignment, the sequences should be aligned for maximum similarity. "Looped" out sequences from deletions or insertions, or mismatches, are considered differences.) The differences are, suitably, differences or changes at a non-essential residue or a conservative substitution.

In certain embodiments, a variant polypeptide includes an amino acid sequence having at least about 50%, 55%, 60%, 65%, 70%, 75%, 80%, 85%, 90%, 91%, 92%, 93%, 94% 95%, 96%, 97%, 98% or more sequence identity or similarity to a corresponding sequence of an AARS polypeptide as, for example, set forth in SEQ ID NOS: 1, 2, 3, 6, 8, 10, 12, 14, 16, 25, 28, 30, 32-108, or 109-115 and has the ability to reduce pulmonary inflammation in a subject, such as by reducing the migration or recruitment of neutrophils or eosinophils to the lung.

Calculations of sequence similarity or sequence identity between sequences (the terms are used interchangeably herein) are performed as follows. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In certain embodiments, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position.

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch, (1970, *J. Mol. Biol.* 48: 444-453) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller (1989, *Cabios*, 4: 11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al., (1990, *J. Mol. Biol,* 215: 403-10). BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997, *Nucleic Acids Res,* 25:

3389-3402). When utilizing BLAST and Gapped BLAST programs, the default parameters of the respective programs (e.g., XBLAST and NBLAST) can be used.

Variants of an AARS polypeptide can be identified by screening combinatorial libraries of mutants of an AARS polypeptide. Libraries or fragments e.g., N terminal, C terminal, or internal fragments, of AARS protein coding sequence can be used to generate a variegated population of fragments for screening and subsequent selection of variants of an AARS polypeptide.

Methods for screening gene products of combinatorial libraries made by point mutation or truncation, and for screening cDNA libraries for gene products having a selected property are known in the art. Such methods are adaptable for rapid screening of the gene libraries generated by combinatorial mutagenesis of AARS polypeptides.

Also included are proteolytic fragments of AARS polypeptides. In certain illustrative embodiments, proteolytic fragments of AARS polypeptides may be produced using a variety of proteolytic enzymes or proteolytic chemical agents, according to techniques known and available in the art. Proteolytic fragments can be produced in vitro, such as by incubating AARS polypeptides with one or more proteases (as described herein and known in the art) under controlled conditions and isolating and characterizing the fragments produced therefrom. Proteolytic fragments can also be produced in vivo, or endogenously, such as by recombinantly expressing the AARS polypeptides in a selected cell (e.g., bacterial cell, eukaryotic cell), and isolating and characterizing the endogenous fragments produced therefrom (see, e.g., Example 10).

Proteases are usually classified according to three major criteria: (i) the reaction catalysed, (ii) the chemical nature of the catalytic site, and (iii) the evolutionary relationship, as revealed by the structure. General examples of proteases or proteinases, as classified by mechanism of catalysis, include aspartic proteases, serine proteases, cysteine proteases, and metalloproteases.

Most aspartic proteases belong to the pepsin family. This family includes digestive enzymes, such as pepsin and chymosin, as well as lysosomal cathepsins D and processing enzymes such as renin, and certain fungal proteases (e.g., penicillopepsin, rhizopuspepsin, endothiapepsin). A second family of aspartic proteases includes viral proteinases such as the protease from the AIDS virus (HIV), also called retropepsin.

Serine proteases include two distinct families. First, the chymotrypsin family, which includes the mammalian enzymes such as chymotrypsin, trypsin, elastase, and kallikrein, and second, the substilisin family, which includes the bacterial enzymes such as subtilisin. The general 3D structure between these two families is different, but they have the same active site geometry, and catalysis proceeds via the same mechanism. The serine proteases exhibit different substrate specificities, differences which relate mainly to amino acid substitutions in the various enzyme subsites (substrate residue interacting sites). Some serine proteases have an extended interaction site with the substrate whereas others have a specificity that is restricted to the P1 substrate residue.

The cysteine protease family includes the plant proteases such as papain, actinidin, and bromelain, several mammalian lysosomal cathepsins, the cytosolic calpains (calcium-activated), as well as several parasitic proteases (e.g., *Trypanosoma, Schistosoma*). Papain is the archetype and the best studied member of the family. Recent elucidation of the X-ray structure of the Interleukin-1-beta Converting Enzyme has revealed a novel type of fold for cysteine proteinases.

The metalloproteases are one of the older classes of proteases, found in bacteria, fungi, and higher organisms. They differ widely in their sequences and their 3D structures, but the great majority of enzymes contain a zinc atom that is catalytically active. In some cases, zinc may be replaced by another metal such as cobalt or nickel without loss of proteolytic activity. Bacterial thermolysin has been well characterized and its crystallographic structure indicates that zinc is bound by two histidines and one glutamic acid. Many metalloproteases contain the sequence motif HEXXH, which provides two histidine ligands for the zinc. The third ligand is either a glutamic acid (thermolysin, neprilysin, alanyl aminopeptidase) or a histidine (astacin, serralysin).

Illustrative proteases include, for example, achromopeptidase, aminopeptidase, ancrod, angiotensin converting enzyme, bromelain, calpain, calpain I, calpain II, carboxypeptidase A, carboxypeptidase B, carboxypeptidase G, carboxypeptidase P, carboxypeptidase W, carboxypeptidase Y, caspase 1, caspase 2, caspase 3, caspase 4, caspase 5, caspase 6, caspase 7, caspase 8, caspase 9, caspase 10, caspase 11, caspase 12, caspase 13, cathepsin B, cathepsin C, cathepsin D, cathepsin E, cathepsin G, cathepsin H, cathepsin L, chymopapain, chymase, chymotrypsin, clostripain, collagenase, complement C1r, complement C1s, complement Factor D, complement factor I, cucumisin, dipeptidyl peptidase IV, elastase (leukocyte), elastase (pancreatic), endoproteinase Arg-C, endoproteinase Asp-N, endoproteinase Glu-C, endoproteinase Lys-C, enterokinase, factor Xa, ficin, furin, granzyme A, granzyme B, HIV Protease, IGase, kallikrein tissue, leucine aminopeptidase (general), leucine aminopeptidase (cytosol), leucine aminopeptidase (microsomal), matrix metalloprotease, methionine aminopeptidase, neutrase, papain, pepsin, plasmin, prolidase, pronase E, prostate specific antigen, protease alkalophilic from *Streptomyces griseus*, protease from *Aspergillus*, protease from *Aspergillus* saitoi, protease from *Aspergillus sojae*, protease (*B. licheniformis*) (alkaline or alcalase), protease from *Bacillus polymyxa*, protease from *Bacillus* sp, protease from *Rhizopus* sp., protease S, proteasomes, proteinase from *Aspergillus oryzae*, proteinase 3, proteinase A, proteinase K, protein C, pyroglutamate aminopeptidase, rennin, rennin, streptokinase, subtilisin, thermolysin, thrombin, tissue plasminogen activator, trypsin, tryptase and urokinase.

Tables C-G illustrate the type of proteolytic fragments that can be produced in vitro by incubating AARS polypeptides with various proteases. In certain embodiments, the incubation conditions can be controlled so that only certain cleavage sites are cleaved by the indicated protease, to achieve only partial cleavage, followed by isolation of the desired proteolytic fragment according to techniques known in the art (e.g., chromatography). Once a desired fragment has been isolated and characterized (e.g., sequenced) according to routine techniques in the art, it can be cloned and produced recombinantly, or produced synthetically, as desired.

Hence, included within the AARS polypeptides of the invention are any proteolytic fragments that can be produced by the exemplary proteases in Tables C-G, in addition to the proteases listed elsewhere herein, including any combination of proteases (e.g., Caspase 1 and hydroxylamine), or any combination of individual cleavage sites. Also, the residue position of cleavage sites may be approximate.

Merely by way of illustration, an AARS proteolytic fragment may include about residues 1-165, about residues 166-445, about residues 166-455, about residues 166-716, about residues 445-716, or about residues 455-716 of GlyRS that has been cleaved or partially cleaved by incubation with iodosobenzoic acid (see Table C). As an additional illustration, an AARS proteolytic fragment may include about residues 1-98, about residues 1-135, about residues 98-135, about residues 1-234, about residues 98-234, about residues 1-379, about residues 234-674, or about residues 135-737 of QRS that has been cleaved or partially cleaved by proline-endopeptidase (see Table D). As a further illustrative example, an AARS polypeptide may include about residues 1-210, about residues 1-273, about residues 1-295, about residues 210-273, about residues 210-295, about residues 273-295 of QRS that has been cleaved or partially cleaved by hydroxylamine. Similar patterns can be applied to any of the AARS polypeptides and any of the proteases in Tables C-G, or to the other proteases listed herein or known in the art.

TABLE C

Glycyl-tRNA synthetase (EC 6.1.1.14) (Glycine-tRNA ligase) (GlyRS)

| Protease | Position of cleavage sites (Residue No.) |
|---|---|
| Arg-C proteinase | 5 10 13 23 27 33 34 52 68 72 79 101 103 121 130 131 166 213 297 310 331 337 342 344 388 391 412 428 430 464 474 560 583 596 602 640 656 657 660 687 689 693 696 722 |
| Asp-N endopeptidase | 55 75 83 89 91 115 116 119 125 134 148 178 195 199 204 214 227 246 255 270 355 360 369 393 424 442 445 462 467 510 522 553 598 647 648 661 672 674 687 689 707 717 |
| Asp-N endopeptidase + N-terminal Glu | 55 60 61 75 82 83 89 91 96 105 108 115 116 119 124 125 134 148 171 172 176 178 185 195 199 204 209 214 227 233 237 239 246 252 255 270 298 312 332 344 349 351 355 358 360 369 393 396 424 433 435 442 445 447 456 462 467 482 487 497 510 516 522 523 528 530 535 538 542 544 553 567 568 575 589 596 598 599 625 632 635 647 648 661 662 672 674 687 689 697 700 707 717 719 726 729 734 737 738 |
| BNPS-Skatole | 165 445 455 716 |
| CNBr | 1 55 124 182 202 226 239 281 292 348 390 433 437 516 530 532 555 585 628 692 |
| Caspase 1 | 215 |
| Chymotrypsin-high specificity (C-term to [FYW], not before P) | 132 133 134 138 141 148 150 165 169 198 201 212 249 258 261 278 282 285 295 305 308 314 321 330 346 354 365 374 376 408 409 414 416 429 440 445 453 455 467 497 508 518 526 540 549 561 566 579 586 589 593 604 605 614 627 630 658 668 674 716 726 |
| Clostripain | 5 10 13 23 27 33 34 52 68 72 79 101 103 121 130 131 166 213 297 310 331 337 342 344 388 391 412 428 430 464 474 560 583 596 602 640 656 657 660 687 689 693 696 722 |
| Formic acid | 56 76 84 90 92 116 117 120 126 135 149 179 196 200 205 215 228 247 256 271 356 361 370 394 425 443 446 463 468 511 523 554 599 648 649 662 673 675 688 690 708 718 |
| Glutamyl endopeptidase | 61 62 83 97 106 109 125 172 173 177 186 210 234 238 240 253 299 313 333 345 350 352 359 397 434 436 448 457 483 488 498 517 524 529 531 536 539 543 545 568 569 576 590 597 600 626 633 636 663 698 701 720 727 730 735 738 739 |
| Hydroxylamine | 208 711 |
| Iodosobenzoic acid | 165 445 455 716 |
| LysC | 80 82 85 93 99 102 108 115 123 129 158 190 197 204 207 219 224 229 230 235 236 264 283 309 318 360 364 379 389 419 426 450 477 484 487 490 501 506 509 510 513 537 547 553 559 563 615 632 646 679 733 734 |
| LysN | 79 81 84 92 98 101 107 114 122 128 157 189 196 203 206 218 223 228 229 234 235 263 282 308 317 359 363 378 388 418 425 449 476 483 486 489 500 505 508 509 512 536 546 552 558 562 614 631 645 678 732 733 |
| NTCB (2-nitro-5-thiocyanobenzoic acid) | 40 154 179 210 230 441 443 460 465 470 521 524 615 |
| Proline-endopeptidase | 6 28 298 363 485 |
| Staphylococcal peptidase I | 61 83 97 106 109 125 172 177 186 210 234 238 240 253 299 313 333 345 350 352 359 397 434 436 448 457 483 488 498 517 524 529 531 536 539 543 545 568 576 590 597 600 626 633 636 663 698 701 720 727 730 735 738 |

TABLE C-continued

Glycyl-tRNA synthetase (EC 6.1.1.14) (Glycine-tRNA ligase) (GlyRS)

| Protease | Position of cleavage sites (Residue No.) |
|---|---|
| Trypsin | 10 13 23 33 34 52 68 72 79 80 82 85 93 99 101 102 103 108 115 121 123 129 |
| | 130 131 158 166 190 197 204 207 213 219 224 229 230 235 236 264 283 309 |
| | 310 318 331 337 342 344 360 364 379 388 389 391 412 419 426 428 430 450 |
| | 464 474 477 487 490 501 506 509 510 513 537 547 553 559 560 563 583 596 |
| | 602 615 632 640 646 656 657 660 679 687 689 693 696 722 733 734 |

TABLE D

Glutaminyl-tRNA synthetase (EC 6.1.1.18) (Glutamine-tRNA ligase) (QRS)

| Protease | Positions of cleavage sites (Residue No.) |
|---|---|
| Arg-C proteinase | 21 34 62 64 67 68 95 109 132 134 141 154 195 201 202 225 265 267 301 351 |
| | 352 361 376 378 391 403 419 427 463 464 486 497 509 515 523 524 525 538 |
| | 558 567 576 616 629 639 666 667 690 694 745 764 |
| Asp-N endopeptidase | 4 48 64 99 102 105 160 169 183 199 205 214 302 303 319 336 339 376 409 413 429 438 445 474 509 511 512 558 562 588 597 617 668 702 713 723 728 |
| | 738 751 753 770 |
| Asp-N endopeptidase + N-terminal Glu | 4 16 21 34 48 64 83 91 99 102 105 107 109 119 122 123 126 139 151 160 167 |
| | 169 181 183 185 196 197 199 205 208 211 214 221 226 235 257 270 302 303 |
| | 307 309 310 319 336 339 347 362 363 376 380 381 387 396 398 408 409 413 |
| | 429 438 445 448 458 474 482 509 511 512 529 548 553 558 562 572 588 597 |
| | 598 614 617 620 621 623 645 658 661 668 671 687 692 701 702 705 713 723 |
| | 728 738 743 751 753 769 770 |
| BNPS-Skatole | 159 324 345 375 432 469 482 511 632 680 |
| CNBr | 1 146 150 164 171 221 250 321 380 390 404 408 413 548 569 686 |
| Caspase1 | 184 |
| Chymotrypsin-high specificity (C-term to [FYW], not before P) | 10 57 71 75 93 107 142 144 159 189 231 238 243 286 288 290 299 302 314 315 324 327 330 334 338 339 343 345 356 375 387 395 418 422 432 438 440 |
| | 460 467 468 469 477 482 484 491 511 517 535 603 608 613 619 627 632 643 |
| | 677 680 692 696 711 738 741 743 748 749 762 |
| Clostripain | 21 34 62 64 67 68 95 109 132 134 141 154 195 201 202 225 265 267 301 351 |
| | 352 361 376 378 391 403 419 427 463 464 486 497 509 515 523 524 525 538 |
| | 558 567 576 616 629 639 666 667 690 694 745 764 |
| Formic acid | 5 49 65 100 103 106 161 170 184 200 206 215 303 304 320 337 340 377 410 |
| | 414 430 439 446 475 510 512 513 559 563 589 598 618 669 703 714 724 729 |
| | 739 752 754 771 |
| Glutamyl endopeptidase | 17 22 35 84 92 108 110 120 123 124 127 140 152 168 182 186 197 198 209 212 222 227 236 258 271 308 310 311 348 363 364 381 382 388 397 399 409 |
| | 449 459 483 530 549 554 573 599 615 621 622 624 646 659 662 672 688 693 |
| | 702 706 744 770 |
| Hydroxylamine | 210 273 295 |
| Iodosobenzoic acid | 159 324 345 375 432 469 482 511 632 680 |
| LysC | 19 25 50 79 80 158 163 166 180 187 188 190 193 205 230 233 239 254 282 292 309 313 331 366 392 394 405 412 421 431 458 496 498 586 601 620 628 |
| | 652 673 675 699 736 740 759 769 774 |
| LysN | 18 24 49 78 79 157 162 165 179 186 187 189 192 204 229 232 238 253 281 291 308 312 330 365 391 393 404 411 420 430 457 495 497 585 600 619 627 |
| | 651 672 674 698 735 739 758 768 773 |
| NTCB (2-nitro-5-thiocyanobenzoic acid) | 110 297 318 357 432 442 444 455 470 477 535 555 656 664 686 729 |

TABLE D-continued

Glutaminyl-tRNA synthetase (EC 6.1.1.18) (Glutamine-tRNA ligase) (QRS)

| Protease | Positions of cleavage sites (Residue No.) |
|---|---|
| Proline-endopeptidase | 98 135 234 379 674 737 |
| Staphylococcal peptidase I | 17 22 35 84 92 108 110 120 123 127 140 152 168 182 186 197 209 212 222 227 236 258 271 308 310 348 363 381 388 397 399 409 449 459 483 530 549 554 573 599 615 621 624 646 659 662 672 688 693 702 706 744 770 |
| Thrombin | 567 |
| Trypsin | 19 21 25 34 50 62 64 67 68 79 80 95 109 132 141 154 158 163 166 180 187 188 190 193 195 201 202 205 225 230 239 254 265 267 282 292 301 309 313 331 351 352 361 366 376 391 392 394 403 405 412 419 421 427 431 458 463 464 486 496 497 498 509 515 523 525 538 558 567 576 586 601 616 620 628 629 639 652 666 667 675 690 694 699 740 745 759 764 769 774 |

TABLE E

Tryptophanyl-tRNA synthetase, cytoplasmic (EC 6.1.1.2) (Tryptophan-tRNA ligase) (WRS) (Interferon-induced protein 53) (IFP53) (hWRS)

| Protease | Positions of cleavage sites (Residue No.) |
|---|---|
| Arg-C proteinase | 24 106 119 122 127 133 134 141 162 298 300 318 321 326 381 388 417 448 449 464 |
| Asp-N endopeptidase | 33 36 56 60 75 82 85 98 100 112 141 147 184 196 197 204 208 220 227 236 238 270 272 298 301 311 313 321 353 362 381 394 396 408 409 410 418 453 468 |
| Asp-N endopeptidase + N-terminal Glu | 4 10 20 33 34 36 55 56 60 75 78 80 81 82 85 98 100 112 114 120 141 147 150 166 184 196 197 198 204 208 216 220 227 236 238 270 272 298 301 311 313 321 353 362 381 384 385 394 396 407 408 409 410 413 418 428 435 443 450 453 454 458 468 |
| BNPS-Skatole | 88 182 203 |
| CNBr | 1 42 48 143 169 195 241 243 319 350 401 425 461 |
| Caspase1 | 61 363 |
| Chymotrypsin-high specificity (C-term to [FYW], not before P) | 13 50 58 84 88 100 107 131 137 138 150 156 157 159 177 179 182 187 201 203 212 214 227 233 235 240 247 248 260 267 269 289 297 316 317 339 360 377 390 400 402 405 406 420 460 468 470 |
| Clostripain | 24 106 119 122 127 133 134 141 162 298 300 318 321 326 381 388 417 448 449 464 |
| Enterokinase | 200 412 |
| Formic acid | 34 37 57 61 76 83 86 99 101 113 142 148 185 197 198 205 209 221 228 237 239 271 273 299 302 312 314 322 354 363 382 395 397 409 410 411 419 454 469 |
| Glutamyl endopeptidase | 5 11 21 35 56 79 81 82 115 121 151 167 199 217 385 386 408 414 429 436 444 451 455 459 |
| Iodosobenzoic acid | 88 182 203 |
| LysC | 27 33 41 47 51 59 96 102 111 114 153 154 181 200 204 220 231 249 253 256 264 277 331 349 366 369 371 374 412 418 431 432 450 458 465 |
| LysN | 26 32 40 46 50 58 95 101 110 113 152 153 180 199 203 219 230 248 252 255 263 276 330 348 365 368 370 373 411 417 430 431 449 457 464 |
| NTCB (2-nitro-5-thiocyanobenzoic acid) | 61 224 273 304 308 393 |
| Proline-endopeptidase | 128 155 332 |
| Staphylococcal peptidase I | 5 11 21 35 56 79 81 115 121 151 167 199 217 385 408 414 429 436 444 451 455 459 |
| Thrombin | 162 326 |
| Trypsin | 24 27 33 41 47 51 59 96 102 106 111 114 119 122 133 134 141 153 162 |

TABLE E-continued

Tryptophanyl-tRNA synthetase, cytoplasmic (EC 6.1.1.2) (Tryptophan-tRNA ligase) (WRS) (Interferon-induced protein 53) (IFP53) (hWRS)

| Protease | Positions of cleavage sites (Residue No.) |
|---|---|
| | 181 200 204 220 231 249 253 256 264 277 298 300 318 321 326 349 366 |
| | 369 371 374 381 388 412 417 418 431 432 448 449 450 458 464 465 |

TABLE F

Tyrosyl-tRNA synthetase (EC 6.1.1.1) (Tyrosyl-tRNA ligase) (YRS)

| Protease | Positions of cleavage sites (Residue No.) |
|---|---|
| Arg-C proteinase | 16 34 93 135 189 207 237 279 325 367 371 400 418 432 450 |
| Asp-N endopeptidase | 2 60 74 80 121 131 143 172 179 186 232 235 239 279 293 297 307 321 342 |
| | 368 382 384 392 416 455 477 493 |
| Asp-N endopeptidase + N-terminal Glu | 2 7 8 19 23 24 28 32 34 60 67 74 80 87 90 97 105 112 121 127 131 143 150 |
| | 156 172 173 174 179 186 195 226 227 228 232 235 238 239 250 255 273 |
| | 279 280 293 295 297 301 307 313 321 325 342 358 360 361 368 378 382 |
| | 384 389 392 395 397 412 413 416 434 445 452 455 464 472 477 478 479 |
| | 488 493 498 499 |
| BNPS-Skatole | 40 87 283 505 |
| CNBr | 1 56 83 104 211 214 223 350 431 439 511 |
| Caspase 1 | 75 494 |
| Chymotrypsin-high specificity (C-term to [FYW], not before P) | 39 40 52 53 62 73 79 87 96 97 117 123 129 134 176 183 192 194 198 204 |
| | 249 263 275 283 289 292 299 328 388 409 468 472 488 495 505 510 |
| Clostripain | 16 34 93 135 189 207 237 279 325 367 371 400 418 432 450 |
| Formic acid | 3 61 75 81 122 132 144 173 180 187 233 236 240 280 294 298 308 322 343 |
| | 369 383 385 393 417 456 478 494 |
| Glutamyl endopeptidase | 8 9 20 24 25 29 33 35 68 88 91 98 106 113 128 151 157 174 175 196 227 |
| | 228 229 239 251 256 274 281 296 302 314 326 359 361 362 379 390 396 |
| | 398 413 414 435 446 453 465 473 479 480 489 499 500 |
| Hydroxylamine | 258 |
| Iodosobenzoic acid | 40 87 283 505 |
| LysC | 10 26 28 32 37 47 58 64 84 102 114 116 119 127 146 147 154 178 190 197 |
| | 206 222 231 238 242 243 244 246 247 265 272 282 287 297 310 319 327 |
| | 334 335 346 348 352 356 374 380 391 412 427 430 470 474 482 484 485 |
| | 486 490 496 506 513 520 523 |
| LysN | 9 25 27 31 36 46 57 63 83 101 113 115 118 126 145 146 153 177 189 196 |
| | 205 221 230 237 241 242 243 245 246 264 271 281 286 296 309 318 326 |
| | 333 334 345 347 351 355 373 379 390 411 426 429 469 473 481 483 484 |
| | 485 489 495 505 512 519 522 |
| NTCB (2-nitro-5-thiocyanobenzoic acid) | 66 249 423 441 500 518 |
| Proline-endopeptidase | 48 159 306 349 382 428 483 |
| Staphylococcal peptidase I | 8 20 24 29 33 35 68 88 91 98 106 113 128 151 157 174 196 227 239 251 |
| | 256 274 281 296 302 314 326 359 361 379 390 396 398 413 435 446 453 |
| | 465 473 479 489 499 |
| Trypsin | 10 16 26 28 32 34 37 58 64 84 93 102 114 116 119 127 135 146 147 154 |
| | 178 189 190 197 206 207 222 231 237 238 242 243 244 246 247 265 272 |
| | 279 282 287 297 310 319 325 327 334 335 346 352 356 367 371 374 380 |
| | 391 400 412 418 430 432 450 470 474 484 485 486 490 496 506 513 520 523 |

TABLE G

Histidyl-tRNA synthetase (EC 6.1.1.21) (Histidine-tRNA ligase) (HisRS)

| Protease | Positions of cleavage sites (Residue No.) |
|---|---|
| Arg-C proteinase | 4 17 19 63 68 73 82 86 128 137 149 157 158 165 167 169 214 215 232 266 |
| | 326 362 375 388 396 405 424 479 484 490 491 500 501 |
| Asp-N endopeptidase | 47 63 77 92 109 115 118 129 158 174 176 182 187 205 212 217 227 238 241 |
| | 264 268 285 300 314 315 320 328 363 370 432 472 487 492 |

TABLE G-continued

Histidyl-tRNA synthetase (EC 6.1.1.21) (Histidine-tRNA ligase) (HisRS)

| Protease | Positions of cleavage sites (Residue No.) |
|---|---|
| Asp-N endopeptidase + N-terminal Glu | 2 7 8 15 28 31 32 33 47 48 63 73 77 89 92 97 100 108 109 115 118 122 129 158 169 174 176 182 187 189 196 205 212 217 227 238 241 246 247 251 255 261 264 268 280 285 296 300 306 314 315 320 328 336 348 349 363 370 386 393 397 400 401 407 421 422 429 432 438 455 456 467 469 472 484 485 487 491 492 495 496 |
| BNPS-Skatole | 246 432 |
| CNBr | 1 70 104 141 163 185 195 220 253 369 |
| Chymotrypsin-high specificity (C-term to [FYW], not before P) | 54 65 77 84 97 107 115 129 135 138 150 156 168 171 172 176 182 207 221 231 246 270 306 308 312 320 330 331 336 363 370 390 432 442 454 |
| Clostripain | 4 17 19 63 68 73 82 86 128 137 149 157 158 165 167 169 214 215 232 266 326 362 375 388 396 405 424 479 484 490 491 500 501 |
| Formic acid | 48 64 78 93 110 116 119 130 159 175 177 183 188 206 213 218 228 239 242 265 269 286 301 315 316 321 329 364 371 433 473 488 493 |
| Glutamyl endopeptidase | 3 8 9 16 29 32 33 34 49 74 90 98 101 109 123 170 190 197 247 248 252 256 262 281 297 307 337 349 350 387 394 398 401 402 408 422 423 430 439 456 457 468 470 485 486 492 496 497 |
| Iodosobenzoic acid | 246 432 |
| LysC | 12 22 25 37 40 42 51 53 57 60 75 85 100 106 112 118 143 148 154 193 210 230 240 243 250 257 288 293 303 317 373 376 403 418 419 426 437 443 444 447 472 477 499 |
| LysN | 11 21 24 36 39 41 50 52 56 59 74 84 99 105 111 117 142 147 153 192 209 229 239 242 249 256 287 292 302 316 372 375 402 417 418 425 436 442 443 446 471 476 498 |
| NTCB (2-nitro-5-thiocyanobenzoic acid) | 82 173 190 195 223 234 378 454 506 508 |
| Staphylococcal peptidase I | 3 8 16 29 32 49 74 90 98 101 109 123 170 190 197 247 252 256 262 281 297 307 337 349 387 394 398 401 408 422 430 439 456 468 470 485 492 496 |
| Trypsin | 4 12 17 19 22 25 37 40 42 51 53 57 60 63 68 73 75 82 85 86 100 106 112 118 128 137 143 148 149 154 157 158 165 167 169 193 210 214 215 230 232 240 243 250 257 266 288 293 303 317 326 362 373 375 376 388 396 403 405 418 419 424 426 437 443 444 447 472 477 479 484 490 491 499 500 501 |

Certain embodiments relate to isolated AARS polypeptides, comprising, consisting essentially of, or consisting of amino acid sequences that have been derived from endogenous, naturally-occurring AARS polypeptide fragments, and pharmaceutical compositions comprising said fragments, and methods of use thereof. In certain embodiments, as noted above, the sequences of naturally-occurring endogenous proteolytic fragments can be generated or identified, for instance, from various cellular fractions (e.g., cytosolic, membrane, nuclear) and/or conditioned medium from various cell-types, including primary cells and cell lines. Examples of such cell types include, without limitation, immune cells such as monocytes, dendritic cells, macrophages (e.g., RAW 264.7 macrophages; see Example 5), neutrophils, eosinophils, basophils, and lymphocytes, such as B-cells and T-cells (e.g., CD4+ helper and CD8+ killer cells), including primary T-cells and T-cell lines such as Jurkat T-cells, as well as natural killer (NK) cells.

In certain embodiments, endogenous proteolytic fragments can be identified by techniques such as mass-spectrometry, or equivalent techniques. Merely by way of illustration and not limitation, in certain embodiments the proteomes from various cell types or fractions thereof may be separated by 1D SDS-PAGE and the gel lanes cut into bands at fixed intervals; after which the bands may be optionally digested with an appropriate protease, such as trypsin, to release the peptides, which may then be analyzed by 1D reverse phase LC-MS/MS. The resulting proteomic data may be integrated into so-called peptographs, which plot, in the left panel, sequence coverage for a given protein in the horizontal dimension (N to C terminus, left to right) versus SDS-PAGE migration in the vertical dimension (high to low molecular weight, top to bottom). The specific peptide fragments can then be sequenced or mapped. Table H provides a set of illustrative mouse QRS polypeptide fragments that were identified from RAW macrophages according to these exemplary techniques. Table I provides the corresponding set of human QRS polypeptide fragments. Table J provides a set of illustrative human QRS polypeptide fragments that were identified from human Jurkat T-cells.

TABLE H

Mouse QRS Polypeptide Fragments

| PEPTIDE SEQUENCE | SEQ ID NO: |
|---|---|
| ETLKNEALSTQLR | 36 |
| EAATQAHQILGSTIDKATGVLLYDLVSR | 37 |
| ETLKNEALSTQLREAATQAHQILGSTIDKATGVLLYDLVSR | 38 |
| DFEQECGVGVVVTPEQIEEAVESTINK | 39 |

TABLE H-continued

Mouse QRS Polypeptide Fragments

| PEPTIDE SEQUENCE | SEQ ID NO: |
|---|---|
| FNMGLLMGEAR* | 40 |
| MIKNEVDMQVLHLLGPK* | 41 |
| NEVDMQVLHLLGPK* | 42 |
| TPGYVITPYTMDLLK | 43 |
| FDDTNPEKEEAK* | 44 |
| VEELKGHNPLPSPWR | 45 |
| DRPKEESLLLFEAMR | 46 |
| VEELKGHNPLPSPWRDRPKEESLLLFEAMR | 47 |
| LVMEDGKMDPVAYR* | 48 |
| VYCPVQWEYGR* | 49 |
| ILQLVAAGAVR | 50 |
| DVLNDAAPRAMAVLEPLQVVITNFPAPK | 51 |
| GFHQVPFASTVFIERSDFKEESEPGYKRLASGQPVGLR | 52 |
| AFIHWVSQPLVCEIR | 53 |
| LGYFSVDPDSHQGQIVFNR | 54 |
| TPGYVITPYTMDLLK | 55 |
| AINFNFGYAK* | 56 |
| FDDTNPEKEEAK* | 57 |
| FFTAIYDMVTWLGYTPYK | 58 |
| FDDTNPEKEEAKFFTAIYDMVTWLGYTPYK | 59 |
| DRPKEESLLLFEAMR | 60 |
| VYCPVQWEYGR* | 61 |
| LNLHYAVVSK* | 62 |
| VYCPVQWEYGRLNLHYAVVSK* | 63 |
| ILQLVAAGAVR | 64 |
| AMAVLEPLQVVITNFPAPK | 65 |
| PLDIRVPNFPADETK | 66 |
| AMAVLEPLQVVITNFPAPKPLDIRVPNFPADETK | 67 |
| SDFKEESEPGYKRLASGQPVGLRHTGYVIELQNIVR | 68 |
| AFIHWVSQPLVCEIR | 69 |
| LGYFSVDPDSHQGQIVFNR | 70 |
| KATGVLLYDLVSR | 71 |
| SFLVSYIANK | 72 |
| DFEQECGVGVVVTPEQIEEAVESTINK | 73 |
| MIKNEVDMQVLHLLGPK* | 74 |
| EAATQAHQILGSTIDKATGVLLYDLVSR | 75 |

*The mouse and human sequences are identical.

TABLE I

Human QRS Polypeptide Fragments

| PEPTIDE SEQUENCE | SEQ ID NO: |
|---|---|
| ETLKNSALSAQLR | 76 |
| EAATQAQQTLGSTIDKATGILLYGLASR | 77 |
| ETLKNSALSAQLREAATQAQQTLGSTIDKATGILLYGLASR | 78 |
| DFERECGVGVIVTPEQIEEAVEAAINR | 79 |
| TPGYVVTPHTMNLLK | 80 |
| GEELKGHNTLPSPWR | 81 |
| DRPMEESLLLFEAMR | 82 |
| GEELKGHNTLPSPWRDRPMEESLLLFEAMR | 83 |
| ILQLVATGAVR | 84 |
| DVLNDTAPRAMAVLESLRVIITNFPAAK | 85 |
| GFHQVPFAPIVFIERTDFKEEPEPGFKRLAWGQPVGLR | 86 |
| AFIHWVSQPLMCEVR | 87 |
| LGYFSVDPDSHQGKLVFNR | 88 |
| TPGYVVTPHTMNLLK | 89 |
| FFTAICDMVAWLGYTPYK | 90 |
| FDDTNPEKEEAKFFTAIYDMVTWLGYTPYK | 91 |
| DRPMEESLLLFEAMR | 92 |
| ILQLVATGAVR | 93 |
| AMAVLESLRVIITNFPAAK | 94 |
| SLDIQVPNFPADETK | 95 |
| AMAVLESLRVIITNFPAAKSLDIQVPNFPADETK | 96 |
| TDFKEEPEPGFKRLAWGQPVGLRHTGYVIELQHVVK | 97 |
| AFIHWVSQPLMCEVR | 98 |
| LGYFSVDPDSHQGKLVFNR | 99 |
| KATGILLYGLASR | 100 |
| SFLVSYIASK | 101 |
| DFERECGVGVIVTPEQIEEAVEAAINR | 102 |
| EAATQAQQTLGSTIDKATGILLYGLASR | 103 |

TABLE J

Human QRS Polypeptide Fragments from Jurkat T-cells

| PEPTIDE SEQUENCE | SEQ ID NO: |
|---|---|
| NSALSAQLREAATQAQQTLGSTIDK | 109 |
| SHPLDPIDTVDFERECGVGVIVTPEQIEEAVEAAINR | 110 |
| LSFLVSYIASK | 111 |
| ECGVGVIVTPEQIEEAVEAAINR | 112 |
| EAATQAQQTLGSTIDKATGILLYGLASR | 113 |

TABLE J-continued

Human QRS Polypeptide Fragments from Jurkat T-cells

| PEPTIDE SEQUENCE | SEQ ID NO: |
|---|---|
| IHTEPQLSAALEYVR | 114 |
| NEVDMQVLHLLGPK | 115 |

Hence, certain specific embodiments include isolated QRS polypeptides that comprise, consist essentially of, or consist of any one or more of SEQ ID NOS:36-103 or 109-115 (in Tables H, I, and J above), which modulate inflammation, such as by reducing pulmonary inflammation, including variants thereof. In certain embodiments, these isolated QRS polypeptide fragments may further comprise 1, 2, 3, 4, 5, 6, 7, 8, 9, 10, 11, 12, 13, 14, 15, 16, 17, 18, 19, or 20 or more of the C-terminal and/or N-terminal residues that surround them, as characterized by their location within the full-length QRS polypeptide. In certain embodiments, these isolated QRS polypeptide fragments may be truncated to contain 1, 2, 3, 4, 5, 6, 7, 8, 9, 10, 11, 12, 13, 14, 15, 16, 17, 18, 19, or 20 fewer of their C-terminal and/or N-terminal residues. Also included are pharmaceutical compositions comprising such QRS polypeptide fragments, and methods of using said polypeptides or compositions to treat a subject in need thereof.

The present invention also contemplates the use of AARS chimeric or fusion proteins for modulating inflammation. As used herein, an AARS "chimeric protein" or "fusion protein" includes an AARS polypeptide or polypeptide fragment linked to either another AARS-polypeptide (e.g., to create multiple fragments), to a non-AARS polypeptide, or to both. A "non-AARS polypeptide" refers to a "heterologous polypeptide" having an amino acid sequence corresponding to a protein which is different from an AARS protein, and which is derived from the same or a different organism. The AARS polypeptide of the fusion protein can correspond to all or a portion of a biologically active AARS amino acid sequence. In certain embodiments, an AARS fusion protein includes at least one (or two) biologically active portion of an AARS protein. The polypeptides forming the fusion protein are typically linked C-terminus to N-terminus, although they can also be linked C-terminus to C-terminus, N-terminus to N-terminus, or N-terminus to C-terminus. The polypeptides of the fusion protein can be in any order.

The fusion partner may be designed and included for essentially any desired purpose provided they do not adversely affect the inflammation-modulating activity of the polypeptide. For example, in one embodiment, a fusion partner may comprise a sequence that assists in expressing the protein (an expression enhancer) at higher yields than the native recombinant protein. Other fusion partners may be selected so as to increase the solubility of the protein or to enable the protein to be targeted to desired intracellular compartments.

The fusion protein can include a moiety which has a high affinity for a ligand. For example, the fusion protein can be a GST-AARS fusion protein in which the AARS sequences are fused to the C-terminus of the GST sequences. As another example, an AARS polypeptide may be fused to an eight amino acid tag at the C-terminus, such as an L-E-H-H-H-H-H (SEQ ID NO:5) tag. In certain specific embodiments, amino acids 1-364 of a YRS polypeptide are fused to a 365-L-E-H-H-H-H-H-H-372 (SEQ ID NO:5) tag at the C-terminus. Such fusion proteins can facilitate the purification and/or identification of an AARS polypeptide. Alternatively, the fusion protein can be an AARS protein containing a heterologous signal sequence at its N-terminus. In certain host cells, expression and/or secretion of AARS proteins can be increased through use of a heterologous signal sequence.

More generally, fusion to heterologous sequences, such as an Fc fragment, may be utilized to remove unwanted characteristics or to improve the desired characteristics (e.g., pharmacokinetic properties) of an AARS polypeptide. For example, fusion to a heterologous sequence may increase chemical stability, decrease immunogenicity, improve in vivo targeting, and/or increase half-life in circulation of an AARS polypeptide.

Fusion to heterologous sequences may also be used to create bi-functional fusion proteins, such as bi-functional proteins that are not only capable of reducing pulmonary inflammation through the AARS polypeptide, but are also capable of modifying (i.e., stimulating or inhibiting) other pathways through the heterologous polypeptide. Examples of such pathways include, but are not limited to, various immune system-related pathways, such as innate or adaptive immune activation pathways, or cell-growth regulatory pathways, such as angiogenesis, or hematopoiesis. In certain aspects, the heterologous polypeptide may act synergistically with the AARS polypeptide to modulate inflammation-related pathways in a subject. Examples of heterologous polypeptides that may be utilized to create a bi-functional fusion protein include, but are not limited to, thrombopoietin, cytokines (e.g., IL-11), chemokines, and various hematopoietic growth factors, in addition to biologically active fragments and/or variants thereof.

Fusion proteins may generally be prepared using standard techniques. For example, DNA sequences encoding the polypeptide components of a desired fusion may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion protein that retains the biological activity of both component polypeptides.

A peptide linker sequence may be employed to separate the first and second polypeptide components by a distance sufficient to ensure that each polypeptide folds into its secondary and tertiary structures, if desired. Such a peptide linker sequence is incorporated into the fusion protein using standard techniques well known in the art. Certain peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39 46 (1985); Murphy et al., *Proc. Natl. Acad. Sci. USA* 83:8258 8262 (1986); U.S. Pat. No. 4,935,233 and U.S. Pat. No. 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences may be operably linked to suitable transcriptional or translational regulatory elements. The regulatory elements responsible for expression of DNA are typically located 5' to the DNA sequence encoding the first polypeptide. Similarly, stop codons required to end translation and transcription termination signals are present 3' to the DNA sequence encoding the second polypeptide.

In general, polypeptides and fusion polypeptides (as well as their encoding polynucleotides) are isolated. An "isolated" polypeptide or polynucleotide is one that is removed from its original environment. For example, a naturally-occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not a part of the natural environment.

Certain embodiments also encompass dimers of AARS polypeptides. Dimers may include, for example, homodimers between two identical AARS polypeptides, heterodimers between two different AARS polypeptides (e.g., a full-length YRS polypeptide and a truncated YRS polypeptide; a truncated YRS polypeptide and a truncated WRS polypeptide), and/or heterodimers between an AARS polypeptide and a heterologous polypeptide. Certain heterodimers, such as those between an AARS polypeptide and a heterologous polypeptide, may be bi-functional, as described herein. Also included are monomers of AARS polypeptides, including isolated AARS polypeptides monomers that do not substantially dimerize with a second AARS polypeptide, whether due to one or more substitutions, truncations, deletions, additions, chemical modifications, or a combination of these alterations. In certain embodiments, monomeric AARS polypeptides possess biological activities, including inflammatory response-modulating activities, which are not possessed by dimeric or multimeric AARS polypeptide complexes.

Certain embodiments of the present invention also contemplate the use of modified AARS polypeptides, including modifications that improved the desired characteristics of an AARS polypeptide, as described herein. Modifications of AARS polypeptides of the invention include chemical and/or enzymatic derivatizations at one or more constituent amino acid, including side chain modifications, backbone modifications, and N- and C-terminal modifications including acetylation, hydroxylation, methylation, amidation, and the attachment of carbohydrate or lipid moieties, cofactors, and the like. Exemplary modifications also include pegylation of an AARS-polypeptide (see, e.g., Veronese and Harris, *Advanced Drug Delivery Reviews* 54: 453-456, 2002, herein incorporated by reference).

In certain aspects, chemoselective ligation technology may be utilized to modify truncated AARS polypeptides of the invention, such as by attaching polymers in a site-specific and controlled manner. Such technology typically relies on the incorporation of chemoselective anchors into the protein backbone by either chemical or recombinant means, and subsequent modification with a polymer carrying a complementary linker. As a result, the assembly process and the covalent structure of the resulting protein—polymer conjugate may be controlled, enabling the rational optimization of drug properties, such as efficacy and pharmacokinetic properties (see, e.g., Kochendoerfer, *Current Opinion in Chemical Biology* 9:555-560, 2005).

The truncated and/or variant AARS polypeptides of the invention may be prepared by any suitable procedure known to those of skill in the art, such as by recombinant techniques. For example, AARS polypeptides may be prepared by a procedure including the steps of: (a) preparing a construct comprising a polynucleotide sequence that encodes a truncated AARS polypeptide and that is operably linked to a regulatory element; (b) introducing the construct into a host cell; (c) culturing the host cell to express the truncated AARS polypeptide; and (d) isolating the truncated and/or variant AARS polypeptide from the host cell. In illustrative examples, the nucleotide sequence encodes at least a biologically active portion of a polypeptide sequence set forth in, or derived from, SEQ ID NOS:1, 2, 3, 6, 8, 10, 12, or 14, or a biologically active variant or fragment thereof. Recombinant AARS polypeptides can be conveniently prepared using standard protocols as described for example in Sambrook, et al., (1989, supra), in particular Sections 16 and 17; Ausubel et al., (1994, supra), in particular Chapters 10 and 16; and Coligan et al., *Current Protocols in Protein Science* (John Wiley & Sons, Inc. 1995-1997), in particular Chapters 1, 5 and 6.

In addition to recombinant production methods, polypeptides of the invention, and fragments thereof, may be produced by direct peptide synthesis using solid-phase techniques (Merrifield, *J. Am. Chem. Soc.* 85:2149-2154 (1963)). Protein synthesis may be performed using manual techniques or by automation. Automated synthesis may be achieved, for example, using Applied Biosystems 431A Peptide Synthesizer (Perkin Elmer). Alternatively, various fragments may be chemically synthesized separately and combined using chemical methods to produce the desired molecule.

Polynucleotide Compositions

The present invention also provides isolated polynucleotides that encode the aminoacyl-tRNA synthetase polypeptides of the invention, including truncations and/or variants thereof, as well as compositions comprising such polynucleotides.

As used herein, the terms "DNA" and "polynucleotide" and "nucleic acid" refer to a DNA molecule that has been isolated free of total genomic DNA of a particular species. Therefore, a DNA segment encoding a polypeptide refers to a DNA segment that contains one or more coding sequences yet is substantially isolated away from, or purified free from, total genomic DNA of the species from which the DNA segment is obtained. Included within the terms "DNA segment" and "polynucleotide" are DNA segments and smaller fragments of such segments, and also recombinant vectors, including, for example, plasmids, cosmids, phagemids, phage, viruses, and the like.

As will be understood by those skilled in the art, the polynucleotide sequences of this invention can include genomic sequences, extra-genomic and plasmid-encoded sequences and smaller engineered gene segments that express, or may be adapted to express, proteins, polypeptides, peptides and the like. Such segments may be naturally isolated, or modified synthetically by the hand of man.

As will be recognized by the skilled artisan, polynucleotides may be single-stranded (coding or antisense) or double-stranded, and may be DNA (genomic, cDNA or synthetic) or RNA molecules. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes an aminoacyl-tRNA synthetase or a portion thereof) or may comprise a variant, or a biological functional equivalent of such a sequence. Polynucleotide variants may contain one or more substitutions, additions, deletions and/or insertions, as further described below, preferably such that the inflammatory response-modulating activity of the encoded polypeptide is not substantially diminished relative to the unmodified polypeptide. The effect on the inflammatory response-modulating activity of the encoded polypeptide may generally be assessed as described herein.

In additional embodiments, the present invention provides isolated polynucleotides comprising various lengths of contiguous stretches of sequence identical to or complementary to an aminoacyl-tRNA synthetase, wherein the isolated polynucleotides encode a truncated aminoacyl tRNA synthetase as described herein.

Exemplary nucleotide sequences that encode the AARS polypeptides of the application encompass coding sequences, such as the polynucleotide sequences of SEQ ID NOS:4, 7, 9, 11, 13, 15, 17, 19, and 31, as well as portions of the full-length or substantially full-length nucleotide sequences of the AARS genes or their transcripts or DNA copies of these transcripts.

Portions of an AARS nucleotide sequence may encode polypeptide portions or segments that retain the biological activity of the reference polypeptide, including the polypeptides of SEQ ID NOS:1, 2, 3, 6, 8, 10, 12, 14, 16, 25, 28, 30, 32-108, and 109-115 or polypeptides having an amino acid sequence that is at least 80%, 85%, 90%, 95%, 97%, or 98% identical to these sequences. A portion of an AARS nucleotide sequence that encodes a biologically active fragment of an AARS polypeptide may encode at least about 20, 21, 22, 23, 24, 25, 30, 40, 50, 60, 70, 80, 90, 100, 120, 150, 300 or 400 contiguous amino acid residues, or almost up to the total number of amino acids present in a full-length AARS polypeptide. It will be readily understood that "intermediate lengths," in this context and in all other contexts used herein, means any length between the quoted values, such as 101, 102, 103, etc.; 151, 152, 153, etc.; 201, 202, 203, etc.

The polynucleotides of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a polynucleotide fragment of almost any length may be employed, with the total length preferably being limited by the ease of preparation and use in the intended recombinant DNA protocol.

The invention also contemplates variants of the AARS nucleotide sequences. Nucleic acid variants can be naturally-occurring, such as allelic variants (same locus), homologs (different locus), and orthologs (different organism) or can be non naturally-occurring. Naturally occurring variants such as these can be identified with the use of well-known molecular biology techniques, as, for example, with polymerase chain reaction (PCR) and hybridization techniques as known in the art. Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product). For nucleotide sequences, conservative variants include those sequences that, because of the degeneracy of the genetic code, encode the amino acid sequence of a reference AARS polypeptide, such as the sequences set forth in SEQ ID NOS: 1, 2, 3, 6, 8, 10, 12, 14, 16, 25, 28, 30, 32-108, or 109-115. Variant nucleotide sequences also include synthetically derived nucleotide sequences, such as those generated, for example, by using site-directed mutagenesis but which still encode an AARS polypeptide. Generally, variants of a particular AARS nucleotide sequence will have at least about 30%, 40% 50%, 55%, 60%, 65%, 70%, generally at least about 75%, 80%, 85%, desirably about 90% to 95% or more, and more suitably about 98% or more sequence identity to that particular nucleotide sequence as determined by sequence alignment programs described elsewhere herein using default parameters.

AARS nucleotide sequences can be used to isolate corresponding sequences and alleles from other organisms, particularly other organisms or microorganisms. Methods are readily available in the art for the hybridization of nucleic acid sequences. Coding sequences from other organisms may be isolated according to well known techniques based on their sequence identity with the coding sequences set forth herein. In these techniques all or part of the known coding sequence is used as a probe which selectively hybridizes to other AARS-coding sequences present in a population of cloned genomic DNA fragments or cDNA fragments (i.e., genomic or cDNA libraries) from a chosen organism.

Accordingly, the present invention also contemplates polynucleotides that hybridize to reference AARS nucleotide sequences, or to their complements, under stringency conditions described below. As used herein, the term "hybridizes under low stringency, medium stringency, high stringency, or very high stringency conditions" describes conditions for hybridization and washing. Guidance for performing hybridization reactions can be found in Ausubel et al., (1998, supra), Sections 6.3.1-6.3.6. Aqueous and non-aqueous methods are described in that reference and either can be used. Reference herein to low stringency conditions include and encompass from at least about 1% v/v to at least about 15% v/v formamide and from at least about 1 M to at least about 2 M salt for hybridization at 42° C., and at least about 1 M to at least about 2 M salt for washing at 42° C. Low stringency conditions also may include 1% Bovine Serum Albumin (BSA), 1 mM EDTA, 0.5 M $NaHPO_4$ (pH 7.2), 7% SDS for hybridization at 65° C., and (i) 2×SSC, 0.1% SDS; or (ii) 0.5% BSA, 1 mM EDTA, 40 mM $NaHPO_4$ (pH 7.2), 5% SDS for washing at room temperature. One embodiment of low stringency conditions includes hybridization in 6× sodium chloride/sodium citrate (SSC) at about 45° □C, followed by two washes in 0.2×SSC, 0.1% SDS at least at 50° C. (the temperature of the washes can be increased to 55° C. for low stringency conditions). Medium stringency conditions include and encompass from at least about 16% v/v to at least about 30% v/v formamide and from at least about 0.5 M to at least about 0.9 M salt for hybridization at 42° C., and at least about 0.1 M to at least about 0.2 M salt for washing at 55° C. Medium stringency conditions also may include 1% Bovine Serum Albumin (BSA), 1 mM EDTA, 0.5 M $NaHPO_4$ (pH 7.2), 7% SDS for hybridization at 65° C., and (i) 2×SSC, 0.1% SDS; or (ii) 0.5% BSA, 1 mM EDTA, 40 mM $NaHPO_4$ (pH 7.2), 5% SDS for washing at 60-65° C. One embodiment of medium stringency conditions includes hybridizing in 6×SSC at about 45° C, followed by one or more washes in 0.2×SSC, 0.1% SDS at 60° C. High stringency conditions include and encompass from at least about 31% v/v to at least about 50% v/v formamide and from about 0.01 M to about 0.15 M salt for hybridization at 42° C., and about 0.01 M to about 0.02 M salt for washing at 55° C. High stringency conditions also may include 1% BSA, 1 mM EDTA, 0.5 M NaHPO$_4$ (pH 7.2), 7% SDS for hybridization at 65° C., and (i) 0.2×SSC, 0.1% SDS; or (ii) 0.5% BSA, 1 mM EDTA, 40 mM NaHPO$_4$ (pH 7.2), 1% SDS for washing at a temperature in excess of 65° C. One embodiment of high stringency conditions includes hybridizing in 6×SSC at about 45° C., followed by one or more washes in 0.2×SSC, 0.1% SDS at 65° C.

In certain embodiments, an AARS polypeptide is encoded by a polynucleotide that hybridizes to a disclosed nucleotide sequence under very high stringency conditions. One embodiment of very high stringency conditions includes hybridizing in 0.5 M sodium phosphate, 7% SDS at 65° C., followed by one or more washes in 0.2×SSC, 1% SDS at 65° C.

Other stringency conditions are well known in the art and a skilled artisan will recognize that various factors can be manipulated to optimize the specificity of the hybridization. Optimization of the stringency of the final washes can serve to ensure a high degree of hybridization. For detailed examples, see Ausubel et al., supra at pages 2.10.1 to 2.10.16 and Sambrook et al. (1989, supra) at sections 1.101 to 1.104.

While stringent washes are typically carried out at temperatures from about 42° C. to 68° C., one skilled in the art will appreciate that other temperatures may be suitable for stringent conditions. Maximum hybridization rate typically occurs at about 20° C. to 25° C. below the $T_m$ for formation of a DNA-DNA hybrid. It is well known in the art that the $T_m$ is the melting temperature, or temperature at which two complementary polynucleotide sequences dissociate. Methods for estimating $T_m$ are well known in the art (see Ausubel et al., supra at page 2.10.8).

In general, the $T_m$ of a perfectly matched duplex of DNA may be predicted as an approximation by the formula: $T_m=81.5+16.6 (\log_{10} M)+0.41 (\% G+C)-0.63 (\% \text{formamide})-(600/\text{length})$ wherein: M is the concentration of Na$^+$, preferably in the range of 0.01 molar to 0.4 molar; % G+C is the sum of guanosine and cytosine bases as a percentage of the total number of bases, within the range between 30% and 75% G+C; % formamide is the percent formamide concentration by volume; length is the number of base pairs in the DNA duplex. The $T_m$ of a duplex DNA decreases by approximately 1° C. with every increase of 1% in the number of randomly mismatched base pairs. Washing is generally carried out at $T_m$−15° C. for high stringency, or $T_m$−30° C. for moderate stringency.

In one example of a hybridization procedure, a membrane (e.g., a nitrocellulose membrane or a nylon membrane) containing immobilized DNA is hybridized overnight at 42° C. in a hybridization buffer (50% deionized formamide, 5×SSC, 5×Denhardt's solution (0.1% ficoll, 0.1% polyvinylpyrollidone and 0.1% bovine serum albumin), 0.1% SDS and 200 mg/mL denatured salmon sperm DNA) containing a labeled probe. The membrane is then subjected to two sequential medium stringency washes (i.e., 2×SSC, 0.1% SDS for 15 min at 45° C., followed by 2×SSC, 0.1% SDS for 15 min at 50° C.), followed by two sequential higher stringency washes (i.e., 0.2×SSC, 0.1% SDS for 12 min at 55° C. followed by 0.2×SSC and 0.1% SDS solution for 12 min at 65-68° C.

Polynucleotides and fusions thereof may be prepared, manipulated and/or expressed using any of a variety of well established techniques known and available in the art. For example, polynucleotide sequences which encode polypeptides of the invention, or fusion proteins or functional equivalents thereof, may be used in recombinant DNA molecules to direct expression of a truncated and/or variant aminoacyl-tRNA synthetase polypeptide in appropriate host cells. Due to the inherent degeneracy of the genetic code, other DNA sequences that encode substantially the same or a functionally equivalent amino acid sequence may be produced and these sequences may be used to clone and express a given polypeptide.

As will be understood by those of skill in the art, it may be advantageous in some instances to produce polypeptide-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

Moreover, the polynucleotide sequences of the present invention can be engineered using methods generally known in the art in order to alter polypeptide encoding sequences for a variety of reasons, including but not limited to, alterations which modify the cloning, processing, expression and/or activity of the gene product.

In order to express a desired polypeptide, a nucleotide sequence encoding the polypeptide, or a functional equivalent, may be inserted into appropriate expression vector, i.e., a vector which contains the necessary elements for the transcription and translation of the inserted coding sequence. Methods which are well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination. Such techniques are described in Sambrook et al., Molecular Cloning, A Laboratory Manual (1989), and Ausubel et al., Current Protocols in Molecular Biology (1989).

A variety of expression vector/host systems are known and may be utilized to contain and express polynucleotide sequences. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" present in an expression vector are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the pBLUESCRIPT phagemid (Stratagene, La Jolla, Calif.) or PSPORT1 plasmid (Gibco BRL, Gaithersburg, Md.) and the like may be used. In mammalian cell systems, promoters from mammalian genes or from mammalian viruses are generally preferred. If it is necessary to generate a cell line that contains multiple copies of the sequence encoding a polypeptide, vectors based on SV40 or EBV may be advantageously used with an appropriate selectable marker.

In bacterial systems, a number of expression vectors may be selected depending upon the use intended for the expressed polypeptide. For example, when large quantities are needed, vectors which direct high level expression of fusion proteins that are readily purified may be used. Such vectors include, but are not limited to, the multifunctional *E. coli* cloning and expression vectors such as BLUESCRIPT (Stratagene), in which the sequence encoding the polypeptide of interest may be ligated into the vector in frame with sequences for the amino-terminal Met and the subsequent 7 residues of β-galactosidase so that a hybrid protein is produced; pIN vectors (Van Heeke & Schuster, *J. Biol. Chem.* 264:5503 5509 (1989)); and the like. pGEX Vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast *Saccharomyces cerevisiae*, a number of vectors containing constitutive or inducible promoters such as alpha factor, alcohol oxidase, and PGH may be used. For reviews, see Ausubel et al. (supra) and Grant et al., *Methods Enzymol.* 153:516-544 (1987).

In cases where plant expression vectors are used, the expression of sequences encoding polypeptides may be driven by any of a number of promoters. For example, viral promoters such as the 35S and 19S promoters of CaMV may be used alone or in combination with the omega leader sequence from TMV (Takamatsu, *EMBO J.* 6:307-311 (1987)). Alternatively, plant promoters such as the small subunit of RUBISCO or heat shock promoters may be used (Coruzzi et al., *EMBO J.* 3:1671-1680 (1984); Broglie et al., *Science* 224:838-843 (1984); and Winter et al., *Results Probl. Cell Differ.* 17:85-105 (1991)). These constructs can be introduced into plant cells by direct DNA transformation or pathogen-mediated transfection. Such techniques are described in a number of generally available reviews (see, e.g., Hobbs in McGraw Hill, *Yearbook of Science and Technology*, pp. 191-196 (1992)).

An insect system may also be used to express a polypeptide of interest. For example, in one such system, *Autographa californica* nuclear polyhedrosis virus (AcNPV) is used as a vector to express foreign genes in *Spodoptera frugiperda* cells or in *Trichoplusia* larvae. The sequences encoding the polypeptide may be cloned into a non-essential region of the virus, such as the polyhedrin gene, and placed under control of the polyhedrin promoter. Successful insertion of the polypeptide-encoding sequence will render the polyhedrin gene inactive and produce recombinant virus lacking coat protein. The recombinant viruses may then be used to infect, for example, *S. frugiperda* cells or *Trichoplusia* larvae in which the polypeptide of interest may be expressed (Engelhard et al., *Proc. Natl. Acad. Sci. U.S.A.* 91:3224-3227 (1994)).

In mammalian host cells, a number of viral-based expression systems are generally available. For example, in cases where an adenovirus is used as an expression vector, sequences encoding a polypeptide of interest may be ligated into an adenovirus transcription/translation complex consisting of the late promoter and tripartite leader sequence. Insertion in a non-essential E1 or E3 region of the viral genome may be used to obtain a viable virus which is capable of expressing the polypeptide in infected host cells (Logan & Shenk, *Proc. Natl. Acad. Sci. U.S.A.* 81:3655-3659 (1984)). In addition, transcription enhancers, such as the Rous sarcoma virus (RSV) enhancer or immediate/early cytomegalovirus (CMV) enhancer/promoter region, may be used to increase expression in mammalian host cells.

Specific initiation signals may also be used to achieve more efficient translation of sequences encoding a polypeptide of interest. Such signals include the ATG initiation codon and adjacent sequences. In cases where sequences encoding the polypeptide, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf et al., *Results Probl. Cell Differ.* 20:125-162 (1994)).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells such as CHO, HeLa, MDCK, HEK293, and W138, which have specific cellular machinery and characteristic mechanisms for such post-translational activities, may be chosen to ensure the correct modification and processing of the foreign protein.

For long-term, high-yield production of recombinant proteins, stable expression is generally preferred. For example, cell lines which stably express a polynucleotide of interest may be transformed using expression vectors which may contain viral origins of replication and/or endogenous expression elements and a selectable marker gene on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler et al., *Cell* 11:223-232 (1977)) and adenine phosphoribosyltransferase (Lowy et al., *Cell* 22:817-823 (1990)) genes which can be employed in tk– or aprt– cells, respectively. Also, antimetabolite, antibiotic or herbicide resistance can be used as the basis for selection; for example, dhfr which confers resistance to methotrexate (Wigler et al., *Proc. Natl. Acad.*

Sci. U.S.A. 77:3567-70 (1980)); npt, which confers resistance to the aminoglycosides, neomycin and G-418 (Colbere-Garapin et al., *J. Mol. Biol.* 150:1-14 (1981)); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman & Mulligan, *Proc. Natl. Acad. Sci. U.S.A.* 85:8047-51 (1988)). The use of visible markers has gained popularity with such markers as anthocyanins, β-glucuronidase and its substrate GUS, and luciferase and its substrate luciferin, being widely used not only to identify transformants, but also to quantify the amount of transient or stable protein expression attributable to a specific vector system (Rhodes et al., *Methods Mol. Biol.* 55:121-131 (1995)).

A variety of protocols for detecting and measuring the expression of polynucleotide-encoded products, using either polyclonal or monoclonal antibodies specific for the product are known in the art. Examples include enzyme-linked immunosorbent assay (ELISA), radioimmunoassay (RIA), and fluorescence activated cell sorting (FACS). These and other assays are described, among other places, in Hampton et al., *Serological Methods, a Laboratory Manual* (1990) and Maddox et al., *J. Exp. Med.* 158:1211-1216 (1983).

A wide variety of labels and conjugation techniques are known by those skilled in the art and may be used in various nucleic acid and amino acid assays. Means for producing labeled hybridization or PCR probes for detecting sequences related to polynucleotides include oligolabeling, nick translation, end-labeling or PCR amplification using a labeled nucleotide. Alternatively, the sequences, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits. Suitable reporter molecules or labels, which may be used include radionuclides, enzymes, fluorescent, chemiluminescent, or chromogenic agents as well as substrates, cofactors, inhibitors, magnetic particles, and the like. Host cells transformed with a polynucleotide sequence of interest may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides of the invention may be designed to contain signal sequences which direct secretion of the encoded polypeptide through a prokaryotic or eukaryotic cell membrane. Other recombinant constructions may be used to join sequences encoding a polypeptide of interest to nucleotide sequence encoding a polypeptide domain which will facilitate purification of soluble proteins.

Antibody Compositions, Fragments Thereof and Other Binding Agents

According to another aspect, the present invention further provides binding agents, such as antibodies and antigen-binding fragments thereof, that exhibit immunological binding to a polypeptide disclosed herein, or to a portion, variant or derivative thereof, and methods of using same. Preferably, such binding agents are effective for modulating one or more of the non-canonical activities mediated by an AARS polypeptide of the invention, or for detecting the presence or absence of selected AARS polypeptides (e.g., truncations, alternate splice variants, mutants) in a sample, such as a biological sample obtained from a subject.

For example, certain embodiments contemplate a method of identifying or characterizing an AARS polypeptide in a subject, comprising obtaining a biological sample from the subject, contacting the biological sample with an antibody, or antigen-binding fragment thereof, wherein the antibody or antigen-binding fragment specifically binds to an AARS polypeptide of the invention, and detecting the presence or absence of the bound antibody, or antigen-binding fragment thereof, thereby identifying or characterizing the AARS polypeptide in the subject. In certain aspects, the antibody, or antigen-binding fragment thereof, specifically binds to a certain variant or truncated AARS polypeptide, such as a selected AARS mutant or alternate splice variant, but does not specifically bind to other AARS polypeptides, such as a full-length, wild type AARS polypeptide.

An antibody, or antigen-binding fragment thereof, is said to "specifically bind," "immunologically bind," and/or is "immunologically reactive" to a polypeptide of the invention if it reacts at a detectable level (within, for example, an ELISA assay) with the polypeptide, and does not react detectably with unrelated polypeptides under similar conditions.

Immunological binding, as used in this context, generally refers to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller Ka represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and on geometric parameters that equally influence the rate in both directions. Thus, both the "on rate constant" ($k_{on}$) and the "off rate constant" ($k_{off}$) can be determined by calculation of the concentrations and the actual rates of association and dissociation. The ratio of $k_{off}/k_{on}$ enables cancellation of all parameters not related to affinity, and is thus equal to the dissociation constant Ka. See, generally, Davies et al. (1990) *Annual Rev. Biochem.* 59:439-473.

An "antigen-binding site," or "binding portion" of an antibody refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions," or "FRs." Thus, the term "FR" refers to amino acid sequences which are naturally found between and adjacent to hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs."

A binding agent may be, for example, a ribosome, with or without a peptide component, an RNA molecule or a polypeptide. In a preferred embodiment, a binding agent is an antibody or an antigen-binding fragment thereof. Antibodies may be prepared by any of a variety of techniques known to those of ordinary skill in the art. See, e.g., Harlow and Lane, *Antibodies: A Laboratory Manual*, Cold Spring Harbor Laboratory, 1988. In general, antibodies can be produced by cell culture techniques, including the generation of monoclonal antibodies as described herein, or via transfection of antibody genes into suitable bacterial or mammalian cell hosts, in order to allow for the production of recombinant antibodies. In one technique, an immunogen comprising the polypeptide is initially injected into any of a wide variety of mammals (e.g., mice, rats, rabbits, sheep or goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for an polypeptide of interest may be prepared, for example, using the technique of Kohler and Milstein, *Eur. J. Immunol.* 6:511-519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

A number of therapeutically useful molecules are known in the art which comprise antigen-binding sites that are capable of exhibiting immunological binding properties of an antibody molecule. The proteolytic enzyme papain preferentially cleaves IgG molecules to yield several fragments, two of which (the "F(ab)" fragments) each comprise a covalent heterodimer that includes an intact antigen-binding site. The enzyme pepsin is able to cleave IgG molecules to provide several fragments, including the "F(ab')2" fragment which comprises both antigen-binding sites. An "Fv" fragment can be produced by preferential proteolytic cleavage of an IgM, and on rare occasions IgG or IgA immunoglobulin molecule. Fv fragments are, however, more commonly derived using recombinant techniques known in the art. The Fv fragment includes a non-covalent $V_H$::$V_L$ heterodimer including an antigen-binding site which retains much of the antigen recognition and binding capabilities of the native antibody molecule. Inbar et al. (1972) *Proc. Nat. Acad. Sci. USA* 69:2659-2662; Hochman et al. (1976) *Biochem* 15:2706-2710; and Ehrlich et al. (1980) *Biochem* 19:4091-4096.

A single chain Fv ("sFv") polypeptide is a covalently linked $V_H$::$V_L$ heterodimer which is expressed from a gene fusion including $V_H$- and $V_L$-encoding genes linked by a peptide-encoding linker. Huston et al. (1988) *Proc. Nat. Acad. Sci. USA* 85(16):5879-5883. A number of methods have been described to discern chemical structures for converting the naturally aggregated—but chemically separated—light and heavy polypeptide chains from an antibody V region into an sFv molecule which will fold into a three dimensional structure substantially similar to the structure of an antigen-binding site. See, e.g., U.S. Pat. Nos. 5,091,513 and 5,132,405, to Huston et al.; and U.S. Pat. No. 4,946,778, to Ladner et al.

Each of the above-described molecules includes a heavy chain and a light chain CDR set, respectively interposed between a heavy chain and a light chain FR set which provide support to the CDRs and define the spatial relationship of the CDRs relative to each other. As used herein, the term "CDR set" refers to the three hypervariable regions of a heavy or light chain V region. Proceeding from the N-terminus of a heavy or light chain, these regions are denoted as "CDR1," "CDR2," and "CDR3" respectively. An antigen-binding site, therefore, includes six CDRs, comprising the CDR set from each of a heavy and a light chain V region. A polypeptide comprising a single CDR, (e.g., a CDR1, CDR2 or CDR3) is referred to herein as a "molecular recognition unit." Crystallographic analysis of a number of antigen-antibody complexes has demonstrated that the amino acid residues of CDRs form extensive contact with bound antigen, wherein the most extensive antigen contact is with the heavy chain CDR3. Thus, the molecular recognition units are primarily responsible for the specificity of an antigen-binding site.

As used herein, the term "FR set" refers to the four flanking amino acid sequences which frame the CDRs of a CDR set of a heavy or light chain V region. Some FR residues may contact bound antigen; however, FRs are primarily responsible for folding the V region into the antigen-binding site, particularly the FR residues directly adjacent to the CDRs. Within FRs, certain amino residues and certain structural features are very highly conserved. In this regard, all V region sequences contain an internal disulfide loop of around 90 amino acid residues. When the V regions fold into a binding-site, the CDRs are displayed as projecting loop motifs which form an antigen-binding surface. It is generally recognized that there are conserved structural regions of FRs which influence the folded shape of the CDR loops into certain "canonical" structures—regardless of the precise CDR amino acid sequence. Further, certain FR residues are known to participate in non-covalent interdomain contacts which stabilize the interaction of the antibody heavy and light chains.

A number of "humanized" antibody molecules comprising an antigen-binding site derived from a non-human immunoglobulin have been described, including chimeric antibodies having rodent V regions and their associated CDRs fused to human constant domains (Winter et al. (1991) *Nature* 349:293-299; Lobuglio et al. (1989) *Proc.*

*Nat. Acad. Sci. USA* 86:4220-4224; Shaw et al. (1987) *J Immunol.* 138:4534-4538; and Brown et al. (1987) *Cancer Res.* 47:3577-3583), rodent CDRs grafted into a human supporting FR prior to fusion with an appropriate human antibody constant domain (Riechmann et al. (1988) *Nature* 332:323-327; Verhoeyen et al. (1988) *Science* 239:1534-1536; and Jones et al. (1986) *Nature* 321:522-525), and rodent CDRs supported by recombinantly veneered rodent FRs (European Patent Publication No. 519,596, published Dec. 23, 1992). These "humanized" molecules are designed to minimize unwanted immunological response toward rodent antihuman antibody molecules which limits the duration and effectiveness of therapeutic applications of those moieties in human recipients.

As used herein, the terms "veneered FRs" and "recombinantly veneered FRs" refer to the selective replacement of FR residues from, e.g., a rodent heavy or light chain V region, with human FR residues in order to provide a xenogeneic molecule comprising an antigen-binding site which retains substantially all of the native FR polypeptide folding structure. Veneering techniques are based on the understanding that the ligand binding characteristics of an antigen-binding site are determined primarily by the structure and relative disposition of the heavy and light chain CDR sets within the antigen-binding surface. Davies et al. (1990) *Ann. Rev. Biochem.* 59:439-473. Thus, antigen binding specificity can be preserved in a humanized antibody only wherein the CDR structures, their interaction with each other, and their interaction with the rest of the V region domains are carefully maintained. By using veneering techniques, exterior (e.g., solvent-accessible) FR residues which are readily encountered by the immune system are selectively replaced with human residues to provide a hybrid molecule that comprises either a weakly immunogenic, or substantially non-immunogenic veneered surface.

In another embodiment of the invention, monoclonal antibodies of the present invention may be coupled to one or more agents of interest. For example, a therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers that provide multiple sites for attachment can be used.

Modulation of Inflammatory Responses and Methods of Use

Embodiments of the present invention relate to the discovery that aminoacyl-tRNA synthetase (AARS) polypeptides, and variants thereof, modulate inflammation in a variety of useful ways, both in vitro and in vivo. For instance, in certain embodiments, the AARS polypeptides of the present invention reduce an inflammatory response, such as by reducing the migration or infiltration of immune cells into selected tissues, increasing the production of anti-inflammatory cytokines, or reducing the production of pro-inflammatory cytokines, among other mechanisms. In certain embodiments, the AARS polypeptides of the present invention increase or stimulate an inflammatory response, such as by increasing the migration or infiltration of immune cells into selected tissues, increasing the production pro-inflammatory cytokines, or reducing the production of anti-inflammatory cytokines, among other mechanisms.

"Inflammation" refers generally to the biological response of tissues to harmful stimuli, such as pathogens, damaged cells (e.g., wounds), and irritants. The term "inflammatory response" refers to the specific mechanisms by which inflammation is achieved and regulated, including, merely by way of illustration, immune cell activation or migration, cytokine production, vasodilation, including kinin release, fibrinolysis, and coagulation, among others described herein and known in the art. Ideally, inflammation is a protective attempt by the body to both remove the injurious stimuli and initiate the healing process for the affected tissue or tissues. In the absence of inflammation, wounds and infections would never heal, creating a situation in which progressive destruction of the tissue would threaten survival. On the other hand, excessive or chronic inflammation may associate with a variety of diseases, such as hay fever, atherosclerosis, and rheumatoid arthritis, among others described herein and known in the art.

AARS polypeptides of the invention may modulate acute inflammation, chronic inflammation, or both. Certain embodiments relate to increasing acute inflammation or acute inflammatory responses, and certain embodiments relate to increasing chronic inflammation or chronic inflammatory responses. Depending on the needs of the subject, certain embodiments relate to reducing acute inflammation or inflammatory responses, and certain embodiments relate to reducing chronic inflammation or chronic inflammatory responses.

Acute inflammation relates to the initial response of the body to presumably harmful stimuli and involves increased movement of plasma and leukocytes from the blood into the injured tissues. It is a short-term process, typically beginning within minutes or hours and ending upon the removal of the injurious stimulus. Acute inflammation may be characterized by any one or more of redness, increased heat, swelling, pain, and loss of function. Redness and heat are due mainly to increased blood flow at body core temperature to the inflamed site, swelling is caused by accumulation of fluid, pain is typically due to release of chemicals that stimulate nerve endings, and loss of function has multiple causes.

Acute inflammatory responses are initiated mainly by local immune cells, such as resident macrophages, dendritic cells, histiocytes, Kuppfer cells and mastocytes. At the onset of an infection, burn, or other injuries, these cells undergo activation and release inflammatory mediators responsible for the clinical signs of inflammation, such as vasoactive amines and eicosanoids. Vasodilation and its resulting increased blood flow cause the redness and increased heat. Increased permeability of the blood vessels results in an exudation or leakage of plasma proteins and fluid into the tissue, which creates swelling. Certain released mediators such as bradykinin increase sensitivity to pain, and alter the blood vessels to permit the migration or extravasation of leukocytes, such as neutrophils, which typically migrate along a chemotactic gradient created by the local immune cells.

Acute inflammatory responses also includes one or more acellular biochemical cascade systems, consisting of preformed plasma proteins modulate, which act in parallel to initiate and propagate the inflammatory response. These systems include the complement system, which is mainly activated by bacteria, and the coagulation and fibrinolysis systems, which are mainly activated by necrosis, such as the type of tissue damage that is caused by certain infections, burns, or other trauma. Hence, AARS polypeptides may be used to modulate acute inflammation, or any of one or more of the individual acute inflammatory responses.

Chronic inflammation, a prolonged and delayed inflammatory response, is characterized by a progressive shift in the type of cells that are present at the site of inflammation, and often leads to simultaneous or near simultaneous destruction and healing of the tissue from the inflammatory process. At the cellular level, chronic inflammatory responses involve a variety of immune cells such as monocytes, macrophages, lymphocytes, plasma cells, and fibroblasts, though in contrast to acute inflammation, which is mediated mainly by granulocytes, chronic inflammation is mainly mediated by mononuclear cells such as monocytes and lymphocytes. Chronic inflammation also involves a variety of inflammatory mediators, such as IFN-γ and other cytokines, growth factors, reactive oxygen species, and hydrolytic enzymes. Chronic inflammation may last for many months or years, and may result in undesired tissue destruction and fibrosis.

Clinical signs of chronic inflammation are dependent upon duration of the illness, inflammatory lesions, cause and anatomical area affected. (see, e.g., Kumar et al., Robbins Basic Pathology-$8^{th}$ Ed., 2009 Elsevier, London; Miller, LM, Pathology Lecture Notes, Atlantic Veterinary College, Charlottetown, PEI, Canada). Chronic inflammation is associated with a variety of pathological conditions or diseases, including, for example, allergies, Alzheimer's disease, anemia, aortic valve stenosis, arthritis such as rheumatoid arthritis and osteoarthritis, cancer, congestive heart failure, fibromyalgia, fibrosis, heart attack, kidney failure, lupus, pancreatitis, stroke, surgical complications, inflammatory lung disease, inflammatory bowel disease, atherosclerosis, and psoriasis, among others described herein and known in the art. Hence, AARS polypeptides may be used to treat or manage chronic inflammation, modulate any of one or more of the individual chronic inflammatory responses, or treat any one or more diseases or conditions associated with chronic inflammation.

AARS polypeptides may also modulate proliferative inflammation, an inflammatory process characterized by an increase in the number of tissue cells. These can encompass skin conditions such as psoriasis, seborrhea or eczema, or can also be thought of in terms of cancers and abnormal growths especially in light of accumulating evidence based on more efficient molecular methods to document even low grade chronic inflammation.

In certain embodiments, AARS polypeptides may modulate inflammatory responses at the cellular level, such as by modulating the activation, inflammatory molecule secretion (e.g., cytokine or kinin secretion), proliferation, activity, migration, or adhesion of various cells involved in inflammation. Examples of such cells include immune cells and vascular cells. Immune cells include, for example, granulocytes such as neutrophils, eosinophils and basophils, macrophages/monocytes, lymphocytes such as B-cells, killer T-cells (i.e., CD8+ T-cells), helper T-cells (i.e., CD4+ T-cells, including $T_h1$ and $T_h2$ cells), natural killer cells, γδ T-cells, dendritic cells, and mast cells. Examples of vascular cells include smooth muscle cells, endothelial cells, and fibroblasts. Also included are methods of modulating an inflammatory condition associated with one or more immune cells or vascular cells, including neutrophil-mediated, macrophage-mediated, and lymphocyte-mediated inflammatory conditions.

In certain embodiments, AARS polypeptides may modulate the levels or activity of inflammatory molecules, including plasma-derived inflammatory molecules and cell-derived inflammatory molecules. Included are pro-inflammatory molecules and anti-inflammatory molecules. Examples of plasma-derived inflammatory molecules include, without limitation, proteins or molecules of any one or more of the complement system, kinin system, coagulation system, and the fibrinolysis system. Examples of members of the complement system include C1, which exists in blood serum as a molecular complex containing about 6 molecules of C1q, 2 molecules of C1r, and 2 molecules of C1s, C2 (a and b), C3(a and B), C4 (a and b), C5, and the membrane attack complex of C5a, C5b, C6, C7, C8, and C9. Examples of the kinin system include bradykinin, kallidin, kallidreins, carboxypeptidases, angiotensin-converting enzyme, and neutral endopeptidase.

Examples of cell-derived inflammatory molecules include, without limitation, enzymes contained within lysosome granules, vasoactive amines, eicosanoids, cytokines, acute-phase proteins, and soluble gases such as nitric oxide. Vasoactive amines contain at least one amino group, and target blood vessels to alter their permeability or cause vasodilation. Examples of vasoactive amines include histamine and serotonin. Eicosanoids refer to signaling molecules made by oxidation of twenty-carbon essential fatty acids, and include prostaglandins, prostacyclins, thromboxanes, and leukotrienes.

Cytokines refer to a variety of substances that are secreted by immune cells, and include polypeptides and glycoproteins. Typically, cytokines are categorized as either autocrine cytokines, which act on the same type of cell from which the cytokine is secreted, or paracrine cytokines, which are restricted to acting on a different cell type from which the cytokine is secreted. Examples of cytokines, examples of their producing cells, examples of their target cells, and exemplary activities are included in Tables J and K below.

TABLE K

Cytokines
Selected Immune Cytokines and Their Activities

| Cytokine | Producing Cell | Target Cell | Activity |
|---|---|---|---|
| GM-CSF | Th cells | progenitor cells | growth and differentiation of monocytes and DC |
| IL-1a | monocytes | Th cells | co-stimulation |
| IL-1b | macrophages<br>B cells<br>DC | B cells<br>NK cells<br>various | maturation and proliferation<br>activation<br>inflammation, acute phase response, fever |
| IL-2 | Th1 cells | activated T and B cells, NK cells | growth, proliferation, activation |
| IL-3 | Th cells<br>NK cells | stem cells<br>mast cells | growth and differentiation<br>growth and histamine release |
| IL-4 | Th2 cells | activated B cells<br><br>macrophages<br>T cells | proliferation and differentiation IgG$_1$ and IgE synthesis<br>MHC Class II<br>proliferation |
| IL-5 | Th2 cells | activated B cells | proliferation and differentiation IgA synthesis |
| IL-6 | monocytes<br>macrophages<br>Th2 cells<br>stromal cells | activated B cells<br>plasma cells<br>stem cells<br>various | differentiation into plasma cells<br>antibody secretion<br>differentiation<br>acute phase response |
| IL-7 | marrow stroma<br>thymus stroma | stem cells | differentiation into progenitor B and T cells |
| IL-8 | macrophages<br>endothelial cells | neutrophils | chemotaxis |
| IL-10 | Th2 cells | macrophages<br>B cells | cytokine production<br>activation |
| IL-12 | macrophages<br>B cells | activated Tc cells<br><br>NK cells | differentiation into CTL (with IL-2)<br>activation |
| IFN-α | leukocytes | various | viral replication<br>MHC I expression |
| IFN-β | fibroblasts | various | viral replication<br>MHC I expression |
| IFN-gamma | Th1 cells,<br>Tc cells, NK cells | various<br>macrophages<br>activated B cells<br>Th2 cells<br>macrophages | Viral replication<br>MHC expression<br>Ig class switch to IgG$_{2a}$<br>proliferation<br>pathogen elimination |
| MIP-1α | macrophages | monocytes, T cells | chemotaxis |
| MIP-1β | lymphocytes | monocytes, T cells | chemotaxis |
| TGF-β | T cells, monocytes | monocytes, macrophages<br>activated macrophages<br>activated B cells<br>various | chemotaxis<br><br>IL-1 synthesis<br>IgA synthesis<br>proliferation |
| TNF-α | macrophages, mast cells, NK cells | macrophages<br>tumor cells | CAM and cytokine expression<br>cell death |
| TNF-β | Th1 and Tc cells | phagocytes<br>tumor cells | phagocytosis, NO production<br>cell death |

TABLE L

Cytokines

| Old Name | New Name |
|---|---|
| ENA-78 | CXCL5 |
| GROα | CXCL1 |
| GROβ | CXCL2 |
| GROγ | CXCL3 |
| PF4 | CXCL4 |
| IP-10 | CXCL10 |
| Mig | CXCL9 |
| I-TAC | CXCL11 |
| SDF-1α/β | CXCL12 |
| BCA-1 | CXCL13 |
|  | CXCL16 |
| BRAK | CXCL14 |
| MCP-1 | CCL2 |
| MCP-4 | CCL13 |
| MCP-3 | CCL7 |
| MCP-2 | CCL8 |
| MIP-1β | CCL4 |
| MIP-1αS | CCL3 |
| MIP-1αP | CCL3LI |
| RANTES | CCL5 |
| MPIF-1 | CCL23 |
| HCC-1 | CCL14 |
| HCC-2 | CCL15 |
| HCC-4 | CCL16 |
| Eotaxin | CCL11 |
| Eotaxin-2 | CCL24 |
| Eotaxin-3 | CCL26 |
| TARC | CCL17 |
| MDC | CCL22 |
| MIP-3α | CCL20 |

TABLE L-continued

Cytokines

| Old Name | New Name |
|---|---|
| ELC | CCL19 |
| SLC | CCL21 |
| I-309 | CCL1 |
| TECK | CCL25 |
| CTACK | CCL27 |
| MEC | CCL28 |
| PARC | CCL18 |
| Lymphotactin | XCL1 |
| SCM-1β | XCL2 |
| Fractalkine | CX3CL1 |

In certain embodiments, AARS polypeptides increase the levels of any one or more of TNF-α, MIP-1b, IL-12(p40), KC, MIP-2, or IL-10. In certain embodiments, AARS polypeptides increase the secretion of at least one of TNF-α and IL-10 by peripheral blood mononuclear cells (PBMCs), including monocytes, lymphocytes, or both. In certain embodiments, AARS polypeptides increase the secretion of IL-2 by lymphocytes such as activated T-cells. In certain embodiments, AARS polypeptides reduce TNF-α secretion by immune cells such as PBMCs, and in certain embodiments reduce lipopolysaccharide-induced TNF-α secretion by these and other cells. In certain embodiments, AARS polypeptides reduce IL-12 secretion by immune cells such as PBMCs, and in certain embodiments reduce lipopolysaccharide induced IL-12 secretion by these and other cells.

Each cytokine typically has a corresponding cytokine receptor. Examples of classes of cytokine receptors include, without limitation, receptors from the immunoglobulin (Ig) superfamily, such as the IL-1 receptor types, which share structural homology with immunoglobulins (antibodies), cell adhesion molecules, and even some cytokines, and receptors from the hematopoietic growth factor family, such as the IL-2 receptor family and the receptors for GM-CSF, IL-3, and IL-5, receptors from the interferon (type 2) family, including receptors for IFN β and γ. Additional examples include receptors from the tumor necrosis factors (TNF) (type 3) family, which share a cysteine-rich common extracellular binding domain and interact with several other non-cytokine ligands such as CD40, CD27 and CD30, receptors from the seven transmembrane helix family, including G-protein coupled receptors, and chemokine receptors such as CXCR4 and CCR5, as well as receptors for IL-8, MIP-1 and RANTES. Hence, in certain embodiments, AARS polypeptides may modulate the levels or activity of one or more selected cytokines, such as those in Tables J and K, the levels or activity of one or more selected cytokine receptors, the interaction between cytokines and their receptors, or any combination thereof.

AARS polypeptides may also modulate levels or activity of acute-phase proteins. Examples of acute-phase proteins include C-reactive protein, serum amyloid A, serum amyloid P, and vasopressin. In certain instances, expression of acute-phase proteins can cause a range of undesired systemic effects including amyloidosis, fever, increased blood pressure, decreased sweating, malaise, loss of appetite, and somnolence. Accordingly, AARS polypeptides may modulate the levels or activity of acute-phase proteins, their systemic effects, or both.

In certain embodiments, AARS polypeptides modulate local inflammation, systemic inflammation, or both. In certain embodiments, AARS polypeptide may reduce or maintain (i.e., prevent further increases) local inflammation or local inflammatory responses. In certain embodiments, depending on the needs of the subject, AARS polypeptides may increase local inflammation or local inflammatory responses. In certain embodiments, AARS polypeptides may reduce or maintain (i.e., prevent further increases) systemic inflammation or systemic inflammatory responses. In certain embodiments, depending on the needs of the subject, AARS polypeptides may increase systemic inflammation or systemic inflammatory responses.

In certain embodiments, the modulation of inflammation or inflammatory responses can be associated with one or more tissues or organs. Non-limiting examples of such tissues or organs include skin (e.g., dermis, epidermis, subcutaneous layer), hair follicles, nervous system (e.g., brain, spinal cord, peripheral nerves), auditory system or balance organs (e.g., inner ear, middle ear, outer ear), respiratory system (e.g., nose, trachea, lungs), gastroesophogeal tissues, the gastrointestinal system (e.g., mouth, esophagus, stomach, small intestines, large intestines, rectum), vascular system (e.g., heart, blood vessels and arteries), liver, gallbladder, lymphatic/immune system (e.g., lymph nodes, lymphoid follicles, spleen, thymus, bone marrow), uro-genital system (e.g., kidneys, ureter, bladder, urethra, cervix, Fallopian tubes, ovaries, uterus, vulva, prostate, bulbourethral glands, epidiymis, prostate, seminal vesicles, testicles), musculoskeletal system (e.g., skeletal muscles, smooth muscles, bone, cartilage, tendons, ligaments), adipose tissue, mammaries, and the endocrine system (e.g., hypothalamus, pituitary, thyroid, pancreas, adrenal glands). Accordingly, AARS polypeptides may be used to modulate inflammation associated with any of these tissues or organs, such as to treat conditions or diseases that are associated with the inflammation of these tissues or organs.

As noted above, certain embodiments may employ AARS polypeptides to reduce or manage (i.e., prevent further increases) inflammation or inflammatory responses associated with particular tissues or organs. Included are inflammatory responses and conditions associated with the skin, including inflammation, infections, and cancers associated with the dermal, epidermal, and subcutaneous layers of the skin. Examples of skin-associated inflammatory conditions include, without limitation, dermatitis, such as psoriasis, irritant dermatitis, seborrheic dermatitis, atopic dermatitis (eczema), allergic contact dermatitis, thermal-induced dermatitis, drug-induced dermatitis, dyshidrotic dermatitis, urticaria, autoimmune dermatitis, skin cancer such as melanoma, and bullous dermatitis. Also included are bacterial, viral and parasitic infections, erythema multiforme, erythema nodosum, granuloma annulare, poison oak/poison ivy, and toxic epidermal necrolysis.

Certain embodiments relate to reducing inflammatory responses and conditions associated with the nervous system, including inflammation, infections, and cancer associated with the brain and spinal cord of the central nervous system, the peripheral nervous system, and the meninges. Expression of inflammatory mediators including complement, adhesion molecules, cyclooxygenase enzymes and their products and cytokines is increased in experimental and clinical neurodegenerative disease, and intervention studies in experimental animals suggest that several of these factors contribute directly to neuronal injury. For instance, specific cytokines, such as interleukin-1 (IL-1), have been implicated heavily in acute neurodegeneration, such as stroke and head injury.

Examples of nervous system associated inflammatory conditions include, without limitation, meningitis (i.e., inflammation of the protective membranes covering the brain and spinal cord), myelitis, encaphaloymyelitis (e.g., myalgic encephalomyelitis, acute disseminated encephalomyelitis, encephalomyelitis disseminata or multiple sclerosis, autoimmune encephalomyelitis), arachnoiditis (i.e., inflammation of the arachnoid, one of the membranes that surround and protect the nerves of the central nervous system), granuloma, drug-induced inflammation or meningitis, neurodegenerative diseases such as Alzheimer's disease, stroke, HIV-dementia, encephalitis such viral encephalitis and bacterial encephalitis, parasitic infections, inflammatory demyeleniating disorders, and auto-immune disorders such as CD8+ T Cell-mediated autoimmune diseases of the CNS. Additional examples include Parkinson's disease, myasthenia gravis, motor neuropathy, Guillain-Barre syndrome, autoimmune neuropathy, Lambert-Eaton myasthenic syndrome, paraneoplastic neurological disease, paraneoplastic cerebellar atrophy, non-paraneoplastic stiff man syndrome, progressive cerebellar atrophy, Rasmussen's encephalitis, amyotrophic lateral sclerosis, Sydeham chorea, Gilles de la Tourette syndrome, autoimmune polyendocrinopathy, dysimmune neuropathy, acquired neuromyotonia, arthrogryposis multiplex, optic neuritis, and stiff-man syndrome.

As noted above, also included is inflammation associated with infections of the nervous system. Specific examples of bacterial infections associated with inflammation of the nervous system include, without limitation, streptococcal infection such as group B streptococci (e.g., subtypes III) and *Streptococcus pneumoniae* (e.g., serotypes 6, 9, 14, 18 and 23), *Escherichia coli* (e.g., carrying K1 antigen), *Listeria monocytogenes* (e.g., serotype IVb), neisserial infection such as *Neisseria meningitidis* (meningococcus), staphylococcal infection, heamophilus infection such as *Haemophilus influenzae* type B, *Klebsiella*, and *Mycobacterium tuberculosis*. Also included are infections by staphylococci and *pseudomonas* and other Gram-negative bacilli, mainly with respect to trauma to the skull, which gives bacteria in the nasal cavity the potential to enter the meningeal space, or in persons with cerebral shunt or related device (e.g., extraventricular drain, Ommaya reservoir). Specific examples of viral infections associated with inflammation of the nervous system include, without limitation, enteroviruses, herpes simplex virus type 1 and 2, human T-lymphotrophic virus, varicella zoster virus (chickenpox and shingles), mumps virus, human immunodeficiency virus (HIV), and lymphocytic choriomeningitis virus (LCMV). Meningitis may also result from infection by spirochetes such as *Treponema pallidum* (syphilis) and *Borrelia burgdorferi* (Lyme disease), parasites such as malaria (e.g., cerebral malaria), fungi such as *Cryptococcus neoformans*, and ameoba such as *Naegleria fowleri*.

Meningitis or other forms of nervous system inflammation may also associate with the spread of cancer to the meninges (malignant meningitis), certain drugs such as non-steroidal anti-inflammatory drugs, antibiotics and intravenous immunoglobulins, sarcoidosis (or neurosarcoidosis), connective tissue disorders such as systemic lupus erythematosus, and certain forms of vasculitis (inflammatory conditions of the blood vessel wall) such as Behçet's disease. Epidermoid cysts and dermoid cysts may cause meningitis by releasing irritant matter into the subarachnoid space. Accordingly, AARS polypeptides may be used to treat or manage any one or more of these conditions.

Certain embodiments relate to reducing inflammatory responses and conditions associated with the auditory system or balance organs, such as the inner ear, middle ear, and the outer ear. Examples of auditory system or balance organ associated inflammatory conditions include, without limitation, outer ear inflammation (e.g., ear infections), middle ear inflammation, which may lead to fluid build-up in the normally air-filled space and associated conductive hearing loss, labyrinthitis, an inner ear infection or inflammation causing both dizziness (vertigo) and hearing loss, vestibular neuronitis, an infection of the vestibular nerve, generally viral, causing vertigo, and cochlear neuronitis, an infection of the cochlear nerve, generally viral, causing sudden deafness but no vertigo. Recipients of cochlear implants for hearing loss are at an increased risk of pneumococcal meningitis and its associated inflammation.

Certain embodiments relate to reducing inflammatory responses and conditions associated with the respiratory system, including inflammation, infections, and cancer associated with the nose, trachea, and lungs. Examples of respiratory system associated inflammatory conditions include, without limitation, atopic asthma, non-atopic asthma, allergic asthma, atopic bronchial IgE-mediated asthma, bronchial asthma, essential asthma, true asthma, intrinsic asthma caused by pathophysiologic disturbances, extrinsic asthma caused by environmental factors, essential asthma of unknown or inapparent cause, non-atopic asthma, bronchitic asthma, emphysematous asthma, exercise-induced asthma, allergen induced asthma, cold air induced asthma, occupational asthma, infective asthma caused by bacterial, fungal, protozoal, or viral infection, non-allergic asthma, incipient asthma, wheezy infant syndrome and bronchiolytis, chronic or acute bronchoconstriction, chronic bronchitis, small airways obstruction, and emphysema. Further examples include obstructive or inflammatory airways diseases such as chronic eosinophilic pneumonia, chronic obstructive pulmonary disease (COPD), COPD that includes chronic bronchitis, pulmonary emphysema or dyspnea associated or not associated with COPD, COPD that is characterized by irreversible, progressive airways obstruction, and adult respiratory distress syndrome (ARDS).

Further examples of conditions associated with pulmonary inflammation include conditions related to exacerbation of airways hyper-reactivity consequent to other drug therapy, airways disease that is associated with pulmonary hypertension, bronchitis such as acute bronchitis, acute laryngotracheal bronchitis, arachidic bronchitis, catarrhal bronchitis, croupus bronchitis, dry bronchitis, infectious asthmatic bronchitis, productive bronchitis, *staphylococcus* or streptococcal bronchitis and vesicular bronchitis, acute lung injury, and bronchiectasis such as cylindric bronchiectasis, sacculated bronchiectasis, fusiform bronchiectasis, capillary bronchiectasis, cystic bronchiectasis, dry bronchiectasis and follicular bronchiectasis.

COPD in particular refers to a group of lung diseases that block airflow and make it increasingly difficult for affected individuals to breathe normally. Emphysema and chronic bronchitis are the two main conditions within the group of COPD diseases, but COPD can also refer to damage caused by chronic asthmatic bronchitis, among other conditions known in the art. In most cases, damage to the airways eventually interferes with the exchange of oxygen and carbon dioxide in the lungs. Standard treatments focus mainly on controlling symptoms and minimizing further damage.

Emphysema represents one aspect of COPD. Emphysema leads to inflammation within the fragile walls of the alveoli, which may destroy some of the walls and elastic fibers, allowing small airways to collapse upon exhaling, and impairing airflow out of the lungs. Signs and symptoms of emphysema include, for instance, shortness of breath, especially during physical activities, wheezing, and chest tightness.

Chronic bronchitis represents another aspect of COPD. Chronic bronchitis is characterized by an ongoing cough, and leads to inflammation and narrowing of the bronchial tubes. This condition also causes increased mucus production, which can further block the narrowed tubes. Chronic bronchitis occurs mainly in smokers, and is typically defined as a cough that lasts for at least three months a year for two consecutive years. Signs and symptoms of chronic bronchitis include, for example, having to clear the throat first thing in the morning, especially for smokers, a chronic cough that produces yellowish sputum, shortness of breath in the later stages, and frequent respiratory infections.

As noted above, COPD refers primarily to obstruction in the lungs resulting from the two above-noted chronic lung conditions. However, many individuals with COPD have both of these conditions.

Chronic asthmatic bronchitis represents another aspect of COPD. Chronic asthmatic bronchitis is usually characterized as chronic bronchitis combined with asthma (bronchospasm). Asthma may occur when inflamed and infected secretions irritate the smooth muscles in the airways. Symptoms are similar to those of chronic bronchitis, but also include intermittent, or even daily, episodes of wheezing. In certain embodiments, COPD is ultimately caused by cigarette smoke and other irritants. In the vast majority of cases, the lung damage that leads to COPD is caused by long-term cigarette smoking. However, other irritants may cause COPD, including cigar smoke, secondhand smoke, pipe smoke, air pollution and certain occupational fumes. Gastroesophageal reflux disease (GERD), which occurs when stomach acids wash back up into the esophagus, can not only aggravate COPD, but may even cause it in some individuals. In rare cases, COPD results from a genetic disorder that causes low levels of a protein called alpha-1-antitrypsin. Hence, risk factors for COPD include exposure to tobacco smoke, occupational exposure to dusts and chemicals (long-term exposure to chemical fumes, vapors and dusts irritates and inflames the lungs), gastroesophageal reflux disease (a severe form of acid reflux—the backflow of acid and other stomach contents into the esophagus), age (COPD develops slowly over years, so most people are at least 40 years old when symptoms begin), and genetics (a rare genetic disorder known as alpha-1-antitrypsin deficiency is the source of a few cases of COPD).

In certain embodiments, COPD may also have an autoimmune component. For instance, lung and peripheral blood T cells in patients with severe emphysema secrete Th1 cytokines and chemokines when stimulated with elastin peptides in vitro, and these patients have increased anti-elastin antibody as compared to controls (see Goswami et al., The Journal of Immunology. 178: 130.41, 2007). Also, IgG autoantibodies with avidity for pulmonary epithelium, and the potential to mediate cytotoxicity, are prevalent in patients with COPD (see Feghali-Bostwick et al., Am J Respir Crit Care Med. 177:156-63, 2008). Since autoreactive immune responses may be important in the etiology of this disease, including, for example, auto-reactive responses to self-antigens such as elastin, may play a role in COPD, the use of AARS polypeptides to desensitize immune cells to these antigens may reduce pulmonary inflammation.

As noted above, certain embodiments relate to the use of AARS polypeptides to desensitize immune cells to selected antigens, including self antigens and foreign antigens, irritants, allergens, or infectious agents related to pulmonary inflammation. By desensitizing these immune cells to a selected antigen, AARS polypeptides may reduce the migration or recruitment of these cells to the lungs, and thereby reduce inflammation. Examples of immune cells include lymphocytes, monocytes, macrophages, dendritic cells, and granulocytes, such as neutrophils, eosinophils, and basophils. Examples of antigens include, without limitation, smoke such as cigarette smoke, air pollution, fumes such as the fumes from welding, dust, including silica dust and workplace dust such as those found in coal mining and gold mining, chemicals such as cadmium and isocyanates. Also included are known allergens and infectious agents, such as bacterial and viral or antigens, including lipopolysaccharide (LPS), which may exacerbate COPD in sensitive individuals.

In addition to others described herein, examples of self-antigens include, without limitation, receptor ligands, chemoattractants, and signaling molecules. In certain embodiments, the response to the antigen or self-antigen signals via a CXCR-2 receptor. Without wishing to be bound by any one theory, certain AARS polypeptides may bind their putative receptor on the surface of neutrophils, such as the CXCR2 receptor, which then results in the desensitization of the receptor (i.e., the receptor is internalized and no longer be present at the cell surface). In these and similar instances, there then exists a population of circulating neutrophils that no longer respond to CXCR-2 ligands, such as IL-8. Since IL-8 is produced as a result of cigarette smoke in COPD, for example, the densitization of certain neutrophils to CXCR-2 ligands such as IL-8 reduces their migration to the lung, and thereby reduces the inflammation associated with COPD, especially that caused by cigarette smoke.

Complications or associated symptoms of COPD may include increased risk of respiratory infections, high blood pressure, heart problems (e.g., heart attacks, arrhythmias, cor pulmonale), lung cancer (smokers with chronic bronchitis are at a higher risk of developing lung cancer than are smokers who don't have chronic bronchitis), pneumonia, pneumothorax, and depression, among others known in the art. Further examples include cough that produces mucus and may be streaked with blood, fatigue, frequent respiratory infections, headaches, shortness of breath (dyspnea) that worsens with mild activity, swelling of the ankles, feet, or legs, which affects both sides of the body, and wheezing. AARS polypeptides may be used to reduce or manage the complications or symptoms associated with COPD or other pulmonary conditions related to inflammation.

Subjects with COPD may be identified according to routine diagnostic techniques known in the art. For instance, pulmonary function tests, such as spirometry, measure how much air the lungs can hold and how fast an individual can blow the air out of their lungs. Spirometry can detect COPD before the appearance of symptoms, and can also be used to track disease progression and monitor treatment. In addition, chest X-rays show emphysema, one of the main causes of COPD, and may also rule out other lung problems or heart failure. In addition, arterial blood gas analysis measures how effectively the lungs bring oxygen into the blood and remove carbon dioxide, providing an indication of COPD. Sputum examination, i.e., the analysis of the cells in the sputum, can identify the cause of certain lung problems and help rule out certain lung cancers. Also, computerized tomography (CT) scan produces highly-detailed images of the internal organs, which can help detect emphysema, and, thus, COPD.

As elsewhere herein, the amount of AARS polypeptide administered to a subject with COPD (or at risk for COPD) will depend on the characteristics of that subject, such as general health, age, sex, body weight, and tolerance to drugs, as well as the degree, severity, and type of reaction to the polypeptide. For instance, in desensitizing immune cells such as circulating neutrophils, multiple administrations may be utilized (1, 2, 3, 4, 5, 6, 7, 8, 9, 10, etc), typically at a defined frequency (number of administrations per day, per week, per month, etc).

Also included are combination therapies. For instance, one or more AARS polypeptides can be utilized in combination with other treatments for pulmonary inflammation or COPD. Examples of such treatments included, without limitation, lifestyle changes, such as quitting or reducing smoking or other exposure to lung irritants, lung rehabilitation, the use of bronchodilators (e.g., ipratropium, tiotropium, salmeterol, formoterol), steroids such as corticosteroids, antibiotics, metered-dose inhalers (MDIs) and dry powder inhalers (DPIs), nebulizers, replacement gene therapy for alpha-1-antitrypsin deficiency, oxygen therapy, and surgery, including bullectomy, lung volume reduction surgery, and lung transplant.

Certain embodiments relate to reducing inflammatory responses and conditions associated the gastrointestinal system, including inflammation, infections, and cancer associated with the mouth, esophagus, stomach, small intestines, large intestines, and rectum. "Gastrointestinal inflammation" as used herein refers to inflammation of a mucosal layer of the gastrointestinal tract, and encompasses acute and chronic inflammatory conditions. Acute inflammation is generally characterized by a short time of onset and infiltration or influx of neutrophils. Chronic inflammation is generally characterized by a relatively longer period of onset and infiltration or influx of mononuclear cells. Chronic inflammation can also typically characterized by periods of spontaneous remission and spontaneous occurrence. "Mucosal layer of the gastrointestinal tract" is meant to include mucosa of the bowel (including the small intestine and large intestine), rectum, stomach (gastric) lining, oral cavity, and the like.

"Chronic gastrointestinal inflammation" refers to inflammation of the mucosal of the gastrointestinal tract that is characterized by a relatively longer period of onset, is long-lasting (e.g., from several days, weeks, months, or years and up to the life of the subject), and is often associated with infiltration or influx of mononuclear cells, and can be further associated with periods of spontaneous remission and spontaneous occurrence. "Chronic gastrointestinal inflammatory conditions" (also referred to as "chronic gastrointestinal inflammatory diseases") having such chronic inflammation include, but are not limited to, inflammatory bowel disease (IBD), colitis induced by environmental insults (e.g., gastrointestinal inflammation associated with a therapeutic regimen, such as chemotherapy, radiation therapy, and the like), colitis in conditions such as chronic granulomatous disease (see, e.g., Schappi et al., *Arch Dis Child.* 84:147-151, 2001), celiac disease, celiac sprue (i.e., a heritable disease in which the intestinal lining is inflamed in response to the ingestion of a protein known as gluten), food allergies, gastritis, infectious gastritis or enterocolitis (e.g., *Helicobacter pylori*-infected chronic active gastritis) and other forms of gastrointestinal inflammation caused by an infectious agent, and other like conditions.

As used herein, "inflammatory bowel disease" or "IBD" refers to any of a variety of diseases characterized by inflammation of all or part of the intestines. Examples of inflammatory bowel disease include, but are not limited to, Crohn's disease and ulcerative colitis. The term IBD includes pseudomembranous colitis, hemorrhagic colitis, hemolytic-uremic syndrome colitis, collagenous colitis, ischemic colitis, radiation colitis, drug and chemically induced colitis, diversion colitis, ulcerative colitis, irritable bowel syndrome, irritable colon syndrome and Crohn's disease; and within Crohn's disease all the subtypes including active, refractory, and fistulizing and Crohn's disease. Hence, AARS polypeptides may be employed to treat or manage any one or more of these conditions.

Certain embodiments relate to reducing inflammatory responses and conditions associated with the vascular system, or vascular inflammation, such as inflammation associated with the blood vessels and the heart. Examples of vascular system associated inflammatory conditions include, without limitation, myocarditis, pericarditis, occlusive disease, atherosclerosis, myocardial infarction, thrombosis, Wegener's granulomatosis, Takayasu's arteritis, Kawasaki syndrome, anti-factor VIII autoimmune disease, necrotizing small vessel vasculitis, microscopic polyangiitis, Churg and Strauss syndrome, pauci-immune focal necrotizing glomerulonephritis, crescentic glomerulonephritis, antiphospholipid syndrome, antibody induced heart failure, thrombocytopenic purpura, autoimmune hemolytic anemia, cardiac autoimmunity in Chagas' disease, and anti-helper T lymphocyte autoimmunity. Also included are endocarditis, or infection of the heart valves with spread of small clusters of bacteria through the bloodstream, phlebitis or vasculitis, inflammation of one or more veins, and thrombophlebitis, vein inflammation related to a thrombus. Thrombophlebitis may occur repeatedly in different locations, and is then referred to as thrombophlebitis migrans, or migrating thrombophlebitis. Phlebitis may associate with a variety of causes, such as bacterial infection, exposure to chemical agents, such as irritating or vesicant solutions, physical trauma from skin puncture such as movement of a cannula into the vein during insertion, medications such as Celebrex, Olanzepine, antidepressants, and others, and alcohol abuse. Certain embodiments may relate to treating or managing heart inflammation caused by any one or more of acute rheumatic fever, congenital toxoplasmosis, enterovirus antenatal infection, lyme disease, and rheumatic fever.

Certain embodiments relate to reducing inflammatory responses and conditions associated with the liver or gallbladder, including acute and chronic liver inflammation, and acute and chronic cholecystis. Examples of liver or gallbladder associated inflammatory conditions include, without limitation, auto-immune hepatitis, viral hepatitis (e.g., Hepatitis A virus, Hepatitis B virus, Hepatitis C virus, Hepatitis D virus, Hepatitis E virus, mononucleosis, rubella, Epstein-Barr virus, and cytomegalovirus), other causes of hepatitis such as severe bacterial infection, ameobic infections, medicines (e.g., agomelatine, allopurinol, amitryptyline, amiodarone, asathioprine, paracetamol, halothane, ibuprofen, indomethacin, isoniazid, rifampicin, pyrazinamide, ketoconazole, loratadine, methotrexate, methyldopa, minocycline, nifedipine, nitrofurantoin, phenytoin, valproic acid, troglitazone, zidovudine), toxins (e.g., alcohol, fungal toxins), and metabolic disorders (e.g., Wilson's disease, a disorder of the body's copper metabolism, haemochromatosis, disorder of the body's iron metabolism, non-alcoholic steatohepatitis, alpha 1-antitrypsin deficiency). Additional examples include non-alcoholic fatty liver disease, cirrhosis such as primary biliary cirrhosis, obstructive jaundice, ischemic hepatitis, and gall bladder disease.

Certain embodiments relate to reducing inflammatory responses and conditions associated with the lymphatic/immune system. Examples of lymphatic/immune system associated inflammatory conditions include, without limitation, auto-immune diseases, such as Chagas disease, chronic obstructive pulmonary disorder (COPD), Crohn's disease, dermatomyositis, diabetes mellitus type I, endometriosis, Goodpasture's syndrome, Graves' disease, Guillain-Barre syndrome, Hachimoto's disease, hidradenitis suppurativa, Kawasaki disease, IgA nephropathy, idiopathic thrombocytopenia purpura, interstitial cystitis, lupus erythematosus, mixed connective tissue disease, morphea, myasthenia gravis, narcolepsy, neuromyotonia, pemphigus vulgaris, pernicous anemia, psoriasis, psoriatic arthritis, poliomyositis, primary biliary cirrhosis, rheumatoid arthritis, schizophrenia, scleroderma, Sjogren's syndrome, stiff person syndrome, temporal arteritis, ulcerative colitis, vitiligo, and Wegener's granulomatosis, in addition to autoimmune hemolytic anemia, and various lymphadenopathies.

Also included are immune-related inflammatory conditions associated with the transplantation of a graft, tissue, cell or organ, such as graft rejection, chronic graft rejection, subacute graft rejection, hyperacute graft rejection, acute graft rejection, and graft versus host disease. In certain embodiments, AARS polypeptides can be administered to a transplant donor before or during tissue removal. In certain embodiments, AARS polypeptides can be administered to a transplant recipient before, during, and/or after transplant therapy to reduce inflammation-related complications of transplant therapy. Examples of transplant therapies include bone marrow, stem cell, peripheral blood, liver, lung, heart, skin, and kidney, among others known in the art. Additional examples include inflammatory conditions associated with allergies, such as asthma, hives, urticaria, pollen allergy, dust mite allergy, venom allergy, cosmetics allergy, latex allergy, chemical allergy, drug allergy, insect bite allergy, animal dander allergy, stinging plant allergy, poison ivy allergy and food allergy.

Certain embodiments relate to reducing inflammatory responses and conditions associated with the uro-genital system. Examples of uro-genital system associated inflammatory conditions include, without limitation, inflammations, infections or cancers of the ureter, bladder, urethra, cervix, Fallopian tubes, ovaries, uterus, womb, vulva, prostate, bulbourethral glands, epidiymis, prostate, seminal vesicles, testicles, or kidneys. Also included are auto-immune interstitial nephritis, renal abscess (intrarenal or extrarenal), acute prostatitis, hematuria, urethritis (e.g., *Chlamydia* and other sexually transmitted diseases), pelvic inflammatory disease (PID), and prostatic abscess. Also included is nephritis associated with one or more of glomerulonephritis, lupus nephritis, nephropathy, gout, poisons or chemicals (e.g., ether, thallium sulfate), certain medications (e.g., piroxicam, candyl, feldene gel, fensaid, pirox), Herrmann syndrome, yellow fever, immune complex diseases, typhoid fever, urethral stricture, renal tuberculosism, and post-streptococcal glomerulonephritis.

Certain embodiments relate to reducing inflammatory responses and conditions associated with the musculoskeletal system. Examples of musculoskeletal system associated inflammatory conditions include, without limitation, arthritis such as rheumatoid arthritis and psoriatic arthritis, ankylosing spondylitis, auto-immune myositis, primary Sjogren's syndrome, smooth muscle auto-immune disease, myositis, polymyositis, tendinitis, ligament inflammation, cartilage inflammation, joint inflammation, synovial inflammation, carpal tunnel syndrome, chronic muscle inflammation, and bone inflammation, including bone inflammation associated with osteoporosis and osteoarthritis. Also included are Tietze's syndrome, a benign, painful, nonsuppurative localized swelling of the costosternal, sternoclavicular, or costochondral joints, costochondritis, sternalis syndrome, xiphoidalgia, spontaneous sternoclavicular subluxation, sternocostoclavicular hyperostosis, fibromyalgia, shoulder tendinitis or bursitis, gouty arthritis, polymyalgia rheumatica, lupus erythematosus, bone spurs, and fractures such as stress fractures.

Certain embodiments relate to reducing inflammatory responses and conditions associated with the endocrine system. Examples of endocrine system associated inflammatory conditions include, without limitation, inflammation, infection, or cancer associated with the hypothalamus, pituitary, thyroid, pancreas, or adrenal glands, glandular diseases such as pancreatic disease, diabetes such as Type I diabetes, thyroid disease, Graves' disease, thyroiditis, spontaneous autoimmune thyroiditis, Hashimoto's thyroiditis, idiopathic myxedema, ovarian autoimmunity, autoimmune anti-sperm infertility, autoimmune prostatitis and Type I autoimmune polyglandular syndrome.

Certain embodiments relate to reducing inflammatory responses and conditions associated with adipose tissues, an active participant in regulating physiologic and pathologic processes, including immunity and inflammation. Macrophages are components of adipose tissue and actively participate in its activities. Furthermore, cross-talk between lymphocytes and adipocytes can lead to immune regulation. Adipose tissue produces and releases a variety of pro-inflammatory and anti-inflammatory factors, including the adipokines leptin, adiponectin, resistin, and visfatin, as well as cytokines and chemokines, such as TNF-alpha, IL-6, monocyte chemoattractant protein 1, and others. Proinflammatory molecules produced by adipose tissue have been implicated as active participants in the development of insulin resistance and the increased risk of cardiovascular disease associated with obesity. In contrast, reduced leptin levels may predispose to increased susceptibility to infection caused by reduced T-cell responses in malnourished individuals. Altered adipokine levels have been observed in a variety of inflammatory conditions (see, e.g., Fantuzzi, *J Allergy Clin Immunol.* 115:911-19, 2005; and Berg et al., *Circulation Research.* 96:939, 2005).

AARS polypeptides may also be employed to treat or manage inflammation associated with hypersensitivity. Examples of such conditions include type I hypersensitivity, type II hypersensitivity, type III hypersensitivity, type IV hypersensitivity, immediate hypersensitivity, antibody mediated hypersensitivity, immune complex mediated hypersensitivity, T-lymphocyte mediated hypersensitivity, and delayed type hypersensitivity.

AARS polypeptides may also be employed to treat or manage auto-inflammatory conditions. Examples of auto-inflammatory conditions include familial Mediterranean fever, TNF receptor associated periodic syndrome (TRAPS), Hyper-IgD syndrome (HIDS), CIAS1-related diseases such as Muckle-Wells syndrome, familial cold auto-inflammatory syndrome, and neonatal onset multisystem inflammatory disease, PAPA syndrome (pyogenic sterile arthritis, pyoderma gangrenosum, acne), and Blau syndrome.

AARS polypeptides may be employed to treat or manage inflammation associated with a variety of cancers. Examples of such cancers include, without limitation, prostate cancer, breast cancer, colon cancer, rectal cancer, lung cancer, ovarian cancer, testicular cancer, stomach cancer, bladder cancer, pancreatic cancer, liver cancer, kidney cancer, brain cancer, melanoma, non-melanoma skin cancer, bone cancer, lymphoma, leukemia, thyroid cancer, endometrial cancer, multiple myeloma, acute myeloid leukemia, neuroblastoma, glioblastoma, and non-Hodgkin's lymphoma.

As noted above, certain embodiments may employ AARS polypeptides to modulate systemic inflammation, such as to reduce or manage systemic inflammation. In certain embodiments, systemic inflammation may by associated with systemic inflammatory response syndrome (SIRS), a whole-body inflammatory condition with a variety of potential causes. SIRS may be characterized or identified according to routine diagnostic techniques. As one non-limiting example, SIRS may be identified by the presence of two or more of the following: (i) a body temperature that is less than 36° C. or greater than 38° C., (ii) a heart rate that is greater than 90 beats per minute, (iii) tachypnea (high respiratory rate), with greater than 20 breaths per minute; or, an arterial partial pressure of carbon dioxide less than 4.3 kPa (32 mmHg), and (iv) white blood cell count less than 4000 cells/mm$^3$ ($4\times10^9$ cells/L) or greater than 12,000 cells/mm$^3$ ($12\times10^9$ cells/L); or the presence of greater than 10% immature neutrophils (band forms).

SIRS is broadly classified as either infectious or noninfectious. Most generally, infectious SIRS is associated with sepsis, a whole-body inflammatory state combined with a known or suspected infection, which includes bacteremia, viremia, parasitemia, and toxic shock syndrome. Sepsis may be associated with a wide variety of infectious agents, including, without limitation, bacteria such as *Streptococcus agalactiae, Escherichia coli, Haemophilus influenzae, Listeria monocytogenes*, Coagulase-negative *Staphylococcus, Staphylococcus aureus, Klebsiella* species, *Pseudomonas aeruginosa, Enterobacter* species, *S. agalactiae, Serratia* species, *Acinetobacter* species, *Streptococcus pneumoniae, Salmonella species*, and *Neisseria meningitidis*; viruses such as rubella, cytomegalovirus, herpes simplex and the chickenpox virus; parasites such as in malarial infection (e.g., *Plasmodium falciparum*), trypanosomiasis, and filariasis; and fungi such as *Candida* species, *Aspergillus* species, *Histoplasma* species, *Cryptococcus neoformans, Coccidioides immitis, Blastomyces dermatitides*, and *Pneumocystis carinii*. In certain instances, infections in the lungs (e.g., pneumonia), bladder and kidneys (e.g., urinary tract infections), skin (e.g., cellulitis), abdomen (e.g., appendicitis), and other areas (e.g., meningitis) can spread and lead to sepsis AARS polypeptides may be used to modulate inflammation associated with any of these infectious agents, whether sepsis is present or otherwise.

Noninfectious SIRS may be associated with trauma, burns, pancreatitis, ischemia, hemorrhage, surgical complications, adrenal insufficiency, pulmonary embolism, aortic aneurysm, cardiac tamponade, anaphylaxis, and drug overdose, among others. SIRS is often complicated by the failure of one or more organs or organ system, including those described herein. Specific examples include acute lung injury, acute kidney injury, shock, and multiple organ dysfunction syndrome, among others. Typically, SIRS is treated by focusing on the underlying problem (e.g., adequate fluid replacement for hypovolemia, IVF/NPO for pancreatitis, epinephrine/steroids/benadryl for anaphylaxis). In certain instances, selenium, glutamine, and eicosapentaenoic acid have shown effectiveness in improving symptoms of SIRS, and antioxidants such as vitamin E may also be helpful. Hence, AARS polypeptides may be used to treat or manage SIRS and the complications of SIRS, alone or in combination with other therapies.

Systemic inflammation may also be associated with "cytokine storm," a dangerous immune reaction caused by a positive feedback loop between cytokines and immune cells, resulting in highly elevated levels of various cytokines. In certain instances, cytokine storm (hypercytokinemia) includes the systemic release of numerous known inflammatory mediators such as cytokines, oxygen free radicals, and coagulation factors). Included are elevated levels of pro-inflammatory cytokines such as TNF-alpha, IL-1, and IL-6, and anti-inflammatory cytokines such as IL-10 and IL-1 receptor antagonist. Cytokine storms can occur in a number of infectious and noninfectious diseases including graft versus host disease (GVHD), acute respiratory distress syndrome (ARDS), sepsis, avian influenza, smallpox, and SIRS. Cytokine storm may also be induced by certain medications. Treatment includes OX40 IG, which reduces T-cell responses, ACE inhibitors, Angiotensin II receptor blockers, corticosteroids, gemfibrozil, free radical scavengers, and TNF-α blockers. Accordingly, AARS polypeptides may be employed to treat or manage cytokine storm, alone or in combination with other therapies.

Certain embodiments may employ AARS polypeptides to reduce any one or more of granulomatous inflammation, fibrinous inflammation, purulent inflammation, serous inflammation, or ulcerative inflammation. Granulomatous inflammation is characterized by the formation of granulomas, typically resulting from a response to infectious agents such as tuberculosis, leprosy, and syphilis. Fibrinous inflammation results from a large increase in vascular permeability, which allows fibrin to pass through the blood vessels. If an appropriate pro-coagulative stimulus is present, such as a cancer cell, a fibrinous exudate is deposited. This process is commonly seen in serous cavities, where the conversion of fibrinous exudate into a scar can occur between serous membranes, limiting their function. Purulent inflammation results from the formation of a large amount of pus, which consists of neutrophils, dead cells, and fluid. Infection by pyogenic bacteria such as staphylococci is characteristic of this kind of inflammation. Large, localized collections of pus enclosed by surrounding tissues are called abscesses. Serous inflammation is characterized by the copious effusion of non-viscous serous fluid, commonly produced by mesothelial cells of serous membranes, but may also be derived from blood plasma. Examples of this type of inflammation include skin blisters. Ulcerative inflammation, which typically occurs near an epithelium, results in the necrotic loss of tissue from the surface, thereby exposing lower layers of tissue. The subsequent excavation of the epithelium is known as an ulcer.

AARS polypeptides may also be employed in the treatment of physical injuries or wounds. Examples abrasions, bruises, cuts, puncture wounds, lacerations, impact wounds, concussions, contusions, thermal burns, frostbite, chemical burns, sunburns, gangrene, necrosis, desiccations, radiation burns, radioactivity burns, smoke inhalation, torn muscles, pulled muscles, torn tendons, pulled tendons, pulled ligaments, torn ligaments, hyperextensions, torn cartilage, bone fractures, pinched nerves, ulcers, and gunshot or other traumatic wounds.

AARS polypeptides may also be employed to treat or manage idiopathic inflammation or inflammation of unknown etiology. Also included are combination therapies, in which one or more AARS polypeptides are administered or utilized in combination with one or more other therapies for any of the inflammatory diseases or conditions described herein, including those therapies that are commonly available and known in the art. Examples of combination therapies include the use of standard anti-inflammatory agents such as non-steroidal anti-inflammatory drugs (NSAIDs), immune selective anti-inflammatory derivatives (ImSAIDs), and steroids (e.g., corticosteroids), anti-infectives such as antibiotics and anti-viral agents, anti-oxidants, cytokines, chemotherapeutic agents and other anti-cancer therapies, and immunosuppressive therapies.

Criteria for assessing the signs and symptoms of inflammatory and other conditions, including for purposes of making differential diagnosis and also for monitoring treatments such as determining whether a therapeutically effective dose has been administered in the course of treatment, e.g., by determining improvement according to accepted clinical criteria, will be apparent to those skilled in the art and are exemplified by the teachings of e.g., Berkow et al., eds., The Merck Manual, 16$^{th}$ edition, Merck and Co., Rahway, N.J., 1992; Goodman et al., eds., Goodman and Gilman's The Pharmacological Basis of Therapeutics, 10$^{th}$ edition, Pergamon Press, Inc., Elmsford, N.Y., (2001); Avery's Drug Treatment: Principles and Practice of Clinical Pharmacology and Therapeutics, 3rd edition, ADIS Press, Ltd., Williams and Wilkins, Baltimore, Md. (1987); Ebadi, Pharmacology, Little, Brown and Co., Boston, (1985); Osolci al., eds., Remington's Pharmaceutical Sciences, 18$^{th}$ edition, Mack Publishing Co., Easton, Pa. (1990); Katzung, Basic and Clinical Pharmacology, Appleton and Lange, Norwalk, Conn. (1992).

Certain embodiments may employ AARS polypeptides to increase inflammation. For instance, depending on the needs of the subject, certain embodiments may increase acute inflammation or increase acute inflammatory responses or both. Certain embodiments may increase chronic inflammation or chronic inflammatory responses or both. Certain embodiments may increase both acute and chronic inflammation. Certain embodiments may increase local or systemic inflammation or both.

In certain embodiments, AARS polypeptides may be used to treat or manage immunodeficiencies, including primary immunodeficiencies and secondary immunodeficiencies, in which the body may not mount an adequate inflammatory response. Examples of primary immunodeficiencies include various autosomal recessive and X-linked genetic conditions such as T-cell and B-cell immunodeficiencies, including combined T-cell and B-cell immunodeficiencies, antibody deficiencies, well-defined syndromes, immune dysregulation diseases, phagocyte disorders, innate immunity disorders, and complement deficiencies.

Examples of T-cell and B-cell immunodeficiencies include T−/B+ deficiencies such as γc deficiency, JAK3 deficiency, interleukin 7 receptor chain a deficiency, CD45 deficiency, CD3δ/CD3ε deficiency; and T−/B− deficiencies such as RAG 1/2 deficiency, DCLRE1C deficiency, adenosine deaminase (ADA) deficiency, reticular dysgenesis. Additional examples include Omenn syndrome, DNA ligase type IV deficiency, CD40 ligand deficiency, CD40 deficiency, purine nucleoside phosphorylase (PNP) deficiency, MHC class II deficiency, CD3γ deficiency, CD8 deficiency, ZAP-70 deficiency, TAP-1/2 deficiency, and winged helix deficiency.

Examples of antibody deficiencies include X-linked agammaglobulinemia (btk deficiency, or Bruton's agammaglobulinemia), μ-Heavy chain deficiency, 1-5 deficiency, Igα deficiency, BLNK deficiency, thymoma with immunodeficiency, common variable immunodeficiency (CVID), ICOS deficiency, CD19 deficiency, TACI (TNFRSF13B) deficiency, and BAFF receptor deficiency. Additional examples include AID deficiency, UNG deficiency, heavy chain deletions, kappa chain deficiency, isolated IgG subclass deficiency, IgA with IgG subclass deficiency, selective immunoglobulin A deficiency, and transient hypogammaglobulinemia of infancy (THI).

Examples of "well-defined syndromes" include Wiskott-Aldrich syndrome, ataxia telangiectasia, ataxia-like syndrome, Nijmegen breakage syndrome, Bloom syndrome, DiGeorge syndrome, immuno-osseous dysplasias such as cartilage-hair hypoplasia, Schimke syndrome, Hermansky-Pudlak syndrome type 2, Hyper-IgE syndrome, chronic mucocutaneous candidiasis.

Examples of immune dysregulation diseases include immunodeficiency with hypopigmentation or albinism such as Chediak-Higashi syndrome and Griscelli syndrome type 2, familial hemophagocytic lymphohistiocytosis such as perforin deficiency, MUNC13D deficiency, and syntaxin 11 deficiency, X-linked lymphoproliferative syndrome, autoimmune lymphoproliferative syndrome such as type 1a (CD95 defects), type 1b (Fas ligand defects), type 2a (CASP10 defects), and type 2b (CASP8 defects), autoimmune polyendocrinopathy with candidiasis and ectodermal dystrophy, and immunodysregulation polyendocrinopathy enteropathy X-linked syndrome. Additionally, diseases affecting the bone marrow may result in abnormal or few leukocytes, such as leukopenia. Leukopenia can be induced by certain infections and diseases, including viral infection, *Rickettsia* infection, some protozoa, tuberculosis, and certain cancers Examples of phagocyte disorders include severe congenital neutropenia such as ELA2 deficiency (e.g., with myelodysplasia), GFI1 deficiency (with T/B lymphopenia) or G-CSFR deficiency (G-CSF-unresponsive), Kostmann syndrome, cyclic neutropenia, X-linked neutropenia/myelodysplasia, leukocyte adhesion deficiency types 1, 2 and 3, RAC2 deficiency, β-actin deficiency, localized juvenile periodontitis, Papillon-Lefevre syndrome, specific granule deficiency, Shwachman-Diamond syndrome, chronic granulomatous disease, including X-linked and autosomal forms, neutrophil glucose-6-phosphate dehydrogenase deficiency, IL-12 and IL-23 β1 chain deficiency, IL-12p40 deficiency, interferon γ receptor 1 deficiency, interferon γ receptor 2 deficiency, and STAT1 deficiency.

Examples of innate immunity deficiencies include hypohidrotic ectodermal dysplasia such as NEMO deficiency and IKBA deficiency, IRAK-4 deficiency, WHIM syndrome (warts, hypogammaglobulinaemia, infections, myleokathexis), and epidermodysplasia verruciformis. Examples of complement deficiencies and exemplary associated conditions include C1q deficiency (e.g., lupus-like syndrome, rheumatoid disease, infections), C1r deficiency, C4 deficiency, C2 deficiency (e.g., lupus-like syndrome, vasculitis, polymyositis, pyogenic infections), C3 deficiency (e.g., recurrent pyogenic infections), C5 deficiency (e.g., neisserial infections), C6 deficiency, C7 deficiency (e.g., vasculitis), C8a and C8b deficiency, C9 deficiency (e.g., neisserial infections), C1-inhibitor deficiency (e.g., hereditary angioedema), Factor I deficiency (pyogenic infections), Factor H deficiency (e.g., haemolytic-uraemic syndrome, membranoproliferative glomerulonephritis), Factor D deficiency (e.g., neisserial infections), Properdin deficiency (e.g., neisserial infections), MBP deficiency (e.g., pyogenic infections), and MASP2 deficiency.

Primary immune deficiencies can be diagnosed according to routine techniques in the art. Exemplary diagnostic tests include, without limitation, performing counts of the different types of mononuclear cells in the blood (e.g., lymphocytes and monocytes, including lymphocytes, different groups of B lymphocytes such as CD19+, CD20+, and CD21+ lymphocytes, natural killer cells, and monocytes positive for CD15+), measuring the presence of activation markers (e.g., HLA-DR, CD25, CD80), performing tests for T cell function such as skin tests for delayed-type hypersensitivity, cell responses to mitogens and allogeneic cells, cytokine production by cells, performing tests for B cell function such as by identifying antibodies to routine immunizations and commonly acquired infections and by quantifying IgG subclasses, and performing tests or phagocyte function, such as by measuring the reduction of nitro blue tetrazolium chloride, and performing assays of chemotaxis and bactericidal activity. AARS polypeptides may therefore be used to stimulate or maintain acute inflammation or acute inflammatory responses in subjects with a primary immunodeficiency, as described herein and known in the art.

Examples of causes of secondary immunodeficiencies include malnutrition, aging, and medications (e.g., chemotherapy, disease-modifying anti-rheumatic drugs, immunosuppressive drugs after organ transplants, glucocorticoids). Additional causes include various cancers, including cancers of the bone marrow and blood cells (e.g., leukemia, lymphoma, multiple myeloma), and certain chronic infections, such as acquired immunodeficiency syndrome (AIDS), caused by the human immunodeficiency virus (HIV). AARS polypeptides may be used to stimulate or maintain acute inflammation or acute inflammatory responses in subjects with an immunodeficiency, as described herein and known in the art. AARS polypeptides may also be used to stimulate or maintain chronic inflammation or chronic inflammatory responses in subjects with a secondary immunodeficiency, as described herein and known in the art.

In certain embodiments, for example, methods are provided for modulating therapeutically relevant cellular activities including, but not limited to, cellular metabolism, cell differentiation, cell proliferation, cell death, cell mobilization, cell migration, gene transcription, mRNA translation, cell impedance, cytokine production, and the like, comprising contacting a cell with an AARS composition as described herein. In certain embodiments, the AARS polypeptides (e.g., QRS polypeptides) or compositions thereof modulate the cytokine response of cells to immune-stimulating antigens, including autoimmune disorder-related antigens and foreign antigens such as lipopolysaccharide (LPS). In certain embodiments, the AARS polypeptides (e.g., QRS polypeptides) or compositions thereof inhibit the cytokine response of cells to immune-stimulating antigens, as above. In certain embodiments, the cells are peripheral blood mononuclear cells (PBMCs).

In certain particular embodiments, AARS polypeptides (e.g., QRS polypeptides) or compositions thereof are provided for inhibiting TNF-α production or secretion in mammalian cells, such as PBMCs, either in vivo or in vitro. In certain particular embodiments, QRS polypeptides or compositions thereof are provided for inhibiting IL-12 production or secretion in mammalian cells, such as PBMCs, either in vivo or in vitro. In certain embodiments, QRS polypeptides inhibit the TNF-α or IL-12-based secretion response of cells to immune-stimulating antigens, including autoimmune disorder-related antigens and foreign antigens such as lipopolysaccharide (LPS). Accordingly, the AARS polypeptides (e.g., QRS polypeptides) may be employed in treating essentially any cell or tissue or subject that would benefit from modulation of one or more such activities.

The AARS polypeptides (e.g., QRS polypeptides) and compositions may also be used in any of a number of therapeutic contexts including, for example, those relating to the treatment or prevention of neoplastic diseases, immune system diseases (e.g., autoimmune diseases and inflammation), infectious diseases, metabolic diseases, neuronal/neurological diseases, muscular/cardiovascular diseases, diseases associated with aberrant hematopoiesis, diseases associated with aberrant angiogenesis, diseases associated with aberrant cell survival, and others.

For example, in certain illustrative embodiments, the AARS polypeptides (e.g., QRS polypeptides) and compositions of the invention may be used to modulate angiogenesis, e.g., via modulation of endothelial cell proliferation and/or signaling. Endothelial cell proliferation and/or cell signaling may be monitored using an appropriate cell line (e.g., Human microvascular endothelial lung cells (HMVEC-L) and Human umbilical vein endothelial cells (HUVEC)), and using an appropriate assay (e.g., endothelial cell migration assays, endothelial cell proliferation assays, tube-forming assays, matrigel plug assays, etc.), many of which are known and available in the art.

Therefore, in related embodiments, the compositions of the invention may be employed in the treatment of essentially any cell or tissue or subject that would benefit from modulation of angiogenesis. For example, in some embodiments, a cell or tissue or subject experiencing or susceptible to angiogenesis (e.g., an angiogenic condition) may be contacted with a suitable composition of the invention to inhibit an angiogenic condition. In other embodiments, a cell or tissue experiencing or susceptible to insufficient angiogenesis (e.g., an angiostatic condition) may be contacted with an appropriate composition of the invention in order to interfere with angiostatic activity and/or promote angiogenesis.

Illustrative examples of angiogenic conditions include, but are not limited to, age-related macular degeneration (AMD), cancer (both solid and hematologic), developmental abnormalities (organogenesis), diabetic blindness, endometriosis, ocular neovascularization, psoriasis, rheumatoid arthritis (RA), and skin disclolorations (e.g., hemangioma, nevus flammeus or nevus simplex). Examples of anti-angiogenic conditions include, but are not limited to, cardiovascular disease, restenosis, tissue damage after reperfusion of ischemic tissue or cardiac failure, chronic inflammation and wound healing.

The compositions of the invention may also be useful as immunomodulators for treating anti- or pro-inflammatory indications by modulating the cells that mediate, either directly or indirectly, autoimmune and/or inflammatory disease, conditions and disorders. The utility of the compositions of the invention as immunomodulators can be monitored using any of a number of known and available techniques in the art including, for example, migration assays (e.g., using leukocytes or lymphocytes), cytokine production assays (e.g., TNF-α, IL-12), or cell viability assays (e.g., using B-cells, T-cells, monocytes or NK cells).

Illustrative immune system diseases, disorders or conditions that may be treated according to the present invention include, but are not limited to, primary immunodeficiencies, immune-mediated thrombocytopenia, Kawasaki syndrome, bone marrow transplant (for example, recent bone marrow transplant in adults or children), chronic B cell lymphocytic leukemia, HIV infection (for example, adult or pediatric HIV infection), chronic inflammatory demyelinating polyneuropathy, post-transfusion purpura, and the like.

Additionally, further diseases, disorders and conditions include Guillain-Barre syndrome, anemia (for example, anemia associated with parvovirus B19, patients with stable multiple myeloma who are at high risk for infection (for example, recurrent infection), autoimmune hemolytic anemia (for example, warm-type autoimmune hemolytic anemia), thrombocytopenia (for example, neonatal thrombocytopenia), and immune-mediated neutropenia), transplantation (for example, cytomegalovirus (CMV)-negative recipients of CMV-positive organs), hypogammaglobulinemia (for example, hypogammaglobulinemic neonates with risk factor for infection or morbidity), epilepsy (for example, intractable epilepsy), systemic vasculitic syndromes, myasthenia gravis (for example, decompensation in myasthenia gravis), dermatomyositis, and polymyositis.

Further autoimmune diseases, disorders and conditions include but are not limited to, autoimmune hemolytic anemia, autoimmune neonatal thrombocytopenia, idiopathic thrombocytopenia purpura, autoimmunocytopenia, hemolytic anemia, antiphospholipid syndrome, dermatitis, allergic encephalomyelitis, myocarditis, relapsing polychondritis, rheumatic heart disease, glomerulonephritis (for example, IgA nephropathy), multiple sclerosis, neuritis, uveitis ophthalmia, polyendocrinopathies, purpura (for example, Henloch-Scoenlein purpura), Reiter's disease, stiff-man syndrome, autoimmune pulmonary inflammation, Guillain-Barre Syndrome, insulin dependent diabetes mellitus, and autoimmune inflammatory eye disease.

Additional autoimmune diseases, disorders or conditions include, but are not limited to, autoimmune thyroiditis; hypothyroidism, including Hashimoto's thyroiditis and thyroiditis characterized, for example, by cell-mediated and humoral thyroid cytotoxicity; SLE (which is often characterized, for example, by circulating and locally generated immune complexes); Goodpasture's syndrome (which is often characterized, for example, by anti-basement membrane antibodies); pemphigus (which is often characterized, for example, by epidermal acantholytic antibodies); receptor autoimmunities such as, for example, Graves' disease (which is often characterized, for example, by antibodies to a thyroid stimulating hormone receptor; myasthenia gravis, which is often characterized, for example, by acetylcholine receptor antibodies); insulin resistance (which is often characterized, for example, by insulin receptor antibodies); autoimmune hemolytic anemia (which is often characterized, for example, by phagocytosis of antibody-sensitized red blood cells); and autoimmune thrombocytopenic purpura (which is often characterized, for example, by phagocytosis of antibody-sensitized platelets).

Further autoimmune diseases, disorders or conditions include, but are not limited to, rheumatoid arthritis (which is often characterized, for example, by immune complexes in joints); scleroderma with anti-collagen antibodies (which is often characterized, for example, by nucleolar and other nuclear antibodies); mixed connective tissue disease, (which is often characterized, for example, by antibodies to extractable nuclear antigens, for example, ribonucleoprotein); polymyositis/dermatomyositis (which is often characterized, for example, by nonhistone anti-nuclear antibodies); pernicious anemia (which is often characterized, for example, by antiparietal cell, antimicrosome, and anti-intrinsic factor antibodies); idiopathic Addison's disease (which is often characterized, for example, by humoral and cell-mediated adrenal cytotoxicity); infertility (which is often characterized, for example, by antispennatozoal antibodies); glomerulonephritis (which is often characterized, for example, by glomerular basement membrane antibodies or immune complexes); by primary glomerulonephritis, by IgA nephropathy; bullous pemphigoid (which is often characterized, for example, by IgG and complement in the basement membrane); Sjogren's syndrome (which is often characterized, for example, by multiple tissue antibodies and/or the specific nonhistone antinuclear antibody (SS-B)); diabetes mellitus (which is often characterized, for example, by cell-mediated and humoral islet cell antibodies); and adrenergic drug resistance, including adrenergic drug resistance with asthma or cystic fibrosis (which is often characterized, for example, by beta-adrenergic receptor antibodies).

Still further autoimmune diseases, disorders or conditions include, but are not limited to chronic active hepatitis (which is often characterized, for example by smooth muscle antibodies); primary biliary cirrhosis (which is often characterized, for example, by anti-mitochondrial antibodies); other endocrine gland failure (which is characterized, for example, by specific tissue antibodies in some cases); vitiligo (which is often characterized, for example, by anti-melanocyte antibodies); vasculitis (which is often characterized, for example, by immunoglobulin and complement in vessel walls and/or low serum complement); post-myocardial infarction conditions (which are often characterized, for example, by anti-myocardial antibodies); cardiotomy syndrome (which is often characterized, for example, by anti-myocardial antibodies); urticaria (which is often characterized, for example, by IgG and IgM antibodies to IgE); atopic dermatitis (which is often characterized, for example, by IgG and IgM antibodies to IgE); asthma (which is often characterized, for example, by IgG and IgM antibodies to IgE); inflammatory myopathies; and other inflammatory, granulomatous, degenerative, and atrophic disorders.

In other embodiments, the AARS polypeptides (e.g., QRS polypeptides) and compositions of the invention may be used to modulate cellular proliferation and/or survival and, accordingly, for treating or preventing diseases, disorders or conditions characterized by abnormalities in cellular proliferation and/or survival. For example, in certain embodiments, the QRS compositions may be used to modulate apoptosis and/or to treat diseases or conditions associated with abnormal apoptosis. Apoptosis is the term used to describe the cell signaling cascade known as programmed cell death. Various therapeutic indications exist for molecules that induce apoptosis (e.g. cancer), as well as those that inhibit apoptosis (i.e. stroke, myocardial infarction, sepsis, etc.). Apoptosis can be monitored by any of a number of available techniques known and available in the art including, for example, assays that measure fragmentation of DNA, alterations in membrane asymmetry, activation of apoptotic caspases and/or release of cytochrome C and AIF.

Illustrative diseases associated with increased cell survival, or the inhibition of apoptosis include, but are not limited to, cancers (such as follicular lymphomas, carcinomas, and hormone-dependent tumors, including, but not limited to colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostate cancer, Kaposi's sarcoma and ovarian cancer); autoimmune disorders (such as, multiple sclerosis, Sjogren's syndrome, Graves' disease, Hashimoto's thyroiditis, autoimmune diabetes, biliary cirrhosis, Behcet's disease, Crohn's disease, polymyositis, systemic lupus erythematosus and immune-related glomerulonephritis, autoimmune gastritis, autoimmune thrombocytopenic purpura, and rheumatoid arthritis) and viral infections (such as herpes viruses, pox viruses and adenoviruses), inflammation, graft vs. host disease (acute and/or chronic), acute graft rejection, and chronic graft rejection.

Further illustrative diseases or conditions associated with increased cell survival include, but are not limited to, progression and/or metastases of malignancies and related disorders such as leukemia (including acute leukemias (for example, acute lymphocytic leukemia, acute myelocytic leukemia, including myeloblastic, promyelocytic, myelomonocytic, monocytic, and erythroleukemia)) and chronic leukemias (for example, chronic myelocytic (granulocytic) leukemia and chronic lymphocytic leukemia), myelodysplastic syndrome polycythemia vera, lymphomas (for example, Hodgkin's disease and non-Hodgkin's disease), multiple myeloma, Waldenstrom's macroglobulinemia, heavy chain diseases, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Illustrative diseases associated with increased apoptosis include, but are not limited to, AIDS (such as HIV-induced nephropathy and HIV encephalitis), neurodegenerative disorders (such as Alzheimer's disease, Parkinson's disease, amyotrophic lateral sclerosis, retinitis pigmentosa, cerebellar degeneration and brain tumor or prior associated disease), autoimmune disorders such as multiple sclerosis, Sjogren's syndrome, Graves' disease, Hashimoto's thyroiditis, autoimmune diabetes, biliary cirrhosis, Behcet's disease, Crohn's disease, polymyositis, systemic lupus erythematosus, immune-related glomerulonephritis, autoimmune gastritis, thrombocytopenic purpura, and rheumatoid arthritis, myelodysplastic syndromes (such as aplastic anemia), graft vs. host disease (acute and/or chronic), ischemic injury (such as that caused by myocardial infarction, stroke and reperfusion injury), liver injury or disease (for example, hepatitis related liver injury, cirrhosis, ischemia/reperfusion injury, cholestosis (bile duct injury) and liver cancer), toxin-induced liver disease (such as that caused by alcohol), septic shock, ulcerative colitis, cachexia, and anorexia.

In still further embodiments, the compositions of the invention may be used in the treatment of neuronal/neurological diseases or disorders, illustrative examples of which include Parkinson's disease, Alzheimer's disease, Pick's disease, Creutzfeldt-Jacob disease, Huntington's chorea, alternating hemiplegia, amyotrophic lateral sclerosis, ataxia, cerebral palsy, chronic fatigue syndrome, chronic pain syndromes, congenital neurological anomalies, cranial nerve diseases, delirium, dementia, demyelinating diseases, dysautonomia, epilepsy, headaches, Huntington's disease, hydrocephalus, meningitis, movement disorders, muscle diseases, nervous system neoplasms, neurocutaneous syndromes, neurodegenerative diseases, neurotoxicity syndromes, ocular motility disorders, peripheral nervous system disorders, pituitary disorders, porencephaly, Rett syndrome, sleep disorders, spinal cord disorders, stroke, sydenham's chorea, tourette syndrome, nervous system trauma and injuries, etc.

Furthermore, additional embodiments relate to the use of the compositions of the invention in the treatment of metabolic disorders such as adrenoleukodystrophy, Krabbe's disease (globoid cell leukodystrophy), metachromatic leukodystrophy, Alexander's disease, Canavan's disease (spongiform leukodystrophy), Pelizaeus-Merzbacher disease, Cockayne's syndrome, Hurler's disease, Lowe's syndrome, Leigh's disease, Wilson's disease, Hallervorden-Spatz disease, Tay-Sachs disease, etc. The utility of the compositions of the invention in modulating metabolic processes may be monitored using any of a variety of techniques known and available in the art including, for example, assays which measure adipocyte lipogenesis or adipocyte lipolysis.

In more specific embodiments of the invention, the AARS polypeptides (e.g., QRS polypeptides) and compositions of the invention may be used to modulate cellular signaling, for example, via cell signaling proteins (e.g., Akt). Cell signaling may be monitored using any of a number of well known assays. For example, the induction of general cell signaling events can be monitored through altered phosphorylation patterns of a variety of target proteins. Detection of cell signaling activities in response to treatment of cells with QRS polypeptides therefore serves as an indicator of distinct biological effects. Target proteins used for this assay may be selected so as to encompass key components of major cellular signaling cascades, thereby providing a broad picture of the cell signaling landscape and its therapeutic relevance. Generally, such assays involve cell treatment with QRS polypeptides followed by immunodetection with antibodies that specifically detect the phosphorylated (activated) forms of the target proteins.

Illustrative target proteins used for monitoring therapeutically relevant cell signaling events may include, but are not limited to: p38 MAPK (mitogen-activated protein kinase; activated by cellular stress and inflammatory cytokines; involved in cell differentiation and apoptosis); SAPK/JNK (stress-activated protein kinase/Jun-amino-terminal kinase; activated by cellular stresses and inflammatory cytokines); Erk1/2, p44/42 MAPK (mitogen-activated protein kinase Erk1 and Erk2; activated by wide variety of extracellular signals; involved in regulation of cell growth and differentiation); and Akt (activated by insulin and various growth or survival factors; involved in inhibition of apoptosis, regulation of glycogen synthesis, cell cycle regulation and cell growth). General phosphorylation of tyrosine residues may also be monitored as a general indicator of changes in cell signaling mediated by phosphorylation.

Of course, it will be recognized that other classes of proteins, such as cell adhesion molecules (e.g., cadherins, integrins, claudins, catenins, selectins, etc.) and/or ion channel proteins may also be assayed for monitoring cellular events or activities modulated by the compositions of the invention.

In other specific embodiments of the invention, the AARS polypeptides (e.g., QRS polypeptides) and compositions of the invention may be used to modulate cytokine production by cells, for example, by leukocytes. Cytokine production may be monitored using any of a number of assays known in the art (i.e., RT-PCR, ELISA, ELISpot, flow cytometry, etc.). Generally, such assays involve cell treatment with AARS polypeptides (e.g., QRS polypeptides) polypeptides followed by detection of cytokine mRNA or polypeptides to measure changes in cytokine production. Detection of increases and/or decreases in cytokine production in response to treatment of cells with AARS polypeptides (e.g., QRS polypeptides) therefore serves as an indicator of distinct biological effects. QRS polypeptides of the invention may induce, enhance, and/or inhibit an immune or inflammatory response by modulating cytokine production. For example, AARS polypeptides (e.g., QRS polypeptides) polypeptides and compositions of the invention may be used to alter a cytokine profile (i.e., type 1 vs. type 2) in a subject. Illustrative cytokines that may measured for monitoring biological effects of the QRS compositions include, but are not limited to IL-1α, IL-1β, IL-2, IL-3, IL-4, IL-5, IL-6, IL-7, IL-10, IL-12, IL-15, IL-18, IL-23 TGF-β, TNF-α, IFN-α, IFN-γ, RANTES, MIP-1α, MIP-1β, MCP-1, GM-CSF, G-CSF, etc.

Generally, a therapeutically effective amount of polypeptide is administered to a subject or patient. In particular embodiments, the amount of polypeptide administered will typically be in the range of about 0.1 µg/kg to about 0.1 mg/kg to about 50 mg/kg of patient body weight. Depending on the type and severity of the disease, about 0.1 µg/kg to about 0.1 mg/kg to about 50 mg/kg body weight (e.g., about 0.1-15 mg/kg/dose) of polypeptide can be an initial candidate dosage for administration to the patient, whether, for example, by one or more separate administrations, or by continuous infusion. For example, a dosing regimen may comprise administering an initial loading dose of about 4 mg/kg, followed by a weekly maintenance dose of about 2 mg/kg of the polypeptide, or about half of the loading dose. However, other dosage regimens may be useful. A typical daily dosage might range from about 0.1 µg/kg to about 1 µg/kg to 100 mg/kg or more, depending on the factors mentioned above. For repeated administrations over several days or longer, depending on the condition, the treatment is sustained until a desired suppression of disease symptoms occurs. The progress of these and other therapies (e.g., ex vivo therapies) can be readily monitored by conventional methods and assays and based on criteria known to the physician or other persons of skill in the art.

Formulations and Pharmaceutical Compositions

The compositions of the invention comprise aminoacyl-tRNA synthetase polypeptides, including truncations and/or variants thereof, formulated in pharmaceutically-acceptable or physiologically-acceptable solutions for administration to a cell or an animal, either alone, or in combination with one or more other modalities of therapy. It will also be understood that, if desired, the compositions of the invention may be administered in combination with other agents as well, such as, e.g., other proteins or polypeptides or various pharmaceutically-active agents. There is virtually no limit to other components that may also be included in the compositions, provided that the additional agents do not adversely affect the inflammatory response-modulating activities or other effects desired to be achieved.

In the pharmaceutical compositions of the invention, formulation of pharmaceutically-acceptable excipients and carrier solutions is well-known to those of skill in the art, as is the development of suitable dosing and treatment regimens for using the particular compositions described herein in a variety of treatment regimens, including e.g., oral, parenteral, intravenous, intranasal, and intramuscular administration and formulation.

In certain applications, the pharmaceutical compositions disclosed herein may be delivered via oral administration to a subject. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain circumstances it will be desirable to deliver the pharmaceutical compositions disclosed herein parenterally, intravenously, intramuscularly, or even intraperitoneally as described, for example, in U.S. Pat. Nos. 5,543,158; 5,641,515 and 5,399,363 (each specifically incorporated herein by reference in its entirety). Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form should be sterile and should be fluid to the extent that easy syringability exists. It should be stable under the conditions of manufacture and storage and should be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion (see, e.g., *Remington's Pharmaceutical Sciences*, 15th Edition, pp. 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity standards as required by FDA Office of Biologics standards.

Sterile injectable solutions can be prepared by incorporating the active compounds in the required amount in the appropriate solvent with the various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

In certain embodiments, the pharmaceutical compositions may be delivered by intranasal sprays, inhalation, and/or other aerosol delivery vehicles. Methods for delivering genes, polynucleotides, and peptide compositions directly to the lungs via nasal aerosol sprays have been described e.g., in U.S. Pat. Nos. 5,756,353 and 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

Also included are topical formulations. Examples of topical formulations include creams, ointments, pastes, lotions, and gels.

In certain embodiments, the delivery may occur by use of liposomes, nanocapsules, microparticles, microspheres, lipid particles, vesicles, and the like, for the introduction of the compositions of the present invention into suitable host cells. In particular, the compositions of the present invention may be formulated for delivery either encapsulated in a lipid particle, a liposome, a vesicle, a nanosphere, a nanoparticle or the like. The formulation and use of such delivery vehicles can be carried out using known and conventional techniques.

All publications, patent applications, and issued patents cited in this specification are herein incorporated by reference as if each individual publication, patent application, or issued patent were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims. The following examples are provided by way of illustration only and not by way of limitation. Those of skill in the art will readily recognize a variety of noncritical parameters that could be changed or modified to yield essentially similar results.

EXAMPLES

Example 1

Amino Acyl-tRNA Synthetase Polypeptides Reduce Neutrophil Migration and Infiltration into the Lungs after Lipopolysaccharide (LPS) Challenge Neutrophil migration from the circulatory system to the lungs is implicated in chronic pulmonary obstructive disease (COPD) (see, e.g., R. A. Stockley, Chest 121:151S-155S, 2002). CXCR-2 expression can play a role in neutrophil migration (see, e.g., Rios-Santos et al., American Journal of Respiratory and Critical Care Medicine 175:490-497, 2007). To determine whether tyrosyl-tRNA synthetase (YRS) polypeptides and histidyl-tRNA synthetase (HisRS) polypeptides can be used to treat neutrophil-mediated disorders, male C57BL/6 mice were anesthetized, injected intra-nasally with 50 µl of a 200 µg/ml lipopolysaccharide (LPS, Sigma-Aldrich Cat# L2880) and sacrificed approximately 8 hours after LPS administration. Prior to exposure to LPS, mice were treated with YRS polypeptides, HisRS polypeptides, or control. A tracheal catheter was inserted to collect bronchoalveolar lavage (BAL) samples by flushing the lungs five times with 1 ml of ice-cold saline solution. Lavage fluid was collected for later cell staining and counting.

Figure 1B:
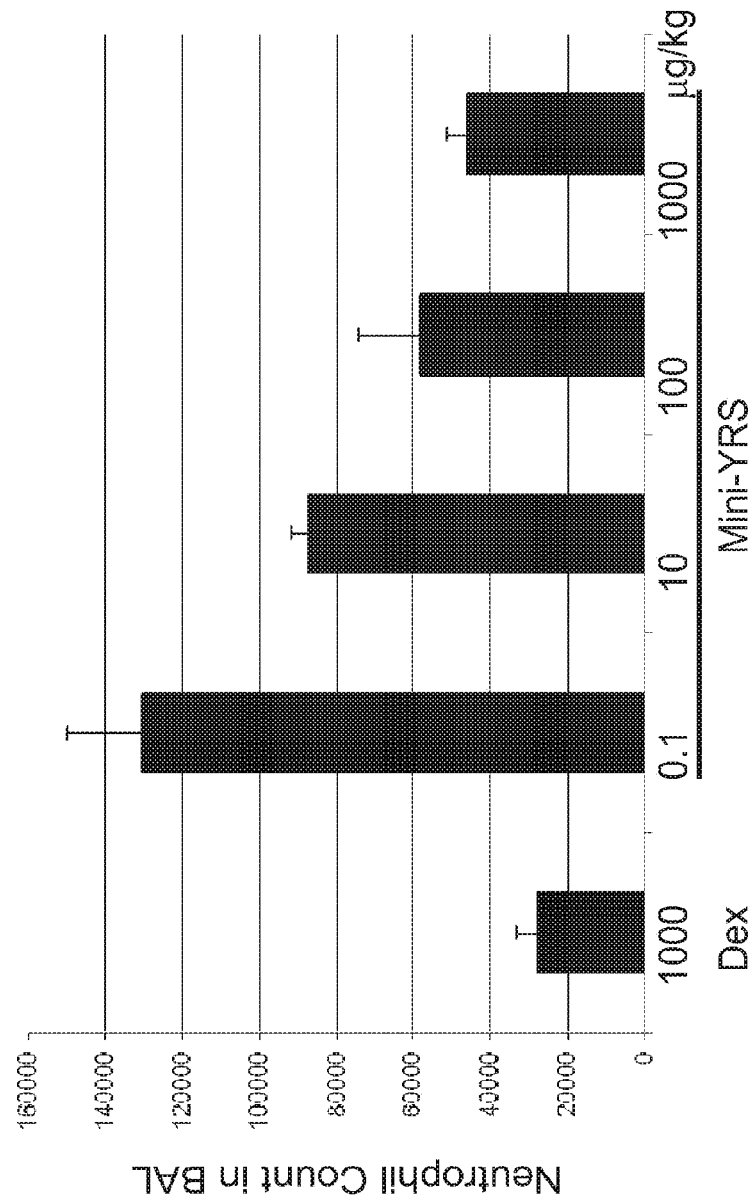
Figure 2A:
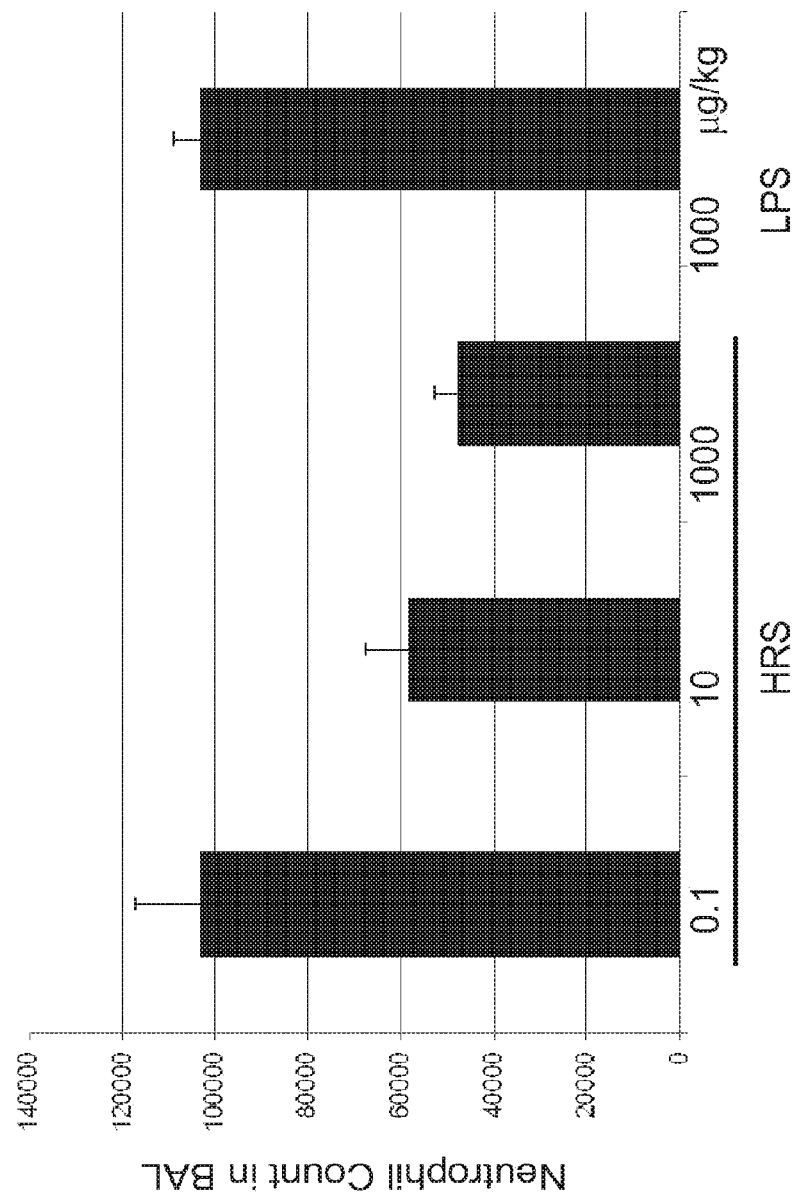
FIGS. 2A-2B show the effects of histidyl-tRNA synthetase polypeptides on granulocyte migration into the lungs.
Figure 2B:
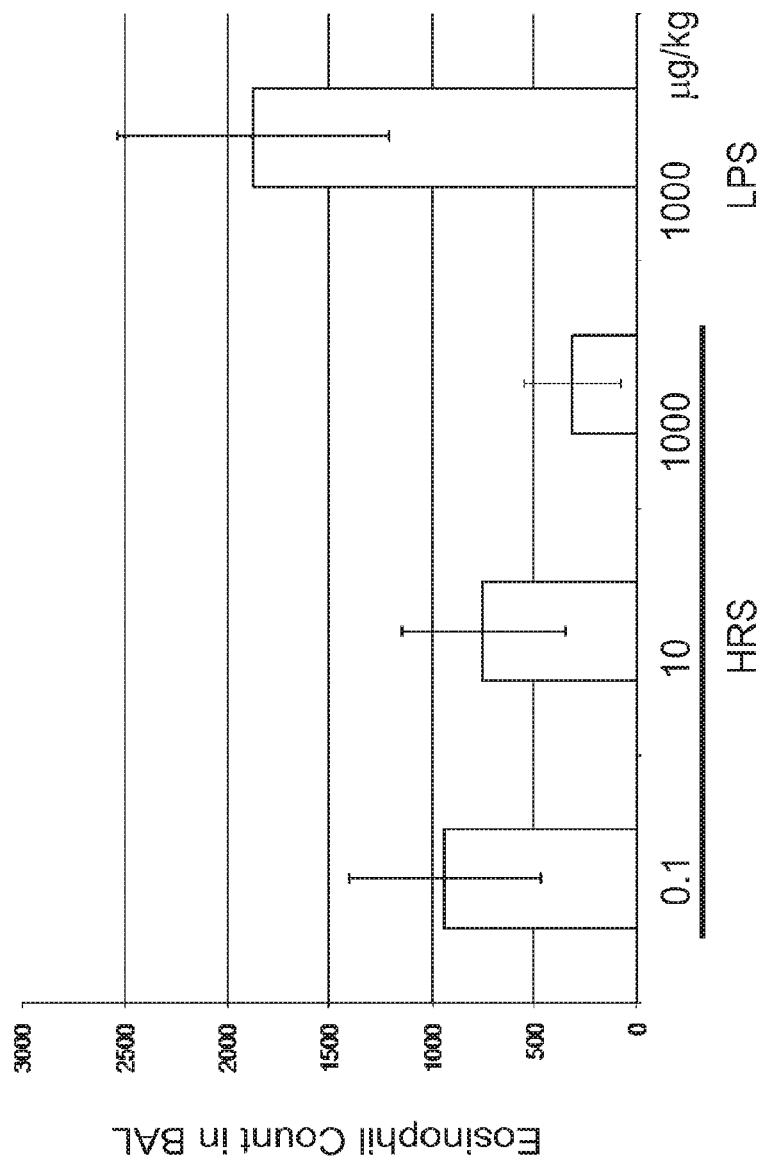

As shown in FIG. 1A, neutrophils are typically absent from the BAL fluid recovered from healthy, untreated animals. Intra-nasal LPS administration resulted in the infiltration of circulating neutrophils into the lungs and in a marked increase in BAL neutrophils (FIG. 1A, LPS group). Intraperitoneal pretreatment with dexamethasone, a synthetic corticosteroid used as positive control in this experiment, resulted in a diminished ability of neutrophils to relocate to the lungs after LPS challenge (FIG. 1A, Dex group). Similarly, intravenous administration of two doses of the YRS and HisRS synthetase polypeptides at 7-8 hours and 1.5 hour prior to LPS administration, respectively, resulted in a drastic reduction in BAL neutrophils. The results for YRS are shown in FIG. 1 (FIG. 1A, Y341A group; and FIG. 1B, Mini-YRS group). Full-length HisRS polypeptide exerted similar effects on neutrophils (FIG. 2A), and was also capable of decreasing eosinophil migration to the lungs (FIG. 2B). Similar results are seen for tryptophanyl-tRNA synthetase (WRS) polypeptides.

Example 2

Tyrosyl-tRNA Synthetase Polypeptides Stimulate Migration of 293 and Cho Cell Lines Transfected with the CXCR-2 Receptor The effects of tyrosyl-tRNA synthetase polypeptides on CXCR-2 signaling was tested by measuring the migration of CXCR-2 expressing cells in response to said polypeptides. 293/CXCR-2 cells were maintained in DMEM medium supplemented with 10% heat-inactivated FBS, 1% Penicillin-Streptomycin and 800 µg/ml Geneticin, all purchased from Invitrogen, Carlsbad, Calif. DMEM medium with 0.1% BSA was used as migration buffer. Prior to migration assay, cells were serum-starved for 30 minutes in migration buffer, centrifuged at 200 g for 5 minutes and resuspended in migration buffer at a final density of 1×10$^6$ cells/ml. 100 µl were added to 6.5 mm transwell filter inserts (Costar, Cambridge, Mass.) and 600 µl migration buffer containing a control chemokine, the tyrosyl-tRNA synthetase polypeptides or buffer only were added to the plate lower chambers. Cells were allowed to migrate for 4 hours and the remaining cells in the upper chamber (transwell filter inserts) were removed with a cotton swap. The filter inserts were then transferred to a new 24-well plate containing 500 µl cell dissociation buffer (Invitrogen, Carlsbad, Calif.) and 12 µg/ml Calcein AM (Invitrogen, Carlsbad, Calif.). After 1 hour incubation at 37° C., cells were collected and resuspended in 100 µl PBS, transferred into a 384-well opaque Greiner plate, and counted by fluorescence in a plate reader.

CHO-K1/CXCR-2 cells were maintained in F12 medium supplemented with 10% heat-inactivated FBS, 1% Penicillin-Streptomycin-Glutamine and 800 µg/ml Geneticin. F12 medium with 0.5% BSA was used as migration buffer. Prior to migration, cells were serum-starved for 30 minutes in migration buffer, collected by using cell dissociation buffer, spun down at 200 g for 5 minutes and resuspended in migration buffer at the final density of 1×10$^6$ cells/ml. 100 µl were added to 6.5 mm transwell filter inserts and 600 µl migration buffer containing a control chemokine, the tyrosyl-tRNA synthetase polypeptides or buffer only were added to the plate lower chambers. Cells were allowed to migrate for 3 hours and the remaining cells in the upper chamber (transwell filter inserts) were removed with a cotton swap. The filter inserts were then transferred to a new 24-well plate containing 500 µl PBS and 12 µg/ml Calcein AM. After 30 minutes incubation at 37° C., filters were transferred again into a new 24-well plate containing 500 µl phenol/red-free trypsin. After 2 to 5 minutes incubation, detached cells were collected and resuspended in 100 µl PBS, transferred into a 384 well opaque Greiner plate and counted by fluorescence in a plate reader.

Figure 3:
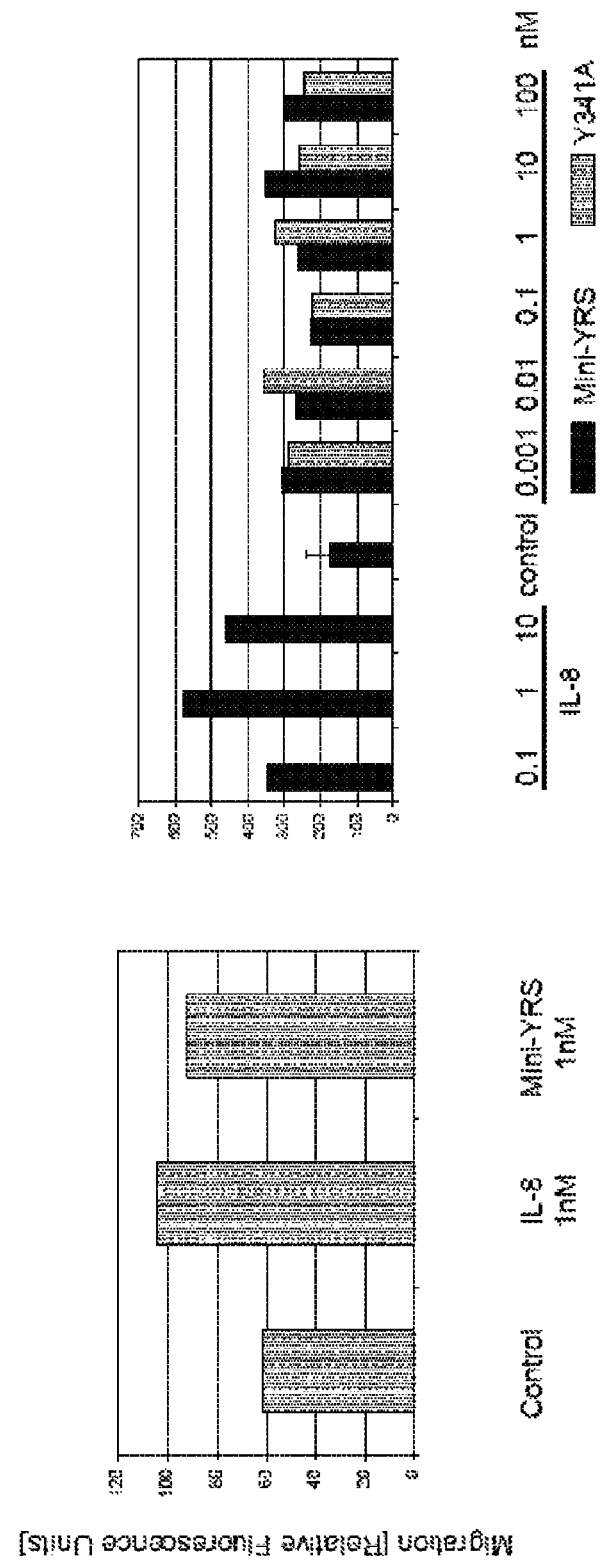
FIG. 3 shows that tyrosyl-tRNA synthetase polypeptides stimulate migration of 293 and CHO cell lines transfected with the CXCR-2 receptor (see Example 2). The left graph in FIG. 24 shows the results for 293/CXCR-2 cells, and the right graph in FIG. 24 shows the results for CHO/CXCR-2 cells.

FIG. 3 shows the ability of the tyrosyl-tRNA synthetase polypeptides to induce migration of CXCR-2 transfected cells.

Example 3

Tyrosyl-tRNA Synthetase Polypeptides Stimulate Polymorphonuclear (PMN) Cell Migration To test the effects of YRS polypeptides on PMN cell migration, human granulocyte cells were purified from fresh human peripheral blood using RosetteSep® Human Granulocyte Enrichment Kit (StemCell Technologies, Vancouver, BC) according to the manufacturer's instructions. Serum-free RPMI medium supplemented with 0.5% FBS was used as migration buffer. 4×10$^7$ cells were resuspended in 1 ml migration buffer and incubated for 30 minutes with 8 µl of a 1 mg/ml Calcein AM solution (Invitrogen, Carlsbad, Calif.). Cells were collected, spun down at 200 g for 5 minutes without brake, washed once with migration buffer and resuspended in the same buffer at a final density of 1×10$^7$/ml.

100 µl were added to 6.5 mm transwell filter inserts (Costar, Cambridge, Mass.) and 600 µl migration buffer containing a control chemokine, the tyrosyl-tRNA synthetase polypeptides or buffer only were added to the plate lower chambers. Cells were allowed to migrate for 45 minutes in the incubator and cells that migrated to the lower chamber were collected, resuspended in 100 µl PBS, transferred into a 384-well opaque Greiner plate and counted by fluorescence in a plate reader.

Figure 4:
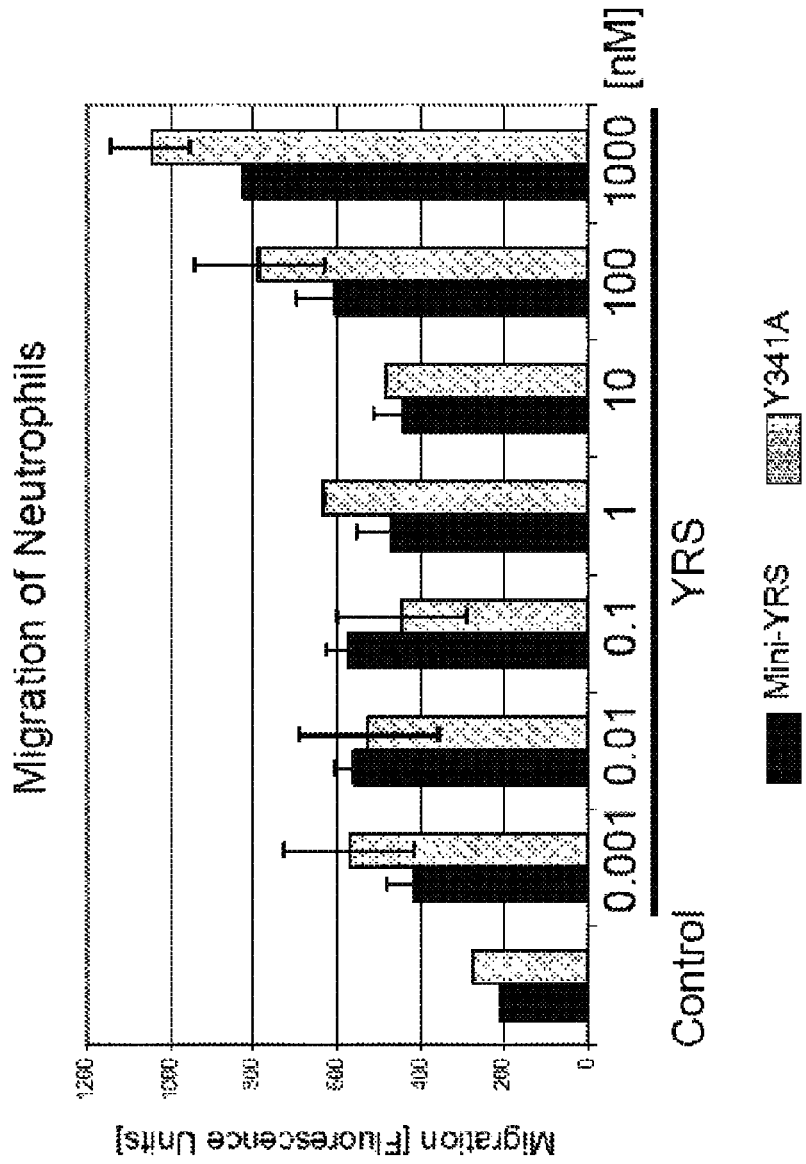
FIG. 4 shows the stimulatory effects of YRS polypeptides on polymorphonuclear (PMN) cell migration (see Example 3).

FIG. 4 shows the bell-shaped migration curve typically observed with chemokines. The tyrosyl-tRNA synthetase polypeptides induced a biphasic migration of PMN both at low pM and at higher µM concentrations.

Example 4

Aspartyl-tRNA Synthetase Polypeptide D1 Induces Secretion of Both Pro- and Anti-Inflammatory Cytokines To probe the possible connection between the D1 fragment (residues 1-154) of full-length AspRS and inflammation, recombinant protein was injected intravenously into healthy mice, and changes in inflammatory cytokines (both pro- and anti-inflammatory) secreted into the bloodstream were observed relative to vehicle controls. Serum was harvested 2 and 6 hours post-injection and TNF-α and IL-10 levels were measured by ELISA.

Figure 5A:
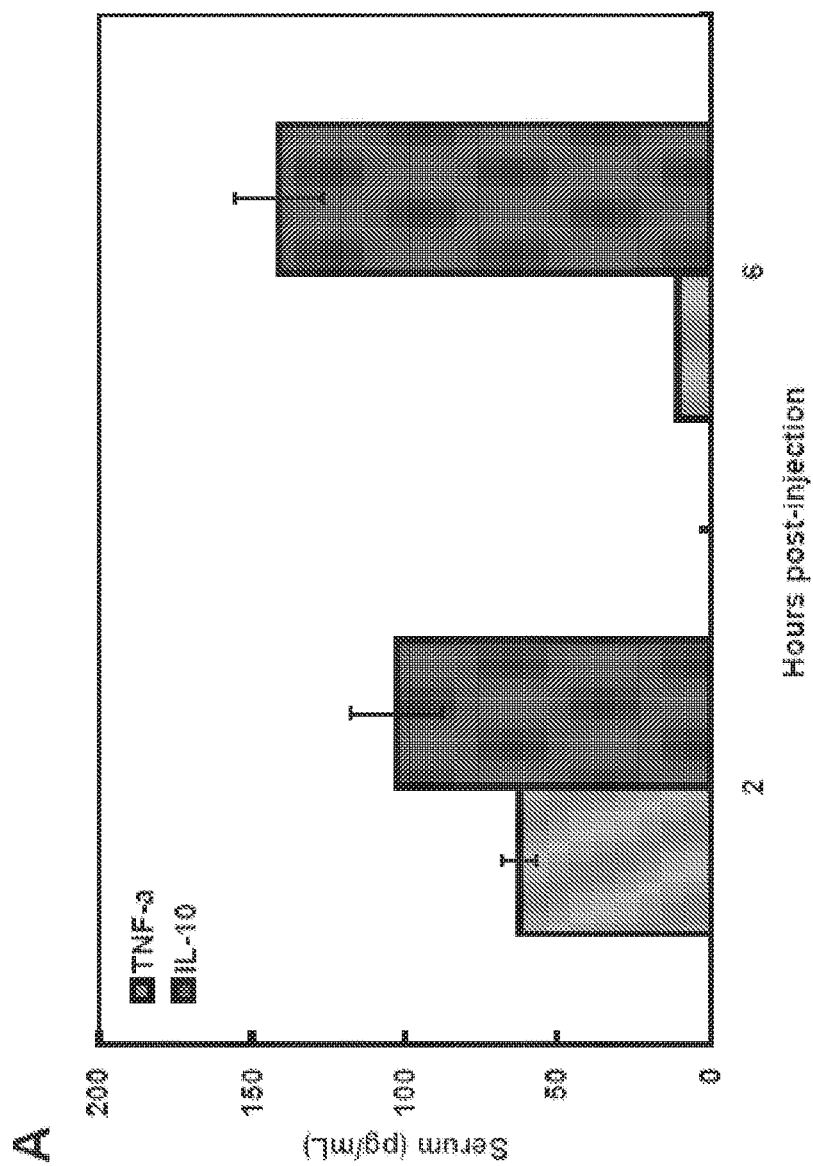
FIGS. 5A-5D show the in vivo and in vitro cytokine release in response to the D1 AspRS polypeptide (amino acids 1-154 of SEQ ID NO:105).
Figure 5B:
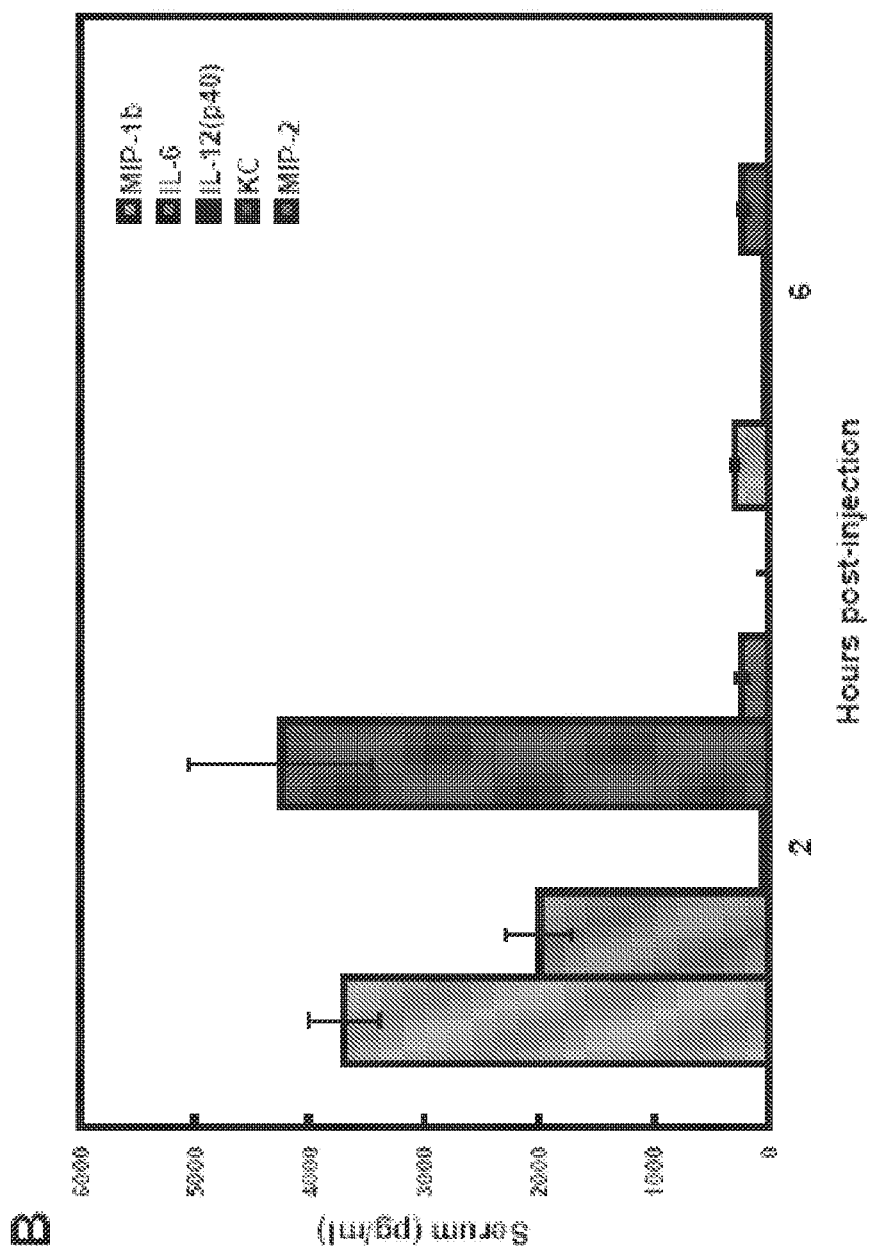

Upon examination at 2 hours post-injection of D1, an increased secretion of both pro-inflammatory cytokines (TNF-α, MIP-1b, IL-12(p40), KC, MIP-2), and IL-10, an anti-inflammatory cytokine, was observed (FIGS. 5A and 5B). At 6 hours post-injection of D1, the pro-inflammatory cytokines could no longer be detected, but the levels of IL-10 anti-inflammatory in the serum continued to increase (see FIGS. 5A and B).

Figure 5C:
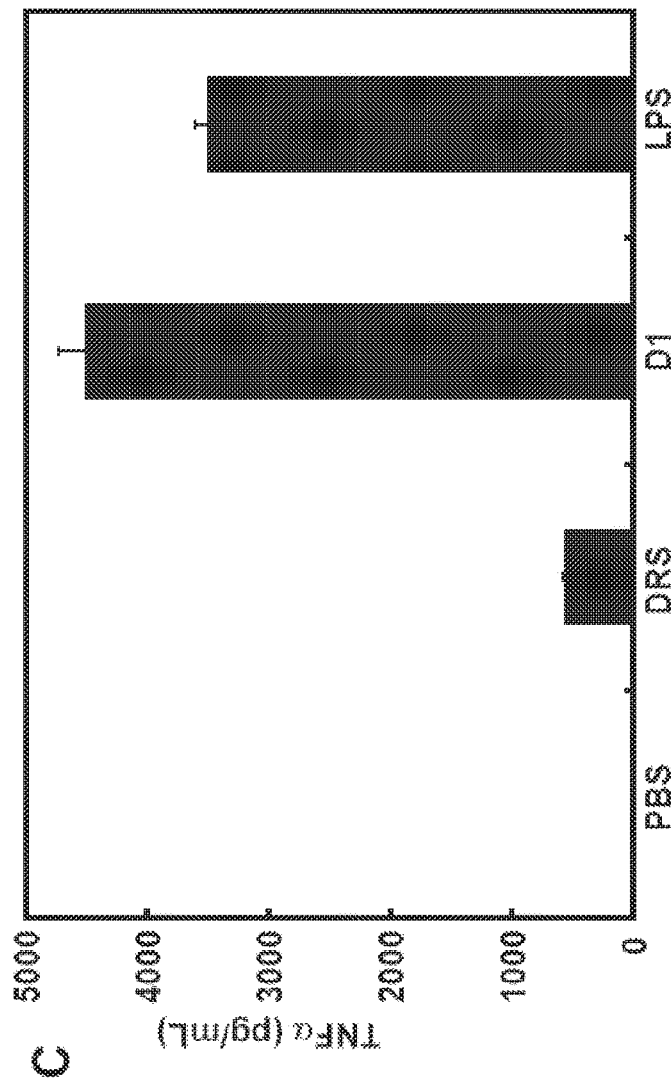
Figure 5D:
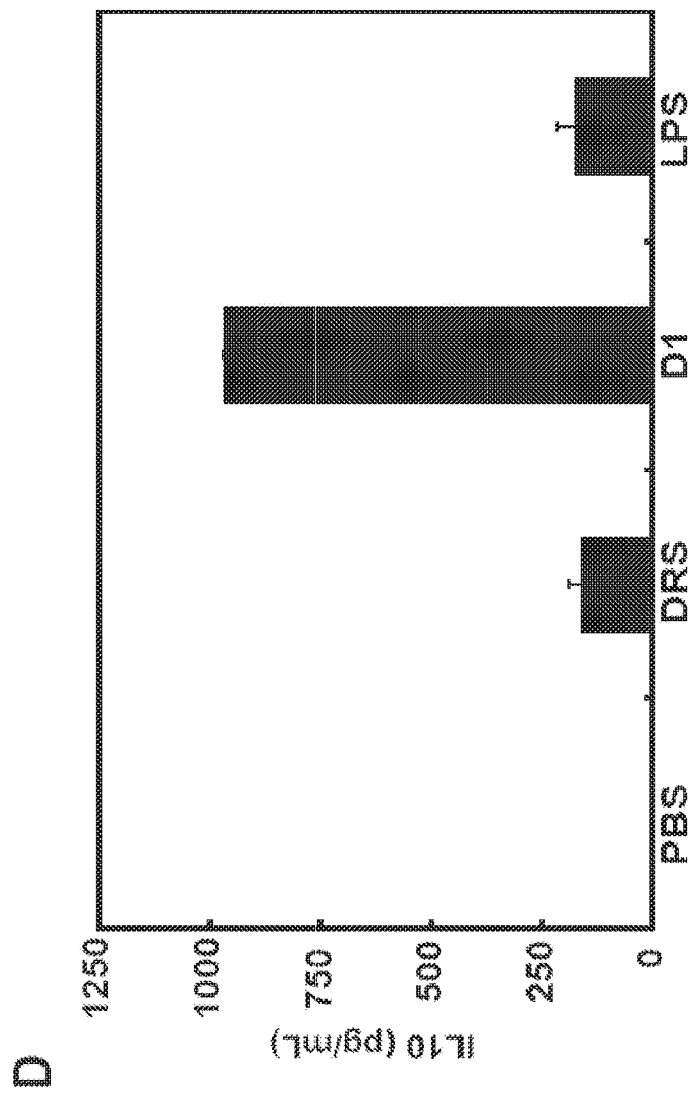

To confirm these results, peripheral blood mononuclear cells (PBMCs) representing a mixture of both monocytes and lymphocytes isolated from human donors were exposed to the D1 protein in vitro (as well as the full-length AspRS protein), and the media was tested for the secretion of either TNF-α or IL-10 in response to treatment. Similar to the effects observed in vivo, treatment with D1 resulted in secretion of both TNF-α (after 4 hours treatment) and IL-10 (after 24 hours treatment) from the mixed cell population (see FIGS. 5C and D).

Example 5

Splice Variants HRS-SV9 and HRS-SV11 Increase IL-2 Secretion in Activated T-Cells When antigen is presented by antigen presenting cells (APC), the earliest detectable response of T cell activation is the secretion of cytokines, such as IL-2. Through autocrine secretion, IL-2 triggers T cells proliferation, thereby generating cells required to eliminate antigen. Thus, regulators of IL-2 secretion serve as immunomodulators for T lymphocyte-mediated immune responses.

Leukemia Jurkat T cells (ATCC No: TIB-152) are widely used for T cell activation research, using IL-2 expression and release as an indication of activation. For T cell activation, Jurkat T cells were stimulated by phorbol esters (PMA) and ionomycin (TOM). IL-2 secretion into media was evaluated by ELISA. As expected, PMA and ionomycin stimulated Jurkat T cells to release IL-2 in a dose dependent manner.

Figure 6:
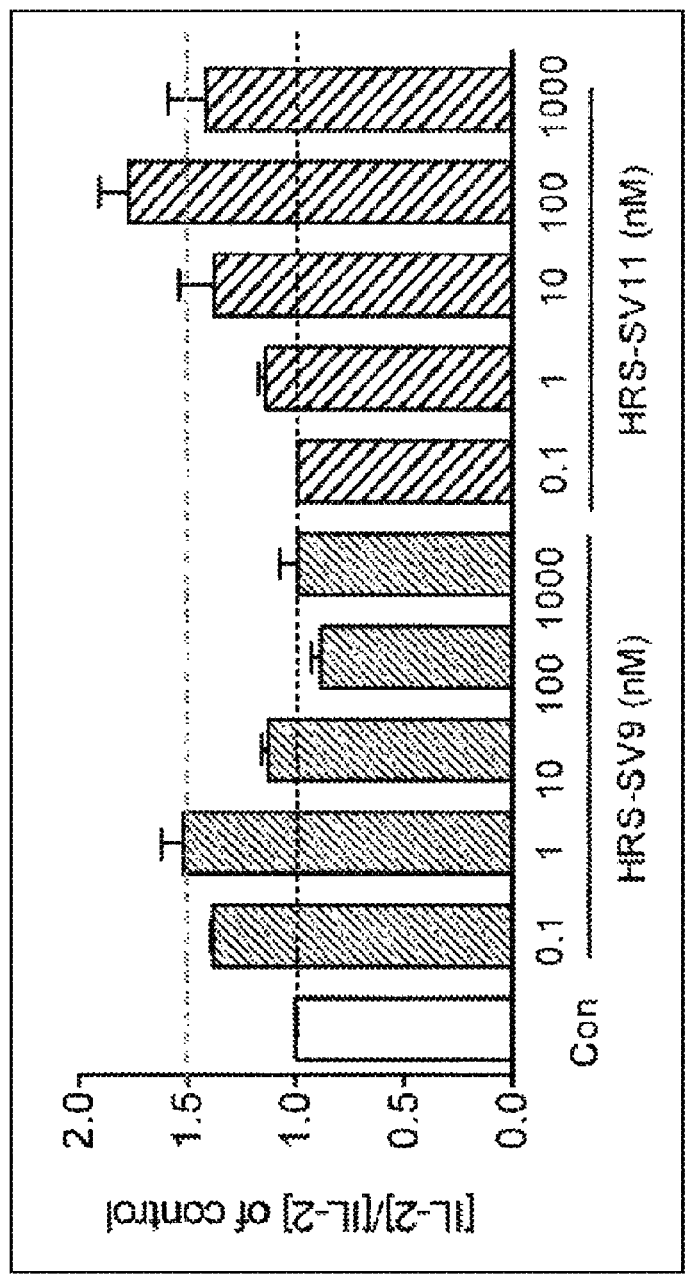
FIG. 6 shows that recombinant HRS-SV9 and HRS-SV11 splice variant polypeptides enhance IL-2 secretion in activated Jurkat T cells. Cells were treated with PMA (25 ng/ml) plus ionomycin (250 ng/ml) with or without HRS-SV9 or HRS-SV11, and media was analyzed 48 hours later by ELISA.

As shown in FIG. 6, HRS-SV9 and HRS-SV11, when co-applied with PMA and IOM significantly increased IL-2 secretion. Thus, both HRS-SV9 and HRS-SV11 exhibited immunomodulatory activity.

Example 6

Splice Variant HRS-SV9 Stimulates TNF-Alpha Secretion in PBMCs

Peripheral blood mononuclear cells (PBMCs) were isolated from human blood. The cells were resuspended in RPMI media with 10% FBS to $1 \times 10^6$ cells/mL. One million cells were treated for 24 hours with HRS-SV9 at 6.25, 12.5, 25, 50, 100, and 250 nM. PBMCs were also treated with Lipopolysaccharide (LPS) at 1 EU/mL, PBS, or 100 nM Negative Control Protein 1 or 2. After 24 hours, cell supernatant was collected by centrifugation at 2000×g for 10 min and evaluated in a TNF-α ELISA assay (R&D Systems; Cat. DTA00C).

Figure 7:
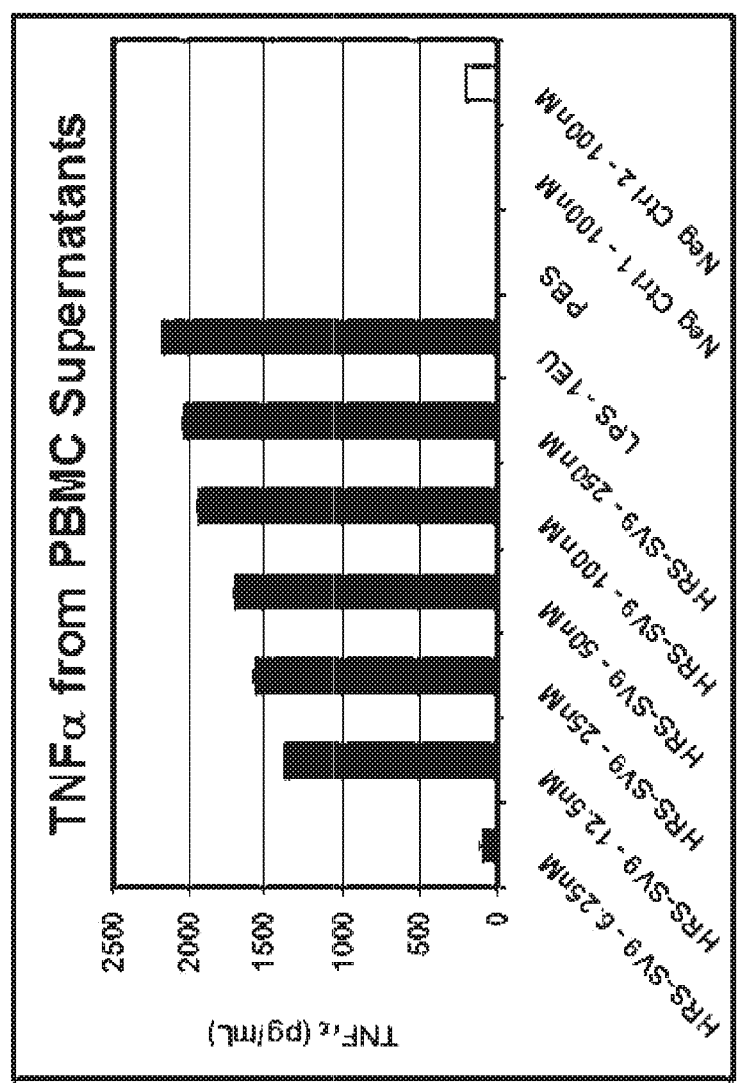
FIG. 7 shows that HRS-SV9 stimulated PBMCs to secrete TNF-α in a dose dependent manner.

As shown in FIG. 7, HRS-SV9 stimulated PBMCs to secrete TNF-α in a dose dependent manner. In contrast, cells treated with PBS or negative control proteins secreted minimal or no TNF-α □□□(PBS, Neg. Ctrl. 1 and Neg. Ctrl. 2). LPS, a known inducer of TNF-α secretion, gave rise to a positive signal at 1 EU/ml. Although a minimal amount of LPS was present in the HRS-SV9 protein (~0.11 EU/mL at 250 nM), the TNF-α signal observed for HRS-SV9 is above that which maybe attributed to LPS. Thus, the results of this example demonstrate that HRS-SV9 acts as a modulator of TNF-α secretion.

Example 7

Generation and Identification of Endogenous Human Glutaminyl-tRNA Synthetase (QRS) Fragments Full-length recombinant human QRS (SEQ ID NO:25) was expressed and purified from *E. coli* using nickel IMAC chromatography. Endogenous proteolytic fragments were generated through the process of purification and subsequently characterized using LC/MS/MS. Without wishing to be bound by any one theory, it is believed that these fragments are indicative of those that would be created in human cells through the process of natural proteolysis.

Figures 8A, 8B, 8C:
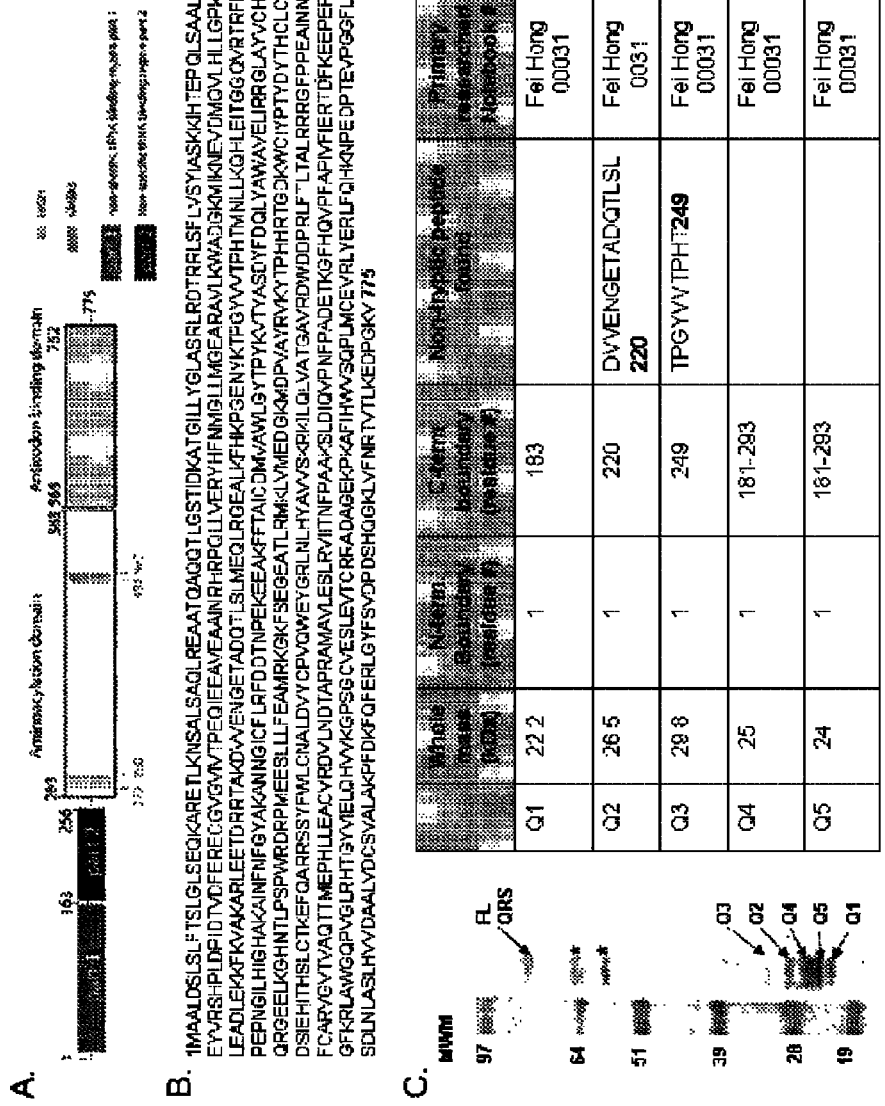
FIGS. 8A-8C shows the domain structure and amino acid sequence of QRS (SEQ ID NO:25), and illustrates the SDS-PAGE separation of fragments of QRS (SEQ ID NOS: 116 and 117) generated by endogenous proteolysis of the full-length QRS.

To identify the residues at which proteolysis occurs for human QRS, the proteins were separated by SDS-PAGE run in 4-12% MOPS, gel slices containing the fragments were excised and subjected to in-gel trypsin digestion followed LC/MS/MS analysis. This process allowed the identification of both the portion of the full-length protein from which the fragments were generated and the non-trypsin cleavage sites that could be attributed to endogenous proteolytic cleavage. All protein fragments identified represented the N-terminal portion of QRS. See Table 1 below, and FIG. 8 (A-C).

TABLE 1

| Endogenous QRS proteolytic fragments | | | |
|---|---|---|---|
| Whole mass (Da) | N-term. boundary | C-term boundary | Non-tryptic peptide found |
| Q1 | 22200 | 1 | 183 | |
| Q2 | 26500 | 1 | 220 | DVVENGETADQTLSL220 (SEQ ID NO: 26) |
| Q3 | 29800 | 1 | 249 | TPGYVVTPHT249 (SEQ ID NO: 27) |
| Q4 | 25000 | 1 | 181-293 (200) | |
| Q5 | 24000 | 1 | 181-293 | |

Figure 9:
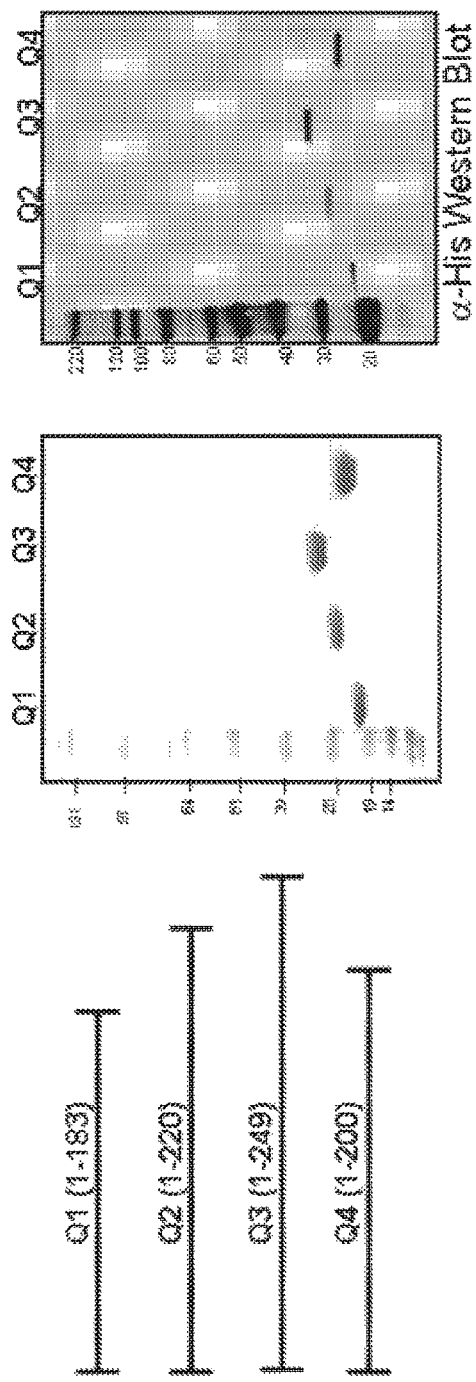
FIG. 9 shows the QRS fragments (designated Q1, Q2, Q3, and Q4) that were cloned into an *E. coli* protein expression vector for over-expression and purification.

QRS fragments closely matching those identified by LC/MS/MS in Table 1 above were cloned into an *E. coli* protein expression vector for over-expression and purification. Proteins were purified using Nickel IMAC chromatography and contaminants were removed using a Sartobind Q membrane (Sartorius). See FIG. 9.

Example 8

N-Terminal Proteolytic Fragments of QRS Inhibit LPS-Induced TNF-Alpha Secretion from PBMCs To measure the effects of QRS polypeptides on TNF-α secretion, peripheral blood mononuclear cells (PBMCs) were isolated from human blood obtained from healthy donors and treated with QRS polypeptides. The cells were resuspended in RPMI media with 10% FBS to $1 \times 10^6$ cells/mL. One million cells were pre-treated for 30 minutes with a dose response of 63 nM, 125 nM, 250 nM and 500 nM (463 nM for Q3) of each Q fragment. After 30 minutes, lipopolysaccharide (LPS, 0.5 EU/mL) was added to pre-treated and untreated cells. After 24h, cell supernatant was collected by centrifugation at 2000×g for 10 minutes and evaluated in a TNF-α ELISA (R&D Systems; Cat. DTA00C) per kit directions.

Figure 10:
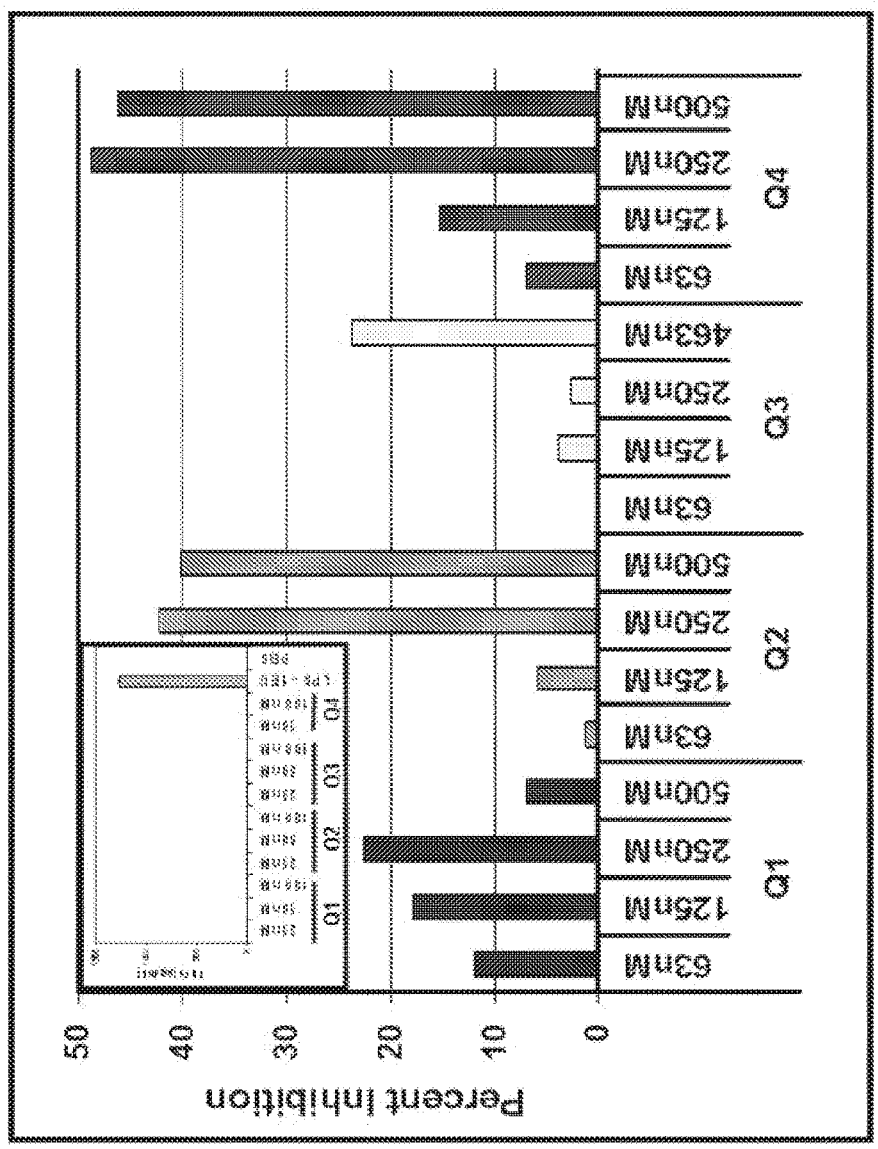
FIG. 10 shows that pretreatment with all four QRS fragments (Q1, Q2, Q3, and Q4) inhibited the amount of TNF-α released from PBMCs upon stimulation with 0.5 EU/ml LPS.

As shown in FIG. 10, pretreatment with all four QRS fragments inhibited the amount of TNF-α released from PBMCs upon stimulation with 0.5 EU/ml LPS.

Example 9

N-Terminal Proteolytic Fragment of QRS Inhibits LPS-Induced TNF-Alpha Secretion from PBMCs at 4 and 24 Hours To measure the longer term effects of QRS polypeptides on TNF-α secretion, peripheral blood mononuclear cells (PBMCs) were isolated from human blood obtained from healthy donors and treated with QRS polypeptides. The cells were resuspended in RPMI media with 10% FBS to $1 \times 10^6$ cells/mL. One million cells were pre-treated for 30 minutes with 500 nM Q4. After 30 minutes, lipopolysaccharide (LPS, 0.5 EU/mL) was added to Q4 pretreated and untreated cells. After 4 hours and 24 hours cell supernatant was collected by centrifugation at 2000×g for 10 minutes and evaluated in a TNF-α ELISA (R&D Systems; Cat. DTA00C) per kit directions.

Figure 11:
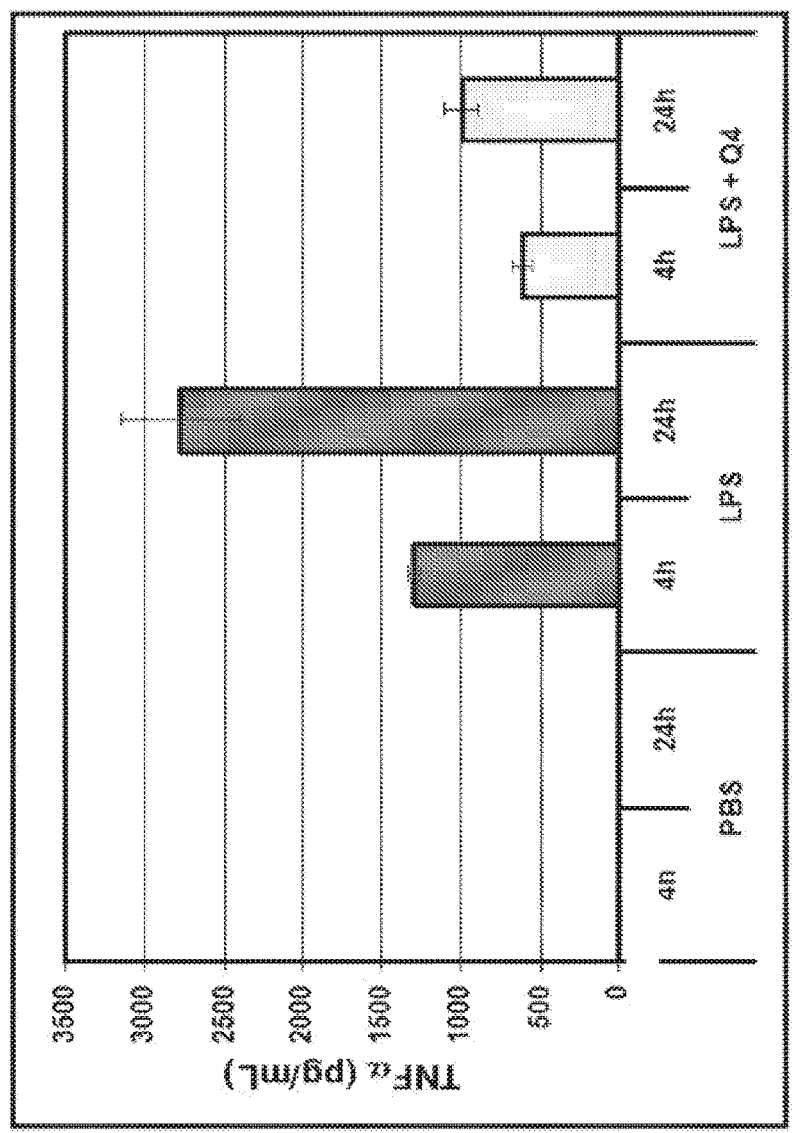
FIG. 11 shows that pretreatment with the Q4 fragment inhibited the amount of TNF-α released from PBMCs upon stimulation with 0.5 EU/ml LPS, after 4 and 24 hours.

As shown in FIG. 11, pretreatment with the Q4 fragment inhibited the amount of TNF-α released from PBMCs upon stimulation with 0.5 EU/ml LPS, even after 4 to 24 hours.

Example 10

N-Terminal Proteolytic Fragment of QRS Inhibit LPS-Induced IL-12 (p40) Secretion from PBMCs To measure the effects of QRS polypeptides on IL-12 secretion, peripheral blood mononuclear cells (PBMCs) were isolated from human blood obtained from healthy donors and treated with QRS polypeptides. The cells were resuspended in RPMI media with 10% FBS to $1 \times 10^6$ cells/mL. One million cells were pre-treated for 30 minutes with 500 nM Q4. After 30 minutes, lipopolysaccharide (LPS, 0.5 EU/mL) was added to Q4 pretreated and untreated cells. After 24 hours of incubation cell supernatant was collected and snap frozen in liquid nitrogen. Samples were shipped frozen to MD Biosciences (St. Paul, Minn.) for multiplex cytokine analysis to detect IL-12 (p40) levels.

Figure 12:
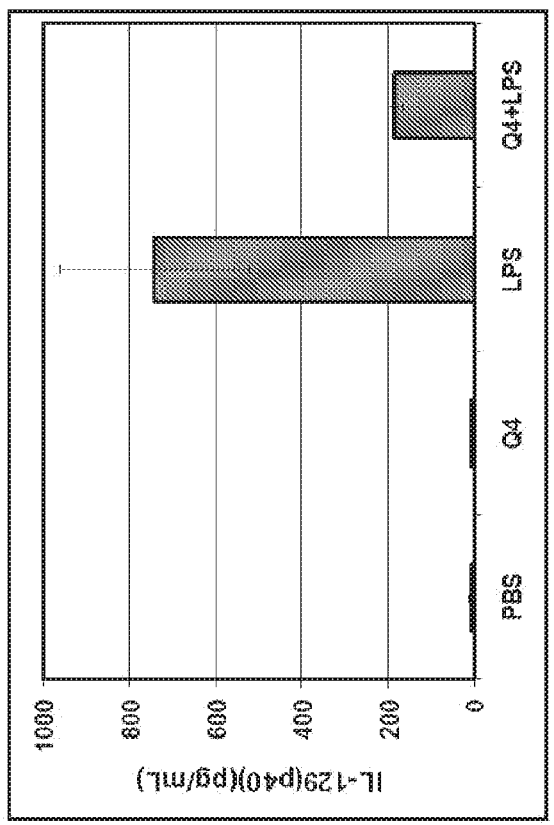
FIG. 12 shows that pretreatment with the Q4 fragment of QRS inhibited the amount of IL-12(p40) released from PBMCs upon stimulation with LPS.

As shown in FIG. 12, pretreatment with the Q4 fragment of QRS inhibited the amount of IL-12(p40) released from PBMCs upon stimulation with LPS.

Example 11

Histidyl-tRNA Synthetase, Aspartyl-tRNA Synthetase and P43 Polypeptides Reduce THP-1 Migration THP-1 cells (ATCC catalog No. TIB-202) were cultured in RPMI-1640 medium (ATCC catalog No. 30-2001) supplemented with 10% heat-inactivated FBS (Invitrogen, Catalog No. 10082147) and 0.05 mM 2-mercaptoethanol. Cell density was kept at <$1 \times 10^6$ cells/ml. Migration was done in Corning Transwell Permeable Supports in 24-well plates (6.5 mm Diameter; 8.0 μm pore size; Fisher Scientific catalog No. 07-200-150).

Before the migration assay, cells were collected by centrifugation at 300 g for 10 minutes, washed with PBS and resuspended in migration medium (RPMI-1640 medium, 0.1% BSA) supplemented with the desired concentration of histidyl-tRNA synthetase (HisRS), aspartyl-tRNA synthetase (AspRS), p43 polypeptide, or with PBS as control, at a density of $6 \times 10^6$ cells/ml. The cells were fluorescently labeled with 6 μg/ml Calcein AM (Invitrogen, catalog No. C3099) and placed in a tissue culture incubator at 37° C. in 5% $CO_2$ for 45 minutes. 100 μl of cells (containing $6 \times 10^5$ cells) were then added to the upper chamber of the migration unit, 600 μl migration medium containing the chemoattractant CCL-5 or CCL-23 (R&D Systems, catalog No. 278-RN-010 and 131-M1-025, respectively) or buffer only (as negative control) were added to each lower chamber, and cells were migrated for 2 hours in the incubator at 37° C. in 5% $CO_2$.

Figure 13A:
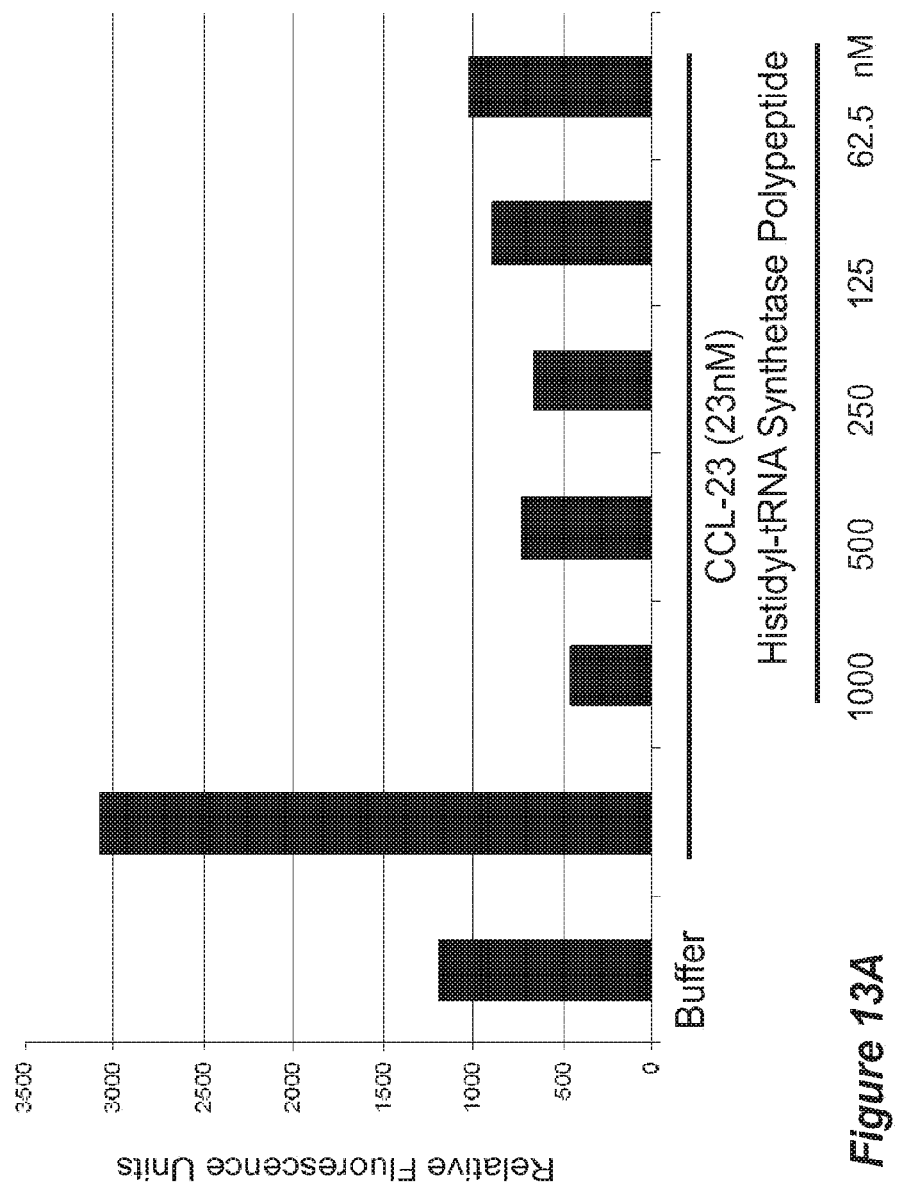
FIGS. 13A to 13C show the inhibitor effects of AARS polypeptides on the migration of THP-1 cells.
Figure 13B:
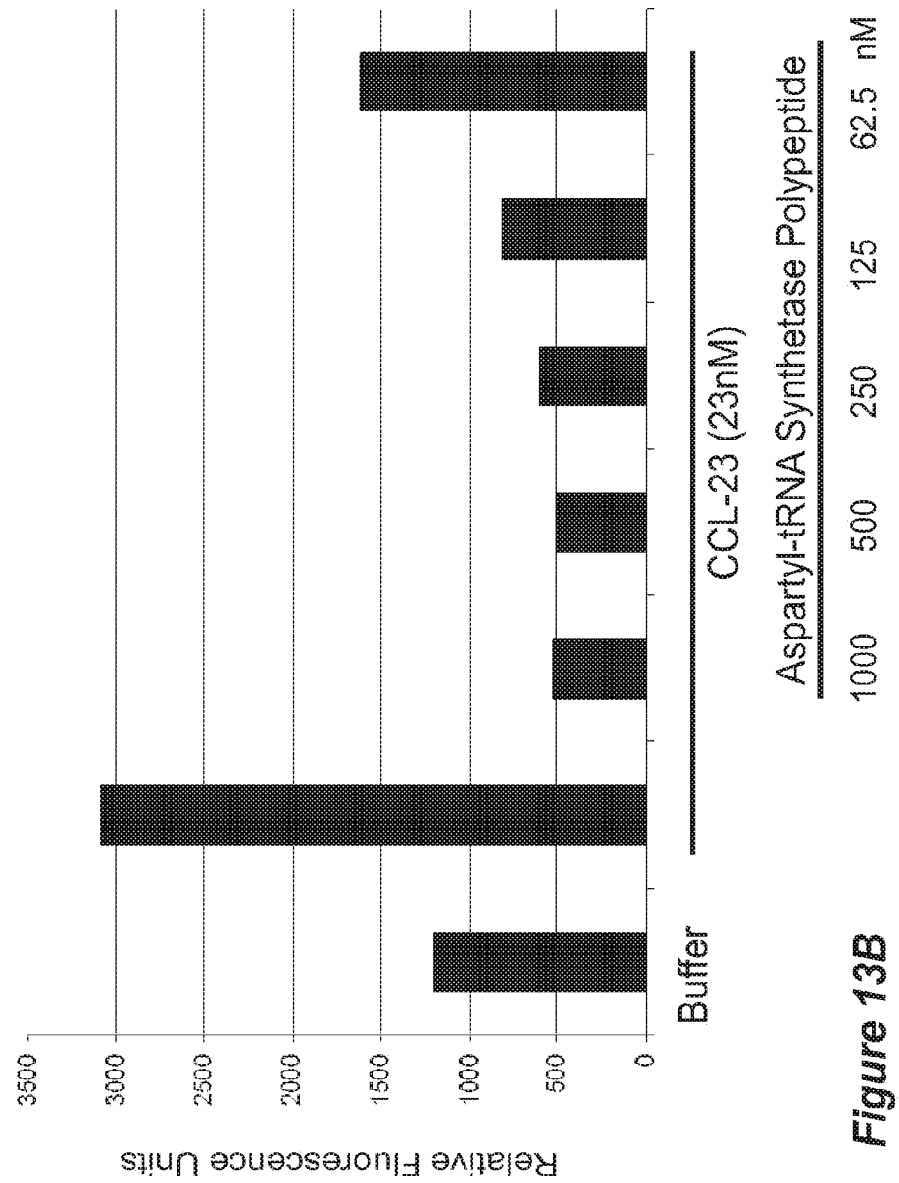
Figure 13C:
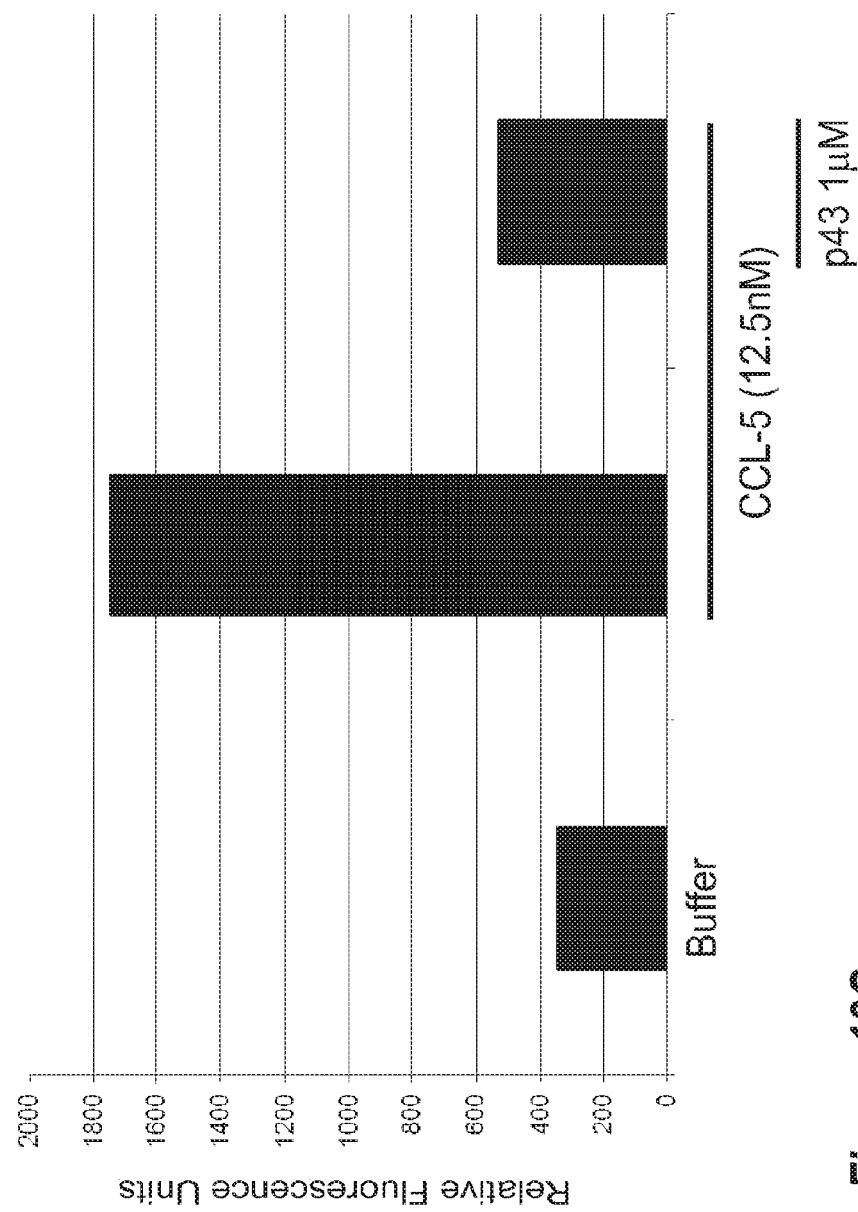

Cells that migrated to the lower chamber were collected, resuspended in 100 μl PBS, put into a 384 well opaque Greiner plate, and fluorescence (485/538/530) was quantified in a plate reader. The results are shown in FIGS. 13A to 13C. FIG. 13A shows the inhibitory effects of HisRS on THP-1 migration to CCL-23, FIG. 13B shows the inhibitory effects of AspRS on THP-1 migration to CCL-23, and FIG. 13C shows the inhibitory effects of p43 polypeptide on THP-1 migration to CCL-5.

Example 12

LC/MS/MS Identification of Endogenous QRS Fragments in Macrophages

To identify endogenous proteolytic QRS fragments having non-canonical activities, Macrophage (RAW 264.7) cell lines were treated with serum free DMEM media at a density of $15 \times 10^6$ cells/flasks. After 48 hours media and cell pellets were collected and processed. 200 μg of protein from secreted and cytosolic proteomic fractions were separated by SDS-PAGE and gel slices were prepared for analysis by mass spectrometry.

In-gel digests were analyzed by LTQ XL ion trap mass spectrometer (ThermoFisher) equipped with ultimate 3000 μLC system (Dionex). The samples were first loaded on PepTrap (michrom) for 10 min with 5% Acetonitrile in 0.1% formic acid using Dionex autosampler. Then the samples were analyzed with a 100 μm (inner diameter) fused silica capillary column containing 10 cm of C18 resin (michrom). Peptides were eluted from the column into mass spectrometer with a flow rate of 0.45 μl/min using a linear gradient of 5-33.5% acetonitrile in 0.1% formic acid within 110 min.

LTQ was operated in data-dependent scanning mode such that one full MS scan is followed by seven MS/MS scans of the seven most abundant ions. Dynamic exclusion was enabled with repeat count equals to 1, repeat duration equals to 20 seconds, exclusion list size is 300 and exclusion duration is 60 seconds.

After LC-MS/MS analysis, the raw data was searched with BioWorks 3.3.1 (SEQUEST) using a concatenated target/decoy cariant of the mouse IPI database. The SEQUEST data were filtered and sorted with DTASelect. Filtered proteomic data were organized and assembled into peptographs using PROTOMAP scripts designed in Professor Benjamin Cravatt's lab at Scripps Research Institute (see, e.g., Dix et al., *Cell.* 134:679-691, 2008, herein incorporated by reference).

Figure 14:
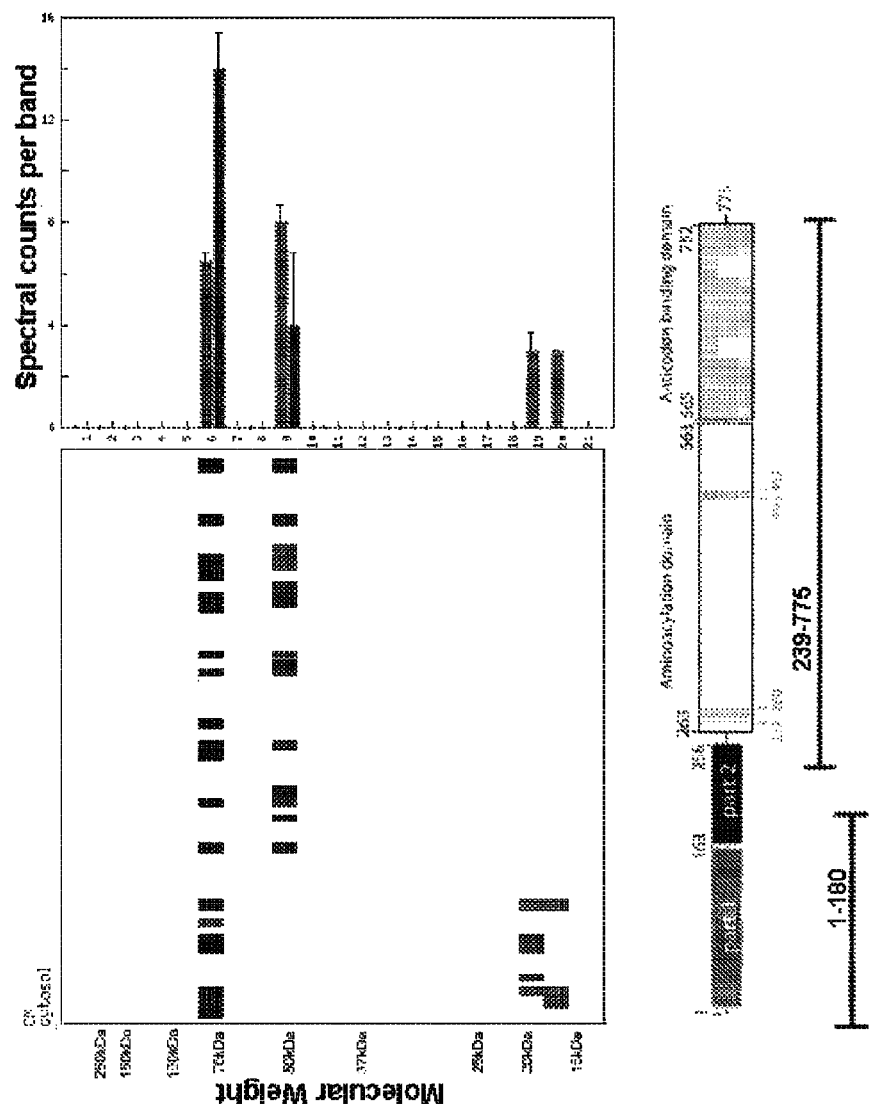
FIG. 14 shows a Protein Topography and Migration Analysis Platform (PROTOMAP) of cytosolic (blue) and conditioned media (red) QRS peptide fractions from macrophages, along with a representation of the QRS polypeptide sequence; (purple) indicates that the peptide was found in both cytosolic and conditioned media fractions. See Example 5.

FIG. 14 shows a Protein Topography and Migration Analysis Platform (PROTOMAP) of cytosolic (blue) and conditioned media (red) fractions, along with a representation of the QRS polypeptide sequence; (purple) indicates that the peptide was found in both cytosolic and conditioned media fractions. FIGS. 15A-15D show the peptides fragments that correspond to the PROTOMAP of FIG. 14. In these figures, (blue; italicized) corresponds to peptides detected in the cytosol, (red; underlined) corresponds to peptides detected in the conditioned media, and (purple; italicized and underlined) corresponds to peptides detected in both samples. FIG. 15A shows the peptide fragments for band 6 (full-length QRS), FIG. 15B shows the peptide fragment for band 9 (C-terminal QRS fragment) and FIGS. 15C-D show the peptide show the peptides form bands 19 and 20 (N-terminal QRS fragment).

As noted, the disclosure above is descriptive, illustrative and exemplary and is not to be taken as limiting the scope defined by the appended claims which follow.

The invention claimed is:

1. A method for reducing inflammation of the respiratory system in a subject in need thereof, comprising administering to the subject a sterile composition, comprising a pharmaceutically-acceptable carrier and an isolated histidyl-tRNA synthetase (HRS) polypeptide selected from (a) a polypeptide that comprises SEQ ID NO:28, (b) a fragment of (a) comprising at least 400 contiguous amino acids of SEQ ID NO:28, and (c) a variant which differs from SEQ ID NO:28 by less than 10% of the residues of SEQ ID NO:28, wherein the HRS polypeptide has an anti-inflammatory activity and is at least about 90% pure.

2. The method of claim 1, wherein (b) is a fragment of SEQ ID NO:28 comprising at least 500 contiguous amino acids of SEQ ID NO:28.

3. The method of claim 1, wherein (c) is a variant which differs from SEQ ID NO:28 by less than 5% of the residues of SEQ ID NO:28.

4. The method of claim 1, wherein the subject in need thereof has inflammatory lung disease (ILD), acute respiratory distress syndrome (ARDS), or pneumonia.

5. The method of claim 1, wherein the subject in need thereof has fibrosis, sarcoidosis, rheumatoid arthritis, lupus erythematosus, polymyositis, dermatomyositis, graft vs. host disease, scleroderma, hypersensitivity, or microscopic polyangiitis.

6. The method of claim 1, wherein the subject in need thereof has a condition selected from atopic asthma, non-atopic asthma, allergic asthma, atopic bronchial IgE-mediated asthma, bronchial asthma, essential asthma, true asthma, intrinsic asthma caused by pathophysiologic disturbances, extrinsic asthma caused by environmental factors, essential asthma of unknown or inapparent cause, non-atopic asthma, bronchitic asthma, emphysematous asthma, exercise-induced asthma, allergen induced asthma, cold air induced asthma, occupational asthma, infective asthma caused by bacterial, fungal, protozoal, or viral infection, non-allergic asthma, incipient asthma, wheezy infant syndrome and bronchiolytis, chronic or acute bronchoconstriction, chronic bronchitis, small airways obstruction, or emphysema.

7. The method of claim 1, wherein the subject in need thereof has an obstructive or inflammatory airway disease.

8. The method of claim 7, wherein the obstructive or inflammatory airways disease is chronic eosinophilic pneumonia, chronic obstructive pulmonary disease (COPD), COPD that includes chronic bronchitis, pulmonary emphysema or dyspnea associated or not associated with COPD, COPD that is characterized by irreversible, progressive airways obstruction, or adult respiratory distress syndrome (ARDS).

9. The method of claim 1, wherein the subject in need thereof has a condition related to exacerbation of airways hyper-reactivity consequent to other drug therapy, airway disease that is associated with pulmonary hypertension, bronchitis or acute bronchitis, acute laryngotracheal bronchitis, arachidic bronchitis, catarrhal bronchitis, croupus bronchitis, dry bronchitis, infectious asthmatic bronchitis, productive bronchitis, staphylococcus or streptococcal bronchitis, vesicular bronchitis, acute lung injury, bronchiectasis or cylindric bronchiectasis, sacculated bronchiectasis, fusiform bronchiectasis, capillary bronchiectasis, cystic bronchiectasis, dry bronchiectasis, or follicular bronchiectasis.

10. The method of claim 1, for desensitizing immune cells to self antigens, foreign antigens, irritants, allergens, or infectious agents related to pulmonary inflammation.

11. The method of claim 1, which is utilized in combination with a treatment for pulmonary inflammation, selected from lung rehabilitation; the use of bronchodilators, steroids or corticosteroids, antibiotics, metered-dose inhalers (MDIs), dry powder inhalers (DPIs), nebulizers, or oxygen therapy; and surgery, optionally bullectomy, lung volume reduction surgery, or lung transplant.

12. The method of claim 11, wherein the bronchodilators are selected from ipratropium, tiotropium, salmeterol, and formoterol.

* * * * *

SEQUENCE LISTING

<160> NUMBER OF SEQ ID NOS: 117

<210> SEQ ID NO 1
<211> LENGTH: 528
<212> TYPE: PRT
<213> ORGANISM: Homo sapiens

<400> SEQUENCE: 1

```
Met Gly Asp Ala Pro Ser Pro Glu Glu Lys Leu His Leu Ile Thr Arg
1               5                   10                  15

Asn Leu Gln Glu Val Leu Gly Glu Glu Lys Leu Lys Glu Ile Leu Lys
            20                  25                  30

Glu Arg Glu Leu Lys Ile Tyr Trp Gly Thr Ala Thr Thr Gly Lys Pro
        35                  40                  45

His Val Ala Tyr Phe Val Pro Met Ser Lys Ile Ala Asp Phe Leu Lys
    50                  55                  60

Ala Gly Cys Glu Val Thr Ile Leu Phe Ala Asp Leu His Ala Tyr Leu
65                  70                  75                  80

Asp Asn Met Lys Ala Pro Trp Glu Leu Leu Glu Leu Arg Val Ser Tyr
                85                  90                  95

Tyr Glu Asn Val Ile Lys Ala Met Leu Glu Ser Ile Gly Val Pro Leu
            100                 105                 110

Glu Lys Leu Lys Phe Ile Lys Gly Thr Asp Tyr Gln Leu Ser Lys Glu
        115                 120                 125

Tyr Thr Leu Asp Val Tyr Arg Leu Ser Ser Val Val Thr Gln His Asp
    130                 135                 140

Ser Lys Lys Ala Gly Ala Glu Val Val Lys Gln Val Glu His Pro Leu
145                 150                 155                 160

Leu Ser Gly Leu Leu Tyr Pro Gly Leu Gln Ala Leu Asp Glu Glu Tyr
                165                 170                 175

Leu Lys Val Asp Ala Gln Phe Gly Gly Ile Asp Gln Arg Lys Ile Phe
            180                 185                 190

Thr Phe Ala Glu Lys Tyr Leu Pro Ala Leu Gly Tyr Ser Lys Arg Val
        195                 200                 205

His Leu Met Asn Pro Met Val Pro Gly Leu Thr Gly Ser Lys Met Ser
    210                 215                 220

Ser Ser Glu Glu Glu Ser Lys Ile Asp Leu Leu Asp Arg Lys Glu Asp
225                 230                 235                 240

Val Lys Lys Lys Leu Lys Lys Ala Phe Cys Glu Pro Gly Asn Val Glu
                245                 250                 255

Asn Asn Gly Val Leu Ser Phe Ile Lys His Val Leu Phe Pro Leu Lys
            260                 265                 270

Ser Glu Phe Val Ile Leu Arg Asp Glu Lys Trp Gly Gly Asn Lys Thr
        275                 280                 285

Tyr Thr Ala Tyr Val Asp Leu Glu Lys Asp Phe Ala Ala Glu Val Val
    290                 295                 300

His Pro Gly Asp Leu Lys Asn Ser Val Glu Val Ala Leu Asn Lys Leu
305                 310                 315                 320

Leu Asp Pro Ile Arg Glu Lys Phe Asn Thr Pro Ala Leu Lys Lys Leu
                325                 330                 335

Ala Ser Ala Ala Tyr Pro Asp Pro Ser Lys Gln Lys Pro Met Ala Lys
            340                 345                 350

Gly Pro Ala Lys Asn Ser Glu Pro Glu Glu Val Ile Pro Ser Arg Leu
        355                 360                 365
```

```
Asp Ile Arg Val Gly Lys Ile Ile Thr Val Glu Lys His Pro Asp Ala
370                 375                 380

Asp Ser Leu Tyr Val Glu Lys Ile Asp Val Gly Glu Ala Glu Pro Arg
385                 390                 395                 400

Thr Val Val Ser Gly Leu Val Gln Phe Val Pro Lys Glu Glu Leu Gln
                405                 410                 415

Asp Arg Leu Val Val Val Leu Cys Asn Leu Lys Pro Gln Lys Met Arg
                420                 425                 430

Gly Val Glu Ser Gln Gly Met Leu Leu Cys Ala Ser Ile Glu Gly Ile
                435                 440                 445

Asn Arg Gln Val Glu Pro Leu Asp Pro Pro Ala Gly Ser Ala Pro Gly
450                 455                 460

Glu His Val Phe Val Lys Gly Tyr Glu Lys Gly Gln Pro Asp Glu Glu
465                 470                 475                 480

Leu Lys Pro Lys Lys Val Phe Glu Lys Leu Gln Ala Asp Phe Lys
                    485                 490                 495

Ile Ser Glu Glu Cys Ile Ala Gln Trp Lys Gln Thr Asn Phe Met Thr
                500                 505                 510

Lys Leu Gly Ser Ile Ser Cys Lys Ser Leu Lys Gly Gly Asn Ile Ser
                515                 520                 525
```

<210> SEQ ID NO 2
<211> LENGTH: 528
<212> TYPE: PRT
<213> ORGANISM: Homo sapiens

<400> SEQUENCE: 2

```
Met Gly Asp Ala Pro Ser Pro Glu Glu Lys Leu His Leu Ile Thr Arg
1               5                   10                  15

Asn Leu Gln Glu Val Leu Gly Glu Lys Leu Lys Glu Ile Leu Lys
                20                  25                  30

Glu Arg Glu Leu Lys Ile Tyr Trp Gly Thr Ala Thr Thr Gly Lys Pro
            35                  40                  45

His Val Ala Tyr Phe Val Pro Met Ser Lys Ile Ala Asp Phe Leu Lys
50                  55                  60

Ala Gly Cys Glu Val Thr Ile Leu Phe Ala Asp Leu His Ala Tyr Leu
65                  70                  75                  80

Asp Asn Met Lys Ala Pro Trp Glu Leu Leu Glu Leu Arg Val Ser Tyr
                85                  90                  95

Tyr Glu Asn Val Ile Lys Ala Met Leu Glu Ser Ile Gly Val Pro Leu
            100                 105                 110

Glu Lys Leu Lys Phe Ile Lys Gly Thr Asp Tyr Gln Leu Ser Lys Glu
        115                 120                 125

Tyr Thr Leu Asp Val Tyr Arg Leu Ser Ser Val Val Thr Gln His Asp
    130                 135                 140

Ser Lys Lys Ala Gly Ala Glu Val Val Lys Gln Val Glu His Pro Leu
145                 150                 155                 160

Leu Ser Gly Leu Leu Tyr Pro Gly Leu Gln Ala Leu Asp Glu Glu Tyr
                165                 170                 175

Leu Lys Val Asp Ala Gln Phe Gly Gly Ile Asp Gln Arg Lys Ile Phe
            180                 185                 190

Thr Phe Ala Glu Lys Tyr Leu Pro Ala Leu Gly Tyr Ser Lys Arg Val
        195                 200                 205

His Leu Met Asn Pro Met Val Pro Gly Leu Thr Gly Ser Lys Met Ser
    210                 215                 220
```

-continued

Ser Ser Glu Glu Glu Ser Lys Ile Asp Leu Leu Asp Arg Lys Glu Asp
225                 230                 235                 240

Val Lys Lys Lys Leu Lys Lys Ala Phe Cys Glu Pro Gly Asn Val Glu
            245                 250                 255

Asn Asn Gly Val Leu Ser Phe Ile Lys His Val Leu Phe Pro Leu Lys
        260                 265                 270

Ser Glu Phe Val Ile Leu Arg Asp Glu Lys Trp Gly Gly Asn Lys Thr
    275                 280                 285

Tyr Thr Ala Tyr Val Asp Leu Glu Lys Asp Phe Ala Ala Glu Val Val
290                 295                 300

His Pro Gly Asp Leu Lys Asn Ser Val Glu Val Ala Leu Asn Lys Leu
305                 310                 315                 320

Leu Asp Pro Ile Arg Glu Lys Phe Asn Thr Pro Ala Leu Lys Lys Leu
            325                 330                 335

Ala Ser Ala Ala Ala Pro Asp Pro Ser Lys Gln Lys Pro Met Ala Lys
        340                 345                 350

Gly Pro Ala Lys Asn Ser Glu Pro Glu Val Ile Pro Ser Arg Leu
    355                 360                 365

Asp Ile Arg Val Gly Lys Ile Ile Thr Val Glu Lys His Pro Asp Ala
370                 375                 380

Asp Ser Leu Tyr Val Glu Lys Ile Asp Val Gly Glu Ala Glu Pro Arg
385                 390                 395                 400

Thr Val Val Ser Gly Leu Val Gln Phe Val Pro Lys Glu Glu Leu Gln
            405                 410                 415

Asp Arg Leu Val Val Leu Cys Asn Leu Lys Pro Gln Lys Met Arg
        420                 425                 430

Gly Val Glu Ser Gln Gly Met Leu Leu Cys Ala Ser Ile Glu Gly Ile
    435                 440                 445

Asn Arg Gln Val Glu Pro Leu Asp Pro Pro Ala Gly Ser Ala Pro Gly
450                 455                 460

Glu His Val Phe Val Lys Gly Tyr Glu Lys Gly Gln Pro Asp Glu Glu
465                 470                 475                 480

Leu Lys Pro Lys Lys Val Phe Glu Lys Leu Gln Ala Asp Phe Lys
            485                 490                 495

Ile Ser Glu Glu Cys Ile Ala Gln Trp Lys Gln Thr Asn Phe Met Thr
        500                 505                 510

Lys Leu Gly Ser Ile Ser Cys Lys Ser Leu Lys Gly Gly Asn Ile Ser
    515                 520                 525

<210> SEQ ID NO 3
<211> LENGTH: 364
<212> TYPE: PRT
<213> ORGANISM: Homo sapiens

<400> SEQUENCE: 3

Met Gly Asp Ala Pro Ser Pro Glu Glu Lys Leu His Leu Ile Thr Arg
1               5                   10                  15

Asn Leu Gln Glu Val Leu Gly Glu Lys Leu Lys Glu Ile Leu Lys
            20                  25                  30

Glu Arg Glu Leu Lys Ile Tyr Trp Gly Thr Ala Thr Gly Lys Pro
        35                  40                  45

His Val Ala Tyr Phe Val Pro Met Ser Lys Ile Ala Asp Phe Leu Lys
    50                  55                  60

Ala Gly Cys Glu Val Thr Ile Leu Phe Ala Asp Leu His Ala Tyr Leu

```
                65                  70                  75                  80
Asp Asn Met Lys Ala Pro Trp Glu Leu Leu Glu Leu Arg Val Ser Tyr
                    85                  90                  95

Tyr Glu Asn Val Ile Lys Ala Met Leu Glu Ser Ile Gly Val Pro Leu
                100                 105                 110

Glu Lys Leu Lys Phe Ile Lys Gly Thr Asp Tyr Gln Leu Ser Lys Glu
                115                 120                 125

Tyr Thr Leu Asp Val Tyr Arg Leu Ser Ser Val Thr Gln His Asp
                130                 135                 140

Ser Lys Lys Ala Gly Ala Glu Val Val Lys Gln Val Glu His Pro Leu
145                 150                 155                 160

Leu Ser Gly Leu Leu Tyr Pro Gly Leu Gln Ala Leu Asp Glu Glu Tyr
                165                 170                 175

Leu Lys Val Asp Ala Gln Phe Gly Gly Ile Asp Gln Arg Lys Ile Phe
                180                 185                 190

Thr Phe Ala Glu Lys Tyr Leu Pro Ala Leu Gly Tyr Ser Lys Arg Val
                195                 200                 205

His Leu Met Asn Pro Met Val Pro Gly Leu Thr Gly Ser Lys Met Ser
                210                 215                 220

Ser Ser Glu Glu Glu Ser Lys Ile Asp Leu Leu Asp Arg Lys Glu Asp
225                 230                 235                 240

Val Lys Lys Lys Leu Lys Lys Ala Phe Cys Glu Pro Gly Asn Val Glu
                245                 250                 255

Asn Asn Gly Val Leu Ser Phe Ile Lys His Val Leu Phe Pro Leu Lys
                260                 265                 270

Ser Glu Phe Val Ile Leu Arg Asp Glu Lys Trp Gly Gly Asn Lys Thr
                275                 280                 285

Tyr Thr Ala Tyr Val Asp Leu Glu Lys Asp Phe Ala Ala Glu Val Val
                290                 295                 300

His Pro Gly Asp Leu Lys Asn Ser Val Glu Val Ala Leu Asn Lys Leu
305                 310                 315                 320

Leu Asp Pro Ile Arg Glu Lys Phe Asn Thr Pro Ala Leu Lys Lys Leu
                325                 330                 335

Ala Ser Ala Ala Tyr Pro Asp Pro Ser Lys Gln Lys Pro Met Ala Lys
                340                 345                 350

Gly Pro Ala Lys Asn Ser Glu Pro Glu Glu Val Ile
                355                 360

<210> SEQ ID NO 4
<211> LENGTH: 1683
<212> TYPE: DNA
<213> ORGANISM: Homo sapiens

<400> SEQUENCE: 4
atgggggacg ctcccagccc tgaagagaaa ctgcacctta tcacccggaa cctgcaggag      60
gttctggggg aagagaagct gaaggagata ctgaaggagc gggaacttaa aatttactgg     120
ggaacggcaa ccacgggcaa accacatgtg gcttactttg tgcccatgtc aaagattgca     180
gacttcttaa aggcagggtg tgaggtaaca attctgtttg cggacctcca cgcatacctg     240
gataacatga agcccccatg gaacttctga gaactccgag tcagttacta tgagaatgtg     300
atcaaagcaa tgctggagag cattggtgtg cccttggaga agctcaagtt catcaaaggc     360
actgattacc agctcagcaa agagtacaca ctagatgtgt acagactctc ctccgtggtc     420
acacagcacg attccaagaa ggctggagct gaggtggtaa agcaggtgga gcacccttg     480
```

```
ctgagtggcc tcttataccc cggactgcag gctttggatg aagagtattt aaaagtagat    540
gcccaatttg gaggcattga tcagagaaag attttcacct ttgcagagaa gtacctccct    600
gcacttggct attcaaaacg ggtccatctg atgaatccta tggttccagg attaacaggc    660
agcaaaatga gctcttcaga agaggagtcc aagattgatc tccttgatcg aaggaggat     720 gtgaagaaaa aactgaagaa ggccttctgt gagccaggaa atgtggagaa caatggggtt    780
ctgtccttca tcaagcatgt cctttttccc cttaagtccg agtttgtgat cctacgagat    840
gagaaatggg gtggaaacaa aacctacaca gcttacgtgg acctggaaaa ggactttgct    900
gctgaggttg tacatcctgg agacctgaag aattctgttg aagtcgcact gaacaagttg    960
ctggatccaa tccgggaaaa gtttaatacc cctgccctga aaaaactggc cagcgctgcc   1020
tacccagatc cctcaaagca gaagccaatg gccaaaggcc ctgccaagaa ttcagaacca   1080
gaggaggtca tcccatcccg gctggatatc cgtgtgggga aatcatcac tgtggagaag    1140 cacccagatg cagacagcct gtatgtagag aagattgacg tgggggaagc tgaaccacgg   1200
actgtggtga gcggcctggt acagttcgtg cccaaggagg aactgcagga caggctggta   1260
gtggtgctgt gcaacctgaa accccagaag atgagaggag tcgagtccca aggcatgctt   1320
ctgtgtgctt ctatagaagg gataaaccgc caggttgaac ctctggaccc tccggcaggc   1380
tctgctcctg gtgagcacgt gtttgtgaag ggctatgaaa agggccaacc agatgaggag   1440
ctcaagccca gaagaaagt cttcgagaag ttgcaggctg acttcaaaat ttctgaggag    1500
tgcatcgcac agtggaagca aaccaacttc atgaccaagc tgggctccat ttcctgtaaa   1560
tcgctgaaag gggggaacat tagctagcca gcccagcatc ttcccccctt cttccaccac   1620
tgagtcatct gctgtctctt cagtctgctc catccatcac ccatttaccc atctctcagg   1680
aca                                                                 1683
```

<210> SEQ ID NO 5
<211> LENGTH: 8
<212> TYPE: PRT
<213> ORGANISM: Artificial Sequence
<220> FEATURE:
<223> OTHER INFORMATION: C-terminal tag

<400> SEQUENCE: 5

Leu Glu His His His His His His
1               5

<210> SEQ ID NO 6
<211> LENGTH: 348
<212> TYPE: PRT
<213> ORGANISM: Homo sapiens
<220> FEATURE:
<221> NAME/KEY: VARIANT
<222> LOCATION: (1)..(9)
<223> OTHER INFORMATION: Xaa = Any Amino Acid

<400> SEQUENCE: 6

Xaa Xaa Xaa Xaa Xaa Xaa Xaa Xaa Xaa Lys Ile Phe Thr Phe Ala Glu
1               5                   10                  15

Lys Tyr Leu Pro Ala Leu Gly Tyr Ser Lys Arg Val His Leu Met Asn
            20                  25                  30

Pro Met Val Pro Gly Leu Thr Gly Ser Lys Met Ser Ser Ser Glu Glu
        35                  40                  45

Glu Ser Lys Ile Asp Leu Leu Asp Arg Lys Glu Asp Val Lys Lys Lys
    50                  55                  60

```
Leu Lys Lys Ala Phe Cys Glu Pro Gly Asn Val Glu Asn Asn Gly Val
 65                  70                  75                  80

Leu Ser Phe Ile Lys His Val Leu Phe Pro Leu Lys Ser Glu Phe Val
             85                  90                  95

Ile Leu Arg Asp Glu Lys Trp Gly Gly Asn Lys Thr Tyr Thr Ala Tyr
            100                 105                 110

Val Asp Leu Glu Lys Asp Phe Ala Ala Glu Val Val His Pro Gly Asp
        115                 120                 125

Leu Lys Asn Ser Val Glu Val Ala Leu Asn Lys Leu Leu Asp Pro Ile
130                 135                 140

Arg Glu Lys Phe Asn Thr Pro Ala Leu Lys Lys Leu Ala Ser Ala Ala
145                 150                 155                 160

Tyr Pro Asp Pro Ser Lys Gln Lys Pro Met Ala Lys Gly Pro Ala Lys
                165                 170                 175

Asn Ser Glu Pro Glu Glu Val Ile Pro Ser Arg Leu Asp Ile Arg Val
            180                 185                 190

Gly Lys Ile Ile Thr Val Glu Lys His Pro Asp Ala Asp Ser Leu Tyr
        195                 200                 205

Val Glu Lys Ile Asp Val Gly Glu Ala Glu Pro Arg Thr Val Val Ser
    210                 215                 220

Gly Leu Val Gln Phe Val Pro Lys Glu Leu Gln Asp Arg Leu Val
225                 230                 235                 240

Val Val Leu Cys Asn Leu Lys Pro Gln Lys Met Arg Gly Val Glu Ser
                245                 250                 255

Gln Gly Met Leu Leu Cys Ala Ser Ile Glu Gly Ile Asn Arg Gln Val
            260                 265                 270

Glu Pro Leu Asp Pro Pro Ala Gly Ser Ala Pro Gly Glu His Val Phe
        275                 280                 285

Val Lys Gly Tyr Glu Lys Gly Gln Pro Asp Glu Glu Leu Lys Pro Lys
    290                 295                 300

Lys Lys Val Phe Glu Lys Leu Gln Ala Asp Phe Lys Ile Ser Glu Glu
305                 310                 315                 320

Cys Ile Ala Gln Trp Lys Gln Thr Asn Phe Met Thr Lys Leu Gly Ser
                325                 330                 335

Ile Ser Cys Lys Ser Leu Lys Gly Gly Asn Ile Ser
            340                 345

<210> SEQ ID NO 7
<211> LENGTH: 2178
<212> TYPE: DNA
<213> ORGANISM: Homo sapiens

<400> SEQUENCE: 7
ttcagaaagt ggtggaggga agacttcctt tttcccagag acagaaggtt atgcacccag      60
tggcctggga ccattgttct gggctttttt tcccttcgac atggatttgc ttctcactgt     120
gtaccccaac caccaaaacc accctgagat caatgctggt gctcctgcat cagatggctt     180
agagatcctt ccacctctta acacaagcat ctaggtccac tttactcaaa tctggcctca     240
gttgagagca gagtatacca tcagagccca ttctcctgtc tgctgtctgg acgtggaaa      300 gaaagttagc tctaggggt ctttccaggg gcctctgtaa ggactggatg ctccttccg       360 gaatccaaga gttcaccagg ctgcttctct aatggacgat gatcctcttc ctcctgacgt     420
ctctccctgg cagcacccag atgcagacag cctgtatgta gagaagattg acgtggggga    480
```

```
agctgaacca cggactgtgg tgagcggcct ggtacagttc gtgcccaagg aggaactgca    540
ggacaggctg gtagtggtgc tgtgcaacct gaaaccccag aagatgagag gagtcgagtc    600
ccaaggcatg cttctgtgtg cttctatgtg agtgaggact tggagtgggg cacaggacct    660
ggggaggcca ggaagagtag ggaatcagcc catatgatgt ccttccacac accaggtgga    720
agctctgaga acacgtgcct cttccttgct gatgccaaaa gttgatgcat gaaggactta    780
tcgtacaagt actgttaatg aagcatttta cctacagtta attttgttaa aatagaaatg    840
gagggctcaa accagtacat acccaagtct tactactagt aaggagtgga gcagggattc    900
aaatcccagt tttgatgtct ataaagtcct cgctacgtta ttttatactt cctcccctag    960
aaacacagat tttggtatct tgacacacaa ttttggtata gcctgggtta atgtaaccct   1020
ggtgatatgc agggatgtag caagataaga ggacctcctg gggctctggt actgaggatg   1080
ccctaaatcc catcagggcc cctgtgtaaa ggcccggatt gctttggcct ccacagtcac   1140
tggaacccat ccatagcctc actcttctct tgtcctgtgt cttcccagag aagggataaa   1200
ccgccaggtt gaacctctgg accctccggc aggctctgct cctggtgagc acgtgtttgt   1260
gaagggctat gaaaagggcc aaccagatga ggagctcaag cccaagagga agtcttcga    1320
gaagttgcag gctgacttca aaatttctga ggagtgcatc gcacagtgga agcaaaccaa   1380
cttcatgacc aagctgggct ccatttcctg taaatcgctg aaagggggga acattagcta   1440
gccagcccca tcttccccc cttcttcca ccactgagtc atctgctgtc tcttcagtct     1500
gctccaccca tcacccattt acccatctct caggacacgg aagcagcggg tttggactct   1560
ttattcggtg cagaactcgg caaggggcag cttaccctcc ccagaaccca ggatcatcct   1620
gtctggctgc agtgagagac caaccccctaa caagggctgg gccacagcag ggagtccagc   1680
cctaccttct tcccttggca gctggagaaa tctggtttca atataactca tttaaaaatt   1740
tatgccacag tccttataat tggaaaaata ctggtgccca ggttttcttg gagttatcca   1800
agcagctgcg cccctagctg ggatctggta cctggactag gctaattaca gcttctcccc   1860
aacaggaaac tgtgggattt gaaaaggaaa gggaagggaa aacagagaac ctagtggtct   1920
accaagtggt tggcaacttt cccaatgtct gcttactctg aggcttggca ctggggggca   1980
gggcctgccc cagggctcct ggaatttccc ttgatccagc taggctggga cactccctaa   2040
atcagctgcg tgttgttagc atcaggcaga atgaatggca gagagtgatt ctgtcttcat   2100
agagggtggg gtacttctcc ataaggcatc tcagtcaaat ccccatcact gtcataaatt   2160
caaataaaat gtctgaac                                                 2178
```

<210> SEQ ID NO 8
<211> LENGTH: 388
<212> TYPE: PRT
<213> ORGANISM: Homo sapiens
<220> FEATURE:
<221> NAME/KEY: VARIANT
<222> LOCATION: (354)..(388)
<223> OTHER INFORMATION: Xaa = Any Amino Acid

<400> SEQUENCE: 8

Met Gly Asp Ala Pro Ser Pro Glu Glu Lys Leu His Leu Ile Thr Arg
1               5                   10                  15

Asn Leu Gln Glu Val Leu Gly Glu Glu Lys Leu Lys Glu Ile Leu Lys
                20                  25                  30

Glu Arg Glu Leu Lys Ile Tyr Trp Gly Thr Ala Thr Thr Gly Lys Pro
        35                  40                  45

His Val Ala Tyr Phe Val Pro Met Ser Lys Ile Ala Asp Phe Leu Lys
            50                  55                  60

Ala Gly Cys Glu Val Thr Ile Leu Phe Ala Asp Leu His Ala Tyr Leu
 65                  70                  75                  80

Asp Asn Met Lys Ala Pro Trp Glu Leu Leu Glu Leu Arg Val Ser Tyr
                 85                  90                  95

Tyr Glu Asn Val Ile Lys Ala Met Leu Glu Ser Ile Gly Val Pro Leu
            100                 105                 110

Glu Lys Leu Lys Phe Ile Lys Gly Thr Asp Tyr Gln Leu Ser Lys Glu
            115                 120                 125

Tyr Thr Leu Asp Val Tyr Arg Leu Ser Ser Val Thr Gln His Asp
130                 135                 140

Ser Lys Ala Gly Ala Glu Val Val Lys Gln Val Glu His Pro Leu
145                 150                 155                 160

Leu Ser Gly Leu Leu Tyr Pro Gly Leu Gln Ala Leu Asp Glu Glu Tyr
                165                 170                 175

Leu Lys Val Asp Ala Gln Phe Gly Gly Ile Asp Gln Arg Lys Ile Phe
            180                 185                 190

Thr Phe Ala Glu Lys Tyr Leu Pro Ala Leu Gly Tyr Ser Lys Arg Val
            195                 200                 205

His Leu Met Asn Pro Met Val Pro Gly Leu Thr Gly Ser Lys Met Ser
            210                 215                 220

Ser Ser Glu Glu Glu Ser Lys Ile Asp Leu Leu Asp Arg Lys Glu Asp
225                 230                 235                 240

Val Lys Lys Lys Leu Lys Lys Ala Phe Cys Glu Pro Gly Asn Val Glu
                245                 250                 255

Asn Asn Gly Val Leu Ser Phe Ile Lys His Val Leu Phe Pro Leu Lys
            260                 265                 270

Ser Glu Phe Val Ile Leu Arg Asp Glu Lys Trp Gly Gly Asn Lys Thr
            275                 280                 285

Tyr Thr Ala Tyr Val Asp Leu Glu Lys Asp Phe Ala Ala Glu Val Val
            290                 295                 300

His Pro Gly Asp Leu Lys Asn Ser Val Glu Val Ala Leu Asn Lys Leu
305                 310                 315                 320

Leu Asp Pro Ile Arg Glu Lys Phe Asn Thr Pro Ala Leu Lys Lys Leu
                325                 330                 335

Ala Ser Ala Ala Tyr Pro Asp Pro Ser Lys Gln Lys Pro Met Ala Lys
            340                 345                 350

Gly Xaa Xaa Xaa Xaa Xaa Xaa Xaa Xaa Xaa Xaa Xaa Xaa Xaa
            355                 360                 365

Xaa Xaa Xaa Xaa Xaa Xaa Xaa Xaa Xaa Xaa Xaa Xaa Xaa Xaa
370                 375                 380

Xaa Xaa Xaa Xaa
385

<210> SEQ ID NO 9
<211> LENGTH: 1167
<212> TYPE: DNA
<213> ORGANISM: Homo sapiens

<400> SEQUENCE: 9
atgggggacg ctcccagccc tgaagagaaa ctgcacctta tcacccggaa cctgcaggag      60
gttctggggg aagagaagct gaaggagata ctgaaggagc gggaacttaa aatttactgg     120
ggaacggcaa ccacgggcaa accacatgtg gcttactttg tgcccatgtc aaagattgca     180

```
gacttcttaa aggcagggtg tgaggtaaca attctgtttg cggacctcca cgcatacctg    240
gataacatga aagccccatg gaacttcta gaactccgag tcagttacta tgagaatgtg    300
atcaaagcaa tgctggagag cattggtgtg cccttggaga agctcaagtt catcaaaggc    360
actgattacc agctcagcaa agagtacaca ctagatgtgt acagactctc ctccgtggtc    420
acacagcacg attccaagaa ggctggagct gaggtggtaa agcaggtgga gcaccctttg    480
ctgagtggcc tcttataccc cggactgcag gctttggatg aagagtattt aaaagtagat    540
gcccaatttg gaggcattga tcagagaaag attttcacct ttgcagagaa gtacctccct    600
gcacttggct attcaaaacg ggtccatctg atgaatccta tggttccagg attaacaggc    660
agcaaaatga gctcttcaga gaggagtcc aagattgatc tccttgatcg aaggaggat    720 gtgaagaaaa aactgaagaa ggccttctgt gagccaggaa atgtggagaa caatgggtt    780 ctgtccttca tcaagcatgt cctttttccc cttaagtccg agtttgtgat cctacgagat    840
gagaaatggg gtgaaacaa aacctacaca gcttacgtgg acctgaaaaa ggactttgct    900
gctgaggttg tacatcctgg agacctgaag aattctgttg aagtcgcact gaacaagttg    960
ctggatccaa tccgggaaaa gtttaatacc cctgccctga aaaaactggc cagcgctgcc   1020
tacccagatc cctcaaagca gaagccaatg gccaaaggcc tgccaagaat tcagaaccag   1080
aggaggtcat cccatcccgg ctggatatcc gtgtggggaa atcatcact gtggagaagc   1140 acccagatgc agacagcctg tatgtag                                      1167

<210> SEQ ID NO 10
<211> LENGTH: 318
<212> TYPE: PRT
<213> ORGANISM: Homo sapiens

<400> SEQUENCE: 10

Met Asn Pro Met Val Pro Gly Leu Thr Gly Ser Lys Met Ser Ser
1               5                   10                  15

Glu Glu Glu Ser Lys Ile Asp Leu Leu Asp Arg Lys Glu Asp Val Lys
            20                  25                  30

Lys Lys Leu Lys Lys Ala Phe Cys Glu Pro Gly Asn Val Glu Asn Asn
        35                  40                  45

Gly Val Leu Ser Phe Ile Lys His Val Leu Phe Pro Leu Lys Ser Glu
    50                  55                  60

Phe Val Ile Leu Arg Asp Glu Lys Trp Gly Gly Asn Lys Thr Tyr Thr
65                  70                  75                  80

Ala Tyr Val Asp Leu Glu Lys Asp Phe Ala Ala Glu Val Val His Pro
                85                  90                  95

Gly Asp Leu Lys Asn Ser Val Glu Val Ala Leu Asn Lys Leu Leu Asp
            100                 105                 110

Pro Ile Arg Glu Lys Phe Asn Thr Pro Ala Leu Lys Lys Leu Ala Ser
        115                 120                 125

Ala Ala Tyr Pro Asp Pro Ser Lys Gln Lys Pro Met Ala Lys Gly Pro
    130                 135                 140

Ala Lys Asn Ser Glu Pro Glu Glu Val Ile Pro Ser Arg Leu Asp Ile
145                 150                 155                 160

Arg Val Gly Lys Ile Ile Thr Val Glu Lys His Pro Asp Ala Asp Ser
                165                 170                 175

Leu Tyr Val Glu Lys Ile Asp Val Gly Glu Ala Glu Pro Arg Thr Val
            180                 185                 190
```

```
Val Ser Gly Leu Val Gln Phe Val Pro Lys Glu Glu Leu Gln Asp Arg
            195                 200                 205
Leu Val Val Leu Cys Asn Leu Lys Pro Gln Lys Met Arg Gly Val
        210                 215                 220
Glu Ser Gln Gly Met Leu Leu Cys Ala Ser Ile Glu Gly Ile Asn Arg
225                 230                 235                 240
Gln Val Glu Pro Leu Asp Pro Pro Ala Gly Ser Ala Pro Gly Glu His
                245                 250                 255
Val Phe Val Lys Gly Tyr Glu Lys Gly Gln Pro Asp Glu Glu Leu Lys
            260                 265                 270
Pro Lys Lys Lys Val Phe Glu Lys Leu Gln Ala Asp Phe Lys Ile Ser
        275                 280                 285
Glu Glu Cys Ile Ala Gln Trp Lys Gln Thr Asn Phe Met Thr Lys Leu
        290                 295                 300
Gly Ser Ile Ser Cys Lys Ser Leu Lys Gly Gly Asn Ile Ser
305                 310                 315
```

<210> SEQ ID NO 11
<211> LENGTH: 1736
<212> TYPE: DNA
<213> ORGANISM: Homo sapiens

<400> SEQUENCE: 11

```
gaaagatttt cacctttgca gagaagtacc tccctgcact ggctattca aaacgggtcc      60
atctgatgaa tcctatggtt ccaggattaa caggcagcaa atgagctct tcagaagagg     120
agtccaagat tgatctcctt gatcggaagg aggatgtgaa gaaaaactg aagaaggcct     180
tctgtgagcc aggaaatgtg gagaacaatg gggttctgtc cttcatcaag catgtccttt     240
ttccccttaa gtccgagttt gtgatcctac gagatgagaa atggggtgga acaaaacct     300
acacagctta cgtggacctg aaaaggact tgctgctga ggttgtacat cctggagacc     360
tgaagaattc tgttgaagtc gcactgaaca agttgctgga tccaatccgg gaaaagttta     420
atacccctgc cctgaaaaaa ctggccagcg ctgcctaccc agatccctca agcagaagc     480
caatggccaa aggccctgcc aagaattcag aaccagagga ggtcatccca tcccggctgg     540
atatccgtgt ggggaaaatc atcactgtgg agaagcaccc agatgcagac agcctgtatg     600
tagagaagat tgacgtgggg gaagctgaac acggactgt ggtgagcggc ctggtacagt     660
tcgtgcccaa ggaggaactg caggacaggc tggtagtggt gctgtgcaac ctgaaacccc     720
agaagatgag aggagtcgag tcccaaggca tgcttctgtg tgcttctata gaagggataa     780
accgccaggt tgaacctctg gaccctccgg caggctctgc tcctggtgag cacgtgtttg     840
tgaagggcta tgaaaagggc caaccagatg aggagctcaa gcccaagaag aaagtcttcg     900
agaagttgca ggctgacttc aaaatttctg aggagtgcat cgcacagtgg aagcaaacca     960
acttcatgac caagctgggc tccatttcct gtaaatcgct gaaggggggg aacattagct    1020
agccagccca gcatcttccc ccttcttcc accactgagt catctgctgt ctcttcagtc    1080
tgctccatcc atcacccatt taccatctc tcaggacacg gaagcagcgg tttggactc    1140
tttattcggt gcagaactcg gcaaggggca gcttaccctc cccagaaccc aggatcatcc    1200
tgtctggctg cagtgagaga ccaaccccta caagggctg ggccacagca gggagtccag    1260
ccctaccttc ttcccttggc agctggagaa atctggtttc aatataactc atttaaaaat    1320
ttatgccaca gtccttataa ttggaaaaat actggtgccc aggttttctt ggagttatcc    1380
aagcagctgc gccctagct gggatctggt acctggacta ggctaattac agcttctccc    1440
```

```
caacaggaaa ctgtgggatt tgaaaaggaa agggaaggga aaacagagaa cctagtggtc   1500
taccaagtgg ttggcaactt tcccaatgtc tgcttactct gaggcttggc actgggggcc   1560
agggcctgcc ccagggctcc tggaatttcc cttgatccag ctaggctggg acactcccta   1620
aatcagctgc gtgttgttag catcaggcag aatgaatggc agagagtgat tctgtcttca   1680
tagagggtgg ggtacttctc cataaggcat ctcagtcaaa tccccatcac tgtcat       1736
```

```
<210> SEQ ID NO 12
<211> LENGTH: 179
<212> TYPE: PRT
<213> ORGANISM: Homo sapiens

<400> SEQUENCE: 12
```

```
Met Ala Lys Gly Pro Ala Lys Asn Ser Glu Pro Glu Val Ile Pro
1               5                   10                  15

Ser Arg Leu Asp Ile Arg Val Gly Lys Ile Ile Thr Val Glu Lys His
            20                  25                  30

Pro Asp Ala Asp Ser Leu Tyr Val Glu Lys Ile Asp Val Gly Glu Ala
        35                  40                  45

Glu Pro Arg Thr Val Val Ser Gly Leu Val Gln Phe Val Pro Lys Glu
    50                  55                  60

Glu Leu Gln Asp Arg Leu Val Val Val Leu Cys Asn Leu Lys Pro Gln
65                  70                  75                  80

Lys Met Arg Gly Val Glu Ser Gln Gly Met Leu Leu Cys Ala Ser Ile
                85                  90                  95

Glu Gly Ile Asn Arg Gln Val Glu Pro Leu Asp Pro Pro Ala Gly Ser
            100                 105                 110

Ala Pro Gly Glu His Val Phe Val Lys Gly Tyr Glu Lys Gly Gln Pro
        115                 120                 125

Asp Glu Glu Leu Lys Pro Lys Lys Val Phe Glu Lys Leu Gln Ala
    130                 135                 140

Asp Phe Lys Ile Ser Glu Glu Cys Ile Ala Gln Trp Lys Gln Thr Asn
145                 150                 155                 160

Phe Met Thr Lys Leu Gly Ser Ile Ser Cys Lys Ser Leu Lys Gly Gly
                165                 170                 175

Asn Ile Ser
```

```
<210> SEQ ID NO 13
<211> LENGTH: 1167
<212> TYPE: DNA
<213> ORGANISM: Homo sapiens

<400> SEQUENCE: 13
```

```
atgggggacg ctcccagccc tgaagagaaa ctgcaccta tcacccggaa cctgcaggag    60
gttctggggg aagagaagct gaaggagata ctgaaggagc gggaacttaa aatttactgg   120
ggaacggcaa ccacgggcaa accacatgtg gcttactttg tgcccatgtc aaagattgca   180
gacttcttaa aggcagggtg tgaggtaaca attctgtttg cggacctcca cgcatacctg   240
gataacatga agcccatg gaacttcta gaactccgag tcagttacta tgagaatgtg   300
atcaaagcaa tgctggagag cattggtgtg cccttggaga agctcaagtt catcaaaggc   360
actgattacc agctcagcaa agagtacaca ctagatgtgt acagactctc ctccgtggtc   420
acacagcacg attccaagaa ggctggagct gaggtggtaa agcaggtgga gcacccttg    480 ctgagtggcc tcttataccc cggactgcag gctttggatg aagagtattt aaaagtagat   540
```

```
gcccaatttg gaggcattga tcagagaaag attttcacct ttgcagagaa gtacctccct    600
gcacttggct attcaaaacg ggtccatctg atgaatccta tggttccagg attaacaggc    660
agcaaaatga gctcttcaga agaggagtcc aagattgatc tccttgatcg aaggaggat     720 gtgaagaaaa aactgaagaa ggccttctgt gagccaggaa atgtggagaa caatggggtt    780
ctgtccttca tcaagcatgt cctttttccc cttaagtccg agtttgtgat cctacgagat    840
gagaaatggg gtggaaacaa aacctacaca gcttacgtgg acctgaaaaa ggactttgct    900
gctgaggttg tacatcctgg agacctgaag aattctgttg aagtcgcact gaacaagttg    960
ctggatccaa tccgggaaaa gtttaatacc cctgccctga aaaaactggc cagcgctgcc   1020
tacccagatc cctcaaagca gaagccaatg gccaaaggcc tgccaagaat tcagaaccag   1080
aggaggtcat cccatcccgg ctggatatcc gtgtggggaa aatcatcact gtggagaagc   1140
acccagatgc agacagcctg tatgtag                                        1167

<210> SEQ ID NO 14
<211> LENGTH: 188
<212> TYPE: PRT
<213> ORGANISM: Homo sapiens
<220> FEATURE:
<221> NAME/KEY: VARIANT
<222> LOCATION: (1)..(8)
<223> OTHER INFORMATION: Xaa = Any Amino Acid

<400> SEQUENCE: 14

Xaa Xaa Xaa Xaa Xaa Xaa Xaa Xaa Pro Met Ala Lys Gly Pro Ala Lys
1               5                   10                  15

Asn Ser Glu Pro Glu Val Ile Pro Ser Arg Leu Asp Ile Arg Val
            20                  25                  30

Gly Lys Ile Ile Thr Val Glu Lys His Pro Asp Ala Asp Ser Leu Tyr
        35                  40                  45

Val Glu Lys Ile Asp Val Gly Glu Ala Glu Pro Arg Thr Val Val Ser
    50                  55                  60

Gly Leu Val Gln Phe Val Pro Lys Glu Glu Leu Gln Asp Arg Leu Val
65                  70                  75                  80

Val Val Leu Cys Asn Leu Lys Pro Gln Lys Met Arg Gly Val Glu Ser
                85                  90                  95

Gln Gly Met Leu Leu Cys Ala Ser Ile Glu Gly Ile Asn Arg Gln Val
            100                 105                 110

Glu Pro Leu Asp Pro Pro Ala Gly Ser Ala Pro Gly Glu His Val Phe
        115                 120                 125

Val Lys Gly Tyr Glu Lys Gly Gln Pro Asp Glu Glu Leu Lys Pro Lys
    130                 135                 140

Lys Lys Val Phe Glu Lys Leu Gln Ala Asp Phe Lys Ile Ser Glu Glu
145                 150                 155                 160

Cys Ile Ala Gln Trp Lys Gln Thr Asn Phe Met Thr Lys Leu Gly Ser
                165                 170                 175

Ile Ser Cys Lys Ser Leu Lys Gly Gly Asn Ile Ser
            180                 185

<210> SEQ ID NO 15
<211> LENGTH: 2262
<212> TYPE: DNA
<213> ORGANISM: Homo sapiens

<400> SEQUENCE: 15
```

```
gccagacaca gtggctcaca cctgtaatct taacactttg gaaggctgag gcaggcggat      60
cacttgagcc caaaagttag agaccaaaac ccagtctcta cccaaaaaaa aaaaaaaaa      120
aaaattagc caggcatagt agcacatgcc tgtagtccca gctacttggg aggctgaggt      180
gagaggatca cctgagcatg gggaagttga gactgcagtg agccatgatc gcaccactgc      240
actccagcct gggcaacaga gtgagactct atgtctcaaa aaagaaaaa tgatagaaat       300
tagattagac ctattatacc caaccggtat atagggtatc gatagtttct tacacagctg      360
ttgggcagag cctgcagagc ttagagaagc ttatctttag attctcccag tttccttcta     420
tgtgcatggg cctggctctt agttggccat ccacttgtgc gtaatgctaa gatattggca     480
ttgatagctt tgtgcgaccc ttccagaaaa aaactcagta actcagtaaa attttttttt    540
ttttttctaa aagagacaga gtctggctct gttgcccagc ctggtcttga agtcctgggc     600
ttaagcaatc ctcccgtctc agcctcccaa agtgctagaa ttacaggtgt gagctaccac     660
acctggccaa gactcagtaa attctatgtg gaatgcatga atggaaatac ctaaaggagg     720
caaagctact actgctccct ccccgctagt ctaataattg agggagagaa cagatgaaaa     780
tcaggtatgt catgtctgaa aggttgccaa cccagtatta agaagttac aactcagtgt       840
ttagactctg gggattctac actaaatctt acctaatctc agtgtcttaa cgtggtggga     900
tcagcagctg acctgccaca gggaagaatt ctacctcatg gggttcttct cattcccaga     960
gccaatggcc aaaggccctg ccaagaattc agaaccagag gaggtcatcc catcccggct    1020
ggatatccgt gtggggaaaa tcatcactgt ggagaagcac ccagatgcag acagcctgta    1080
tgtagagaag attgacgtgg gggaagctga accacggact gtggtgagcg gcctggtaca    1140
gttcgtgccc aaggaggaac tgcaggacag gctggtagtg gtgctgtgca acctgaaacc    1200
ccagaagatg agaggagtcg agtcccaagg catgcttctg tgtgcttcta tagaagggat    1260
aaaccgccag gttgaacctc tggaccctcc ggcaggctct gctcctggtg agcacgtgtt    1320
tgtgaagggc tatgaaaagg gccaaccaga tgaggagctc aagcccaaga gaaaagtctt    1380
cgagaagttg caggctgact tcaaaatttc tgaggagtgc atcgcacagt ggaagcaaac    1440
caacttcatg accaagctgg gctccatttc ctgtaaatcg ctgaaagggg ggaacattag    1500
ctagccagcc cagcatcttc cccccttctt ccaccactga gtcatctgct gtctcttcag    1560
tctgctccat ccatcaccca tttacccatc tctcaggaca cggaagcagc gggtttggac    1620
tctttattcg gtgcagaact cggcaagggg cagcttaccc tccccagaac ccaggatcat    1680
cctgtctggc tgcagtgaga gaccaacccc taacaagggc tgggccacag cagggagtcc    1740
agccctacct tcttcccttg gcagctggag aaatctggtt tcaatataac tcatttaaaa    1800
atttatgcca cagtccttat aattggaaaa atactggtgc ccaggttttc ttggagttat    1860
ccaagcagct gcgcccctag ctgggatctg gtacctggac taggctaatt acagcttctc    1920
cccaacagga aactgtggga tttgaaaagg aaagggaagg gaaaacagag aacctagtgg    1980
tctaccaagt ggttggcaac tttcccaatg tctgcttact ctgaggcttg gcactggggg    2040
ccagggcctg ccccagggct cctggaattt cccttgatcc agctaggctg ggacactccc    2100
taaatcagct gcgtgttgtt agcatcaggc agaatgaatg gcagagagtg attctgtctt    2160
catagagggt ggggtacttc tccataaggc atctcagtca aatcccatc actgtcataa      2220
attcaaataa aatgtctgaa caagggaaaa aaaaaaaaa aa                         2262
```

<210> SEQ ID NO 16
<211> LENGTH: 685

<212> TYPE: PRT
<213> ORGANISM: Homo sapiens

<400> SEQUENCE: 16

Met Asp Gly Ala Gly Ala Glu Glu Val Leu Ala Pro Leu Arg Leu Ala
1               5                   10                  15

Val Arg Gln Gln Gly Asp Leu Val Arg Lys Leu Lys Glu Asp Lys Ala
            20                  25                  30

Pro Gln Val Asp Val Asp Lys Ala Val Ala Glu Leu Lys Ala Arg Lys
        35                  40                  45

Arg Val Leu Glu Ala Lys Glu Leu Ala Leu Gln Pro Lys Asp Asp Ile
    50                  55                  60

Val Asp Arg Ala Lys Met Glu Asp Thr Leu Lys Arg Arg Phe Phe Tyr
65                  70                  75                  80

Asp Gln Ala Phe Ala Ile Tyr Gly Gly Val Ser Gly Leu Tyr Asp Phe
                85                  90                  95

Gly Pro Val Gly Cys Ala Leu Lys Asn Asn Ile Ile Gln Thr Trp Arg
            100                 105                 110

Gln His Phe Ile Gln Glu Glu Gln Ile Leu Glu Ile Asp Cys Thr Met
        115                 120                 125

Leu Thr Pro Glu Pro Val Leu Lys Thr Ser Gly His Val Asp Lys Phe
    130                 135                 140

Ala Asp Phe Met Val Lys Asp Val Lys Asn Gly Glu Cys Phe Arg Ala
145                 150                 155                 160

Asp His Leu Leu Lys Ala His Leu Gln Lys Leu Met Ser Asp Lys Lys
                165                 170                 175

Cys Ser Val Glu Lys Lys Ser Glu Met Glu Ser Val Leu Ala Gln Leu
            180                 185                 190

Asp Asn Tyr Gly Gln Gln Glu Leu Ala Asp Leu Phe Val Asn Tyr Asn
        195                 200                 205

Val Lys Ser Pro Ile Thr Gly Asn Asp Leu Ser Pro Pro Val Ser Phe
    210                 215                 220

Asn Leu Met Phe Lys Thr Phe Ile Gly Pro Gly Gly Asn Met Pro Gly
225                 230                 235                 240

Tyr Leu Arg Pro Glu Thr Ala Gln Gly Ile Phe Leu Asn Phe Lys Arg
                245                 250                 255

Leu Leu Glu Phe Asn Gln Gly Lys Leu Pro Phe Ala Ala Ala Gln Ile
            260                 265                 270

Gly Asn Ser Phe Arg Asn Glu Ile Ser Pro Arg Ser Gly Leu Ile Arg
        275                 280                 285

Val Arg Glu Phe Thr Met Ala Glu Ile Glu His Phe Val Asp Pro Ser
    290                 295                 300

Glu Lys Asp His Pro Lys Phe Gln Asn Val Ala Asp Leu His Leu Tyr
305                 310                 315                 320

Leu Tyr Ser Ala Lys Ala Gln Val Ser Gly Gln Ser Ala Arg Lys Met
                325                 330                 335

Arg Leu Gly Asp Ala Val Glu Gln Gly Val Ile Asn Asn Thr Val Leu
            340                 345                 350

Gly Tyr Phe Ile Gly Arg Ile Tyr Leu Tyr Leu Thr Lys Val Gly Ile
        355                 360                 365

Ser Pro Asp Lys Leu Arg Phe Arg Gln His Met Glu Asn Glu Met Ala
    370                 375                 380

His Tyr Ala Cys Asp Cys Trp Asp Ala Glu Ser Lys Thr Ser Tyr Gly
385                 390                 395                 400

```
Trp Ile Glu Ile Val Gly Cys Ala Asp Arg Ser Cys Tyr Asp Leu Ser
                405                 410                 415
Cys His Ala Arg Ala Thr Lys Val Pro Leu Val Ala Glu Lys Pro Leu
            420                 425                 430
Lys Glu Pro Lys Thr Val Asn Val Gln Phe Glu Pro Ser Lys Gly
        435                 440                 445
Ala Ile Gly Lys Ala Tyr Lys Lys Asp Ala Lys Leu Val Met Glu Tyr
    450                 455                 460
Leu Ala Ile Cys Asp Glu Cys Tyr Ile Thr Glu Met Glu Met Leu Leu
465                 470                 475                 480
Asn Glu Lys Gly Glu Phe Thr Ile Glu Thr Gly Lys Thr Phe Gln
            485                 490                 495
Leu Thr Lys Asp Met Ile Asn Val Lys Arg Phe Gln Lys Thr Leu Tyr
        500                 505                 510
Val Glu Glu Val Val Pro Asn Val Ile Glu Pro Ser Phe Gly Leu Gly
    515                 520                 525
Arg Ile Met Tyr Thr Val Phe Glu His Thr Phe His Val Arg Glu Gly
    530                 535                 540
Asp Glu Gln Arg Thr Phe Phe Ser Phe Pro Ala Val Val Ala Pro Phe
545                 550                 555                 560
Lys Cys Ser Val Leu Pro Leu Ser Gln Asn Gln Glu Phe Met Pro Phe
            565                 570                 575
Val Lys Glu Leu Ser Glu Ala Leu Thr Arg His Gly Val Ser His Lys
        580                 585                 590
Val Asp Asp Ser Ser Gly Ser Ile Gly Arg Arg Tyr Ala Arg Thr Asp
    595                 600                 605
Glu Ile Gly Val Ala Phe Gly Val Thr Ile Asp Phe Asp Thr Val Asn
    610                 615                 620
Lys Thr Pro His Thr Ala Thr Leu Arg Asp Arg Asp Ser Met Arg Gln
625                 630                 635                 640
Ile Arg Ala Glu Ile Ser Glu Leu Pro Ser Ile Val Gln Asp Leu Ala
            645                 650                 655
Asn Gly Asn Ile Thr Trp Ala Asp Val Glu Ala Arg Tyr Pro Leu Phe
        660                 665                 670
Glu Gly Gln Glu Thr Gly Lys Lys Glu Thr Ile Glu Glu
    675                 680                 685

<210> SEQ ID NO 17
<211> LENGTH: 2058
<212> TYPE: DNA
<213> ORGANISM: Homo sapiens

<400> SEQUENCE: 17
atggacggcg cggggctga ggaggtgctg cacctctga ggctagcagt gcgccagcag      60
ggagatcttg tgcgaaaact caagaagat aaagcacccc aagtagacgt agacaaagca    120
gtggctgagc tcaaagcccg caagagggtt ctggaagcaa aggagctggc gttacagccc    180
aaagatgata ttgtagaccg agcaaaaatg gaagataccc tgaagaggag gtttttctat    240
gatcaagctt ttgctatta tggaggtgtt agtggtctgt atgactttgg gccagttggc    300
tgtgctttga gaacaatat tattcagacc tggaggcagc actttatcca agaggaacag    360
atcctggaga tcgattgcac catgctcacc cctgagccag ttttaaagac ctctggccat    420
gtagacaaat ttgctgactt catggtgaaa gacgtaaaaa atggagaatg ttttcgtgct    480
```

```
gaccatctat taaaagctca tttacagaaa ttgatgtctg ataagaagtg ttctgtcgaa    540
aagaaatcag aaatggaaag tgttttggcc cagcttgata actatggaca gcaagaactt    600
gcggatcttt ttgtgaacta taatgtaaaa tctcccatta ctggaaatga tctatcccct    660
ccagtgtctt ttaacttaat gttcaagact ttcattgggc tggaggaaa catgcctggg     720 tacttgagac cagaaactgc acaggggatt tcttgaatt tcaaacgact tttggagttc     780
aaccaaggaa agttgccttt tgctgctgcc cagattggaa attcttttag aaatgagatc    840
tcccctcgat ctggactgat cagagtcaga gaattcacaa tggcagaaat tgagcacttt    900
gtagatccca gtgagaaaga ccaccccaag ttccagaatg tggcagacct tcacctttat    960
ttgtattcag caaaagccca ggtcagcgga cagtccgctc ggaaaatgcg cctgggagat   1020
gctgttgaac agggtgtgat taataacaca gtattaggct atttcattgg ccgcatctac   1080
ctctacctca cgaaggttgg aatatctcca gataaactcc gcttccggca gcacatggag   1140
aatgagatgg cccattatgc ctgtgactgt tgggatgcag aatccaaaac atcctacggt   1200
tggattgaga ttgttggatg tgctgatcgt tcctgttatg acctctcctg tcatgcacga   1260
gccaccaaag tcccacttgt agctgagaaa cctctgaaag acccaaaaac agtcaatgtt   1320
gttcagtttg aacccagtaa gggagcaatt ggtaaggcat ataagaagga tgcaaaactg   1380
gtgatggagt atcttgccat ttgtgatgag tgctacatta cagaaatgga gatgctgctg   1440
aatgagaaag gggaattcac aattgaaact gaagggaaaa catttcagtt aacaaaagac   1500
atgatcaatg tgaagagatt ccagaaaaca ctatatgtgg aagaagttgt tccgaatgta   1560
attgaacctt ccttcggcct gggtaggatc atgtatacgg tatttgaaca tacattccat   1620
gtacgagaag gagatgaaca gagaacattc ttcagtttcc ctgctgtagt tgctccattc   1680
aaatgttccg tcctcccact gagccaaaac caggagttca tgccatttgt caaggaatta   1740
tcggaagccc tgaccaggca tggagtatct cacaaagtag acgattcctc tgggtcaatc   1800
ggaaggcgct atgccaggac tgatgagatt ggcgtggctt ttggtgtcac cattgactt    1860 gacacagtga acaagacccc ccacactgca actctgaggg accgtgactc aatgcggcag   1920
ataagagcag agatctctga gctgcccagc atagtccaag acctagccaa tggcaacatc   1980
acatgggctg atgtggaggc caggtatcct ctgtttgaag ggcaagagac tggtaaaaaa   2040
gagacaatcg aggaatga                                                 2058
```

```
<210> SEQ ID NO 18
<211> LENGTH: 17
<212> TYPE: PRT
<213> ORGANISM: Homo sapiens

<400> SEQUENCE: 18

Pro Gly Tyr Leu Arg Pro Glu Thr Ala Gln Gly Ile Phe Leu Asn Phe
1               5                  10                  15

Lys

<210> SEQ ID NO 19
<211> LENGTH: 16
<212> TYPE: PRT
<213> ORGANISM: Homo sapiens

<400> SEQUENCE: 19

Thr Gly Asn Asp Leu Ser Pro Pro Val Ser Phe Asn Leu Met Phe Lys
1               5                  10                  15
```

<210> SEQ ID NO 20
<211> LENGTH: 9
<212> TYPE: PRT
<213> ORGANISM: Homo sapiens

<400> SEQUENCE: 20

Asn Val Val Gln Phe Glu Pro Ser Lys
1               5

<210> SEQ ID NO 21
<211> LENGTH: 19
<212> TYPE: PRT
<213> ORGANISM: Homo sapiens

<400> SEQUENCE: 21

Leu Tyr Val Glu Glu Val Val Pro Asn Val Ile Glu Pro Ser Phe Gly
1               5                   10                  15

Leu Gly Arg

<210> SEQ ID NO 22
<211> LENGTH: 20
<212> TYPE: PRT
<213> ORGANISM: Homo sapiens

<400> SEQUENCE: 22

Ala Ile Tyr Gly Gly Val Ser Gly Leu Tyr Asp Phe Gly Pro Val Gly
1               5                   10                  15

Cys Ala Leu Lys
            20

<210> SEQ ID NO 23
<211> LENGTH: 15
<212> TYPE: PRT
<213> ORGANISM: Homo sapiens

<400> SEQUENCE: 23

Gln His Phe Ile Gln Glu Glu Gln Ile Leu Gly Ile Asp Cys Thr
1               5                   10                  15

<210> SEQ ID NO 24

<400> SEQUENCE: 24

000

<210> SEQ ID NO 25
<211> LENGTH: 775
<212> TYPE: PRT
<213> ORGANISM: Homo sapiens

<400> SEQUENCE: 25

Met Ala Ala Leu Asp Ser Leu Ser Leu Phe Thr Ser Leu Gly Leu Ser
1               5                   10                  15

Glu Gln Lys Ala Arg Glu Thr Leu Lys Asn Ser Ala Leu Ser Ala Gln
                20                  25                  30

Leu Arg Glu Ala Ala Thr Gln Ala Gln Gln Thr Leu Gly Ser Thr Ile
            35                  40                  45

Asp Lys Ala Thr Gly Ile Leu Leu Tyr Gly Leu Ala Ser Arg Leu Arg
        50                  55                  60

Asp Thr Arg Arg Leu Ser Phe Leu Val Ser Tyr Ile Ala Ser Lys Lys
65                  70                  75                  80

Ile His Thr Glu Pro Gln Leu Ser Ala Ala Leu Glu Tyr Val Arg Ser

```
                    85                  90                  95
His Pro Leu Asp Pro Ile Asp Thr Val Asp Phe Glu Arg Glu Cys Gly
                100                 105                 110

Val Gly Val Ile Val Thr Pro Glu Gln Ile Glu Glu Ala Val Glu Ala
            115                 120                 125

Ala Ile Asn Arg His Arg Pro Gln Leu Leu Val Glu Arg Tyr His Phe
        130                 135                 140

Asn Met Gly Leu Leu Met Gly Glu Ala Arg Ala Val Leu Lys Trp Ala
145                 150                 155                 160

Asp Gly Lys Met Ile Lys Asn Glu Val Asp Met Gln Val Leu His Leu
                165                 170                 175

Leu Gly Pro Lys Leu Glu Ala Asp Leu Glu Lys Lys Phe Lys Val Ala
            180                 185                 190

Lys Ala Arg Leu Glu Glu Thr Asp Arg Arg Thr Ala Lys Asp Val Val
        195                 200                 205

Glu Asn Gly Glu Thr Ala Asp Gln Thr Leu Ser Leu Met Glu Gln Leu
210                 215                 220

Arg Gly Glu Ala Leu Lys Phe His Lys Pro Gly Glu Asn Tyr Lys Thr
225                 230                 235                 240

Pro Gly Tyr Val Val Thr Pro His Thr Met Asn Leu Leu Lys Gln His
                245                 250                 255

Leu Glu Ile Thr Gly Gly Gln Val Arg Thr Arg Phe Pro Pro Glu Pro
            260                 265                 270

Asn Gly Ile Leu His Ile Gly His Ala Lys Ala Ile Asn Phe Asn Phe
        275                 280                 285

Gly Tyr Ala Lys Ala Asn Asn Gly Ile Cys Phe Leu Arg Phe Asp Asp
        290                 295                 300

Thr Asn Pro Glu Lys Glu Ala Lys Phe Phe Thr Ala Ile Cys Asp
305                 310                 315                 320

Met Val Ala Trp Leu Gly Tyr Thr Pro Tyr Lys Val Thr Tyr Ala Ser
                325                 330                 335

Asp Tyr Phe Asp Gln Leu Tyr Ala Trp Ala Val Glu Leu Ile Arg Arg
            340                 345                 350

Gly Leu Ala Tyr Val Cys His Gln Arg Gly Glu Glu Leu Lys Gly His
        355                 360                 365

Asn Thr Leu Pro Ser Pro Trp Arg Asp Arg Pro Met Glu Glu Ser Leu
        370                 375                 380

Leu Leu Phe Glu Ala Met Arg Lys Gly Lys Phe Ser Glu Gly Glu Ala
385                 390                 395                 400

Thr Leu Arg Met Lys Leu Val Met Glu Asp Gly Lys Met Asp Pro Val
                405                 410                 415

Ala Tyr Arg Val Lys Tyr Thr Pro His His Arg Thr Gly Asp Lys Trp
            420                 425                 430

Cys Ile Tyr Pro Thr Tyr Asp Tyr Thr His Cys Leu Cys Asp Ser Ile
        435                 440                 445

Glu His Ile Thr His Ser Leu Cys Thr Lys Glu Phe Gln Ala Arg Arg
        450                 455                 460

Ser Ser Tyr Phe Trp Leu Cys Asn Ala Leu Asp Val Tyr Cys Pro Val
465                 470                 475                 480

Gln Trp Glu Tyr Gly Arg Leu Asn Leu His Tyr Ala Val Val Ser Lys
                485                 490                 495

Arg Lys Ile Leu Gln Leu Val Ala Thr Gly Ala Val Arg Asp Trp Asp
            500                 505                 510
```

-continued

```
Asp Pro Arg Leu Phe Thr Leu Thr Ala Leu Arg Arg Gly Phe Pro
        515                 520                 525

Pro Glu Ala Ile Asn Asn Phe Cys Ala Arg Val Gly Val Thr Val Ala
    530                 535                 540

Gln Thr Thr Met Glu Pro His Leu Leu Glu Ala Cys Val Arg Asp Val
545                 550                 555                 560

Leu Asn Asp Thr Ala Pro Arg Ala Met Ala Val Leu Glu Ser Leu Arg
                565                 570                 575

Val Ile Ile Thr Asn Phe Pro Ala Ala Lys Ser Leu Asp Ile Gln Val
                580                 585                 590

Pro Asn Phe Pro Ala Asp Glu Thr Lys Gly Phe His Gln Val Pro Phe
            595                 600                 605

Ala Pro Ile Val Phe Ile Glu Arg Thr Asp Phe Lys Glu Glu Pro Glu
            610                 615                 620

Pro Gly Phe Lys Arg Leu Ala Trp Gly Gln Pro Val Gly Leu Arg His
625                 630                 635                 640

Thr Gly Tyr Val Ile Glu Leu Gln His Val Val Lys Gly Pro Ser Gly
                645                 650                 655

Cys Val Glu Ser Leu Glu Val Thr Cys Arg Arg Ala Asp Ala Gly Glu
                660                 665                 670

Lys Pro Lys Ala Phe Ile His Trp Val Ser Gln Pro Leu Met Cys Glu
            675                 680                 685

Val Arg Leu Tyr Glu Arg Leu Phe Gln His Lys Asn Pro Glu Asp Pro
            690                 695                 700

Thr Glu Val Pro Gly Gly Phe Leu Ser Asp Leu Asn Leu Ala Ser Leu
705                 710                 715                 720

His Val Val Asp Ala Ala Leu Val Asp Cys Ser Val Ala Leu Ala Lys
                725                 730                 735

Pro Phe Asp Lys Phe Gln Phe Glu Arg Leu Gly Tyr Phe Ser Val Asp
            740                 745                 750

Pro Asp Ser His Gln Gly Lys Leu Val Phe Asn Arg Thr Val Thr Leu
            755                 760                 765

Lys Glu Asp Pro Gly Lys Val
770                 775

<210> SEQ ID NO 26
<211> LENGTH: 15
<212> TYPE: PRT
<213> ORGANISM: Homo sapiens

<400> SEQUENCE: 26

Asp Val Val Glu Asn Gly Glu Thr Ala Asp Gln Thr Leu Ser Leu
1               5                   10                  15

<210> SEQ ID NO 27
<211> LENGTH: 10
<212> TYPE: PRT
<213> ORGANISM: Homo sapiens

<400> SEQUENCE: 27

Thr Pro Gly Tyr Val Val Thr Pro His Thr
1               5                   10

<210> SEQ ID NO 28
<211> LENGTH: 509
<212> TYPE: PRT
<213> ORGANISM: Homo sapiens
```

<400> SEQUENCE: 28

```
Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Gly Thr Arg Asp
    50                  55                  60

Tyr Ser Pro Arg Gln Met Ala Val Arg Glu Lys Val Phe Asp Val Ile
65                  70                  75                  80

Ile Arg Cys Phe Lys Arg His Gly Ala Glu Val Ile Asp Thr Pro Val
                85                  90                  95

Phe Glu Leu Lys Glu Thr Leu Met Gly Lys Tyr Gly Glu Asp Ser Lys
                100                 105                 110

Leu Ile Tyr Asp Leu Lys Asp Gln Gly Gly Glu Leu Leu Ser Leu Arg
            115                 120                 125

Tyr Asp Leu Thr Val Pro Phe Ala Arg Tyr Leu Ala Met Asn Lys Leu
130                 135                 140

Thr Asn Ile Lys Arg Tyr His Ile Ala Lys Val Tyr Arg Arg Asp Asn
145                 150                 155                 160

Pro Ala Met Thr Arg Gly Arg Tyr Arg Glu Phe Tyr Gln Cys Asp Phe
                165                 170                 175

Asp Ile Ala Gly Asn Phe Asp Pro Met Ile Pro Asp Ala Glu Cys Leu
            180                 185                 190

Lys Ile Met Cys Glu Ile Leu Ser Ser Leu Gln Ile Gly Asp Phe Leu
        195                 200                 205

Val Lys Val Asn Asp Arg Arg Ile Leu Asp Gly Met Phe Ala Ile Cys
    210                 215                 220

Gly Val Ser Asp Ser Lys Phe Arg Thr Ile Cys Ser Ser Val Asp Lys
225                 230                 235                 240

Leu Asp Lys Val Ser Trp Glu Glu Val Lys Asn Glu Met Val Gly Glu
                245                 250                 255

Lys Gly Leu Ala Pro Glu Val Ala Asp Arg Ile Gly Asp Tyr Val Gln
            260                 265                 270

Gln His Gly Gly Val Ser Leu Val Glu Gln Leu Leu Gln Asp Pro Lys
        275                 280                 285

Leu Ser Gln Asn Lys Gln Ala Leu Glu Gly Leu Gly Asp Leu Lys Leu
    290                 295                 300

Leu Phe Glu Tyr Leu Thr Leu Phe Gly Ile Asp Asp Lys Ile Ser Phe
305                 310                 315                 320

Asp Leu Ser Leu Ala Arg Gly Leu Asp Tyr Tyr Thr Gly Val Ile Tyr
                325                 330                 335

Glu Ala Val Leu Leu Gln Thr Pro Ala Gln Ala Gly Glu Glu Pro Leu
            340                 345                 350

Gly Val Gly Ser Val Ala Ala Gly Gly Arg Tyr Asp Gly Leu Val Gly
        355                 360                 365

Met Phe Asp Pro Lys Gly Arg Lys Val Pro Cys Val Gly Leu Ser Ile
    370                 375                 380

Gly Val Glu Arg Ile Phe Ser Ile Val Glu Gln Arg Leu Glu Ala Leu
385                 390                 395                 400

Glu Glu Lys Ile Arg Thr Thr Glu Thr Gln Val Leu Val Ala Ser Ala
```

```
                    405                 410                 415
Gln Lys Lys Leu Leu Glu Glu Arg Leu Lys Leu Val Ser Glu Leu Trp
        420                 425                 430

Asp Ala Gly Ile Lys Ala Glu Leu Leu Tyr Lys Lys Asn Pro Lys Leu
            435                 440                 445

Leu Asn Gln Leu Gln Tyr Cys Glu Glu Ala Gly Ile Pro Leu Val Ala
    450                 455                 460

Ile Ile Gly Glu Gln Glu Leu Lys Asp Gly Val Ile Lys Leu Arg Ser
465                 470                 475                 480

Val Thr Ser Arg Glu Glu Val Asp Val Arg Arg Glu Asp Leu Val Glu
                485                 490                 495

Glu Ile Lys Arg Arg Thr Gly Gln Pro Leu Cys Ile Cys
            500                 505

<210> SEQ ID NO 29
<211> LENGTH: 183
<212> TYPE: DNA
<213> ORGANISM: Homo sapiens

<400> SEQUENCE: 29
atggcagagc gtgcggcgct ggaggagctg gtgaaacttc agggagagcg cgtgcgaggc    60
ctcaagcagc agaaggccag cgccgagctg atcgaggagg aggtggcgaa actcctgaaa   120
ctgaaggcac agctgggtcc tgatgaaagc aaacagaaat ttgtgctcaa aaccccaag    180 tag                                                                 183

<210> SEQ ID NO 30
<211> LENGTH: 60
<212> TYPE: PRT
<213> ORGANISM: Homo sapiens

<400> SEQUENCE: 30

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys
    50                  55                  60

<210> SEQ ID NO 31
<211> LENGTH: 516
<212> TYPE: DNA
<213> ORGANISM: Homo sapiens

<400> SEQUENCE: 31
atggcagagc gtgcggcgct ggaggagctg gtgaaacttc agggagagcg cgtgcgaggc    60
ctcaagcagc agaaggccag cgccgagctg atcgaggagg aggtggcgaa actcctgaaa   120
ctgaaggcac agctgggtcc tgatgaaagc aaacagaaat ttgtgctcaa aaccccaag    180 gctttggagg agaagatacg gaccacggag acacaggtgc ttgtggcatc tgcacagaag   240
aagctgctag aggaaagact aaagcttgtc tcagaactgt gggatgctgg gatcaaggct   300
gagctgctgt acaagaagaa cccaaagcta ctgaaccagt acagtactg tgaggaggca    360 ggcatcccac tggtggctat catcggcgag caggaactca aggatggggt catcaagctc   420
cgttcagtga cgagcaggga agaggtggat gtccgaagag aagaccttgt ggaggaaatc   480
```
aaaaggagaa caggccagcc cctctgcatc tgctga         516

<210> SEQ ID NO 32
<211> LENGTH: 171
<212> TYPE: PRT
<213> ORGANISM: Homo sapiens

<400> SEQUENCE: 32

Met Ala Glu Arg Ala Ala Leu Glu Glu Leu Val Lys Leu Gln Gly Glu
1               5                   10                  15

Arg Val Arg Gly Leu Lys Gln Gln Lys Ala Ser Ala Glu Leu Ile Glu
            20                  25                  30

Glu Glu Val Ala Lys Leu Leu Lys Leu Lys Ala Gln Leu Gly Pro Asp
        35                  40                  45

Glu Ser Lys Gln Lys Phe Val Leu Lys Thr Pro Lys Ala Leu Glu Glu
    50                  55                  60

Lys Ile Arg Thr Thr Glu Thr Gln Val Leu Val Ala Ser Ala Gln Lys
65                  70                  75                  80

Lys Leu Leu Glu Glu Arg Leu Lys Leu Val Ser Glu Leu Trp Asp Ala
                85                  90                  95

Gly Ile Lys Ala Glu Leu Leu Tyr Lys Lys Asn Pro Lys Leu Leu Asn
            100                 105                 110

Gln Leu Gln Tyr Cys Glu Glu Ala Gly Ile Pro Leu Val Ala Ile Ile
        115                 120                 125

Gly Glu Gln Glu Leu Lys Asp Gly Val Ile Lys Leu Arg Ser Val Thr
    130                 135                 140

Ser Arg Glu Glu Val Asp Val Arg Glu Asp Leu Val Glu Glu Ile
145                 150                 155                 160

Lys Arg Arg Thr Gly Gln Pro Leu Cys Ile Cys
                165                 170

<210> SEQ ID NO 33
<211> LENGTH: 471
<212> TYPE: PRT
<213> ORGANISM: Homo sapiens

<400> SEQUENCE: 33

Met Pro Asn Ser Glu Pro Ala Ser Leu Leu Glu Leu Phe Asn Ser Ile
1               5                   10                  15

Ala Thr Gln Gly Glu Leu Val Arg Ser Leu Lys Ala Gly Asn Ala Ser
            20                  25                  30

Lys Asp Glu Ile Asp Ser Ala Val Lys Met Leu Val Ser Leu Lys Met
        35                  40                  45

Ser Tyr Lys Ala Ala Gly Glu Asp Tyr Lys Ala Asp Cys Pro Pro
    50                  55                  60

Gly Asn Pro Ala Pro Thr Ser Asn His Gly Pro Asp Ala Thr Glu Ala
65                  70                  75                  80

Glu Glu Asp Phe Val Asp Pro Trp Thr Val Gln Thr Ser Ser Ala Lys
                85                  90                  95

Gly Ile Asp Tyr Asp Lys Leu Ile Val Arg Phe Gly Ser Ser Lys Ile
            100                 105                 110

Asp Lys Glu Leu Ile Asn Arg Ile Glu Arg Ala Thr Gly Gln Arg Pro
        115                 120                 125

His His Phe Leu Arg Arg Gly Ile Phe Phe Ser His Arg Asp Met Asn
    130                 135                 140

-continued

Gln Val Leu Asp Ala Tyr Glu Asn Lys Lys Pro Phe Tyr Leu Tyr Thr
145                 150                 155                 160

Gly Arg Gly Pro Ser Ser Glu Ala Met His Val Gly His Leu Ile Pro
            165                 170                 175

Phe Ile Phe Thr Lys Trp Leu Gln Asp Val Phe Asn Val Pro Leu Val
            180                 185                 190

Ile Gln Met Thr Asp Asp Glu Lys Tyr Leu Trp Lys Asp Leu Thr Leu
            195                 200                 205

Asp Gln Ala Tyr Ser Tyr Ala Val Glu Asn Ala Lys Asp Ile Ile Ala
            210                 215                 220

Cys Gly Phe Asp Ile Asn Lys Thr Phe Ile Phe Ser Asp Leu Asp Tyr
225                 230                 235                 240

Met Gly Met Ser Ser Gly Phe Tyr Lys Asn Val Val Lys Ile Gln Lys
                245                 250                 255

His Val Thr Phe Asn Gln Val Lys Gly Ile Phe Gly Phe Thr Asp Ser
            260                 265                 270

Asp Cys Ile Gly Lys Ile Ser Phe Pro Ala Ile Gln Ala Ala Pro Ser
            275                 280                 285

Phe Ser Asn Ser Phe Pro Gln Ile Phe Arg Asp Arg Thr Asp Ile Gln
290                 295                 300

Cys Leu Ile Pro Cys Ala Ile Asp Gln Asp Pro Tyr Phe Arg Met Thr
305                 310                 315                 320

Arg Asp Val Ala Pro Arg Ile Gly Tyr Pro Lys Pro Ala Leu Leu His
                325                 330                 335

Ser Thr Phe Phe Pro Ala Leu Gln Gly Ala Gln Thr Lys Met Ser Ala
            340                 345                 350

Ser Asp Pro Asn Ser Ser Ile Phe Leu Thr Asp Thr Ala Lys Gln Ile
            355                 360                 365

Lys Thr Lys Val Asn Lys His Ala Phe Ser Gly Gly Arg Asp Thr Ile
370                 375                 380

Glu Glu His Arg Gln Phe Gly Gly Asn Cys Asp Val Asp Val Ser Phe
385                 390                 395                 400

Met Tyr Leu Thr Phe Phe Leu Glu Asp Asp Lys Leu Glu Gln Ile
                405                 410                 415

Arg Lys Asp Tyr Thr Ser Gly Ala Met Leu Thr Gly Glu Leu Lys Lys
            420                 425                 430

Ala Leu Ile Glu Val Leu Gln Pro Leu Ile Ala Glu His Gln Ala Arg
            435                 440                 445

Arg Lys Glu Val Thr Asp Glu Ile Val Lys Glu Phe Met Thr Pro Arg
450                 455                 460

Lys Leu Ser Phe Asp Phe Gln
465                 470

<210> SEQ ID NO 34
<211> LENGTH: 379
<212> TYPE: PRT
<213> ORGANISM: Homo sapiens

<400> SEQUENCE: 34

Met Ser Ala Lys Gly Ile Asp Tyr Asp Lys Leu Ile Val Arg Phe Gly
1               5                   10                  15

Ser Ser Lys Ile Asp Lys Glu Leu Ile Asn Arg Ile Glu Arg Ala Thr
            20                  25                  30

Gly Gln Arg Pro His His Phe Leu Arg Arg Gly Ile Phe Phe Ser His
        35                  40                  45

Arg Asp Met Asn Gln Val Leu Asp Ala Tyr Glu Asn Lys Lys Pro Phe
 50                  55                  60

Tyr Leu Tyr Thr Gly Arg Gly Pro Ser Ser Glu Ala Met His Val Gly
 65                  70                  75                  80

His Leu Ile Pro Phe Ile Phe Thr Lys Trp Leu Gln Asp Val Phe Asn
                 85                  90                  95

Val Pro Leu Val Ile Gln Met Thr Asp Asp Glu Lys Tyr Leu Trp Lys
            100                 105                 110

Asp Leu Thr Leu Asp Gln Ala Tyr Ser Tyr Ala Val Glu Asn Ala Lys
        115                 120                 125

Asp Ile Ile Ala Cys Gly Phe Asp Ile Asn Lys Thr Phe Ile Phe Ser
130                 135                 140

Asp Leu Asp Tyr Met Gly Met Ser Ser Gly Phe Tyr Lys Asn Val Val
145                 150                 155                 160

Lys Ile Gln Lys His Val Thr Phe Asn Gln Val Lys Gly Ile Phe Gly
                165                 170                 175

Phe Thr Asp Ser Asp Cys Ile Gly Lys Ile Ser Phe Pro Ala Ile Gln
            180                 185                 190

Ala Ala Pro Ser Phe Ser Asn Ser Phe Pro Gln Ile Phe Arg Asp Arg
        195                 200                 205

Thr Asp Ile Gln Cys Leu Ile Pro Cys Ala Ile Asp Gln Asp Pro Tyr
210                 215                 220

Phe Arg Met Thr Arg Asp Val Ala Pro Arg Ile Gly Tyr Pro Lys Pro
225                 230                 235                 240

Ala Leu Leu His Ser Thr Phe Phe Pro Ala Leu Gln Gly Ala Gln Thr
                245                 250                 255

Lys Met Ser Ala Ser Asp Pro Asn Ser Ser Ile Phe Leu Thr Asp Thr
            260                 265                 270

Ala Lys Gln Ile Lys Thr Lys Val Asn Lys His Ala Phe Ser Gly Gly
        275                 280                 285

Arg Asp Thr Ile Glu Glu His Arg Gln Phe Gly Gly Asn Cys Asp Val
290                 295                 300

Asp Val Ser Phe Met Tyr Leu Thr Phe Phe Leu Glu Asp Asp Asp Lys
305                 310                 315                 320

Leu Glu Gln Ile Arg Lys Asp Tyr Thr Ser Gly Ala Met Leu Thr Gly
                325                 330                 335

Glu Leu Lys Lys Ala Leu Ile Glu Val Leu Gln Pro Leu Ile Ala Glu
            340                 345                 350

His Gln Ala Arg Arg Lys Glu Val Thr Asp Glu Ile Val Lys Glu Phe
        355                 360                 365

Met Thr Pro Arg Lys Leu Ser Phe Asp Phe Gln
370                 375

<210> SEQ ID NO 35
<211> LENGTH: 424
<212> TYPE: PRT
<213> ORGANISM: Homo sapiens

<400> SEQUENCE: 35

Met Ser Tyr Lys Ala Ala Ala Gly Glu Asp Tyr Lys Ala Asp Cys Pro
 1               5                  10                  15

Pro Gly Asn Pro Ala Pro Thr Ser Asn His Gly Pro Asp Ala Thr Glu
            20                  25                  30

Ala Glu Glu Asp Phe Val Asp Pro Trp Thr Val Gln Thr Ser Ser Ala

```
            35                  40                  45
Lys Gly Ile Asp Tyr Asp Lys Leu Ile Val Arg Phe Gly Ser Ser Lys
 50                  55                  60

Ile Asp Lys Glu Leu Ile Asn Arg Ile Glu Arg Ala Thr Gly Gln Arg
 65                  70                  75                  80

Pro His His Phe Leu Arg Arg Gly Ile Phe Phe Ser His Arg Asp Met
                 85                  90                  95

Asn Gln Val Leu Asp Ala Tyr Glu Asn Lys Lys Pro Phe Tyr Leu Tyr
                100                 105                 110

Thr Gly Arg Gly Pro Ser Ser Glu Ala Met His Val Gly His Leu Ile
                115                 120                 125

Pro Phe Ile Phe Thr Lys Trp Leu Gln Asp Val Phe Asn Val Pro Leu
            130                 135                 140

Val Ile Gln Met Thr Asp Asp Glu Lys Tyr Leu Trp Lys Asp Leu Thr
145                 150                 155                 160

Leu Asp Gln Ala Tyr Ser Tyr Ala Val Glu Asn Ala Lys Asp Ile Ile
                165                 170                 175

Ala Cys Gly Phe Asp Ile Asn Lys Thr Phe Ile Phe Ser Asp Leu Asp
                180                 185                 190

Tyr Met Gly Met Ser Ser Gly Phe Tyr Lys Asn Val Val Lys Ile Gln
                195                 200                 205

Lys His Val Thr Phe Asn Gln Val Lys Gly Ile Phe Gly Phe Thr Asp
210                 215                 220

Ser Asp Cys Ile Gly Lys Ile Ser Phe Pro Ala Ile Gln Ala Ala Pro
225                 230                 235                 240

Ser Phe Ser Asn Ser Phe Pro Gln Ile Phe Arg Asp Arg Thr Asp Ile
                245                 250                 255

Gln Cys Leu Ile Pro Cys Ala Ile Asp Gln Asp Pro Tyr Phe Arg Met
                260                 265                 270

Thr Arg Asp Val Ala Pro Arg Ile Gly Tyr Pro Lys Pro Ala Leu Leu
                275                 280                 285

His Ser Thr Phe Phe Pro Ala Leu Gln Gly Ala Gln Thr Lys Met Ser
            290                 295                 300

Ala Ser Asp Pro Asn Ser Ser Ile Phe Leu Thr Asp Thr Ala Lys Gln
305                 310                 315                 320

Ile Lys Thr Lys Val Asn Lys His Ala Phe Ser Gly Gly Arg Asp Thr
                325                 330                 335

Ile Glu Glu His Arg Gln Phe Gly Gly Asn Cys Asp Val Asp Val Ser
                340                 345                 350

Phe Met Tyr Leu Thr Phe Phe Leu Glu Asp Asp Lys Leu Glu Gln
                355                 360                 365

Ile Arg Lys Asp Tyr Thr Ser Gly Ala Met Leu Thr Gly Glu Leu Lys
            370                 375                 380

Lys Ala Leu Ile Glu Val Leu Gln Pro Leu Ile Ala Glu His Gln Ala
385                 390                 395                 400

Arg Arg Lys Glu Val Thr Asp Glu Ile Val Lys Glu Phe Met Thr Pro
                405                 410                 415

Arg Lys Leu Ser Phe Asp Phe Gln
            420

<210> SEQ ID NO 36
<211> LENGTH: 13
<212> TYPE: PRT
<213> ORGANISM: Mus musculus
```

<400> SEQUENCE: 36

Glu Thr Leu Lys Asn Glu Ala Leu Ser Thr Gln Leu Arg
1               5                   10

<210> SEQ ID NO 37
<211> LENGTH: 28
<212> TYPE: PRT
<213> ORGANISM: Mus musculus

<400> SEQUENCE: 37

Glu Ala Ala Thr Gln Ala His Gln Ile Leu Gly Ser Thr Ile Asp Lys
1               5                   10                  15

Ala Thr Gly Val Leu Leu Tyr Asp Leu Val Ser Arg
            20                  25

<210> SEQ ID NO 38
<211> LENGTH: 41
<212> TYPE: PRT
<213> ORGANISM: Mus musculus

<400> SEQUENCE: 38

Glu Thr Leu Lys Asn Glu Ala Leu Ser Thr Gln Leu Arg Glu Ala Ala
1               5                   10                  15

Thr Gln Ala His Gln Ile Leu Gly Ser Thr Ile Asp Lys Ala Thr Gly
            20                  25                  30

Val Leu Leu Tyr Asp Leu Val Ser Arg
        35                  40

<210> SEQ ID NO 39
<211> LENGTH: 27
<212> TYPE: PRT
<213> ORGANISM: Mus musculus

<400> SEQUENCE: 39

Asp Phe Glu Gln Glu Cys Gly Val Gly Val Val Thr Pro Glu Gln
1               5                   10                  15

Ile Glu Glu Ala Val Glu Ser Thr Ile Asn Lys
            20                  25

<210> SEQ ID NO 40
<211> LENGTH: 11
<212> TYPE: PRT
<213> ORGANISM: Mus musculus

<400> SEQUENCE: 40

Phe Asn Met Gly Leu Leu Met Gly Glu Ala Arg
1               5                   10

<210> SEQ ID NO 41
<211> LENGTH: 17
<212> TYPE: PRT
<213> ORGANISM: Mus musculus

<400> SEQUENCE: 41

Met Ile Lys Asn Glu Val Asp Met Gln Val Leu His Leu Leu Gly Pro
1               5                   10                  15

Lys

<210> SEQ ID NO 42
<211> LENGTH: 14
<212> TYPE: PRT

<213> ORGANISM: Mus musculus

<400> SEQUENCE: 42

Asn Glu Val Asp Met Gln Val Leu His Leu Leu Gly Pro Lys
1               5                   10

<210> SEQ ID NO 43
<211> LENGTH: 15
<212> TYPE: PRT
<213> ORGANISM: Mus musculus

<400> SEQUENCE: 43

Thr Pro Gly Tyr Val Ile Thr Pro Tyr Thr Met Asp Leu Leu Lys
1               5                   10                  15

<210> SEQ ID NO 44
<211> LENGTH: 12
<212> TYPE: PRT
<213> ORGANISM: Mus musculus

<400> SEQUENCE: 44

Phe Asp Asp Thr Asn Pro Glu Lys Glu Glu Ala Lys
1               5                   10

<210> SEQ ID NO 45
<211> LENGTH: 15
<212> TYPE: PRT
<213> ORGANISM: Mus musculus

<400> SEQUENCE: 45

Val Glu Glu Leu Lys Gly His Asn Pro Leu Pro Ser Pro Trp Arg
1               5                   10                  15

<210> SEQ ID NO 46
<211> LENGTH: 15
<212> TYPE: PRT
<213> ORGANISM: Mus musculus

<400> SEQUENCE: 46

Asp Arg Pro Lys Glu Glu Ser Leu Leu Leu Phe Glu Ala Met Arg
1               5                   10                  15

<210> SEQ ID NO 47
<211> LENGTH: 30
<212> TYPE: PRT
<213> ORGANISM: Mus musculus

<400> SEQUENCE: 47

Val Glu Glu Leu Lys Gly His Asn Pro Leu Pro Ser Pro Trp Arg Asp
1               5                   10                  15
Arg Pro Lys Glu Glu Ser Leu Leu Leu Phe Glu Ala Met Arg
            20                  25                  30

<210> SEQ ID NO 48
<211> LENGTH: 14
<212> TYPE: PRT
<213> ORGANISM: Mus musculus

<400> SEQUENCE: 48

Leu Val Met Glu Asp Gly Lys Met Asp Pro Val Ala Tyr Arg
1               5                   10

<210> SEQ ID NO 49
<211> LENGTH: 11

-continued

<212> TYPE: PRT
<213> ORGANISM: Mus musculus

<400> SEQUENCE: 49

Val Tyr Cys Pro Val Gln Trp Glu Tyr Gly Arg
1               5                   10

<210> SEQ ID NO 50
<211> LENGTH: 11
<212> TYPE: PRT
<213> ORGANISM: Mus musculus

<400> SEQUENCE: 50

Ile Leu Gln Leu Val Ala Ala Gly Ala Val Arg
1               5                   10

<210> SEQ ID NO 51
<211> LENGTH: 28
<212> TYPE: PRT
<213> ORGANISM: Mus musculus

<400> SEQUENCE: 51

Asp Val Leu Asn Asp Ala Ala Pro Arg Ala Met Ala Val Leu Glu Pro
1               5                   10                  15

Leu Gln Val Val Ile Thr Asn Phe Pro Ala Pro Lys
            20                  25

<210> SEQ ID NO 52
<211> LENGTH: 38
<212> TYPE: PRT
<213> ORGANISM: Mus musculus

<400> SEQUENCE: 52

Gly Phe His Gln Val Pro Phe Ala Ser Thr Val Phe Ile Glu Arg Ser
1               5                   10                  15

Asp Phe Lys Glu Glu Ser Glu Pro Gly Tyr Lys Arg Leu Ala Ser Gly
            20                  25                  30

Gln Pro Val Gly Leu Arg
            35

<210> SEQ ID NO 53
<211> LENGTH: 15
<212> TYPE: PRT
<213> ORGANISM: Mus musculus

<400> SEQUENCE: 53

Ala Phe Ile His Trp Val Ser Gln Pro Leu Val Cys Glu Ile Arg
1               5                   10                  15

<210> SEQ ID NO 54
<211> LENGTH: 19
<212> TYPE: PRT
<213> ORGANISM: Mus musculus

<400> SEQUENCE: 54

Leu Gly Tyr Phe Ser Val Asp Pro Asp Ser His Gln Gly Gln Ile Val
1               5                   10                  15

Phe Asn Arg

<210> SEQ ID NO 55
<211> LENGTH: 15
<212> TYPE: PRT
<213> ORGANISM: Mus musculus

```
<400> SEQUENCE: 55

Thr Pro Gly Tyr Val Ile Thr Pro Tyr Thr Met Asp Leu Leu Lys
1               5                   10                  15

<210> SEQ ID NO 56
<211> LENGTH: 10
<212> TYPE: PRT
<213> ORGANISM: Mus musculus

<400> SEQUENCE: 56

Ala Ile Asn Phe Asn Phe Gly Tyr Ala Lys
1               5                   10

<210> SEQ ID NO 57
<211> LENGTH: 12
<212> TYPE: PRT
<213> ORGANISM: Mus musculus

<400> SEQUENCE: 57

Phe Asp Asp Thr Asn Pro Glu Lys Glu Glu Ala Lys
1               5                   10

<210> SEQ ID NO 58
<211> LENGTH: 18
<212> TYPE: PRT
<213> ORGANISM: Mus musculus

<400> SEQUENCE: 58

Phe Phe Thr Ala Ile Tyr Asp Met Val Thr Trp Leu Gly Tyr Thr Pro
1               5                   10                  15

Tyr Lys

<210> SEQ ID NO 59
<211> LENGTH: 30
<212> TYPE: PRT
<213> ORGANISM: Mus musculus

<400> SEQUENCE: 59

Phe Asp Asp Thr Asn Pro Glu Lys Glu Glu Ala Lys Phe Phe Thr Ala
1               5                   10                  15

Ile Tyr Asp Met Val Thr Trp Leu Gly Tyr Thr Pro Tyr Lys
            20                  25                  30

<210> SEQ ID NO 60
<211> LENGTH: 15
<212> TYPE: PRT
<213> ORGANISM: Mus musculus

<400> SEQUENCE: 60

Asp Arg Pro Lys Glu Glu Ser Leu Leu Leu Phe Glu Ala Met Arg
1               5                   10                  15

<210> SEQ ID NO 61
<211> LENGTH: 11
<212> TYPE: PRT
<213> ORGANISM: Mus musculus

<400> SEQUENCE: 61

Val Tyr Cys Pro Val Gln Trp Glu Tyr Gly Arg
1               5                   10

<210> SEQ ID NO 62
```

```
<210> SEQ ID NO 62
<211> LENGTH: 10
<212> TYPE: PRT
<213> ORGANISM: Mus musculus

<400> SEQUENCE: 62

Leu Asn Leu His Tyr Ala Val Val Ser Lys
1               5                   10

<210> SEQ ID NO 63
<211> LENGTH: 21
<212> TYPE: PRT
<213> ORGANISM: Mus musculus

<400> SEQUENCE: 63

Val Tyr Cys Pro Val Gln Trp Glu Tyr Gly Arg Leu Asn Leu His Tyr
1               5                   10                  15

Ala Val Val Ser Lys
            20

<210> SEQ ID NO 64
<211> LENGTH: 11
<212> TYPE: PRT
<213> ORGANISM: Mus musculus

<400> SEQUENCE: 64

Ile Leu Gln Leu Val Ala Ala Gly Ala Val Arg
1               5                   10

<210> SEQ ID NO 65
<211> LENGTH: 19
<212> TYPE: PRT
<213> ORGANISM: Mus musculus

<400> SEQUENCE: 65

Ala Met Ala Val Leu Glu Pro Leu Gln Val Val Ile Thr Asn Phe Pro
1               5                   10                  15

Ala Pro Lys

<210> SEQ ID NO 66
<211> LENGTH: 15
<212> TYPE: PRT
<213> ORGANISM: Mus musculus

<400> SEQUENCE: 66

Pro Leu Asp Ile Arg Val Pro Asn Phe Pro Ala Asp Glu Thr Lys
1               5                   10                  15

<210> SEQ ID NO 67
<211> LENGTH: 34
<212> TYPE: PRT
<213> ORGANISM: Mus musculus

<400> SEQUENCE: 67

Ala Met Ala Val Leu Glu Pro Leu Gln Val Val Ile Thr Asn Phe Pro
1               5                   10                  15

Ala Pro Lys Pro Leu Asp Ile Arg Val Pro Asn Phe Pro Ala Asp Glu
            20                  25                  30

Thr Lys

<210> SEQ ID NO 68
<211> LENGTH: 36
<212> TYPE: PRT
<213> ORGANISM: Mus musculus
```

<400> SEQUENCE: 68

Ser Asp Phe Lys Glu Glu Ser Glu Pro Gly Tyr Lys Arg Leu Ala Ser
1               5                   10                  15

Gly Gln Pro Val Gly Leu Arg His Thr Gly Tyr Val Ile Glu Leu Gln
            20                  25                  30

Asn Ile Val Arg
        35

<210> SEQ ID NO 69
<211> LENGTH: 15
<212> TYPE: PRT
<213> ORGANISM: Mus musculus

<400> SEQUENCE: 69

Ala Phe Ile His Trp Val Ser Gln Pro Leu Val Cys Glu Ile Arg
1               5                   10                  15

<210> SEQ ID NO 70
<211> LENGTH: 19
<212> TYPE: PRT
<213> ORGANISM: Mus musculus

<400> SEQUENCE: 70

Leu Gly Tyr Phe Ser Val Asp Pro Asp Ser His Gln Gly Gln Ile Val
1               5                   10                  15

Phe Asn Arg

<210> SEQ ID NO 71
<211> LENGTH: 13
<212> TYPE: PRT
<213> ORGANISM: Mus musculus

<400> SEQUENCE: 71

Lys Ala Thr Gly Val Leu Leu Tyr Asp Leu Val Ser Arg
1               5                   10

<210> SEQ ID NO 72
<211> LENGTH: 10
<212> TYPE: PRT
<213> ORGANISM: Mus musculus

<400> SEQUENCE: 72

Ser Phe Leu Val Ser Tyr Ile Ala Asn Lys
1               5                   10

<210> SEQ ID NO 73
<211> LENGTH: 27
<212> TYPE: PRT
<213> ORGANISM: Mus musculus

<400> SEQUENCE: 73

Asp Phe Glu Gln Glu Cys Gly Val Gly Val Val Thr Pro Glu Gln
1               5                   10                  15

Ile Glu Glu Ala Val Glu Ser Thr Ile Asn Lys
            20                  25

<210> SEQ ID NO 74
<211> LENGTH: 17
<212> TYPE: PRT
<213> ORGANISM: Mus musculus

<400> SEQUENCE: 74

```
Met Ile Lys Asn Glu Val Asp Met Gln Val Leu His Leu Leu Gly Pro
1               5                   10                  15

Lys

<210> SEQ ID NO 75
<211> LENGTH: 28
<212> TYPE: PRT
<213> ORGANISM: Mus musculus

<400> SEQUENCE: 75

Glu Ala Ala Thr Gln Ala His Gln Ile Leu Gly Ser Thr Ile Asp Lys
1               5                   10                  15

Ala Thr Gly Val Leu Leu Tyr Asp Leu Val Ser Arg
            20                  25

<210> SEQ ID NO 76
<211> LENGTH: 13
<212> TYPE: PRT
<213> ORGANISM: Homo sapiens

<400> SEQUENCE: 76

Glu Thr Leu Lys Asn Ser Ala Leu Ser Ala Gln Leu Arg
1               5                   10

<210> SEQ ID NO 77
<211> LENGTH: 28
<212> TYPE: PRT
<213> ORGANISM: Homo sapiens

<400> SEQUENCE: 77

Glu Ala Ala Thr Gln Ala Gln Gln Thr Leu Gly Ser Thr Ile Asp Lys
1               5                   10                  15

Ala Thr Gly Ile Leu Leu Tyr Gly Leu Ala Ser Arg
            20                  25

<210> SEQ ID NO 78
<211> LENGTH: 41
<212> TYPE: PRT
<213> ORGANISM: Homo sapiens

<400> SEQUENCE: 78

Glu Thr Leu Lys Asn Ser Ala Leu Ser Ala Gln Leu Arg Glu Ala Ala
1               5                   10                  15

Thr Gln Ala Gln Gln Thr Leu Gly Ser Thr Ile Asp Lys Ala Thr Gly
            20                  25                  30

Ile Leu Leu Tyr Gly Leu Ala Ser Arg
        35                  40

<210> SEQ ID NO 79
<211> LENGTH: 27
<212> TYPE: PRT
<213> ORGANISM: Homo sapiens

<400> SEQUENCE: 79

Asp Phe Glu Arg Glu Cys Gly Val Gly Val Ile Val Thr Pro Glu Gln
1               5                   10                  15

Ile Glu Glu Ala Val Glu Ala Ala Ile Asn Arg
            20                  25

<210> SEQ ID NO 80
<211> LENGTH: 15
```

```
<212> TYPE: PRT
<213> ORGANISM: Homo sapiens

<400> SEQUENCE: 80

Thr Pro Gly Tyr Val Val Thr Pro His Thr Met Asn Leu Leu Lys
1               5                   10                  15

<210> SEQ ID NO 81
<211> LENGTH: 15
<212> TYPE: PRT
<213> ORGANISM: Homo sapiens

<400> SEQUENCE: 81

Gly Glu Glu Leu Lys Gly His Asn Thr Leu Pro Ser Pro Trp Arg
1               5                   10                  15

<210> SEQ ID NO 82
<211> LENGTH: 15
<212> TYPE: PRT
<213> ORGANISM: Homo sapiens

<400> SEQUENCE: 82

Asp Arg Pro Met Glu Glu Ser Leu Leu Leu Phe Glu Ala Met Arg
1               5                   10                  15

<210> SEQ ID NO 83
<211> LENGTH: 30
<212> TYPE: PRT
<213> ORGANISM: Homo sapiens

<400> SEQUENCE: 83

Gly Glu Glu Leu Lys Gly His Asn Thr Leu Pro Ser Pro Trp Arg Asp
1               5                   10                  15

Arg Pro Met Glu Glu Ser Leu Leu Leu Phe Glu Ala Met Arg
            20                  25                  30

<210> SEQ ID NO 84
<211> LENGTH: 11
<212> TYPE: PRT
<213> ORGANISM: Homo sapiens

<400> SEQUENCE: 84

Ile Leu Gln Leu Val Ala Thr Gly Ala Val Arg
1               5                   10

<210> SEQ ID NO 85
<211> LENGTH: 28
<212> TYPE: PRT
<213> ORGANISM: Homo sapiens

<400> SEQUENCE: 85

Asp Val Leu Asn Asp Thr Ala Pro Arg Ala Met Ala Val Leu Glu Ser
1               5                   10                  15

Leu Arg Val Ile Ile Thr Asn Phe Pro Ala Ala Lys
            20                  25

<210> SEQ ID NO 86
<211> LENGTH: 38
<212> TYPE: PRT
<213> ORGANISM: Homo sapiens

<400> SEQUENCE: 86

Gly Phe His Gln Val Pro Phe Ala Pro Ile Val Phe Ile Glu Arg Thr
1               5                   10                  15
```

```
Asp Phe Lys Glu Glu Pro Glu Pro Gly Phe Lys Arg Leu Ala Trp Gly
            20                  25                  30

Gln Pro Val Gly Leu Arg
        35

<210> SEQ ID NO 87
<211> LENGTH: 15
<212> TYPE: PRT
<213> ORGANISM: Homo sapiens

<400> SEQUENCE: 87

Ala Phe Ile His Trp Val Ser Gln Pro Leu Met Cys Glu Val Arg
1               5                   10                  15

<210> SEQ ID NO 88
<211> LENGTH: 19
<212> TYPE: PRT
<213> ORGANISM: Homo sapiens

<400> SEQUENCE: 88

Leu Gly Tyr Phe Ser Val Asp Pro Asp Ser His Gln Gly Lys Leu Val
1               5                   10                  15

Phe Asn Arg

<210> SEQ ID NO 89
<211> LENGTH: 15
<212> TYPE: PRT
<213> ORGANISM: Homo sapiens

<400> SEQUENCE: 89

Thr Pro Gly Tyr Val Val Thr Pro His Thr Met Asn Leu Leu Lys
1               5                   10                  15

<210> SEQ ID NO 90
<211> LENGTH: 18
<212> TYPE: PRT
<213> ORGANISM: Homo sapiens

<400> SEQUENCE: 90

Phe Phe Thr Ala Ile Cys Asp Met Val Ala Trp Leu Gly Tyr Thr Pro
1               5                   10                  15

Tyr Lys

<210> SEQ ID NO 91
<211> LENGTH: 30
<212> TYPE: PRT
<213> ORGANISM: Homo sapiens

<400> SEQUENCE: 91

Phe Asp Asp Thr Asn Pro Glu Lys Glu Ala Lys Phe Phe Thr Ala
1               5                   10                  15

Ile Tyr Asp Met Val Thr Trp Leu Gly Tyr Thr Pro Tyr Lys
            20                  25                  30

<210> SEQ ID NO 92
<211> LENGTH: 15
<212> TYPE: PRT
<213> ORGANISM: Homo sapiens

<400> SEQUENCE: 92

Asp Arg Pro Met Glu Glu Ser Leu Leu Leu Phe Glu Ala Met Arg
1               5                   10                  15
```

```
<210> SEQ ID NO 93
<211> LENGTH: 11
<212> TYPE: PRT
<213> ORGANISM: Homo sapiens

<400> SEQUENCE: 93

Ile Leu Gln Leu Val Ala Thr Gly Ala Val Arg
1               5                   10

<210> SEQ ID NO 94
<211> LENGTH: 19
<212> TYPE: PRT
<213> ORGANISM: Homo sapiens

<400> SEQUENCE: 94

Ala Met Ala Val Leu Glu Ser Leu Arg Val Ile Ile Thr Asn Phe Pro
1               5                   10                  15

Ala Ala Lys

<210> SEQ ID NO 95
<211> LENGTH: 15
<212> TYPE: PRT
<213> ORGANISM: Homo sapiens

<400> SEQUENCE: 95

Ser Leu Asp Ile Gln Val Pro Asn Phe Pro Ala Asp Glu Thr Lys
1               5                   10                  15

<210> SEQ ID NO 96
<211> LENGTH: 34
<212> TYPE: PRT
<213> ORGANISM: Homo sapiens

<400> SEQUENCE: 96

Ala Met Ala Val Leu Glu Ser Leu Arg Val Ile Ile Thr Asn Phe Pro
1               5                   10                  15

Ala Ala Lys Ser Leu Asp Ile Gln Val Pro Asn Phe Pro Ala Asp Glu
                20                  25                  30

Thr Lys

<210> SEQ ID NO 97
<211> LENGTH: 36
<212> TYPE: PRT
<213> ORGANISM: Homo sapiens

<400> SEQUENCE: 97

Thr Asp Phe Lys Glu Glu Pro Glu Pro Gly Phe Lys Arg Leu Ala Trp
1               5                   10                  15

Gly Gln Pro Val Gly Leu Arg His Thr Gly Tyr Val Ile Glu Leu Gln
                20                  25                  30

His Val Val Lys
            35

<210> SEQ ID NO 98
<211> LENGTH: 15
<212> TYPE: PRT
<213> ORGANISM: Homo sapiens

<400> SEQUENCE: 98

Ala Phe Ile His Trp Val Ser Gln Pro Leu Met Cys Glu Val Arg
1               5                   10                  15
```

<210> SEQ ID NO 99
<211> LENGTH: 19
<212> TYPE: PRT
<213> ORGANISM: Homo sapiens

<400> SEQUENCE: 99

Leu Gly Tyr Phe Ser Val Asp Pro Asp Ser His Gln Gly Lys Leu Val
1               5                   10                  15

Phe Asn Arg

<210> SEQ ID NO 100
<211> LENGTH: 13
<212> TYPE: PRT
<213> ORGANISM: Homo sapiens

<400> SEQUENCE: 100

Lys Ala Thr Gly Ile Leu Leu Tyr Gly Leu Ala Ser Arg
1               5                   10

<210> SEQ ID NO 101
<211> LENGTH: 10
<212> TYPE: PRT
<213> ORGANISM: Homo sapiens

<400> SEQUENCE: 101

Ser Phe Leu Val Ser Tyr Ile Ala Ser Lys
1               5                   10

<210> SEQ ID NO 102
<211> LENGTH: 27
<212> TYPE: PRT
<213> ORGANISM: Homo sapiens

<400> SEQUENCE: 102

Asp Phe Glu Arg Glu Cys Gly Val Gly Val Ile Val Thr Pro Glu Gln
1               5                   10                  15

Ile Glu Glu Ala Val Glu Ala Ala Ile Asn Arg
            20                  25

<210> SEQ ID NO 103
<211> LENGTH: 28
<212> TYPE: PRT
<213> ORGANISM: Homo sapiens

<400> SEQUENCE: 103

Glu Ala Ala Thr Gln Ala Gln Gln Thr Leu Gly Ser Thr Ile Asp Lys
1               5                   10                  15

Ala Thr Gly Ile Leu Leu Tyr Gly Leu Ala Ser Arg
            20                  25

<210> SEQ ID NO 104
<211> LENGTH: 86
<212> TYPE: PRT
<213> ORGANISM: Homo sapiens

<400> SEQUENCE: 104

Met Pro Thr Val Ser Val Lys Arg Asp Leu Leu Phe Gln Ala Leu Gly
1               5                   10                  15

Arg Thr Tyr Thr Asp Glu Glu Phe Glu Leu Cys Phe Glu Phe Gly
            20                  25                  30

Leu Glu Leu Asp Glu Ile Lys Asp Leu Glu Leu Leu Cys Pro Arg Cys

```
                35                  40                  45
Ser Leu Ser Thr Asp His Gln His Arg Cys Val Trp Pro Ile Lys Lys
 50                  55                  60

Ala Ala Ser Tyr Gln Glu Lys Thr Gly Ala Ile Gln Cys Thr Val Glu
 65                  70                  75                  80

Gly Glu Ser Gly Thr Asn
                 85

<210> SEQ ID NO 105
<211> LENGTH: 501
<212> TYPE: PRT
<213> ORGANISM: Homo sapiens

<400> SEQUENCE: 105

Met Pro Ser Ala Ser Ala Ser Arg Lys Ser Gln Glu Lys Pro Arg Glu
 1               5                   10                  15

Ile Met Asp Ala Ala Glu Asp Tyr Ala Lys Glu Arg Tyr Gly Ile Ser
                 20                  25                  30

Ser Met Ile Gln Ser Gln Glu Lys Pro Asp Arg Val Leu Val Arg Val
                 35                  40                  45

Arg Asp Leu Thr Ile Gln Lys Ala Asp Glu Val Val Trp Val Arg Ala
 50                  55                  60

Arg Val His Thr Ser Arg Ala Lys Gly Lys Gln Cys Phe Leu Val Leu
 65                  70                  75                  80

Arg Gln Gln Gln Phe Asn Val Gln Ala Leu Val Ala Val Gly Asp His
                 85                  90                  95

Ala Ser Lys Gln Met Val Lys Phe Ala Ala Asn Ile Asn Lys Glu Ser
                 100                 105                 110

Ile Val Asp Val Glu Gly Val Val Arg Lys Val Asn Gln Lys Ile Gly
                 115                 120                 125

Ser Cys Thr Gln Gln Asp Val Glu Leu His Val Gln Lys Ile Tyr Val
                 130                 135                 140

Ile Ser Leu Ala Glu Pro Arg Leu Pro Leu Gln Leu Asp Asp Ala Val
145                  150                 155                 160

Arg Pro Glu Ala Glu Gly Glu Glu Gly Arg Ala Thr Val Asn Gln
                 165                 170                 175

Asp Thr Arg Leu Asp Asn Arg Val Ile Asp Leu Arg Thr Ser Thr Ser
                 180                 185                 190

Gln Ala Val Phe Arg Leu Gln Ser Gly Ile Cys His Leu Phe Arg Glu
                 195                 200                 205

Thr Leu Ile Asn Lys Gly Phe Val Glu Ile Gln Thr Pro Lys Ile Ile
                 210                 215                 220

Ser Ala Ala Ser Glu Gly Gly Ala Asn Val Phe Thr Val Ser Tyr Phe
225                  230                 235                 240

Lys Asn Asn Ala Tyr Leu Ala Gln Ser Pro Gln Leu Tyr Lys Gln Met
                 245                 250                 255

Cys Ile Cys Ala Asp Phe Glu Lys Val Phe Ser Ile Gly Pro Val Phe
                 260                 265                 270

Arg Ala Glu Asp Ser Asn Thr His Arg His Leu Thr Glu Phe Val Gly
                 275                 280                 285

Leu Asp Ile Glu Met Ala Phe Asn Tyr His Tyr His Glu Val Met Glu
                 290                 295                 300

Glu Ile Ala Asp Thr Met Val Gln Ile Phe Lys Gly Leu Gln Glu Arg
305                  310                 315                 320
```

```
Phe Gln Thr Glu Ile Gln Thr Val Asn Lys Gln Phe Pro Cys Glu Pro
                325                 330                 335

Phe Lys Phe Leu Glu Pro Thr Leu Arg Leu Glu Tyr Cys Glu Ala Leu
            340                 345                 350

Ala Met Leu Arg Glu Ala Gly Val Glu Met Gly Asp Glu Asp Asp Leu
                355                 360                 365

Ser Thr Pro Asn Glu Lys Leu Leu Gly His Leu Val Lys Glu Lys Tyr
    370                 375                 380

Asp Thr Asp Phe Tyr Ile Leu Asp Lys Tyr Pro Leu Ala Val Arg Pro
385                 390                 395                 400

Phe Tyr Thr Met Pro Asp Pro Arg Asn Pro Lys Gln Ser Asn Ser Tyr
                405                 410                 415

Asp Met Phe Met Arg Gly Glu Ile Leu Ser Gly Ala Gln Arg Ile
                420                 425                 430

His Asp Pro Gln Leu Leu Thr Glu Arg Ala Leu His His Gly Ile Asp
            435                 440                 445

Leu Glu Lys Ile Lys Ala Tyr Ile Asp Ser Phe Arg Phe Gly Ala Pro
    450                 455                 460

Pro His Ala Gly Gly Gly Ile Gly Leu Glu Arg Val Thr Met Leu Phe
465                 470                 475                 480

Leu Gly Leu His Asn Val Arg Gln Thr Ser Met Phe Pro Arg Asp Pro
                485                 490                 495

Lys Arg Leu Thr Pro
                500

<210> SEQ ID NO 106
<211> LENGTH: 471
<212> TYPE: PRT
<213> ORGANISM: Homo sapiens

<400> SEQUENCE: 106

Met Pro Asn Ser Glu Pro Ala Ser Leu Leu Glu Leu Phe Asn Ser Ile
1               5                   10                  15

Ala Thr Gln Gly Glu Leu Val Arg Ser Leu Lys Ala Gly Asn Ala Ser
            20                  25                  30

Lys Asp Glu Ile Asp Ser Ala Val Lys Met Leu Val Ser Leu Lys Met
        35                  40                  45

Ser Tyr Lys Ala Ala Gly Glu Asp Tyr Lys Ala Asp Cys Pro Pro
    50                  55                  60

Gly Asn Pro Ala Pro Thr Ser Asn His Gly Pro Asp Ala Thr Glu Ala
65                  70                  75                  80

Glu Glu Asp Phe Val Asp Pro Trp Thr Val Gln Thr Ser Ser Ala Lys
                85                  90                  95

Gly Ile Asp Tyr Asp Lys Leu Ile Val Arg Phe Gly Ser Ser Lys Ile
            100                 105                 110

Asp Lys Glu Leu Ile Asn Arg Ile Glu Arg Ala Thr Gly Gln Arg Pro
        115                 120                 125

His His Phe Leu Arg Arg Gly Ile Phe Phe Ser His Arg Asp Met Asn
    130                 135                 140

Gln Val Leu Asp Ala Tyr Glu Asn Lys Lys Pro Phe Tyr Leu Tyr Thr
145                 150                 155                 160

Gly Arg Gly Pro Ser Ser Glu Ala Met His Val Gly His Leu Ile Pro
                165                 170                 175

Phe Ile Phe Thr Lys Trp Leu Gln Asp Val Phe Asn Val Pro Leu Val
            180                 185                 190
```

-continued

```
Ile Gln Met Thr Asp Asp Glu Lys Tyr Leu Trp Lys Asp Leu Thr Leu
        195                 200                 205

Asp Gln Ala Tyr Ser Tyr Ala Val Glu Asn Ala Lys Asp Ile Ile Ala
    210                 215                 220

Cys Gly Phe Asp Ile Asn Lys Thr Phe Ile Phe Ser Asp Leu Asp Tyr
225                 230                 235                 240

Met Gly Met Ser Ser Gly Phe Tyr Lys Asn Val Val Lys Ile Gln Lys
                245                 250                 255

His Val Thr Phe Asn Gln Val Lys Gly Ile Phe Gly Phe Thr Asp Ser
            260                 265                 270

Asp Cys Ile Gly Lys Ile Ser Phe Pro Ala Ile Gln Ala Ala Pro Ser
        275                 280                 285

Phe Ser Asn Ser Phe Pro Gln Ile Phe Arg Asp Arg Thr Asp Ile Gln
    290                 295                 300

Cys Leu Ile Pro Cys Ala Ile Asp Gln Asp Pro Tyr Phe Arg Met Thr
305                 310                 315                 320

Arg Asp Val Ala Pro Arg Ile Gly Tyr Pro Lys Pro Ala Leu Leu His
                325                 330                 335

Ser Thr Phe Phe Pro Ala Leu Gln Gly Ala Gln Thr Lys Met Ser Ala
            340                 345                 350

Ser Asp Pro Asn Ser Ser Ile Phe Leu Thr Asp Thr Ala Lys Gln Ile
        355                 360                 365

Lys Thr Lys Val Asn Lys His Ala Phe Ser Gly Gly Arg Asp Thr Ile
    370                 375                 380

Glu Glu His Arg Gln Phe Gly Gly Asn Cys Asp Val Asp Val Ser Phe
385                 390                 395                 400

Met Tyr Leu Thr Phe Phe Leu Glu Asp Asp Lys Leu Glu Gln Ile
                405                 410                 415

Arg Lys Asp Tyr Thr Ser Gly Ala Met Leu Thr Gly Glu Leu Lys Lys
                420                 425                 430

Ala Leu Ile Glu Val Leu Gln Pro Leu Ile Ala Glu His Gln Ala Arg
            435                 440                 445

Arg Lys Glu Val Thr Asp Glu Ile Val Lys Glu Phe Met Thr Pro Arg
        450                 455                 460

Lys Leu Ser Phe Asp Phe Gln
465                 470

<210> SEQ ID NO 107
<211> LENGTH: 424
<212> TYPE: PRT
<213> ORGANISM: Homo sapiens

<400> SEQUENCE: 107

Met Ser Tyr Lys Ala Ala Ala Gly Glu Asp Tyr Lys Ala Asp Cys Pro
1               5                   10                  15

Pro Gly Asn Pro Ala Pro Thr Ser Asn His Gly Pro Asp Ala Thr Glu
                20                  25                  30

Ala Glu Glu Asp Phe Val Asp Pro Trp Thr Val Gln Thr Ser Ser Ala
            35                  40                  45

Lys Gly Ile Asp Tyr Asp Lys Leu Ile Val Arg Phe Gly Ser Ser Lys
        50                  55                  60

Ile Asp Lys Glu Leu Ile Asn Arg Ile Glu Arg Ala Thr Gly Gln Arg
65                  70                  75                  80

Pro His His Phe Leu Arg Arg Gly Ile Phe Phe Ser His Arg Asp Met
```

```
                    85                  90                  95
Asn Gln Val Leu Asp Ala Tyr Glu Asn Lys Pro Phe Tyr Leu Tyr
                100                 105                 110

Thr Gly Arg Gly Pro Ser Ser Glu Ala Met His Val Gly His Leu Ile
                115                 120                 125

Pro Phe Ile Phe Thr Lys Trp Leu Gln Asp Val Phe Asn Val Pro Leu
        130                 135                 140

Val Ile Gln Met Thr Asp Asp Glu Lys Tyr Leu Trp Lys Asp Leu Thr
145                 150                 155                 160

Leu Asp Gln Ala Tyr Ser Tyr Ala Val Glu Asn Ala Lys Asp Ile Ile
                165                 170                 175

Ala Cys Gly Phe Asp Ile Asn Lys Thr Phe Ile Phe Ser Asp Leu Asp
                180                 185                 190

Tyr Met Gly Met Ser Ser Gly Phe Tyr Lys Asn Val Val Lys Ile Gln
                195                 200                 205

Lys His Val Thr Phe Asn Gln Val Lys Gly Ile Phe Gly Phe Thr Asp
                210                 215                 220

Ser Asp Cys Ile Gly Lys Ile Ser Phe Pro Ala Ile Gln Ala Ala Pro
225                 230                 235                 240

Ser Phe Ser Asn Ser Phe Pro Gln Ile Phe Arg Asp Arg Thr Asp Ile
                    245                 250                 255

Gln Cys Leu Ile Pro Cys Ala Ile Asp Gln Asp Pro Tyr Phe Arg Met
                260                 265                 270

Thr Arg Asp Val Ala Pro Arg Ile Gly Tyr Pro Lys Pro Ala Leu Leu
                275                 280                 285

His Ser Thr Phe Phe Pro Ala Leu Gln Gly Ala Gln Thr Lys Met Ser
                290                 295                 300

Ala Ser Asp Pro Asn Ser Ser Ile Phe Leu Thr Asp Thr Ala Lys Gln
305                 310                 315                 320

Ile Lys Thr Lys Val Asn Lys His Ala Phe Ser Gly Gly Arg Asp Thr
                    325                 330                 335

Ile Glu Glu His Arg Gln Phe Gly Gly Asn Cys Asp Val Asp Val Ser
                340                 345                 350

Phe Met Tyr Leu Thr Phe Phe Leu Glu Asp Asp Lys Leu Glu Gln
                355                 360                 365

Ile Arg Lys Asp Tyr Thr Ser Gly Ala Met Leu Thr Gly Glu Leu Lys
                370                 375                 380

Lys Ala Leu Ile Glu Val Leu Gln Pro Leu Ile Ala Glu His Gln Ala
385                 390                 395                 400

Arg Arg Lys Glu Val Thr Asp Glu Ile Val Lys Glu Phe Met Thr Pro
                    405                 410                 415

Arg Lys Leu Ser Phe Asp Phe Gln
                420

<210> SEQ ID NO 108
<211> LENGTH: 401
<212> TYPE: PRT
<213> ORGANISM: Homo sapiens

<400> SEQUENCE: 108

Ser Asn His Gly Pro Asp Ala Thr Glu Ala Glu Glu Asp Phe Val Asp
1               5                   10                  15

Pro Trp Thr Val Gln Thr Ser Ser Ala Lys Gly Ile Asp Tyr Asp Lys
                20                  25                  30
```

```
Leu Ile Val Arg Phe Gly Ser Ser Lys Ile Asp Lys Glu Leu Ile Asn
             35                  40                  45
Arg Ile Glu Arg Ala Thr Gly Gln Arg Pro His His Phe Leu Arg Arg
 50                  55                  60
Gly Ile Phe Phe Ser His Arg Asp Met Asn Gln Val Leu Asp Ala Tyr
 65                  70                  75                  80
Glu Asn Lys Lys Pro Phe Tyr Leu Tyr Thr Gly Arg Gly Pro Ser Ser
                 85                  90                  95
Glu Ala Met His Val Gly His Leu Ile Pro Phe Ile Phe Thr Lys Trp
            100                 105                 110
Leu Gln Asp Val Phe Asn Val Pro Leu Val Ile Gln Met Thr Asp Asp
            115                 120                 125
Glu Lys Tyr Leu Trp Lys Asp Leu Thr Leu Asp Gln Ala Tyr Ser Tyr
130                 135                 140
Ala Val Glu Asn Ala Lys Asp Ile Ile Ala Cys Gly Phe Asp Ile Asn
145                 150                 155                 160
Lys Thr Phe Ile Phe Ser Asp Leu Asp Tyr Met Gly Met Ser Ser Gly
                165                 170                 175
Phe Tyr Lys Asn Val Val Lys Ile Gln Lys His Val Thr Phe Asn Gln
            180                 185                 190
Val Lys Gly Ile Phe Gly Phe Thr Asp Ser Asp Cys Ile Gly Lys Ile
            195                 200                 205
Ser Phe Pro Ala Ile Gln Ala Ala Pro Ser Phe Ser Asn Ser Phe Pro
            210                 215                 220
Gln Ile Phe Arg Asp Arg Thr Asp Ile Gln Cys Leu Ile Pro Cys Ala
225                 230                 235                 240
Ile Asp Gln Asp Pro Tyr Phe Arg Met Thr Arg Asp Val Ala Pro Arg
                245                 250                 255
Ile Gly Tyr Pro Lys Pro Ala Leu Leu His Ser Thr Phe Phe Pro Ala
            260                 265                 270
Leu Gln Gly Ala Gln Thr Lys Met Ser Ala Ser Asp Pro Asn Ser Ser
            275                 280                 285
Ile Phe Leu Thr Asp Thr Ala Lys Gln Ile Lys Thr Lys Val Asn Lys
            290                 295                 300
His Ala Phe Ser Gly Gly Arg Asp Thr Ile Glu Glu His Arg Gln Phe
305                 310                 315                 320
Gly Gly Asn Cys Asp Val Asp Val Ser Phe Met Tyr Leu Thr Phe Phe
                325                 330                 335
Leu Glu Asp Asp Asp Lys Leu Glu Gln Ile Arg Lys Asp Tyr Thr Ser
            340                 345                 350
Gly Ala Met Leu Thr Gly Glu Leu Lys Lys Ala Leu Ile Glu Val Leu
            355                 360                 365
Gln Pro Leu Ile Ala Glu His Gln Ala Arg Arg Lys Glu Val Thr Asp
370                 375                 380
Glu Ile Val Lys Glu Phe Met Thr Pro Arg Lys Leu Ser Phe Asp Phe
385                 390                 395                 400
Gln

<210> SEQ ID NO 109
<211> LENGTH: 25
<212> TYPE: PRT
<213> ORGANISM: Homo sapiens

<400> SEQUENCE: 109
```

Asn Ser Ala Leu Ser Ala Gln Leu Arg Glu Ala Ala Thr Gln Ala Gln
1               5                   10                  15

Gln Thr Leu Gly Ser Thr Ile Asp Lys
            20                  25

<210> SEQ ID NO 110
<211> LENGTH: 37
<212> TYPE: PRT
<213> ORGANISM: Homo sapiens

<400> SEQUENCE: 110

Ser His Pro Leu Asp Pro Ile Asp Thr Val Asp Phe Glu Arg Glu Cys
1               5                   10                  15

Gly Val Gly Val Ile Val Thr Pro Glu Gln Ile Glu Glu Ala Val Glu
            20                  25                  30

Ala Ala Ile Asn Arg
        35

<210> SEQ ID NO 111
<211> LENGTH: 11
<212> TYPE: PRT
<213> ORGANISM: Homo sapiens

<400> SEQUENCE: 111

Leu Ser Phe Leu Val Ser Tyr Ile Ala Ser Lys
1               5                   10

<210> SEQ ID NO 112
<211> LENGTH: 23
<212> TYPE: PRT
<213> ORGANISM: Homo sapiens

<400> SEQUENCE: 112

Glu Cys Gly Val Gly Val Ile Val Thr Pro Glu Gln Ile Glu Glu Ala
1               5                   10                  15

Val Glu Ala Ala Ile Asn Arg
            20

<210> SEQ ID NO 113
<211> LENGTH: 28
<212> TYPE: PRT
<213> ORGANISM: Homo sapiens

<400> SEQUENCE: 113

Glu Ala Ala Thr Gln Ala Gln Gln Thr Leu Gly Ser Thr Ile Asp Lys
1               5                   10                  15

Ala Thr Gly Ile Leu Leu Tyr Gly Leu Ala Ser Arg
            20                  25

<210> SEQ ID NO 114
<211> LENGTH: 15
<212> TYPE: PRT
<213> ORGANISM: Homo sapiens

<400> SEQUENCE: 114

Ile His Thr Glu Pro Gln Leu Ser Ala Ala Leu Glu Tyr Val Arg
1               5                   10                  15

<210> SEQ ID NO 115
<211> LENGTH: 14
<212> TYPE: PRT
<213> ORGANISM: Homo sapiens

```
<400> SEQUENCE: 115

Asn Glu Val Asp Met Gln Val Leu His Leu Leu Gly Pro Lys
1               5                   10

<210> SEQ ID NO 116
<211> LENGTH: 775
<212> TYPE: PRT
<213> ORGANISM: Mus musculus

<400> SEQUENCE: 116

Met Ala Thr Pro Asp Ser Leu Ala Leu Phe Thr Gly Leu Gly Leu Ser
1               5                   10                  15

Glu Asn Lys Ala Arg Glu Thr Leu Lys Asn Glu Ala Leu Ser Thr Gln
                20                  25                  30

Leu Arg Glu Ala Ala Thr Gln Ala His Gln Ile Leu Gly Ser Thr Ile
            35                  40                  45

Asp Lys Ala Thr Gly Val Leu Leu Tyr Asp Leu Val Ser Arg Leu Arg
    50                  55                  60

Asp Thr Arg Arg Arg Ser Phe Leu Val Ser Tyr Ile Ala Asn Lys Lys
65                  70                  75                  80

Ile His Thr Gly Leu Gln Leu Ser Ala Ala Leu Glu Tyr Val Arg Ser
                85                  90                  95

His Pro Gln Asp Pro Ile Asp Thr Lys Asp Phe Glu Gln Glu Cys Gly
                100                 105                 110

Val Gly Val Val Val Thr Pro Glu Gln Ile Glu Glu Ala Val Glu Ser
            115                 120                 125

Thr Ile Asn Lys His Gln Leu Gln Leu Leu Ala Glu Arg Tyr Arg Phe
    130                 135                 140

Asn Met Gly Leu Leu Met Gly Glu Ala Arg Ala Ala Leu Arg Trp Ala
145                 150                 155                 160

Asp Gly Lys Met Ile Lys Asn Glu Val Asp Met Gln Val Leu His Leu
                165                 170                 175

Leu Gly Pro Lys Met Glu Ala Asp Leu Val Lys Lys Pro Lys Val Ala
            180                 185                 190

Lys Ala Arg Leu Glu Glu Thr Asp Arg Lys Thr Ala Lys Asp Val Val
        195                 200                 205

Glu Lys Gly Glu Val Ala Gly Gln Ile Leu Ser Leu Met Glu Gln Leu
    210                 215                 220

Arg Gly Glu Ala Leu Lys Phe His Lys Pro Gly Glu Asn Tyr Lys Thr
225                 230                 235                 240

Pro Gly Tyr Val Ile Thr Pro Tyr Thr Met Asp Leu Leu Lys Gln His
                245                 250                 255

Leu Glu Ile Thr Gly Gly Gln Val Arg Thr Arg Phe Pro Pro Glu Pro
            260                 265                 270

Asn Gly Ile Leu His Ile Gly His Ala Lys Ala Ile Asn Phe Asn Phe
        275                 280                 285

Gly Tyr Ala Lys Ala Asn Asn Gly Ile Cys Phe Leu Arg Phe Asp Asp
    290                 295                 300

Thr Asn Pro Glu Lys Glu Glu Ala Lys Phe Phe Thr Ala Ile Tyr Asp
305                 310                 315                 320

Met Val Thr Trp Leu Gly Tyr Thr Pro Tyr Lys Val Thr Tyr Ala Ser
                325                 330                 335

Asp Tyr Phe Asp Gln Leu Tyr Ala Trp Ala Val Glu Leu Ile His Gly
            340                 345                 350
```

-continued

```
Gly Leu Ala Tyr Val Cys His Gln Arg Val Glu Glu Leu Lys Gly His
            355                 360                 365

Asn Pro Leu Pro Ser Pro Trp Arg Asp Arg Pro Lys Glu Glu Ser Leu
370                 375                 380

Leu Leu Phe Glu Ala Met Arg Lys Gly Lys Phe Ala Glu Gly Glu Ala
385                 390                 395                 400

Thr Leu Arg Met Lys Leu Val Met Glu Asp Gly Lys Met Asp Pro Val
                405                 410                 415

Ala Tyr Arg Val Lys Tyr Thr Pro His His Arg Thr Gly Asp Lys Trp
            420                 425                 430

Cys Ile Tyr Pro Thr Tyr Asp Tyr Thr His Cys Leu Cys Asp Ser Ile
            435                 440                 445

Glu His Ile Thr His Ser Leu Cys Thr Lys Glu Phe Gln Ala Arg Arg
            450                 455                 460

Ser Ser Tyr Phe Trp Leu Cys Asn Ala Leu Lys Val Tyr Cys Pro Val
465                 470                 475                 480

Gln Trp Glu Tyr Gly Arg Leu Asn Leu His Tyr Ala Val Val Ser Lys
                485                 490                 495

Arg Lys Ile Leu Gln Leu Val Ala Ala Gly Ala Val Arg Asp Trp Asp
            500                 505                 510

Asp Pro Arg Leu Phe Thr Leu Thr Ala Leu Arg Arg Arg Gly Phe Pro
            515                 520                 525

Pro Glu Ala Ile Asn Asn Phe Cys Ala Arg Val Gly Val Thr Val Ala
            530                 535                 540

Gln Thr Thr Met Glu Pro His Leu Leu Glu Ala Cys Val Arg Asp Val
545                 550                 555                 560

Leu Asn Asp Ala Ala Pro Arg Ala Met Ala Val Leu Glu Pro Leu Gln
                565                 570                 575

Val Val Ile Thr Asn Phe Pro Ala Pro Lys Pro Leu Asp Ile Arg Val
            580                 585                 590

Pro Asn Phe Pro Ala Asp Glu Thr Lys Gly Phe His Gln Val Pro Phe
            595                 600                 605

Ala Ser Thr Val Phe Ile Glu Arg Ser Asp Phe Lys Glu Glu Ser Glu
            610                 615                 620

Pro Gly Tyr Lys Arg Leu Ala Ser Gly Gln Pro Val Gly Leu Arg His
625                 630                 635                 640

Thr Gly Tyr Val Ile Glu Leu Gln Asn Ile Val Arg Gly Ser Ser Gly
                645                 650                 655

Cys Val Glu Arg Leu Glu Val Thr Cys Arg Arg Ala Asp Ala Gly Glu
            660                 665                 670

Lys Pro Lys Ala Phe Ile His Trp Val Ser Gln Pro Leu Val Cys Glu
            675                 680                 685

Ile Arg Leu Tyr Glu Arg Leu Phe Gln His Lys Asn Pro Glu Asp Pro
            690                 695                 700

Val Glu Val Pro Gly Gly Phe Leu Ser Asp Leu Asn Pro Ala Ser Leu
705                 710                 715                 720

Gln Val Val Glu Gly Ala Leu Val Asp Cys Ser Val Ala Leu Ala Lys
                725                 730                 735

Pro Phe Asp Lys Phe Gln Phe Glu Arg Leu Gly Tyr Phe Ser Val Asp
            740                 745                 750

Pro Asp Ser His Gln Gly Gln Ile Val Phe Asn Arg Thr Val Thr Leu
            755                 760                 765

Lys Glu Asp Pro Gly Glu Ile
```

<210> SEQ ID NO 117
<211> LENGTH: 2437
<212> TYPE: DNA
<213> ORGANISM: Homo sapiens

<400> SEQUENCE: 117

```
ctgcaatggc ggctctagac tccctgtcgc tcttcactag cctcggcctg agcgagcaga      60
aggcccgcga gacgctcaag aactcggctc tgagcgcgca gctgcgcgag gccgctactc     120
aggctcagca gaccctgggt tccaccattg acaaagctac cgggatcctg ttatatggct     180
tggcctcccg actcagggat acccggcgtc tctccttcct tgtaagctac atagccagta     240
agaagatcca cactgagccc cagctaagcg ctgcccttga gtatgtgcgg agtcaccct      300
tggaccccat cgacactgtg gacttcgagc gggaatgtgg cgtgggtgtc attgtgaccc     360
cagagcagat tgaggaggct gtggaggctc tattaacag gcaccggccc cagctcctgg      420
tggaacgtta ccatttcaac atggggctgc tgatgggaga ggctcgggct gtgctgaagt     480
gggcagatgg caaaatgatc aagaatgaag tggacatgca ggtcctccac cttctgggcc     540
ccaagttgga ggctgatctg gagaagaagt tcaaggtggc aaaagctcgg ctagaagaaa     600
cagaccggag gacggcaaag gatgtggtgg agaatggcga gactgctgac cagaccctgt     660
ctctgatgga gcagctccgg ggggaggccc ttaagttcca caagcctggt gagaactaca     720
agaccccagg ctatgtggtc actccacaca ccatgaatct actaaagcag cacctggaga     780
ttactggtgg gcaggtacgt acccggttcc cgccagaacc caatggaatc ctgcatattg     840
gacatgccaa agccatcaat ttcaactttg ctatgccaa ggccaacaat ggcatctgtt     900
ttctgcgttt tgatgacacc aaccctgaga aggaggaagc aaagttcttc acggccatct     960
gtgacatggt agcctggcta ggctacacac cttacaaagt cacatatgcg tctgactatt    1020
ttgaccagct atatgcgtgg gctgtggagc tcatccgcag gggtctggct tatgtgtgcc    1080
accagcgagg agaggagctc aaaggccata atactctgcc ttcaccctgg agagaccgtc    1140
ccatggagga gtcactgctg ctctttgagg caatgcgcaa gggcaagttt tcagagggcg    1200
aggccacact acggatgaag ctggtgatgg aggatggcaa gatggaccct gtagcctatc    1260
gagtcaagta taccacacac accgcacag ggacaaatg tgtcatctat cccacctacg     1320
actacacaca ctgcctctgt gactccatcg agcacatcac tcactcactc tgcaccaagg    1380
aattccaggc ccgacgctct tcctacttct ggctttgcaa tgcactggac gtctattgcc    1440
ctgtgcagtg ggagtatggc cgcctcaacc tgcactatgc tgttgtctct aagaggaaga    1500
tcctccagct tgtagcaact ggtgctgtgc gggactggga tgcccacgg ctctttacac     1560
tcacggccct gcgacggcgg ggcttccac ctgaggccat caacaacttc tgtgcccggg     1620
tgggagtgac tgtggcacaa accacaatgg agccacatct tctagaagcc tgtgtgcgtg    1680
atgtgctgaa tgacacagcc ccacgagcca tggctgtgct ggagtcacta cgggtcatca    1740
tcaccaactt tcctgctgcc aagtccttgg acatccaggt gcccaacttc ccagctgatg    1800
agaccaaagg cttccatcag gttcccttttg cacccattgt cttcattgag aggactgact    1860
tcaaggagga gccagagcca ggatttaagc gcctggcttg gggccagcct gtgggcctga    1920
ggcatacagg ctacgtcatt gagctgcagc atgttgtcaa gggccccagt ggttgtgtag    1980
agagtctgga ggtgacctgc agacgggcag atgctggaga gaagccaaag gccttttattc   2040
actgggtgtc acagcctttg atgtgtgagg ttcgcctcta tgagcgacta ttccagcaca   2100
```

```
agaaccctga agatcctact gaggtgcctg gtggattttt aagtgacctg aacctggcat    2160
cactacacgt ggtggatgca gcattagtgg actgctctgt ggccctggca aaacccttcg    2220
acaagttcca gtttgagcgt cttggatatt tctccgtgga tccagacagc catcagggaa    2280
agcttgtctt taaccgaact gtcacactga aggaagaccc aggaaaggtg tgagctggaa    2340
gcactgaacc tacctcatcc tcctggaggg tgtggctacc ctcgccaccc caaattccat    2400
gtcaataaag aacagctaaa ttctcctaga aaaaaa                              2437
```